(12) United States Patent
Hardy et al.

(10) Patent No.: US 8,518,694 B2
(45) Date of Patent: Aug. 27, 2013

(54) NUCLEIC ACID VECTOR COMPRISING A PROMOTER AND A SEQUENCE ENCODING A POLYPEPTIDE FROM THE ENDOGENOUS RETROVIRUS PCAV

(75) Inventors: Stephen Hardy, San Francisco, CA (US); John Donnelly, Siena (IT); Jan zur Megede, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1674 days.

(21) Appl. No.: 10/587,032

(22) PCT Filed: Jun. 13, 2003

(86) PCT No.: PCT/US03/18666
§ 371 (c)(1),
(2), (4) Date: Dec. 9, 2009

(87) PCT Pub. No.: WO03/106634
PCT Pub. Date: Dec. 24, 2003

(65) Prior Publication Data
US 2010/0086565 A1    Apr. 8, 2010

Related U.S. Application Data

(60) Provisional application No. 60/388,831, filed on Jun. 13, 2002, provisional application No. 60/472,189, filed on May 20, 2003.

(51) Int. Cl.
*A61K 48/00* (2006.01)
*C12N 15/00* (2006.01)

(52) U.S. Cl.
USPC ........................ 435/320.1; 514/44 R

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,777,127 A | 10/1988 | Suni |
| 4,816,567 A | 3/1989 | Cabilly et al. |
| 4,959,314 A | 9/1990 | Mark et al. |
| 5,010,175 A | 4/1991 | Rutter et al. |
| 5,124,246 A | 6/1992 | Urdea et al. |
| 5,149,655 A | 9/1992 | McCabe et al. |
| 5,206,152 A | 4/1993 | Sukhatme |
| 5,219,740 A | 6/1993 | Miller |
| 5,422,120 A | 6/1995 | Kim |
| 5,445,934 A | 8/1995 | Fodor et al. |
| 5,530,101 A | 6/1996 | Queen et al. |
| 5,556,752 A | 9/1996 | Lockhart et al. |
| 5,578,832 A | 11/1996 | Trulson et al. |
| 5,580,859 A | 12/1996 | Felgner et al. |
| 5,593,839 A | 1/1997 | Hubbell et al. |
| 5,599,695 A | 2/1997 | Pease et al. |
| 5,631,734 A | 5/1997 | Stern et al. |
| 5,650,277 A | 7/1997 | Navot et al. |
| 5,707,829 A | 1/1998 | Jacobs et al. |
| 5,800,992 A | 9/1998 | Fodor et al. |
| 5,807,522 A | 9/1998 | Brown et al. |
| 5,814,482 A | 9/1998 | Dubensky, Jr. et al. |
| 5,858,723 A | 1/1999 | Mueller-Lantzsch |
| 5,939,598 A | 8/1999 | Kucherlapati et al. |
| 6,747,137 B1 | 6/2004 | Weinstock et al. |
| 6,753,314 B1 | 6/2004 | Giot et al. |
| 7,776,523 B2 | 8/2010 | Garcia |
| 2004/0259086 A1 | 12/2004 | Schlegel et al. |
| 2005/0196754 A1 | 9/2005 | Drmanac et al. |

FOREIGN PATENT DOCUMENTS

| | | |
|---|---|---|
| EP | 0345242 A2 | 12/1989 |
| EP | 0505012 | 9/1992 |
| EP | 0509112 | 10/1992 |
| EP | 0524968 | 2/1993 |
| EP | 0689454 | 1/1996 |
| EP | 0721016 | 7/1996 |
| EP | 0785280 | 7/1997 |
| EP | 0799897 | 10/1997 |
| EP | 0835318 | 4/1998 |
| EP | 0735898 | 3/1999 |
| EP | 0761231 | 1/2000 |
| EP | 1074617 | 2/2001 |
| GB | 2200651 A | 8/1988 |

(Continued)

OTHER PUBLICATIONS

Tonjes et al. Genome-Wide Screening, Cloning, Chromosomal Assignment, and Expression of Full-Length Human Endogenous Retrovirus Type K. Journal of Virology, Nov. 1999, vol. 73, pp. 9187-9195.*

Zur Megede et. al. Increased Expression and Immunogenicity of Sequence-Modified Human Immunodeficiency Virus Type 1 gag Gene. J. Virology, 2000, p. 2628-2635.*

Tonjes et al. Genome-Wide Screening, Cloning, Chromosomal Assignment, and Expression of Full-Length Human Endogenous Retrovirus Type K. J. Virology, 1999, vol. 73, pp. 9187-9195.*

Boese et al. The Rev/Rex homolog HERV-K cORF multimerizes via a C-terminal domain FEBS Letters, 2001, vol. 493, pp. 117-121.*

(Continued)

*Primary Examiner* — Deborah Crouch
(74) *Attorney, Agent, or Firm* — Mei Hong; Patricia Tsao

(57) ABSTRACT

A nucleic acid vector comprising: (i) a promoter; (ii) a sequence encoding a HML-2 polypeptide operably linked to said promoter; and (iii) a selectable marker. Preferred vectors comprise: (I) a eukaryotic promoter; (ii) a sequence encoding a HML-2 polypeptide downstream of and operably linked to said promoter, (iii) a prokaryotic selectable marker; (iv) a prokaryotic origin of replication; and (v) a eukaryotic transcription terminator downstream of and operably linked to said sequence encoding a HML-2 polypeptide. Vectors of the invention are particularly useful for expression of HML-2 polypeptides either in vitro (e.g. for later purification). Or in vivo (e.g. for nucleic acid immunization). They are well suited to nucleic acid immunization against prostrate tumors. A preferred HML-2 is PCAV, which is located in chromosome 22 at 20.428 megabases (22q11.2).

41 Claims, 7 Drawing Sheets

(56) References Cited

FOREIGN PATENT DOCUMENTS

| | | |
|---|---|---|
| WO | 90/07936 | 7/1990 |
| WO | WO-90/11092 | 10/1990 |
| WO | WO-90/14837 | 12/1990 |
| WO | 91/02805 | 3/1991 |
| WO | WO-91/10741 | 7/1991 |
| WO | WO-91/14445 | 10/1991 |
| WO | WO-91/17823 | 11/1991 |
| WO | WO-92/02526 | 2/1992 |
| WO | WO-92/11033 | 7/1992 |
| WO | WO-92/13949 | 8/1992 |
| WO | 93/03769 | 3/1993 |
| WO | 93/10218 | 5/1993 |
| WO | 93/11230 | 6/1993 |
| WO | WO-93/13202 | 7/1993 |
| WO | WO-93/14778 | 8/1993 |
| WO | 93/19191 | 9/1993 |
| WO | 93/25234 | 12/1993 |
| WO | 93/25698 | 12/1993 |
| WO | 94/03622 | 2/1994 |
| WO | WO-94/02602 | 2/1994 |
| WO | 94/12649 | 6/1994 |
| WO | WO-94/23697 | 10/1994 |
| WO | 94/28938 | 12/1994 |
| WO | 95/00655 | 1/1995 |
| WO | WO-95/07994 | 3/1995 |
| WO | 95/11984 | 5/1995 |
| WO | WO-95/13796 | 5/1995 |
| WO | WO-95/22058 | 8/1995 |
| WO | WO-95/30763 | 11/1995 |
| WO | WO-95/35505 | 12/1995 |
| WO | WO-96/17072 | 6/1996 |
| WO | WO-96/30498 | 10/1996 |
| WO | WO-96/33735 | 10/1996 |
| WO | WO-97/02357 | 1/1997 |
| WO | WO-97/25431 | 7/1997 |
| WO | WO-97/27317 | 7/1997 |
| WO | WO-97/29212 | 8/1997 |
| WO | WO-97/42338 | 11/1997 |
| WO | WO-98/03192 | 1/1998 |
| WO | WO-98/24893 | 6/1998 |
| WO | WO-98/57659 | 12/1998 |
| WO | WO-99/11241 | 3/1999 |
| WO | WO-99/52549 | 10/1999 |
| WO | WO-00/07621 | 2/2000 |
| WO | WO-00/09709 | 2/2000 |
| WO | WO-00/23105 | 4/2000 |
| WO | WO-00/62800 | 10/2000 |
| WO | WO-00/73801 | 12/2000 |
| WO | WO-01/21152 | 3/2001 |
| WO | WO-01/21207 | 3/2001 |
| WO | 02/46477 | 6/2001 |
| WO | WO-01/42467 | 6/2001 |
| WO | WO-01/51623 | 7/2001 |
| WO | WO-01/57182 | 8/2001 |
| WO | WO-01/57270 | 8/2001 |
| WO | WO-01/57272 | 8/2001 |
| WO | WO-01/57274 | 8/2001 |
| WO | WO-01/57275 | 8/2001 |
| WO | WO-01/57276 | 8/2001 |
| WO | WO-01/57277 | 8/2001 |
| WO | WO-01/57278 | 8/2001 |
| WO | WO-01/60860 | 8/2001 |
| WO | WO-01/73032 | 10/2001 |
| WO | WO-01/75067 | 10/2001 |
| WO | WO-01/79518 | 10/2001 |
| WO | WO-01/81581 | 11/2001 |
| WO | WO-02/29065 | 4/2002 |
| WO | WO-03/029460 | 4/2003 |
| WO | 03/050258 | 6/2003 |
| WO | WO-03/106634 | 12/2003 |
| WO | 2004/037972 | 5/2004 |

OTHER PUBLICATIONS

Klein et al. Gag-Specific Immune Responses after Immunization with p17/p24:Ty Virus-Like Particles in HIV Type 1-Seropositive Individuals. Aids Research Human Retrovir., 1996, vol. 13, pp. 393-400.*

Rudolf et al. Human Dendritic Cells Are Activated by Chimeric Human Papillomavirus Type-16 Virus-Like Particles and Induce Epitope-Specific Human T Cell Responses In Vitro. J. Immun., 2001, vol. 166, pp. 5917-5925.*

Herbst et al. Expression of Human Endogenous Retrovirus K Elements in Germ Cell and Trophoblastic Tumors. American J. Pathol., 1996, vol. 149, pp. 1727-1735.*

Tristem et al. Identification and Characterization of Novel Human Endogenous Retrovirus Families by Phylogenetic Screening of the Human Genome Mapping Project Database. J. Virology, 2000, vol. 74, pp. 3715-3730.*

Andersson, Marie-Louise et al. "Diversity of human endogenous retrovirus class II-like sequences", J. of General Virology (1999), 80, 255-260.

Artamonova, T.N., et al. Nonrandom Distribution of the Endogenous Retroviral Regulatory Elements HERV-K LTR on Human Chromosome 22, Doklady Biochemistry, vol. 372, 2000 pp. 87-89.

Barbulescu, Madalina "Many human endogenous retrovirus K (HEERV-K) proviruses are unique to humans" Current Biology 1999, 9:861-868.

Berkhout, Ben, "Identification of an Active Reverse Transcriptqase Enzyme Encoded by a Human Endogenous HERV-K Retrovirus", Journal of Virology, Mar. 1999, p. 2365-2375.

Bieda, Katrin, "Phenotypic heterogeneity of human endogenous retrovirus particles produced by teratocarcinoma cell lines", Journal of General Virology, (2001) 82, 591-596.

Boller, Klaus : "Evidence That HERV-K is the Endogenous Retrovirus Sequence That Codes for the Human Teratocarcinoma-Dervied Rtrovirus HTDV" Virology 196, 349-353 (1993).

Donnelly, John J. "DNA Vaccines", Annu. Rev. Immunol. 1997 15:617-48.

GENBANK, Human endogenous retrovirus HERV-K(II) DNA, complete sequence and flanking region, accession No. AB047240Genomics 72 (2), 137-144 (2001).

Goedert, Jame J. "High prevalence of antibodies against HERV-K10 in patients with testicular cancer but not with AIDS", Cancer Epidemiology, Biomarkers and Prevention, vol. 8, No. 4, Apr. 1, 1999 PA, US.

Gotzinger, Nicole, "Regulation of human endogenous retrovirus-K Gag expression in teratocarcinoma cell lines and human tumours", Journal of General Virology (1996) , 77, 2983-2990.

Kuhelj, Robert, "Inhibition of Human Endogenous Retrovirus-K10 Protease in Cell-free and Cell-based Assays", The Journal of Biological Chemistry, vol. 276, No. 20, Issue of May 18, pp. 16674-16682, 2001.

Kurdyukov, Sergey G. "Full-sized HERV_K (HML-2) human endogenous retrovital LTR sequences on human chromosome 21: map locations and evolutionary history", Gene 273 (2001) 51-61.

Lower, Roswitha, Identification of human endogenous retroviruses with complex mRNA expression and particle formation:, Proc. Natl. Acad. Sci, vol. 90, pp. 4480-4484, May 1993.

Lower, Roswitha, et al. "Identification of a Rev-Related Protein by Analysis of Spliced Transcripts of the Human Endogenous Retroviruses HTDV/HERV-K" Journal of Virology, vol. 69, No. 1 Jan. 1995, p. 141-149.

Lower, Roswitha, et al. "The viruses in all of us: Characteristics and biological significance of human endogenouse retrovirus sequences", Proc. Natl. Acad. Sci vol. 93, pp. 5177-5184, May 1996.

Magin, Christine, Et al. "cORF and RcRE, the Rev/Rex and RRE/RxRE Homologues of the Human Endogenous Retrovirus Family HTDV/HERV-K" J. of Virology, Nov. 1999, p. 9496-9507.

Magin-Lachmann, Christine, "Rec (Formerly Corf) Function Requires Interaction with a Complex, Folded RNA Structure within Its Responsive Element rather than Binding to a Discrete Specific Binding Site", J. of Virology, Nov. 2001, p. 10359-10371.

Mayer, et al. "An almost-intact human endogenous retrovirus K on human chromosome 7" Nature Genetics, vol. 21, Mar. 1999.

Medstrand, Patrik, et al., "Human-Specific Integrations of the HERV-K Endogenous Retrovirus Family", J. of Virology, Dec. 1998, p. 9782-9787.

Mueller-Lantzsch, Nikolaus, et al., "Human Endogenous Retrovial Element K10 (HERV-K10) Encodes a Full-Length Gag Homologous 73-kDa Protein and a Functional Protease", AIDS Research and Human Retroviruses, vol. 9, No. 4, 1993.
Johnston, James B., et al., "Monocyte Activation and Differentiation Augment Human Endogenous Retrovirus Expression: Implications for Inflammatory Brain Diseases", Ann Neurol 2001; 50: 434-442.
Ono, Masao, et al., "Nucleotide Sequence of Human Endogenous Retrovirus Genome Related to the Mouse Mammary Tumor Virus Genome", J. of Virology, Nov. 1986, vol. 60, No. 2 p. 589-598.
Paces, Jan, et al., "HERVd: database of human endogenous retroviruses", Nucleic Acids Research, 2002, vol. 30, No. 1 205-206.
Reus, Katrin "Genomic Organization of the Human Endogenous Retrovirus HERV-K(HML-2.HOM) (ERVK6) on Chromosome 7", Genomics 72, 314-320 (2001).
Robinson, Harriet L., et al "DNA vaccines", seminars in Immunology, vol. 9, 1997, pp. 271-283.
Sauter, Marlies, "Human Endogenous Retrovirus K10: Expression Gag Protein and Detection of Antibodies in Patients with Seminomas" J. of Virology, Jan. 1995, p. 414-421.
Smith, Richard D., et al. "Human Endogenous Retrovirus HERV-K Expression in Prostate Cancer" J. of Urology, Fol. 165, No. 5, Supplement, Jun. 2001.
Smith, RD et al."The Human Endogenous Retrovirus HERV-K in Prostate Cancer" American Journal of Human Genetics, vol. 69, No. 4, Oct. 12, 2001 275.
Stauffer, Yves, et al.,"Digital expression profiles of human endogenous retroviral families in normal and cancerous tissues", Cancer Immunity, vol. 4, p. 2 (Feb. 11, 2004).
Sugimoto, J., et al., gag[Human endogenous retrovirus HERV-K(II)] GenBank: BAB11759.1 m Genomics 72 (2) 137-144 (2001).
Tonjes, Ralf R., et al., "Characterization of Human Endogenous Retrovirus Type K Virus-like Particles Generated from Recombinant Baculoviruses", Virology 233, 280-291 (1997).
Tonjes, Ralf R., et al., gag protein [Human endogenous retrovirus K], GenBank CAA76884.1 J. Virology, 73 (11) 9187-9195 (1999).
Wang-Johanning F. et al., Detection of Human Endogenous Retrovirus Envelope, HERV-E4-1, MRNA Transcriptional Activity/ Prostate Adenocarcinoma by RT-PCR etc. 90th Annual Meeting of American Assoc. of Cancer Research, Philadelphia, PA Apr. 10-14, 1999.
Zsiros, J., et al., "Evolutionary relationships within a subgroup of HERV-K-related human endogenous retroviruses", J. of General Virology (1998) 79, 61-70.
Boese, et al., "Human endogenous retrovirus protein cORF supports cell transformation and associates with the promyelocytic leukemia zinc finger protein", Oncogene (2000) 19, 4328-4336.
Alignment for SEQ ID No: 55 (Accession No. ABG17449) from U.S. Appl. No. 10/498,033, published Dec. 7, 2006, with WO-01/75067, published Oct. 11, 2001. Alignment cited in Office Action for U.S. Appl. No. 10/498,033, mailed on Oct. 15, 2008.
Alignment for SEQ ID No: 54 (Accession No. ABG19124) from U.S. Appl. No. 10/498,033, published Dec. 7, 2006, with WO-01/75067, published Oct. 11, 2001. Alignment cited in Office Action for U.S. Appl. No. 10/498,033, mailed on Oct. 15, 2008.
Alignment of SEQ ID No: 69 (Accession No. AAE26954) from U.S. Appl. No. 10/498,033, published Dec. 7, 2006, with WO-92/13949, published Aug. 20, 1992. Alignment cited in Office Action for U.S. Appl. No. 10/498,033, mailed on Apr. 18, 2012.
Alignments of SEQ ID No: 26 (Accession No. ABV24390) from U.S. Appl. No. 10/497,786, published Feb. 5, 2007, with WO-01/60860, published Aug. 23, 2001. Alignment cited in Office Action for U.S. Appl. No. 10/497,786, mailed on Sep. 14, 2011.
Alignment of SEQ ID No: 27 from U.S. Appl. No. 10/498,033, published Dec. 7, 2006, with US Patent 5,650,277, published Jul. 22, 1997. Alignment cited in Office Action for U.S. Appl. No. 10/498,033, mailed on Apr. 18, 2012.
Alignment of SEQ ID No: 68 from U.S. Appl. No. 10/497,786, published Feb. 5, 2007, with SEQ ID No: 87 from U.S. Appl. No. 10/498,033, published Dec. 7, 2006. Alignment cited in Office Action for U.S. Appl. No. 10/497,786, mailed on Apr. 25, 2012.
Alignment of SEQ ID No: 68 from U.S. Appl. No. 10/497,786, published Feb. 5, 2007, with SEQ ID No: 98 from U.S. Appl. No. 10/498,033, published Dec. 7, 2006. Alignment cited in Office Action for U.S. Appl. No. 10/497,786, mailed on Apr. 25, 2012.
Alignment of SEQ ID No: 68 from U.S. Appl. No. 10/498,033, published Dec. 7, 2006, with Seher et al. (EMBL/GenBank database submission dated Nov. 1999). Alignment cited in Office Action for U.S. Appl. No. 10/498,033, mailed on Apr. 28, 2010.
Alignment of SEQ ID No: 68 from U.S. Appl. No. 10/498,033, published Dec. 7, 2006, with US Patent No. 6,747,137, published Jun. 8, 2004. Alignment cited in Office Action for U.S. Appl. No. 10/498,033, mailed on Apr. 28, 2010.
Alignment of SEQ ID No: 69 from U.S. Appl. No. 10/498,033, published Dec. 7, 2006, with Lyne et al. (EMBL/GenBank database submission dated Jul. 1999). Alignment cited in Office Action for U.S. Appl. No. 10/498,033, mailed on Apr. 18, 2012.
Alignment of SEQ ID No: 61 from U.S. Appl. No. 10/498,033, published Dec. 7, 2006, to WO-2000/09709-A2 (Bandman, et al., published Feb. 24, 2000). Alignment cited in Office Action for U.S. Appl. No. 10/498,033, mailed on Jul. 7, 2009.
Alignment of SEQ ID No: 64 from U.S. Appl. No. 10/498,033, published Dec. 7, 2006, to Barbulescu, et al. (Curr. Biol, 1999, 9:861-868). Alignment cited in Office Action for U.S. Appl. No. 10/498,033, mailed on Jul. 7, 2009.
Alignment of SEQ ID No: 67 from U.S. Appl. No. 10/498,033, published Dec. 7, 2006, to WO-98/03192-A1 (Chang et al., published Jan. 29, 1998). Alignment cited in Office Action for U.S. Appl. No. 10/498,033, mailed on Jul. 7, 2009.
Alignment of SEQ ID No: 54 of U.S. Appl. No. 10/498,033, published Dec. 7, 2006, to Dunham, et al. (Nature, 1999, 402:489-495). Alignment cited in Office Action for U.S. Appl. No. 10/498,033, mailed on Jul. 7, 2009.
Alignment of SEQ ID No: 55 of U.S. Appl. No. 10/498,033, published Dec. 7, 2006, to Dunham, et al. alignment (Nature, 1999, 402:489-495). Alignment cited in Office Action for U.S. Appl. No. 10/498,033, mailed on Jul. 7, 2009.
Alignment of SEQ ID No. 59 of U.S. Appl. No. 10/498,033, published Dec. 7, 2006, to Giot, et al, alignment (US Patent No. 6,753,314). Alignment cited in Office Action for U.S. Appl. No. 10/498,033, mailed on Jul. 7, 2009.
Alignment of SEQ IDs No: 54 of EP Application No. 10153737.1, published Jul. 21, 2010, to WO03/029460, published Apr. 10, 2003. Alignment cited in Examination Report for EP Application No. 10153737.1, mailed on Sep. 4, 2012.
Database Geneseq [Online] Mar. 23, 2001. EBI accession No. GSN: AAF43752. "Yeast NORF gene SAGE tag oligonucleotide, SEQ ID No. 11891."
Database EMBL [Online] Nov. 30, 2000. EBI accession No. BF378661. "MR2-UM0060-170400-204-e11 UM0060 Momo Sapiens cONNNA, mRNA sequence."
Database EMBL [Online] Sep. 27, 2001. EBI accession No. EMBL: B1781192. "EBma03_SQ001_L 14_R maternal, 8 OPA, no treatment, cv Optic, EBma03 Hordeum vulgare cONA clone EBma03_SQ001_L 145', mRNA sequence."
Genbank Database Accession AB015466, Mar. 7, 2007.
Genbank Database Accession Q96897, Feb. 1, 1997 (first seen at NCBI on Sep. 14, 2005).
Database EMBL [Online] Jun. 16, 1999 "Homo sapiens genomic DNA, chromosome 22q11., clone KB1572G7" Accession No. AP000346.
Genbank Database Accession P10266, Jul. 1, 1989 (first seen at NCBI on Apr. 24, 1993).
Database EMBL Accession No. AAM75812, Nov. 6, 2001.
Database EMBL Accession No. B1858348 (Oct. 12, 2001).
Database EMBL Database Accession No. X82271 (Mar. 30, 1995).
Database Geneseq [Online] Mar. 26, 2001 "Human prostate cancer associated antigen protein sequence SEQ 10 No. 1210" Accession No. AAB63848.
Database Geneseq [Online] Mar. 26, 2001 "Human prostate cancer associated antigen protein sequence SEQ 10 No. 1220" Accession No. AAB63858.
Database Geneseq [Online] Mar. 26, 2001 "Human prostate cancer associated antigen nucleotide sequence SEQ ID:506." Accession No. AAF22927.

Database Genseq Derwent: Aug. 23, 2001, Schlegel et al.: Human prostate expression marker cDNA 24381: accession No. ABV24390.
Database Genseq Derwent; Sep. 13, 2002, Schlegel, et al.: "Human prostate expression marker cDNA 21509" Accession No. ABV21518.
Database Genseq Derwent; Sep. 13, 2002, Schlegel, et al: "Human prostate expression marker cDNA 21999" Accession No. ABV22008.
Extend European search report for EP application No. 10153737.1, dated Sep. 29, 2010.
Extend European search report for EP application No. 10176402.5, dated May 4, 2011.
Extend European search report for EP application No. 10176900.8, dated Apr. 8, 2011.
Supplementary European Search Report for EP Patent Application No. 02786981.7, mailed Feb. 20, 2007.
Supplementary European Search Report for EP Patent Application No. 02807929.1, mailed Jun. 22, 2007.
International Preliminary Examination Report for International Application No. PCT/US02/39344, dated Apr. 20, 2011.
International Search Report for International Application No. PCT/US2001/047824, mailed May 13, 2003.
International Search Report for International Application PCT/2002/039136, mailed Mar. 9, 2006.
Office Action for U.S. Appl. No. 12/819,648, mailed Feb. 29, 2012.
Office Action for U.S. Appl. No. 12/819,648, mailed Nov. 21, 2012.
Office Action for U.S. Appl. No. 10/498,033, mailed Oct. 15, 2008.
Office Action for U.S. Appl. No. 10/498,033, mailed Jul. 7, 2009.
Office Action for U.S. Appl. No. 10/498,033, mailed Apr. 28, 2010.
Office Action for U.S. Appl. No. 10/498,033, mailed Feb. 29, 2012.
Office Action for U.S. Appl. No. 10/498,033, mailed Apr. 18, 2012.
Office Action for U.S. Appl. No. 10/016,604, mailed Mar. 10, 2004.
Office Action for U.S. Appl. No. 10/016,604, mailed Nov. 15, 2004.
Office Action for U.S. Appl. No. 10/016,604, mailed Jun. 27, 2005.
Office Action for U.S. Appl. No. 10/016,604, mailed Mar. 21, 2006.
Office Action for U.S. Appl. No. 10/016,604, mailed Aug. 23, 2006.
Office Action for U.S. Appl. No. 10/016,604, mailed Mar. 22, 2007.
Office Action for U.S. Appl. No. 10/016,604, mailed May 28, 2008.
Office Action for U.S. Appl. No. 10/016,604, mailed Mar. 4, 2009.
Office Action for U.S. Appl. No. 10/016,604, mailed Aug. 20, 2009.
Notice of Allowance for U.S. Appl. No. 10/016,604, mailed Feb. 24, 2010.
Andersson et al. (1996). "Differential Expression of Human Endogenous Retroviral Sequences Similar to Mouse Mammary Tumor Virus in Normal Peripheral Blood Mononuclear Cells," AIDS Research and Human Retroviruses 12(9):833-840.
Armbruester et al. (2002). "A Novel Gene from the Human Endogenous Retrovirus K Expressed in Transformed Cells," Clinical Cancer Research 8(6):1800-1807.
Arnon et al. (1992). "Synthetic peptides as vaccines," Current Opinion in Immunology 4(4):449-453.
Bell et al. (Jan. 1992). "Definition of an immunodominant T cell epitope contained in the envelope gp41 sequence of HIV-1," Clin Exp Immunol. 87(1):37-45.
Belldegrun et al. (Oct. 2001). "Society of Urologic Oncology Biotechnology Forum: New Approaches and Targets for Advanced Prostate Cancer," Journal of Urology, vol. 166, 1316-1321.
Boller et al. (1997). "Characterization of the antibody response specific for the human endogenous retrovirus HTDV/HERV-K," Journal of Virology vol. 71, No. 6, p. 4581-4588.
Bussemakers, et al. (1992). "Increased expression of retroviral sequences in progressionally advanced rat prostatic tumors," Biochemical and Biophysical Research Communications, 182(1):318-24.
Charles et al. (2000). "Antitumor efficacy of tumor-antigen-encoding recombinant poxvirus immunization in Dunning rat prostate cancer: implications for clinical genetic vaccine development," World J Urol. 18(2):136-42.
Chen, et al. (2002). "Discordant Protein and mRNA Expression in Lung Adenocarcinomas," Mol Cell Proteomics. 1(4):304-13.
Comments to the human chromosome 22 article (Oct. 5, 2001). Human Endogenous Retrovirus Database, (retrieved on Jun. 21, 2012 from the Internet: <http://herv.img.cas.cz/comments/> from Japanese Patent Application No. 2005-501590 Office Action Sep. 17, 2008.
Dannull et al. (2000). "Prostate stem cell antigen is a promising candidate for immunotherapy of advanced prostate cancer," Cancer Res. 60(19):5522-8.
Depil, et al. (2002)."Expression of a human endogenous retrovirus, HERV-K, in the blood cells of leukemia patients," Leukemia 16(2):254-9.
Dunham et al. (1999). "The DNA sequence of human chromosome 22," Nature 402(6761):489-95.
Flockerzi et al. (2008). "Expression patterns of transcribed human endogenous retrovirus HERV-K(HML2) loci in human tissues and the need for a HERV Transcriptome Project" BMC Genomics 9:354.
Gray et al. (2008). "A paradigm shift in therapeutic vaccination of cancer patients: the need to apply therapeutic vaccination strategies in the preventive setting." Immunol Rev. 222:316-27.
Greenspan et al. (1999). "Defining epitopes: Its not as easy as it seems," Nat Biotechnol. 17(10):936-7.
Griffifths (2001). "Endogenous retroviruses in the human genome sequence," Genome Biology 2(6):reviews 1017.1-1017.5.
Gu et al. (2000). "Prostate stem cell antigen (PSCA) expression increases with high gleason score, advanced stage and bone metastasis in prostate cancer." Oncogene. 19(10):1288-96.
Guinet et al. (2003). "Do retroviruses preferentially integrate within highly plastic regions of the human genome?" Medical Hypotheses 60(2), 293-297.
Guo et al. (2008). "How is mRNA expression predictive for protein expression? A correlation study on human circulating monocytes," Acta Biochim Biophys Sin (Shanghai) 40(5):426-36.
Hamdan et al. (2002). "Codon optimization improves heterologous expression of a Schistosoma mansoni cDNA in HEK293 cells." Parasitol Res. 88(6):583-6.
Hanahan et al. (2000). "The hallmarks of cancer," Cell 100(1):57-70.
Herbst et al. (1998). "Human endogenous retrovirus (HERV)-K transcripts in germ cell and trophoblastic tumours," APMIS. 106(1):216-20.
Hoon, et al. (1995). "Detection of occult melanoma cells in blood with a multiple-marker polymerase chain reaction assay," J Clin Oncol. 13(8):2109-16.
Huang et al. (1998). "FRA7G extends over a broad region: coincidence of human endogenous retroviral sequences (HERV-H) and small polydispersed circular DNAs (spcDNA) and fragile sites," Oncogene 16(18):2311-19.
Huang et al. (2006). "Human endogenous retroviral pol RNA and protein detected and identified in the blood of individuals with schizophrenia," Schizophr Res. 83(2-3):193-9.
Hubert et al. (1999). "STEAP: A prostate-specific cell-surface antigen highly expressed in human prostate tumors," PNAS vol. 96 No. 25 14523-14528.
Javaherian et al. (Dec. 1990). "Broadly neutralizing antibodies elicited by the hypervariable neutralizing determinant of HIV-1," Science. 250(4987):1590-3.
Kedl et al. (Jan. 1995). "Comparative sequence analysis of the reovirus S4 genes from 13 serotype 1 and serotype 3 field isolates," J Virol. 69(1):552-9.
Klupp et al. (May 1992). "Identification and Characterization of Pseudorabies Virus Glycoprotein H," Journal of Virology, p. 3048-3055.
Larsson (1989). "Human endogenous proviruses," Curr Top Microbiol Immunol. 148:115-32.
Letvin et al. (1993). "Simian immunodeficiency virus-specific cytotoxic T lymphocytes in rhesus monkeys: characterization and vaccine induction," Semin Immunol. 5(3):215-23.
Lichtinghagen et al. (2002). "Different mRNA and Protein Expression of Matrix Metalloproteinases 2 and 9 and Tissue Inhibitor of Metalloproteinases 1 in Benign and Malignant Prostate Tissue ," European Urology 42(4): 398-406.
Liebermann et al. (Nov. 1998). "Receptor Binding Sites and Antigenic Epitopes on the Fiber Know of Human Adenovirus Serotype 3" J. of Virology, p. 9121-9130.

Lower et al. (1993). "A general method for the identification of transcribed retrovirus sequences (R-U5 PCR) reveals the expression of the human endogenous retrovirus loci HERV-H and HERV-K in teratocarcinoma cells," Virology 192(2):501-11.

Magin et al. (2000). "Corf, the Rev/Rex homologue of HTDV/HERV-K, encodes an arginine-rich nuclear localization signal that exerts a trans-dominant phenotype when mutated," Virology 274(1):11-16.

Mariani-Costantini et al. (1989). "Ancestry of a human endogenous retrovirus family," Journal of Virology 63(11):4982-85.

Mata et al. (1998). "The MHC class I-restricted immune response to HIV-gag in BALB/c mice selects a single epitope that does not have a predictable MHC-binding motif and binds to Kd through interactions between a glutamine at P3 and pocket D," J Immunol. 161(6):2985-93.

Mateu et al. (1992). "Non-additive effects of multiple amino acid substitutions on antigen-antibody recognition," Eur J Immunol. 22(6):1385-9.

Mayer et al. (1997). "Chromosomal assignment of human endogenous retrovirus K (HERV-K) env open reading frames," Cytogenet Cell Genet. 79(1-2):157-61.

Mayer et al. (2005). "Human endogenous retroviruses in the primate lineage and their influence on host genomes," Cytogenet Genome Res. 110(1-4):448-56.

McSharry (1999). "Antiviral drug susceptibility assays: going with the flow," Antiviral Res 43(1):1-21.

Medstrand et al. (1993). "Characterization of novel reverse transcriptase encoding human endogenous retroviral sequences similar to type A and type B retroviruses: differential transcription in normal human tissues," Journal of Virology 67(11):6778-87.

Meier et al. (1994). "Novel conserved sequence motifs in plant G-box binding proteins and implications for interactive domains," Nucleic Acids Research, vol. 22, No. 3 470-478.

N. de Parseval et al. (2005). "Human endogenous retroviruses: from infectious elements to human genes" Cytogenet Genome Res 110:318-332.

Ojala et al. (May 1993). "Protein P4 of Double-Stranded RNA Bacteriophage 06 Is Accessible on the Nucleocapsid Surface" Epitope Mapping and Orientation of the Protein J. of Virology, p. 2879-2886.

Ono et al. (1986). "Molecular cloning and long terminal repeat sequences of human endogenous retrovirus genes related to types A and B retrovirus genes," Journal of Virology 58(3):937-944.

Ono et al. (1987). "Stimulation of expression of the human endogenous retrovirus genome by female steroid hormones in human breast cancer cell line T47D," J Virol. 61(6):2059-62.

Pakula et al. (1989). "Genetic Analysis of Protein Stability and Function," Annual Review of Genetics 23:289-310.

Palker et al. (Apr. 1, 1986). "C-Terminal Region of Human T Cell Lymphotropic Virus Type I (HTLV) P19 Core Protein is Immunogenic in Humans and Contains an HTLV-Specific Eptiope" J. of Immunology, vol. 136, No. 7.

Pascal et al. (2008). "Correlation of mRNA and protein levels: Cell type-specific gene expression of cluster designation antigens in the prostate," BMC Genomics 9:246-258.

Perkins et al. (2003). "Breast Cancer in Men," BMJ 327(7409):239-240.

Schommer et al (1996). "Characterization of the human endogenous retrovirus K proteinase," J Gen Virol 77 (Pt 2):375-9.

Seifarth et al (1998). "Proviral structure, chromosomal location, and expression of HERV-K-T47D, a novel human endogenous retrovirus derived from T47D particles," Journal of Virology 72(10):8384-91.

Shih et al. (1991). "Evolutionary implications of primate endogenous retroviruses," Virology 182(2):495-502.

Slade et al. (1999). "Quantitative Polymerase Chain Reaction for the Detection of Micrometastases in Patients With Breast Cancer, "Journal of Clinical Oncology, 17(3):870-879.

Spencer. (Feb. 2002). "Antigenic Specificity of the *Mycobacterium leprae* Homologue of ESAT-6," Infection and Immunity, pp. 1010-1013.

Sverdlo (2000). "Retroviruses and primate evolution," BioEssays 22(2):161-71.

Tomlins et al. (2007). "Distinct classes of chromosomal reqrrangements create oncogenic ETS gene fusions in prostate cancer," Nature 448:595-599.

Tonjes et al. (1996). "HERV-K: the biologically most active human endogenous retrovirus family," J Acquir Immune Defic Syndr Hum Retrovirol. 13 Suppl 1:S261-7.

Turner et al. (2001). "Insertional polymorphisms of full-length endogenous retroviruses in humans," Curr Biol. 1 1(19):1531-5.

Urnovitz et al. (1996). "Human endogenous retroviruses: nature, occurrence, and clinical implications in human disease," Clinical Microbiology Reviews 9(1):72-99.

Vaccine Adjuvant: Incomplete Freund's Adjuvant. Product information sheet [online]. InvivoGen, 2011 [retrieved on Feb. 24, 2012]. Retrieved from the Internet <URL:www.invivogen.com/ifa>.

Viglianti et al. (1990). "Simian Immunodeficiency virus Displays Complex Patterns of RNA Splicing" J. Virol. 64(9):4207-4216.

Wang-Johanning et al (2001). "Expression of human endogenous retrovirus k envelope transcripts in human breast cancer," Clinical Cancer Research 7(6):1553-60.

Wiche (1991). "Cloning and Sequencing of Rat Plectin Indicates a 466-kD Polypeptide Chain with a Three-Domain Structure Based on a Central Alpha-Helical Coiled Coil," J. of Cell Biology, 114(1):83-99.

Wiker (1998). "Immunochemical Characterization of the MPB70/80 and MPB83 Proteins of *Mycobacterium bovis*," Infection and Immunity, p. 1445-1452.

Willer, et al. (1997). "Two Groups of Endogenous MMTV Related Retroviral env Transcripts Expressed in Human Tissues," Virus Genes 15(2):123-133.

Xu (Jun. 2011). "Evaluation of a Novel Chimeric B Cell Epitope-Based Vaccine against Mastitis Induced by Either *Streptococcus agalactiae* or *Staphylococcus aureus* in Mice", Clinical & Vaccine Immunology, pp. 398-900.

Yang et al (1999). "An ancient family of human endogenous retroviruses encodes a functional homolog of the HIV-1 Rev protein," Proc Natl Acad Sci USA 96(23):13404-13408.

Yao et al. (1996). "Reverse transcriptase-polymerase chain reaction (RT-PCR) to detect prostate cancer micrometastasis in the blood," Cancer Treat Res. 88:77-91.

Yin et al. (1997). "Transcription of human endogenous retroviral sequences related to mouse mammary tumor virus in human breast and placenta: similar pattern in most malignant and nonmalignant breast tissues," AIDS Res Hum Retroviruses. 13(6):507-16. (Abstract Only).

* cited by examiner

US 8,518,694 B2

NUCLEIC ACID VECTOR COMPRISING A PROMOTER AND A SEQUENCE ENCODING A POLYPEPTIDE FROM THE ENDOGENOUS RETROVIRUS PCAV

This application is a National Stage application of PCT application PCT/US2003/18666 filed Jun. 13, 2003, which was published in English under PCT Article 21(2) on Dec. 24, 2003, and which claims the benefit of European patent application Ser. No. 60/388,831 filed Jun. 13, 2002 and Ser. No. 60/472,189 filed May 20, 2003. These applications are incorporated herein by reference in their entireties.

All publications and patent applications mentioned in this specification are incorporated herein by reference to the same extent as if each individual document were specifically and individually indicated to be incorporated by reference.

TECHNICAL FIELD

The present invention relates to nucleic acid vectors for polypeptide expression.

BACKGROUND ART

Prostate cancer is the most common type of cancer in men in the USA. Benign prostatic hyperplasia (BPH) is the abnormal growth of benign prostate cells in which the prostate grows and pushes against the urethra and bladder, blocking the normal flow of urine. More than half of the men in the USA, aged 60-70 and as many as 90% percent aged 70-90 have symptoms of BPH. Although BPH is seldom a threat to life, it may require treatment to relieve symptoms.

References 1 and 2 disclose that human endogenous retroviruses (HERVs) of the HML-2 subgroup of the HERV-K family show up-regulated expression in prostate tumors. This finding is disclosed as being useful in prostate cancer screening, diagnosis and therapy. In particular, higher levels of an HML-2 expression product relative to normal tissue are said to indicate that the patient from whom the sample was taken has cancer.

Reference 3 discloses that a specific member of the HML-2 family located in chromosome 22 at 20.428 megabases (22q11.2) is preferentially and significantly up-regulated in prostate tumors. This endogenous retrovirus (termed 'PCAV') has several features not found in other members of the HERV-K family: (1) it has a specific nucleotide sequence which distinguishes it from other HERVs within the genome; (2) it has tandem 5'LTRs; (3) it has a fragmented 3'LTR; (4) its env gene is interrupted by an alu insertion; and (5) its gag contains a unique insertion. Reference 3 teaches that these features can be exploited in prostate cancer screening, diagnosis and therapy.

References 1 to 3 disclose in general terms vectors for expression of HML-2 and PCAV polypeptides. It is an object of the invention to provide additional and improved vectors for in vitro or in vivo expression of HML-2 and PCAV polypeptides.

DISCLOSURE OF THE INVENTION

The invention provides a nucleic acid vector comprising: (i) a promoter; (ii) a sequence encoding a HML-2 polypeptide operably linked to said promoter; and (iii) a selectable marker. Preferred vectors further comprise (iv) an origin of replication; and (v) a transcription terminator downstream of and operably linked to (ii).

Vectors of the invention are particularly useful for expression of HML-2 polypeptides either in vitro (e.g. for later purification) or in vivo (e.g. for nucleic acid immunization). For use in nucleic acid immunization it is preferred that (i) & (v) should be eukaryotic and (iii) and (iv) should be prokaryotic.

The Promoter

Vectors of the invention include a promoter. It is preferred that the promoter is functional in (i.e. can drive transcription in) a eukaryote. The eukaryote is preferably a mammal and more preferably a human. The promoter is preferably active in vivo.

The promoter may be a constitutive promoter or it may be a regulated promoter.

The promoter may be specific to particular tissues or cell types, or it may be active in many tissues.

Preferred promoters are viral promoters e.g. from cytomegalovirus (CMV). Where viral-based systems are used for delivery, the promoter can be a promoter associated with the respective virus e.g. a vaccinia promoter can be used with a vaccinia virus delivery system, etc.

The vector may also include transcriptional regulatory sequences (e.g. enhancers) in addition to the promoter and which interact functionally with the promoter.

Preferred vectors include the immediate-early CMV enhancer/promoter, and more preferred vectors also include CMV intron A. This was originally isolated from the Towne strain and is very strong. The complete native human immediate-early CMV transcription control unit is divided schematically into four regions from 5' to the ATG of the sequence whose transcription is controlled: I—modulator region (clusters of nuclear factor 1 binding sites); II—enhancers region; III—promoter region; and IV—5' UTR with intron A. In the native virus, Region I includes upstream sequences that modulate expression in specific cell types and clusters of nuclear factor 1 (NF1) binding sites. Region I can be inhibitory in many cell lines and is generally omitted from vectors of the invention. Regions II and III are generally included in vectors of the invention. Intron A (in Region IV) positively regulates expression in many transformed cell lines and its inclusion enhances expression.

The promoter in vectors of the invention is operably linked to a downstream sequence encoding a HML-2 polypeptide, such that expression of the encoding sequence is under the promoter's control.

The Sequence Encoding a HML-2 Polypeptide

Vectors of the invention include a sequence which encodes a HML-2 polypeptide. The HML-2 is preferably PCAV.

HML-2 is a subgroup of the HERV-K family [4]. HERV isolates which are members of the HML-2 subgroup include HML-2.HOM [5] (also called ERVK6), HERV-K10 [6, 7], HERV-K108 [8], the 27 HML-2 viruses shown in FIG. 4 of reference 9, HERV-K(C7) [10], HERV-K(II) [11], HERV-K (CH) [1, 2]. Because HML-2 is a well-recognized family, the skilled person will be able to determine without difficulty whether any particular HERV-K is or is not a HML-2 e.g. by reference to the HERVd database [12].

It is preferred to use sequences from HML-2.HOM, located on chromosome 7 [5, 13], or PCAV [3]. PCAV is a member of the HERV-K sub-family HML2.0, and SEQ ID 75 is the 12366 bp sequence of PCAV, based on available human chromosome 22 sequence [14], from the beginning of its first 5' LTR to the end of its fragmented 3' LTR. It is the sense strand of the double-stranded genomic DNA. The transcription start site seems to be at nucleotide 635+5, and its polyadenylation site is at nucleotide 11735.

The HML-2 polypeptide may be from the gag, prt, pol, env, or cORF regions. HML-2 transcripts which encode these polypeptides are generated by alternative splicing of the full-length mRNA copy of the endogenous viral genome [e.g. FIG. 4 of ref. 15, FIG. 1A of ref. 16, FIG. 9 herein]. Although some HML-2 viruses encode all five polypeptides (e.g. ERVK6 [5]), the coding regions of most contain mutations which result in one or more coding regions being either mutated or absent. Thus not all HML-2 HERVs have the ability to encode all five polypeptides.

HML-2 gag polypeptide is encoded by the first long ORF in a complete HML-2 genome [17]. Full-length gag polypeptide is proteolytically cleaved. Examples of gag nucleotide sequences are: SEQ ID 1 (HERV-K108); SEQ ID 2 (HERV-K(C7)); SEQ ID 3 (HERV-K(II)); SEQ ID 4 (HERV-K10); and SEQ ID 76 (PCAV). Examples of gag polypeptide sequences are: SEQ ID 5 (HERV-K(C7)); SEQ ID 6 (HERV-K(II)); SEQ IDs 7 & 8 (HERV-K10); SEQ ID 9 ('ERVK6'); SEQ ID 69; and SEQ ID 78 (PCAV).

HML-2 prt polypeptide is encoded by the second long ORF in a complete HML-2 genome. It is translated as a gag-prt fusion polypeptide. The fusion polypeptide is proteolytically cleaved to give a protease. Examples of prt nucleotide sequences are: SEQ ID 10 [HERV-K(108)]; SEQ ID 11 [HERV-K(II)]; SEQ ID 12 [HERV-K10]. Examples of prt polypeptide sequences are: SEQ ID 13 [HERV-K10]; SEQ ID 14 ['ERVK6']; SEQ ID 71.

HML-2 pol polypeptide is encoded by the third long ORF in a complete HMI-2 genome. It is translated as a gag-prt-pol fusion polypeptide. The fusion polypeptide is proteolytically cleaved to give three pol products—reverse transcriptase, endonuclease and integrase [18]. Examples of pol nucleotide sequences are: SEQ ID 15 [HERV-K(108)]; SEQ ID 16 [HERV-K(C7)]; SEQ ID 17 [HERV-K(II)]; SEQ ID 18 [HERV-K10]. Examples of pol polypeptide sequences are: SEQ ID 19 [HERV-K(C7)]; SEQ ID 20 [HERV-K10]; SEQ ID 21 ['ERVK6']; SEQ ID 73.

HML-2 env polypeptide is encoded by the fourth long ORF in a complete HML-2 genome. The translated polypeptide is proteolytically cleaved. Examples of env nucleotide sequences are: SEQ ID 22 [HERV-K(108)]; SEQ ID 23 [HERV-K(C7)]; SEQ ID 24 [HERV-K(II)]; SEQ ID 25 [HERV-K10]. Examples of env polypeptide sequences are: SEQ ID 26 [HERV-K(C7)]; SEQ ID 27 [HERV-K10]; SEQ ID 28 ['ERVK6'].

HML-2 cORF polypeptide is encoded by an ORF which shares the same 5' region and start codon as env. After around 87 codons, a splicing event removes env-coding sequences and the cORF-coding sequence continues in the reading frame +1 relative to that of env [19, 20]. cORF has also been called Rec [21]. Examples of cORF nucleotide sequences are: SEQ IDs 29 & 30 [HERV-K(108)]. An example of a cORF polypeptide sequence is SEQ ID 31.

The HML-2 polypeptide may alternatively be from a PCAP open-reading frame [22], such as PCAP1, PCAP2, PCAP3, PCAP4, PCAP4a or PCAP5 (SEQ IDs 32 to 37 herein). PCAP3 (SEQ. IDs 34 & 46) and PCAP5 are preferred (SEQ ID 37).

The HML-2 polypeptide may alternatively be one of SEQ IDs 38 to 50 [22].

Sequences encoding any HML-2 polypeptide expression product may be used in accordance with the invention (e.g. sequences encoding any one of SEQ IDs 5, 6, 7, 8, 9, 13, 14, 19, 20, 21, 26, 27, 28, 31-50, 69-74, 78 or 79).

The invention may also utilize sequences encoding polypeptides having at least $\alpha$% identity to such wild-type HML-2 polypeptide sequences. The value of $\alpha$ may be 65 or more (e.g. 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9). These sequences include allelic variants, SNP variants, homologs, orthologs, paralogs, mutants etc. of the SEQ IDs listed in the previous paragraph.

The invention may also utilize sequences having at least b % identity to wild-type HML-2 nucleotide sequences. The value of b may be 65 or more (e.g. 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9). These sequences include allelic variants, SNP variants, homologs, orthologs, paralogs, mutants etc. of SEQ IDs 1, 2, 3, 4, 10, 11, 12, 15, 16, 17, 18, 22, 23, 24, 25, 29 and 30.

The invention may also utilize sequences comprising a fragment of at least c nucleotides of such wild-type HML-2 nucleotide sequences. The value of c may be 7 or more (e.g. 8, 9, 10, 11, 12, 13, 14, 15, 16, 17, 18, 19, 20, 21, 22, 23, 24, 25, 30, 35, 40, 45, 50, 60, 70, 75, 80, 90, 100, 125, 150, 175, 200, 250, 300 or more). The fragment is preferably a proteolytic cleavage product of a HML-2 polyprotein. The fragment preferably comprises a sequence encoding a T-cell or, preferably, a B-cell epitope from HML-2. T- and B-cell epitopes can be identified empirically (e.g. using the PEPSCAN method [23, 24] or similar methods), or they can be predicted e.g. using the Jameson-Wolf antigenic index [25], matrix-based approaches [26], TEPITOPE [27], neural networks [28], OptiMer & EpiMer [29, 30], ADEPT [31], Tsites [32], hydrophilicity [33], antigenic index [34] or the methods disclosed in reference 35 etc.

The invention may also utilize sequences encoding a polypeptide which comprises a fragment of at least d amino acids of wild-type HML-2 polypeptide sequences. The value of d may be 7 or more (e.g. 8, 9, 10, 11, 12, 13, 14, 15, 16, 17, 18, 19, 20, 21, 22, 23, 24, 25, 30, 35, 40, 45, 50, 60, 70, 75, 80, 90, 100, 125, 150, 175, 200, 250, 300 or more). The fragment preferably comprises a T-cell or, preferably, a B-cell epitope from HML-2.

The invention may also utilize sequences comprising (i) a first sequence which is a wild-type HML-2 sequence or a sequence as disclosed above and (ii) a second non-HML-2 sequence. Examples of (ii) include sequences encoding: signal peptides, protease cleavage sites, epitopes, leader sequences, tags, fusion partners, N-terminal methionine, arbitrary sequences etc. Sequence (ii) will generally be located at the N- and/or C-terminus of (i).

Even though a nucleotide sequence may encode a HML-2 polypeptide which is found naturally, it may differ from the corresponding natural nucleotide sequence. For example, the nucleotide sequence may include mutations e.g. to take into account codon preference in a host of interest, or to add restriction sites or tag sequences.

The Selectable Marker

Vectors of the invention include a selectable marker.

The marker preferably functions in a microbial host (e.g. in a prokaryote, in a bacteria, in a yeast). The marker is preferably a prokaryotic selectable marker (e.g. transcribed under the control of a prokaryotic promoter).

For convenience, typical markers are antibiotic resistance genes.

Further Features of Nucleic Acid Vectors of The Invention

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the HML-2 coding sequence. The vectors will therefore (a) be amplified and selected in prokaryotic hosts without HML-2 polypeptide expression, but (b) be expressed in eukaryotic hosts without being amplified. This is ideal for nucleic acid immunization vectors.

The vector of the invention may comprise a eukaryotic transcriptional terminator sequence downstream of the HML2-coding sequence. This can enhance transcription levels. Where the HML2-coding sequence does not have its own, the vector of the invention preferably comprises a polyadenylation sequence. A preferred polyadenylation sequence is from bovine growth hormone.

The vector of the invention may comprise a multiple cloning site

In addition to sequences encoding a HML-2 polypeptide and a marker, the vector may comprise a second eukaryotic coding sequence. The vector may also comprise an IRES upstream of said second sequence in order to permit translation of a second eukaryotic polypeptide from the same transcript as the HML-2 polypeptide. Alternatively, the HML-2 polypeptide may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Pharmaceutical Compositions

The invention provides a pharmaceutical composition comprising a vector of the invention. The invention also provides the vectors' use as medicaments, and their use in the manufacture of medicaments for treating prostate cancer. The invention also provides a method for treating a patient with a prostate tumor, comprising administering to them a pharmaceutical composition of the invention. The patient is generally a human, preferably a human male, and more preferably an adult human male. Other diseases in which HERV-Ks have been implicated include testicular cancer [36], multiple sclerosis [37], and insulin-dependent diabetes mellitus (IDDM) [38], and the vectors may also be used against these diseases.

The invention also provides a method for raising an immune response, comprising administering an immunogenic dose of a vector of the invention to an animal (e.g. to a human).

Pharmaceutical compositions encompassed by the present invention include as active agent, the vectors of the invention in a therapeutically effective amount. An "effective amount" is an amount sufficient to effect beneficial or desired results, including clinical results. An effective amount can be administered in one or more administrations. For purposes of this invention, an effective amount is an amount that is sufficient to palliate, ameliorate, stabilize, reverse, slow or delay the symptoms and/or progression of prostate cancer. The effect can be detected by, for example, chemical markers or antigen levels. Therapeutic effects also include reduction in physical symptoms.

The precise effective amount for a subject will depend upon the subject's size and health, the nature and extent of the condition, and the therapeutics or combination of therapeutics selected for administration. The effective amount for a given situation is determined by routine experimentation and is within the judgment of the clinician. For purposes of the present invention, an effective dose will generally be from about 0.01 mg/kg to about 5 mg/kg, or about 0.01 mg/kg to about 50 mg/kg or about 0.05 mg/kg to about 10 mg/kg of the compositions of the present invention in the individual to which it is administered.

The compositions can be used to treat cancer as well as metastases of primary cancer. In addition, the pharmaceutical compositions can be used in conjunction with conventional methods of cancer treatment, e.g. to sensitize tumors to radiation or conventional chemotherapy. The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e. arresting its development; or (c) relieving the disease symptom, i.e. causing regression of the disease or symptom.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g. mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in reference 39.

The composition is preferably sterile and/or pyrogen-free. It will typically be buffered at about pH 7.

Once formulated, the compositions contemplated by the invention can be (1) administered directly to the subject; or (2) delivered ex vivo, to cells derived from the subject (e.g. as in ex vivo gene therapy). Direct delivery of the compositions will generally be accomplished by parenteral injection, e.g. subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Intramuscular injection is preferred.

Methods for the ex vivo delivery and reimplantation of transformed cells into a subject are known in the art [e.g. ref.

40]. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the nucleic acid(s) in liposomes, and direct microinjection of the DNA into nuclei, all well known in the art.

Targeted Delivery

Vectors of the invention may be delivered in a targeted way.

Receptor-mediated DNA delivery techniques are described in, for example, references 41 to 46. Therapeutic compositions containing a nucleic acid are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions of e.g. a tumor site, may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally references 47 to 50).

Viral-based vectors for delivery of a desired nucleic acid and expression in a desired cell are well known in the art. Exemplary viral-based vehicles include, but are not limited to, recombinant retroviruses (e.g. references 51 to 61), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see refs. 62 to 67). Administration of DNA linked to killed adenovirus [68] can also be employed.

Non-viral delivery vehicles and methods can also be employed, including, but not limited to, polycationic condensed DNA linked or unlinked to killed adenovirus alone [e.g. 68], ligand-linked DNA [69], eukaryotic cell delivery vehicles cells [e.g. refs. 70 to 74] and nucleic charge neutralization or fusion with cell membranes. Naked DNA can also be employed. Exemplary naked DNA introduction methods are described in refs. 75 and 76. Liposomes (e.g. immunoliposomes) that can act as gene delivery vehicles are described in refs. 77 to 81. Additional approaches are described in refs. 82 & 83.

Further non-viral delivery suitable for use includes mechanical delivery systems such as the approach described in ref. 83. Moreover, the coding sequence and the product of expression of such can be delivered through deposition of photopolymerized hydrogel materials or use of ionizing radiation [e.g. refs. 84 & 85]. Other conventional methods for gene delivery that can be used for delivery of the coding sequence include, for example, use of hand-held gene transfer particle gun [86] or use of ionizing radiation for activating transferred genes [84 & 87].

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Vaccine Compositions

The pharmaceutical composition is preferably an immunogenic composition and is more preferably a vaccine composition. Such compositions can be used to raise antibodies in a mammal (e.g. a human) and/or to raise a cellular immune response (e.g. a response involving T-cells such as CTLs, a response involving natural killer cells, a response involving macrophages etc.)

The invention provides the use of a vector of the invention in the manufacture of medicaments for preventing prostate cancer. The invention also provides a method for protecting a patient from prostate cancer, comprising administering to them a pharmaceutical composition of the invention.

Nucleic acid immunization is well known [e.g. refs. 88 to 94 etc.]

The composition may additionally comprise an adjuvant. For example, the composition may comprise one or more of the following adjuvants: (1) oil-in-water emulsion formulations (with or without other specific immunostimulating agents such as muramyl peptides (see below) or bacterial cell wall components), such as for example (a) MF59™ [95; Chapter 10 in ref. 96], containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent [97]; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) [e.g. 98, 99]; (6) combinations of 3dMPL with, for example, QS21 and/or oil-in-water emulsions [e.g. 100, 101, 102]; (7) oligonucleotides comprising CpG motifs i.e. containing at least one CG dinucleotide, with 5-methylcytosine optionally being used in place of cytosine; (8) a polyoxyethylene ether or a polyoxyethylene ester [103]; (9) a polyoxyethylene sorbitan ester surfactant in combination with an octoxynol [104] or a polyoxyethylene alkyl ether or ester surfactant in combination with at least one additional non-ionic surfactant such as an octoxynol [105]; (10) an immunostimulatory oligonucleotide (e.g. a CpG oligonucleotide) and a saponin [106]; (11) an immunostimulant and a particle of metal salt [107]; (12) a saponin and an oil-in-water emulsion [108]; (13) a saponin (e.g. QS21)+3dMPL+IL-12 (optionally+a sterol) [109]; (14) aluminium salts, preferably hydroxide or phosphate, but any other suitable salt may also be used (e.g. hydroxyphosphate, oxyhydroxide, orthophosphate, sulphate etc. [chapters 8 & 9 of ref. 96]). Mixtures of different aluminium salts may also be used. The salt may take any suitable form (e.g. gel, crystalline, amorphous etc.); (15) chitosan; (16) cholera toxin or E.coli heat labile toxin, or detoxified mutants thereof [110]; (17) microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone etc., such as poly(lactide-co-glycolide) etc.) optionally treated to have a negatively-charged surface (e.g. with SDS) or a positively-charged surface (e.g. with a cationic detergent, such as CTAB); (18) monophosphoryl lipid A mimics, such as aminoalkyl glucosaminide phosphate derivatives e.g. RC-529 [111]; (19) polyphosphazene (PCPP); (20) a bioadhesive [112] such as esterified hyaluronic acid microspheres [113] or a mucoadhesive selected from the group consisting of cross-linked derivatives of poly(acrylic acid), polyvinyl alcohol, polyvinyl pyrollidone, polysaccharides and carboxymethylcellulose; (21) double-stranded RNA; or (22) other substances that act as immunostimulating agents to enhance the efficacy of the composition. Aluminium salts and/or MF59™ are preferred.

Vaccines of the invention may be prophylactic (i.e. to prevent disease) or therapeutic (i.e. to reduce or eliminate the symptoms of a disease).

Specific Vectors of the Invention

Preferred vectors of the invention comprise: (i) a eukaryotic promoter; (ii) a sequence encoding a HML-2 polypeptide downstream of and operably linked to said promoter; (iii) a prokaryotic selectable marker; (iv) a prokaryotic origin of replication; and (v) a eukaryotic transcription terminator downstream of and operably linked to said sequence encoding a HML-2 polypeptide.

Particularly preferred vectors are shown in FIGS. 2 to 8 (SEQ IDs 51 to 56 & 80).

Virus-Like Particles

HML-2 gag polypeptide has been found to assemble into virus-like particles (VLPs). This particulate form of the polypeptide has enhanced immunogenicity when compared to soluble polypeptide and is a preferred form of polypeptide for use in immunization and/or diagnosis.

Thus the invention provides a virus-like particle, comprising HML-2 gag polypeptide. The gag polypeptide may be myristoylated at its N-terminus.

The invention also provides a VLP of the invention for use as an immunogen or for use as a diagnostic antigen. The invention also provides the use of a VLP of the invention in the manufacture of a medicament for immunizing an animal.

The invention also provides a method of raising an immune response in an animal, comprising administering to the animal a VLP of the invention. The immune response may comprise a humoral immune response and/or a cellular immune response.

For raising an immune response, the VLP may be administered with or without an adjuvant as disclosed above. The immune response may treat or protect against cancer (e.g. prostate cancer).

The invention also provides a method for diagnosing cancer (e.g. prostate cancer) in a patient, comprising the step of contacting antibodies from the patient with VLPs of the invention. Similarly, the invention provides a method for diagnosing cancer (e.g. prostate cancer) in a patient, comprising the step of contacting anti-VLP antibodies with a patient sample.

The invention also provides a process for preparing VLPs of the invention, comprising the step of expressing gag polypeptide in a cell, and collecting VLPs from the cell. Expression may be achieved using a vector of the invention.

The VLP of the invention may or may not include packaged nucleic acid.

The gag polypeptide from which the VLPs are made can be from any suitable HML-2 virus (e.g. SEQ IDs 1-9, 69 & 78).

Definitions

The term "comprising" means "including" as well as "consisting" e.g. a composition "comprising" X may consist exclusively of X or may include something additional e.g. X+Y.

The term "about" in relation to a numerical value x means, for example, x±10%.

The terms "neoplastic cells", "neoplasia", "tumor", "tumor cells", "cancer" and "cancer cells" (used interchangeably) refer to cells which exhibit relatively autonomous growth, so that they exhibit an aberrant growth phenotype characterized by a significant loss of control of cell proliferation (i.e. deregulated cell division). Neoplastic cells can be malignant or benign and include prostate cancer derived tissue.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 114. A preferred alignment program is GCG Gap (Genetics Computer Group, Wisconsin, Suite Version 10.1), preferably using default parameters, which are as follows: open gap=3; extend gap=1.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 114. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 115.

MODES FOR CARRYING OUT THE INVENTION

Certain aspects of the present invention are described in greater detail in the non-limiting examples that follow. The examples are put forth so as to provide those of ordinary skill in the art with a disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Vectors for Expressing HML-2 Polypeptides

Figure 1:
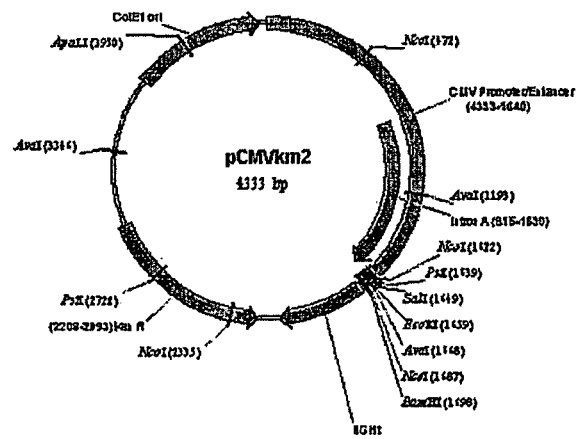
FIG. 1 shows the pCMVkm2 vector.

The basic pCMVkm2 vector is shown in FIG. 1. This vector has an immediate-early CMV enhancer/promoter and a bovine growth hormone transcription terminator, with a multiple cloning site in between. The vector also has a kanamycin resistance gene and a ColE1 origin of replication.

Sequences coding for HML-2 polypeptides being inserted between SalI and EcoRI in the multiple cloning site:

| FIG. | SEQ ID | HML-2 polypeptide |
|------|--------|-------------------|
| 2    | 51     | cORF              |
| 3    | 52     | PCAP5             |
| 4    | 53     | gag               |
| 5    | 54     | gag               |
| 6    | 55     | Prt               |
| 7    | 56     | Pol               |

Figure 4:
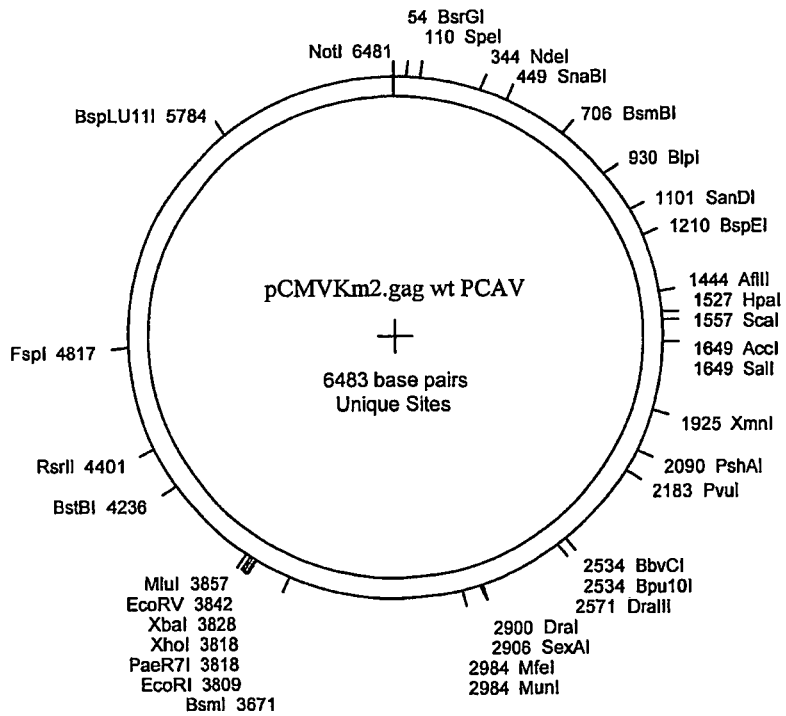

Except for the vector shown in FIG. 4 (SEQ ID 53), the inserted sequences were manipulated for codon preference, including addition of an optimal stop codon:

cORF Manipulation:
Start with SEQ ID 57 (SEQ ID 43); manipulate to SEQ ID 58 (SEQ ID 67):

```
ATGAACCCATCAGAGATGCAAAGAAAAGCACCTCCGCGGAGACGGAGACATC    cORFwt_hml (1)

ATGAACCCCAGCGAGATGCAGCGCAAGGCCCCCCCCGCCGCCGCCGCCACC     corfopt_hml (1)

GCAATCGAGCACCGTTGACTCACAAGATGAACAAAATGGTGACGTCAGAAGA    cORFwt_hml (53)

GCAACCGCGCCCCCCTGACCCACAAGATGAACAAGATGGTGACCAGCGAGGA    corfopt_hml (53)

ACAGATGAAGTTGCCATCCACCAAGAAGGCAGAGCCGCCAACTTGGGCACAA    cORFwt_hml (105)

GCAGATGAAGCTGCCCAGCACCAAGAAGGCCGAGCCCCCACCTGGGCCCAG     corfopt_hml (105)

CTAAAGAAGCTGACGCAGTTAGCTACAAAATATCTAGAGAACACAAAGGTGA    cORFwt_hml (157)

CTGAAGAAGCTGACCCAGCTGGCCACCAAGTACCTGGAGAACACCAAGGTGA    corfopt_hml (157)

CACAAACCCCAGAGAGTATGCTGCTTGCAGCCTTGATGATTGTATCAATGGT    cORFwt_hml (209)

CCCAGACCCCCGAGAGCATGCTGCTGGCCGCCCTGATGATCGTGAGCATGGT    corfopt_hml (209)

GTCTGCAGGTGTACCCAACAGCTCCGAAGAGACAGCGACCATCGAGAACGGG    cORFwt_hml (261)

GAGCGCCGGCGTGCCCAACAGCAGCGAGGAGACCGCCACCATCGAGAACGGC    corfopt_hml (261)

CCA---TGA                                               cORFwt_hml (313)

CCCGCTTAA                                               corfopt_hml (313)
```

PCAP5 Manipulation:
Start with SEQ ID 59 (SEQ ID 37); manipulate to SEQ ID 60 (SEQ ID 68):

```
ATGAACCCATCGGAGATGCAAAGAAAAGCACCTCCGCGGAGACGGAGACAT     pCAP5wt_hml (1)

ATGAACCCCAGCGAGATGCAGCGCAAGGCCCCCCCCGCCGCCGCCGCCAC      pcap5opt_hml (1)

CGCAATCGAGCACCGTTGACTCACAAGATGAACAAAATGGTGACGTCAGAA     pCAP5wt_hml (52)

CGCAACCGCGCCCCCCTGACCCACAAGATGAACAAGATGGTGACCAGCGAG     pcap5opt_hml (52)

GAACAGATGAAGTTGCCATCCACCAAGAAGGCAGAGCCGCCAACTTGGGCA     pCAP5wt_hml (103)

GAGCAGATGAAGCTGCCCAGCACCAAGAAGGCCGAGCCCCCACCTGGGCC      pcap5opt_hml (103)

CAACTAAAGAAGCTGACGCAGTTAGCTACAAAATATCTAGAGAACACAAAG     pCAP5wt_hml (154)

CAGCTGAAGAAGCTGACCCAGCTGGCCACCAAGTACCTGGAGAACACCAAG     pcap5opt_hml (154)

GTGACACAAACCCCAGAGAGTATGCTGCTTGCAGCCTTGATGATTGTATCA     pCAP5wt_hml (205)
```

```
GTGACCCAGACCCCCGAGAGCATGCTGCTGGCCGCCCTGATGATCGTGAGC    pcap5opt_hml  (205)

ATGGTGGTGTACCCAACAGCTCCGAAGAGACAGCGACCATCGAGAACGGGC    pCAP5wt_hml   (256)

ATGGTGGTGTACCCCACCGCCCCCAAGCGCCAGCGCCCCAGCCGCACCGGC    pcap5opt_hml  (256)

CATGATGACGATGGCGGTTTTGTCGAAAAGAAAAGGGGGAAATGTGGGGAA    pCAP5wt_hml   (307)

CACGACGACGACGGCGGCTTCGTGGAGAAGAAGCGCGGCAAGTGCGGCGAG    pcap5opt_hml  (307)

AAGCAAGAGAGATCAGATTGTTACTGTGTCTGTGTAGAAAGAAGTAGACAT    pCAP5wt_hml   (358)

AAGCAGGAGCGCAGCGACTGCTACTGCGTGTGCGTGGAGCGCAGCCGCCAC    pcap5opt_hml  (358)

AGGAGACTCCATTTTGTTCTGTAC---TAA                        pCAP5wt_hml   (409)

CGCCGCCTGCACTTCGTGCTGTACGCTTAA                        pcap5opt_hml  (409)
```

Gag Manipulation:
Start with SEQ ID 61 (SEQ ID 69); manipulate to SEQ ID 62 (SEQ ID 70):

```
ATGGGGCAAACTAAAAGTAAAATTAAAAGTAAATATGCCTCTTATCTCAGCT    gagwt_hml   (1)

ATGGGCCAGACCAAGAGCAAGATCAAGAGCAAGTACGCCAGCTACCTGAGCT    gagopt_hml  (1)

TTATTAAAATTCTTTTAAAAAGAGGGGGAGTTAAAGTATCTACAAAAAATCT    gagwt_hml   (53)

TCATCAAGATCCTGCTGAAGCGCGGCGGCGTGAAGGTGAGCACCAAGAACCT    gagopt_hml  (53)

AATCAAGCTATTTCAAATAATAGAACAATTTTGCCCATGGTTTCCAGAACAA    gagwt_hml   (105)

GATCAAGCTGTTCCAGATCATCGAGCAGTTCTGCCCCTGGTTCCCCGAGCAG    gagopt_hml  (105)

GGAACTTTAGATCTAAAAGATTGGAAAAGAATTGGTAAGGAACTAAAACAAG    gagwt_hml   (157)

GGCACCCTGGACCTGAAGGACTGGAAGCGCATCGGCAAGGAGCTGAAGCAGG    gagopt_hml  (157)

CAGGTAGGAAGGGTAATATCATTCCACTTACAGTATGGAATGATTGGGCCAT    gagwt_hml   (209)

CCGGCCGCAAGGGCAACATCATCCCCCTGACCGTGTGGAACGACTGGGCCAT    gagopt_hml  (209)

TATTAAAGCAGCTTTAGAACCATTTCAAACAGAAGAAGATAGCGTTTCAGTT    gagwt_hml   (261)

CATCAAGGCCGCCCTGGAGCCCTTCCAGACCGAGGAGGACAGCGTGAGCGTG    gagopt_hml  (261)

TCTGATGCCCCTGGAAGCTGTATAATAGATTGTAATGAAAACACAAGGAAAA    gagwt_hml   (313)

AGCGACGCCCCCGGCAGCTGCATCATCGACTGCAACGAGAACACCCGCAAGA    gagopt_hml  (313)

AATCCCAGAAAGAAACGGAAGGTTTACATTGCGAATATGTAGCAGAGCCGGT    gagwt_hml   (365)

AGAGCCAGAAGGAGACCGAGGGCCTGCACTGCGAGTACGTGGCCGAGCCCGT    gagopt_hml  (365)

AATGGCTCAGTCAACGCAAAATGTTGACTATAATCAATTACAGGAGGTGATA    gagwt_hml   (417)

GATGGCCCAGAGCACCCAGAACGTGGACTACAACCAGCTGCAGGAGGTGATC    gagopt_hml  (417)

TATCCTGAAACGTTAAAATTAGAAGGAAAAGGTCCAGAATTAGTGGGGCAT    gagwt_hml   (469)

TACCCCGAGACCCTGAAGCTGGAGGGCAAGGGCCCCGAGCTGGTGGGCCCCA    gagopt_hml  (469)

CAGAGTCTAAACCACGAGGCACAAGTCCTCTTCCAGCAGGTCAGGTGCCTGT    gagwt_hml   (521)

GCGAGAGCAAGCCCCGCGGCACCAGCCCCCTGCCCGCCGGCCAGGTGCCCGT    gagopt_hml  (521)

AACATTACAACCTCAAAAGCAGGTTAAAGAAAATAAGACCCAACCGCCAGTA    gagwt_hml   (573)

GACCCTGCAGCCCCAGAAGCAGGTGAAGGAGAACAAGACCCAGCCCCCCGTG    gagopt_hml  (573)

GCCTATCAATACTGGCCTCCGGCTGAACTTCAGTATCGGCCACCCCCAGAAA    gagwt_hml   (625)

GCCTACCAGTACTGGCCCCCCGCCGAGGTGCAGTACCGCCCCCCCCCCGAGA    gagopt_hml  (625)

GTCAGTATGGATATCCAGGAATGCCCCCAGCACCACAGGGCAGGGCGCCATA    gagwt_hml   (677)

GCCAGTACGGCTACCCCGGCATGCCCCCCGCCCCCCAGGGCCGCGCCCCCTA    gagopt_hml  (677)
```

```
CCCTCAGCCGCCCACTAGGAGACTTAATCCTACGGCACCACCTAGTAGACAG  gagwt_hml  (729)

CCCCCAGCCCCCCACCCGCCGCCTGAACCCCACCGCCCCCCCCAGCCGCCAG  gagopt_hml (729)

GGTAGTAAATTACATGAAATTATTGATAAATCAAGAAAGGAAGGAGATACTG  gagwt_hml  (781)

GGCAGCAAGCTGCACGAGATCATCGACAAGAGCCGCAAGGAGGGCGACACCG  gagopt_hml (781)

AGGCATGGCAATTCCCAGTAACGTTAGAACCGATGCCACCTGGAGAAGGAGC  gagwt_hml  (833)

AGGCCTGGCAGTTCCCCGTGACCCTGGAGCCCATGCCCCCGGCGAGGGCGC   gagopt_hml (833)

CCAAGAGGGAGAGCCTCCCACAGTTGAGGCCAGATACAAGTCTTTTTCGATA  gagwt_hml  (885)

CCAGGAGGGCGAGCCCCCCACCGTGGAGGCCCGCTACAAGAGCTTCAGCATC  gagopt_hml (885)

AAAAAGCTAAAAGATATGAAAGAGGGAGTAAAACAGTATGGACCCAACTCCC  gagwt_hml  (937)

AAGAAGCTGAAGGACATGAAGGAGGGCGTGAAGCAGTACGGCCCCAACAGCC  gagopt_hml (937)

CTTATATGAGGACATTATTAGATTCCATTGCTCATGGACATAGACTCATTCC  gagwt_hml  (989)

CCTACATGCGCACCCTGCTGGACAGCATCGCCCACGGCCACCGCCTGATCCC  gagopt_hml (989)

TTATGATTGGGAGATTCTGGCAAAATCGTCTCTCTCACCCTCTCAATTTTTA  gagwt_hml  (1041)

CTACGACTGGGAGATCCTGGCCAAGAGCAGCCTGAGCCCCAGCCAGTTCCTG  gagopt_hml (1041)

CAATTTAAGACTTGGTGGATTGATGGGGTACAAGAACAGGTCCGAAGAAATA  gagwt_hml  (1093)

CAGTTCAAGACCTGGTGGATCGACGGCGTGCAGGAGCAGGTGCGCCGCAACC  gagopt_hml (1093)

GGGCTGCCAATCCTCCAGTTAACATAGATGCAGATCAACTATTAGGAATAGG  gagwt_hml  (1145)

GCGCCGCCAACCCCCCCGTGAACATCGACGCCGACCAGCTGCTGGGCATCGG  gagopt_hml (1145)

TCAAAATTGGAGTACTATTAGTCAACAAGCATTAATGCAAAATGAGGCCATT  gagwt_hml  (1197)

CCAGAACTGGAGCACCATCAGCCAGCAGGCCCTGATGCAGAACGAGGCCATC  gagopt_hml (1197)

GAGCAAGTTAGAGCTATCTGCCTTAGAGCCTGGGAAAAAATCCAAGACCCAG  gagwt_hml  (1249)

GAGCAGGTGCGCGCCATGTGCCTGCGCGCCTGGGAGAAGATCCAGGACCCCG  gagopt_hml (1249)

GAAGTACCTGCCCCTCATTTAATACAGTAAGACAAGGTTCAAAAGAGCCCTA  gagwt_hml  (1301)

GCAGCACCTGCCCCAGCTTCAACACCGTGCGCCAGGGCAGCAAGGAGCCCTA  gagopt_hml (1301)

TCCTGATTTTGTGGCAAGGCTCCAAGATGTTGCTCAAAAGTCAATTGCTGAT  gagwt_hml  (1353)

CCCCGACTTCGTGGCCCGCCTGCAGGACGTGGCCCAGAAGAGCATCGCCGAC  gagopt_hml (1353)

GAAAAAGCCCGTAAGGTCATAGTGGAGTTGATGGCATATGAAAACGCCAATC  gagwt_hml  (1405)

GAGAAGGCCCGCAAGGTGATGGTGGAGCTGATGGCCTACGAGAACGCCAACC  gagopt_hml (1405)

CTGAGTGTCAATCAGCCATTAAGCCATTAAAAGGAAAGGTTCCTGCAGGATC  gagwt_hml  (1457)

CCGAGTGCCAGAGCGCCATCAAGCCCCTGAAGGGCAAGGTGCCCGCCGGCAG  gagopt_hml (1457)

AGATGTAATCTCAGAATATGTAAAAGCCTGTGATGGAATCGGAGGAGCTATG  gagwt_hml  (1509)

CGACGTGATCAGCGAGTACGTGAAGGCCTGCGACGGCATCGGCGGCGCCATG  gagopt_hml (1509)

CATAAAGCTATGCTTATGGCTCAAGCAATAACAGGAGTTGTTTTAGGAGGAC  gagwt_hml  (1561)

CACAAGGCCATGCTGATGGCCCAGGCCATCACCGGCGTGGTGCTGGGCGGCC  gagopt_hml (1561)

AAGTTAGAACATTTGGAAGAAAATGTTATAATTGTGGTCAAATTGGTCACTT  gagwt_hml  (1613)

AGGTGCGCACCTTCGGCCGCAAGTGCTACAACTGCGGCCAGATCGGCCACCT  gagopt_hml (1613)

AAAAAAGAATTGCCCAGTCTTAAATAAACAGAATATAACTATTCAAGCAACT  gagwt_hml  (1665)

GAAGAAGAACTGCCCCGTGCTGAACAAGCAGAACATCACCATCCAGGCCACC  gagopt_hml (1665)

ACAACAGGTAGAGAGCCACCTGACTTATGTCCAAGATGTAAAAAAGGAAAAC  gagwt_hml  (1717)

ACCACCGGCCGCGAGCCCCCCGACCTGTGCCCCCGCTGCAAGAAGGGCAAGC  gagopt_hml (1717)

ATTGGGCTAGTCAATGTCGTTCTAAATTTGATAAAAATGGGCAACCATTGTC  gagwt_hml  (1769)
```

-continued

```
ACTGGGCCAGCCAGTGCCGCAGCAAGTTCGACAAGAACGGCCAGCCCCTGAG  gagopt_hml (1769)

GGGAAACGAGCAAAGGGGCCAGCCTCAGGCCCCACAACAAACTGGGGCATTC  gagwt_hml (1821)

CGGCAACGAGCAGCGCGGCCAGCCCCAGGCCCCCCAGCAGACCGGCGCCTTC  gagopt_hml (1821)

CCAATTCAGCCATTTGTTCCTCAGGGTTTTCAGGGACAACAACCCCCACTGT  gagwt_hml (1873)

CCCATCCAGCCCTTCGTGCCCCAGGGCTTCCAGGGCCAGCAGCCCCCCCTGA  gagopt_hml (1873)

CCCAAGTGTTTCAGGGAATAAGCCAGTTACCACAATACAACAATTGTCCCCC  gagwt_hml (1925)

GCCAGGTGTTCCAGGGCATCAGCCAGCTGCCCCAGTACAACAACTGCCCCCC  gagopt_hml (1925)

GCCACAAGCGGCAGTGCAGCAG---TAG                         gagwt_hml (1977)

CCCCCAGGCCGCCGTGCAGCAGGCTTAA                         gagopt_hml (1977)
```

Prt Manipulation:
Start with SEQ ID 63 (SEQ ID 71); manipulate to SEQ ID 64 (SEQ ID 72):

```
ATGTGGGCAACCATTGTCGGGAAACGAGCAAAGGGGCCAGCCTCAGGCCCCA  Protwt_hml (1)

ATGTGGGCCACCATCGTGGGCAAGCGCGCCAAGGGCCCCGCCAGCGGCCCCA  protopt_hml (1)

CAACAAACTGGGGCATTCCCAATTCAGCCATTTGTTCCTCAGGGTTTTCAGG  Protwt_hml (53)

CCACCAACTGGGGCATCCCCAACAGCGCCATCTGCAGCAGCGGCTTCAGCGG  protopt_hml (53)

GACAACAACCCCCACTGTCCCAAGTGTTTCAGGGAATAAGCCAGTTACCACA  Protwt_hml (105)

CACCACCACCCCCACCGTGCCCAGCGTGAGCGGCAACAAGCCCGTGACCACC  protopt_hml (105)

ATACAACAATTGTCCCCCGCCACAAGCGGCAGTGCAGCAGTAGATTTATGTA  Protwt_hml (157)

ATCCAGCAGCTGAGCCCCGCCACCAGCGGCAGCGCCGCCGTGGACCTGTGCA  protopt_hml (157)

CTATACAAGCAGTCTCTCTGCTTCCAGGGGAGCCCCCACAAAAAACCCCCAC  Protwt_hml (209)

CCATCCAGGCCGTGAGCCTGCTGCCCGGCGAGCCCCCCCAGAAGACCCCCAC  protopt_hml (209)

AGGGGTATATGGACCCCTGCCTAAGGGGACTGTAGGACTAATCTTGGGACGA  Protwt_hml (261)

CGGCGTGTACGGCCCCCTGCCCAAGGGCACCGTGGGCCTGATCCTGGGCCGC  protopt_hml (261)

TCAAGTCTAAATCTAAAAGGAGTTCAAATTCATACTAGTGTGGTTGATTCAG  Protwt_hml (313)

AGCAGCCTGAACCTGAAGGGCGTGCAGATCCACACCAGCGTGGTGGACAGCG  protopt_hml (313)

ACTATAAAGGCGAAATTCAATTGGTTATTAGCTCTTCAATTCCTTGGAGTGC  Protwt_hml (365)

ACTACAAGGGCGAGATCCAGCTGGTGATCAGCAGCAGCATCCCCTGGAGCGC  protopt_hml (365)

CAGTCCAAGAGACAGGATTGCTCAATTATTACTCCTGCCATACATTAAGGGT  Protwt_hml (417)

CAGCCCCCGCGACCGCATCGCCCAGCTGCTGCTGCTGCCCTACATCAAGGGC  protopt_hml (417)

GGAAATAGTGAAATAAAAAGAATAGGAGGGCTTGGAAGCACTGATCCAACAG  Protwt_hml (469)

GGCAACAGCGAGATCAAGCGCATCGGCGGCCTGGGCAGCACCGACCCCACCG  protopt_hml (469)

GAAAGGCTGCATATTGGGCAAGTCAGGTCTCAGAGAACAGACCTGTGTGTAA  Protwt_hml (521)

GCAAGGCCGCCTACTGGGCCAGCCAGGTGAGCGAGAACCGCCCCGTGTGCAA  protopt_hml (521)

GGCCATTATTCAAGGAAAACAGTTTGAAGGGTTGGTAGACACTGGAGCAGAT  Protwt_hml (573)

GGCCATCATCCAGGGCAAGCAGTTCGAGGGCCTGGTGGACACCGGCGCCGAC  protopt_hml (573)

GTCTCTATCATTGCTTTAAATCAGTGGCCAAAAAATTGGCCTAAACAAAAGG  Protwt_hml (625)

GTGAGCATCATCGCCCTGAACCAGTGGCCCAAGAACTGGCCCAAGCAGAAGG  protopt_hml (625)

CTGTTACAGGACTTGTCGGCATAGGCACAGCCTCAGAAGTGTATCAAAGTAC  Protwt_hml (677)

CCGTGACCGGCCTGGTGGGCATCGGCACCGCCAGCGAGGTGTACCAGAGCAC  protopt_hml (677)
```

-continued

```
GGAGATTTTACATTGCTTAGGGCCAGATAATCAAGAAAGTACTGTTCAGCCA  Protwt_hml (729)

CGAGATCCTGCACTGCCTGGGCCCCGACAACCAGGAGAGCACCGTGCAGCCC  protopt_hml (729)

ATGATTACTTCAATTCCTCTTAATCTGTGGGGTCGAGATTTATTACAACAAT  Protwt_hml (781)

ATGATCACCAGCATCCCCCTGAACCTGTGGGGCCGCGACCTGCTGCAGCAGT  protopt_hml (781)

GGGGTGCGGAAATCACCATGCCCGCTCCATCATATAGCCCCACGAGTCAAAA  Protwt_hml (833)

GGGGCGCCGAGATCACCATGCCCGCCCCCAGCTACAGCCCCACCAGCCAGAA  protopt_hml (833)

AATCATGACCAAGATGGGATATATACCAGGAAAGGGACTAGGGAAAAATGAA  Protwt_hml (885)

GATCATGACCAAGATGGGCTACATCCCCGGCAAGGGCCTGGGCAAGAACGAG  protopt_hml (885)

GATGGCATTAAAATTCCAGTTGAGGCTAAAATAAATCAAGAAAGAGAAGGAA  Protwt_hml (937)

GACGGCATCAAGATCCCCGTGGAGGCCAAGATCAACCAGGAGCGCGAGGGCA  protopt_hml (937)

TAGGGAATCCTTGC---TAG                                  Protwt_hml (989)

TCGGCAACCCCTGCGCTTAA                                  protopt_hml (989)
```

Pol Manipulation:
Start with SEQ ID 65 (SEQ ID 73); manipulate to SEQ ID 66 (SEQ ID 74):

```
ATGAATAAATCAAGAAAGAGAAGGAATAGGGAATCCTTGCTAGGGGCGGCCA  polwt_hml (1)

ATGAACAAGAGCCGCAAGCGCCGCAACCGCGAGAGCCTGCTGGGCGCCGCCA  polopt_hml (1)

CTGTAGAGCCTCCTAAACCCATACCATTAACTTGGAAAACAGAAAAACCAGT  polwt_hml (53)

CCGTGGAGCCCCCCAAGCCCATCCCCCTGACCTGGAAGACCGAGAAGCCCGT  polopt_hml (53)

GTGGGTAAATCAGTGGCCGCTACCAAAACAAAAACTGGAGGCTTTACATTTA  polwt_hml (105)

GTGGGTGAACCAGTGGCCCCTGCCCAAGCAGAAGCTGGAGGCCCTGCACCTG  polopt_hml (105)

TTAGCAAATGAACAGTTAGAAAAGGGTCATATTGAGCCTTCGTTCTCACCTT  polwt_hml (157)

CTGGCCAACGAGCAGCTGGAGAAGGGCCACATCGAGCCCAGCTTCAGCCCCT  polopt_hml (157)

GGAATTCTCCTGTGTTTGTAATTCAGAAGAAATCAGGCAAATGGCGTATGTT  polwt_hml (209)

GGAACAGCCCCGTGTTCGTGATCCAGAAGAAGAGCGGCAAGTGGCGCATGCT  polopt_hml (209)

AACTGACTTAAGGGCTGTAAACGCCGTAATTCAACCCATGGGGCCTCTCCAA  polwt_hml (261)

GACCGACCTGCGCGCCGTGAACGCGGTGATCCAGCCCATGGGCCCCCTGCAG  polopt_hml (261)

CCCGGGTTGCCCTCTCCGGCCATGATCCCAAAAGATTGGCCTTTAATTATAA  polwt_hml (313)

CCCGGCCTGCCCAGCCCCGCCATGATCCCCAAGGACTGGCCCCTGATCATCA  polopt_hml (313)

TTGATCTAAAGGATTGCTTTTTTACCATCCCTCTGGCAGAGCAGGATTGCGA  polwt_hml (365)

TCGACCTGAAGGACTGCTTCTTCACCATCCCCCTGGCCGAGCAGGACTGCGA  polopt_hml (365)

AAAATTTGCCTTTACTATACCAGCCATAAATAATAAAGAACCAGCCACCAGG  polwt_hml (417)

GAAGTTCGCCTTCACCATCCCCGCCATCAACAACAAGGAGCCCGCCACCCGC  polopt_hml (417)

TTTCAGTGGAAAGTGTTACCTCAGGGAATGCTTAATAGTCCAACTATTTGTC  polwt_hml (469)

TTCCAGTGGAAGGTGCTGCCCCAGGGCATGCTGAACAGCCCCACCATCTGCC  polopt_hml (469)

AGACTTTTGTAGGTCGAGCTCTTCAACCAGTTAGAGAAAAGTTTTCAGACTG  polwt_hml (521)

AGACCTTCGTGGGCCGCGCCCTGCAGCCCGTGCGCGAGAAGTTCAGCGACTG  polopt_hml (521)

TTATATTATTCATTGTATTGATGATATTTTATGTGCTGCAGAAACGAAAGAT  polwt_hml (573)

CTACATCATCCACTGCATCGACGACATCCTGTGCGCCGCCGAGACCAAGGAC  polopt_hml (573)

AAATTAATTGACTGTTATACATTTCTGCAAGCAGAGGTTGCCAATGCTGGAC  polwt_hml (625)
```

-continued

```
AAGCTGATCGACTGCTACACCTTCCTGCAGGCCGAGGTGGCCAACGCCGGCC  polopt_hml (625)

TGGCAATAGCATCTGATAAGATCCAAACCTCTACTCCTTTTCATTATTTAGG  polwt_hml (677)

TGGCCATCGCCAGCGACAAGATCCAGACCAGCACCCCCTTCCACTACCTGGG  polopt_hml (677)

GATGCAGATAGAAAATAGAAAAATTAAGCCACAAAAAATAGAAATAAGAAAA  polwt_hml (729)

CATGCAGATCGAGAACCGCAAGATCAAGCCCCAGAAGATCGAGATCCGCAAG  polopt_hml (729)

GACACATTAAAAACACTAAATGATTTTCAAAAATTACTAGGAGATATTAATT  polwt_hml (781)

GACACCCTGAAGACCCTGAACGACTTCCAGAAGCTGCTGGGCGACATCAACT  polopt_hml (781)

GGATTCGGCCAACTCTAGGCATTCCTACTTATGCCATGTCAAATTTGTTCTC  polwt_hml (833)

GGATCCGCCCCACCCTGGGCATCCCCACCTACGCCATGAGCAACCTGTTCAG  polopt_hml (833)

TATCTTAAGAGGAGACTCAGACTTAAATAGTAAAAGAATGTTAACCCCAGAG  polwt_hml (885)

CATCCTGCGCGGCGACAGCGACCTGAACAGCAAGCGCATGCTGACCCCCGAG  polopt_hml (885)

GCAACAAAAGAAATTAAATTAGTGGAAGAAAAAATTCAGTCAGCGCAAATAA  polwt_hml (937)

GCCACCAAGGAGATCAAGCTGGTGGAGGAGAAGATCCAGAGCGCCCAGATCA  polopt_hml (937)

ATAGAATAGATCCCTTAGCCCCACTCCAACTTTTGATTTTTGCCACTGCACA  polwt_hml (989)

ACCGCATCGACCCCCTGGCCCCCCTGCAGCTGCTGATCTTCGCCACCGCCCA  polopt_hml (989)

TTCTCCAACAGGCATCATTATTCAAAATACTGATCTTGTGGAGTGGTCATTC  polwt_hml (1041)

CAGCCCCACCGGCATCATCATCCAGAACACCGACCTGGTGGAGTGGAGCTTC  polopt_hml (1041)

CTTCCTCACAGTACAGTTAAGACTTTTACATTGTACTTGGATCAAATAGCTA  polwt_hml (1093)

CTGCCCCACAGCACCGTGAAGACCTTCACCCTGTACCTGGACCAGATCGCCA  polopt_hml (1093)

CATTAATCGGTCAGACAAGATTACGAATAATAAAATTATGTGGGAATGACCC  polwt_hml (1145)

CCCTGATCGGCCAGACCCGCCTGCGCATCATCAAGCTGTGCGGCAACGACCC  polopt_hml (1145)

AGACAAAATAGTTGTCCCTTTAACCAAGGAACAAGTTAGACAAGCCTTTATC  polwt_hml (1197)

CGACAAGATCGTGGTGCCCCTGACCAAGGAGCAGGTGCGCCAGGCCTTCATC  polopt_hml (1197)

AATTCTGGTGCATGGAAGATTGGTCTTGCTAATTTTGTGGGAATTATTGATA  polwt_hml (1249)

AACAGCGGCGCCTGGAAGATCGGCCTGGCCAACTTCGTGGGCATCATCGACA  polopt_hml (1249)

ATCATTACCCAAAAACAAAGATCTTCCAGTTCTTAAAATTGACTACTTGGAT  polwt_hml (1301)

ACCACTACCCCAAGACCAAGATCTTCCAGTTCCTGAAGCTGACCACCTGGAT  polopt_hml (1301)

TCTACCTAAAATTACCAGACGTGAACCTTTAGAAAATGCTCTAACAGTATTT  polwt_hml (1353)

CCTGCCCAAGATCACCCGCCGCGAGCCCCTGGAGAACGCCCTGACCGTGTTC  polopt_hml (1353)

ACTGATGGTTCCAGCAATGGAAAAGCAGCTTACACAGGACCGAAAGAACGAG  polwt_hml (1405)

ACCGACGGCAGCAGCAACGGCAAGGCCGCCTACACCGGCCCCAAGGAGCGCG  polopt_hml (1405)

TAATCAAAACTCCATATCAATCGGCTCAAAGAGCAGAGTTGGTTGCAGTCAT  polwt_hml (1457)

TGATCAAGACCCCCTACCAGAGCGCCCAGCGCGCCGAGCTGGTGGCCGTGAT  polopt_hml (1457)

TACAGTGTTACAAGATTTTGACCAACCTATCAATATTATATCAGATTCTGCA  polwt_hml (1509)

CACCGTGCTGCAGGACTTCGACCAGCCCATCAACATCATCAGCGACAGCGCC  polopt_hml (1509)

TATGTAGTACAGGCTACAAGGGATGTTGAGACAGCTCTAATTAAATATAGCA  polwt_hml (1561)

TACGTGGTGCAGGCCACCCGCGACGTGGAGACCGCCCTGATCAAGTACAGCA  polopt_hml (1561)

TGGATGATCAGTTAAACCAGCTATTCAATTTATTACAACAAACTGTAAGAAA  polwt_hml (1613)

TGGACGACCAGCTGAACCAGCTGTTCAACCTGCTGCAGCAGACCGTGCGCAA  polopt hml (1613)

AAGAAATTTCCCATTTTATATTACACATATTCGAGCACACACTAATTTACCA  polwt_hml (1665)
```

```
GCGCAACTTCCCCTTCTACATCACCCACATCCGCGCCCACACCAACCTGCCC  polopt_hml (1665)
GGGCCTTTGACTAAAGCAAATGAACAAGCTGACTTACTGGT-ATCATCTGCA  polwt_hml  (1717)
GGCCCCCTGACCAAGGCCAACGAGCAGGCCGACCTGCTGGTGAGCAGC-GCC  polopt_hml (1717)
CTCATAAAAGCACAAGAACTTCATGCTTTGACTCATGTAAATGCAGCAGGAT  polwt_hml  (1768)
CTGATCAAGGCCCAGGAGCTGCACGCCCTGACCCACGTGAACGCCGCCGGCC  polopt_hml (1768)
TAAAAAACAAATTTGATGTCACATGGAAACAGGCAAAAGATATTGTACAACA  polwt_hml  (1820)
TGAAGAACAAGTTCGACGTGACCTGGAAGCAGGCCAAGGACATCGTGCAGCA  polopt_hml (1820)
TTGCACCCAGTGTCAAGTCTTACACCTGCCCACTCAAGAGGCAGGAGTTAAT  polwt_hml  (1872)
CTGCACCCAGTGCCAGGTGCTGCACCTGCCCACCCAGGAGGCCGGCGTGAAC  polopt_hml (1872)
CCCAGAGGTCTGTGTCCTAATGCATTATGGCAAATGGATGTCACGCATGTAC  polwt_hml  (1924)
CCCCGCGGCCTGTGCCCCAACGCCCTGTGGCAGATGGACGTGACCCACGTGC  polopt_hml (1924)
CTTCATTTGGAAGATTATCATATGTTCACGTAACAGTTGATACTTATTCACA  polwt_hml  (1976)
CCAGCTTCGGCCGCCTGAGCTACGTGCACGTGACCGTGGACACCTACAGCCA  polopt_hml (1976)
TTTCATATGGGCAACTTGCCAAACAGGAGAAAGTACTTCCCATGTTAAAAAA  polwt_hml  (2028)
CTTCATCTGGGCCACCTGCCAGACCGGCGAGAGCACCAGCCACGTGAAGAAG  polopt_hml (2028)
CATTTATTGTCTTGTTTTGCTGTAATGGGAGTTCCAGAAAAAATCAAAACTG  polwt_hml  (2080)
CACCTGCTGAGCTGCTTCGCCGTGATGGGCGTGCCCGAGAAGATCAAGACCG  polopt_hml (2080)
ACAATGGACCAGGATATTGTAGTAAAGCTTTCCAAAAATTCTTAAGTCAGTG  polwt_hml  (2132)
ACAACGGCCCCGGCTACTGCAGCAAGGCCTTCCAGAAGTTCCTGAGCCAGTG  polopt_hml (2132)
GAAAATTTCACATACAACAGGAATTCCTTATAATTCCCAAGGACAGGCCATA  polwt_hml  (2184)
GAAGATCAGCCACACCACCGGCATCCCCTACAACAGCCAGGGCCAGGCCATC  polopt_hml (2184)
GTTGAAAGAACTAATAGAACACTCAAAACTCAATTAGTTAAACAAAAAGAAG  polwt_hml  (2236)
GTGGAGCGCACCAACCGCACCCTGAAGACCCAGCTGGTGAAGCAGAAGGAGG  polopt_hml (2236)
GGGGAGACAGTAAGGAGTGTACCACTCCTCAGATGCAACTTAATCTAGCACT  polwt_hml  (2288)
GCGGCGACAGCAAGGAGTGCACCACCCCCCAGATGCAGCTGAACCTGGCCCT  polopt_hml (2288)
CTATACTTTAAATTTTTTAAACATTTATAGAAATCAGACTACTACTTCTGCA  polwt_hml  (2340)
GTACACCCTGAACTTCCTGAACATCTACCGCAACCAGACCACCACCAGCGCC  polopt_hml (2340)
GAACAACATCTTACTGGTAAAAAGAACAGCCCACATGAAGGAAAACTAATTT  polwt_hml  (2392)
GAGCAGCACCTGACCGGCAAGAAGAACAGCCCCCACGAGGGCAAGCTGATCT  polopt_hml (2392)
GGTGGAAAGATAATAAAAATAAGACATGGGAAATAGGGAAGGTGATAACGTG  polwt_hml  (2444)
GGTGGAAGGACAACAAGAACAAGACCTGGGAGATCGGCAAGGTGATCACCTG  polopt_hml (2444)
GGGGAGAGGTTTTGCTTGTGTTTCACCAGGAGAAAATCAGCTTCCTGTTTGG  polwt_hml  (2496)
GGGCCGCGGCTTCGCCTGCGTGAGCCCCGGCGAGAACCAGCTGCCCGTGTGG  polopt_hml (2496)
ATACCCACTAGACATTTGAAGTTCTACAATGAACCCATCAGAGATGCAAAGA  polwt_hml  (2548)
ATCCCCACCCGCCACCTGAAGTTCTACAACGAGCCCATCCGCGACGCCAAGA  polopt_hml (2548)
AAAGCACCTCCGCGGAGACGGAGACATCGCAATCGAGCACCGTTGACTCACA  polwt_hml  (2600)
AGAGCACCAGCGCCGAGACCGAGACCAGCCAGAGCAGCACCGTGGACAGCCA  polopt_hml (2600)
AGATGAACAAAATGGTGACGTCAGAAGAACAGATGAAGTTGCCATCCACCAA  polwt_hml  (2652)
GGACGAGCAGAACGGCGACGTGCGCCGCACCGACGAGGTGGCCATCCACCAG  polopt_hml (2652)
GAAGGCAGAGCCGCCAACTTGGGCACAACTAAAGAAGCTGACGCAGTTAGCT  polwt_hml  (2704)
GAGGGCCGCGCCGCCAACCTGGGCACCACCAAGGAGGCCGACGCCGTGAGCT  polopt_hml (2704)
```

-continued

```
ACAAAATATCTAGAGAACACAAAGGTGACACAAACCCCAGAGAGTATGCTGC      polwt_hml  (2756)

ACAAGATCAGCCGCGAGCACAAGGGCGACACCAACCCCCGCGAGTACGCCGC      polopt_hml (2756)

TTGCAGCCTTGATGATTGTATCAATGGTGGTAAGTCTCCCTATGCCTGCAGG      polwt_hml  (2808)

CTGCAGCCTGGACGACTGCATCAACGGCGGCAAGAGCCCCTACGCCTGCCGC      polopt_hml (2808)

AGCAGCTGCAGC---TAA                                        polwt_hml  (2860)

AGCAGCTGCAGCGCTTAA                                        polopt_hml (2860)
```

Env Manipulation:
Start with SEQ ID 81 (SEQ ID 83); manipulate to SEQ ID 82:

```
envwt_HML2   ATGAACCCAAGCGAGATGCAAAGAAAAGCACCTCCGCGGAGACGGAGACATCGCAATCGA envopt_HML2  ATGAACCCCAGCGAGATGCAGCGCAAGGCCCCCCCCCCCGCCGCCGCCACCGCAACCGC envwt_HML2   GCACCGTTGACTCACAAGATGAACAAAATGGTGACGTCAGAAGAACAGATGAAGTTGCCA envopt_HML2  GCCCCCCTGACCCACAAGATGAACAAGATGGTGACCAGCGAGGAGCAGATGAAGCTGCCC envwt_HML2   TCCACCAAGAAGGCAGAGCCGCCAACTTGGGCACAACTAAAGAAGCTGACGCAGTTAGCT envopt_HML2  AGCACCAAGAAGGCCGAGCCCCCCACCTGGGCCCAGCTGAAGAAGCTGACCCAGCTGGCC envwt_HML2   ACAAAATATCTAGAGAACACAAAGGTGACACAAACCCCAGAGAGTATGCTGCTTGCAGCC envopt_HML2  ACCAAGTACCTGGAGAACACCAAGGTGACCCAGACCCCCGAGAGCATGCTGCTGGCCGCC envwt_HML2   TTGATGATTGTATCAATGGTGGTAAGTCTCCCTATGCCTGCAGGAGCAGCTGCAGCTAAC envopt_HML2  CTGATGATCGTGAGCATGGTGGTGAGCCTGCCCATGCCCGCCGGCGCCGCCGCCGCCAAC envwt_HML2   TATACCTACTGGGCCTATGTGCCTTTCCCGCCCTTAATTCGGGCAGTCACATGGATGGAT envopt_HML2  TACACCTACTGGGCCTACGTGCCCTTCCCCCCCCTGATCCGCGCCGTGACCTGGATGGAC envwt_HML2   AATCCTACAGAAGTATATGTTAATGATAGTGTATGGGTACCTGGCCCCATAGATGATCGC envopt_HML2  AACCCCACCGAGGTGTACGTGAACGACAGCGTGTGGGTGCCCGGCCCCATCGACGACCGC envwt_HML2   TGCCCTGCCAAACCTGAGGAAGAAGGGATGATGATAAATATTTCCATTGGGTATCATTAT envopt_HML2  TGCCCCGCCAAGCCCGAGGAGGAGGGCATGATGATCAACATCAGCATCGGCTACCACTAC envwt_HML2   CCTCCTATTTGCCTAGGGAGAGCACCAGGATGTTTAATGCCTGCAGTCCAAAATTGGTTG envopt_HML2  CCCCCCATCTGCCTGGGCCGCGCCCCCGGCTGCCTGATGCCCGCCGTGCAGAACTGGCTG envwt_HML2   GTAGAAGTACCTACTGTCAGTCCCATCTGTAGATTCACTTATCACATGGTAAGCGGGATG envopt_HML2  GTGGAGGTGCCCACCGTGAGCCCCATCTGCCGCTTCACGTACCACATGGTGAGCGGCATG envwt_HML2   TCACTCAGGCCACGGGTAAATTATTTACAAGACTTTTCTTATCAAAGATCATTAAAATTT envopt_HML2  AGCCTGCGCCCCCGCGTGAACTACCTGCAGGACTTCAGCTACCAGCGCAGCCTGAAGTTC envwt_HML2   AGACCTAAAGGGAAACCTTGCCCCAAGGAAATTCCCAAAGAATCAAAAAATACAGAAGTT envopt_HML2  CGCCCCAAGGGCAAGCCCTGCCCCAAGGAGATCCCCAAGGAGAGCAAGAACACCGAGGTG envwt_HML2   TTAGTTTGGGAAGAATGTGTGGCCAATAGTGCGGTGATATTACAAACAATGAATTCGGA envopt_HML2  CTGGTGTGGGAGGAGTGCGTGGCCAACAGCGCCGTGATCCTGCAGAACAACGAGTTCGGC envwt_HML2   ACTATTATAGATTGGGCACCTCGAGGTCAATTCTACCACAATTGCTCAGGACAAACTCAG envopt_HML2  ACCATCATCGACTGGGCCCCCCGCGGCCAGTTCTACCACAACTGCAGCGGCCAGACCCAG envwt_HML2   TCGTGTCCAAGTGCACAAGTGAGTCCAGCTGTTGATAGCGACTTAACAGAAAGTTTAGAC envopt_HML2  AGCTGCCCCAGCGCCCAGGTGAGCCCCGCCGTGGACAGCGACCTGACCGAGAGCCTGGAC envwt_HML2   AAACATAAGCATAAAAAATTGCAGTCTTTCTACCCTTGGGAATGGGGAGAAAAAGGAATC
```

-continued

Figure 5:
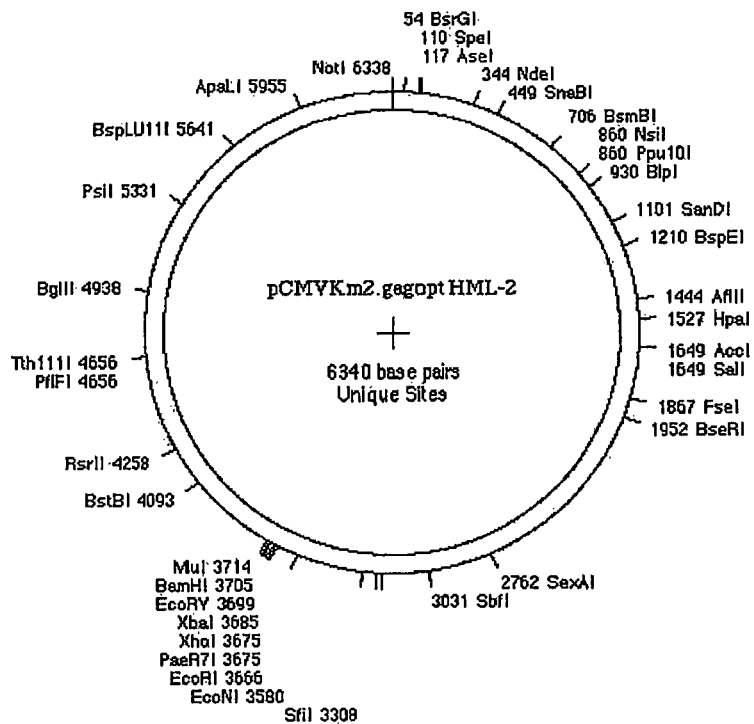
Figure 8:
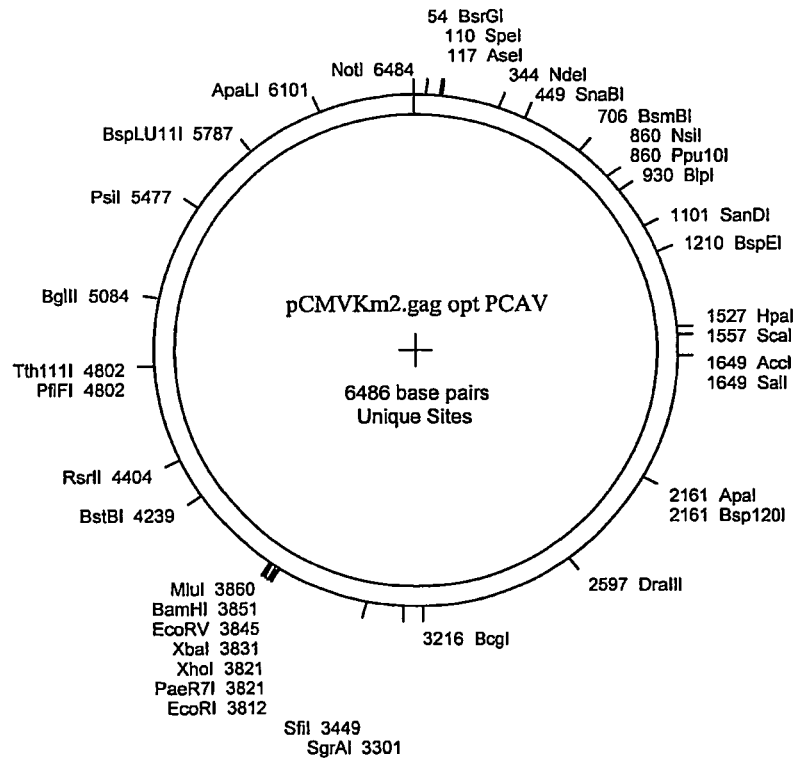
Figure 9:
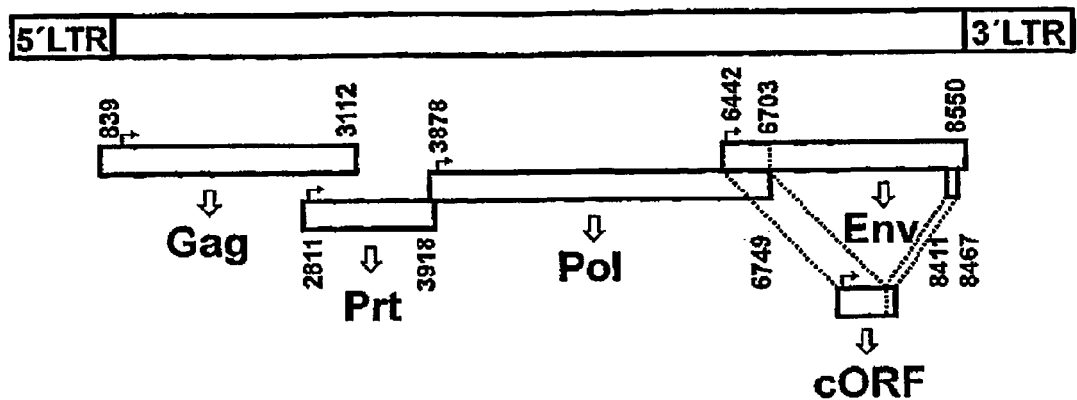
FIG. 9 shows the location of coding sequences in the HML2.HOM genome, with nucleotide numbering according to ref. 5.

```
envopt_HML2  AAGCACAAGCACAAGAAGCTGCAGAGCTTCTACCCCTGGGAGTGGGGCGAGAAGGGCATC envwt_HML2   TCTACCCCAAGACCAAAAATAGTAAGTCCTGTTTCTGGTCCTGAACATCCAGAATTATGG envopt_HML2  AGCACCCCCGCCCCAAGATCGTGAGCCCCGTGAGCGGCCCCGAGCACCCCGAGCTGTGG envwt_HML2   AGGCTTACTGTGGCTTCACACCACATTAGAATTTGGTCTGGAAATCAAACTTTAGAAACA envopt_HML2  CGCCTGACCGTGGCCAGCCACCACATCCGCATCTGGAGCGGCAACCAGACCCTGGAGACC envwt_HML2   AGAGATCGTAAGCCATTTTATACTATTGACCTGAATTCCAGTCTAACAGTTCCTTTACAA envopt_HML2  CGCGACCGCAAGCCCTTCTACACCATCGACCTGAACAGCAGCCTGACCGTGCCCCTGCAG envwt_HML2   AGTTGCGTAAAGCCCCCTTATATGCTAGTTGTAGGAAATATAGTTATTAAACCAGACTCC envopt_HML2  AGCTGCGTGAAGCCCCCCTACATGCTGGTGGTGGGCAACATCGTGATCAAGCCCGACAGC envwt_HML2   CAGACTATAACCTGTGAAAATTGTAGATTGCTTACTTGCATTGATTCAACTTTTAATTGG envopt_HML2  CAGACCATCACCTGCGAGAACTGCCGCCTGCTGACCTGCATCGACAGCACCTTCAACTGG envwt_HML2   CAACACCGTATTCTGCTGGTGAGAGCAAGAGAGGGCGTGTGGATCCCTGTGTCCATGGAC envopt_HML2  CAGCACCGCATCCTGCTGGTGCGCGCCCGCGAGGGCGTGTGGATCCCCGTGAGCATGGAC envwt_HML2   CGACCGTGGGAGGCCTCGCCATCCGTCCATATTTTGACTGAAGTATTAAAAGGTGTTTTA envopt_HML2  CGCCCCTGGGAGGCCAGCCCCAGCGTGCACATCCTGACCGAGGTGCTGAAGGGCGTGCTG envwt_HML2   AATAGATCCAAAAGATTCATTTTTACTTTAATTGCAGTGATTATGGGATTAATTGCAGTC envopt_HML2  AACCGCAGCAAGCGCTTCATCTTCACCCTGATCGCCGTGATCATGGGCCTGATCGCCGTG envwt_HML2   ACAGCTACGGCTGCTGTAGCAGGAGTTGCATTGCACTCTTCTGTTCAGTCAGTAAACTTT envopt_HML2  ACCGCCACCGCCGCCGTGGCCGGCGTGGCCCTGCACAGCAGCGTGCAGAGCGTGAACTTC envwt_HML2   GTTAATGATTGGCAAAAAAATTCTACAAGATTGTGGAATTCACAATCTAGTATTGATCAA envopt_HML2  GTGAACGAC In Vitro Expression of Gag Sequences Three different gag-encoding sequences were cloned into the pCMVKm2 vector:
(1) gag opt HML-2 (SEQ ID 54, including SEQ ID 62 and encoding SEQ ID 70—FIG. 5).
(2) gag opt PCAV (SEQ ID 80, including SEQ ID 77 and encoding SEQ ID 79—FIG. 8).
(3) gag wt PCAV (SEQ ID 53, including SEQ ID 76 and encoding SEQ ID 78—FIG. 4).

The vectors were used to transfect 293 cells in duplicate in 6-well plates, using the polyamine reagent TransIt™ LT-1 (PanVera Corp, Madison Wis.) plus 2 µg DNA.

Figure 10:
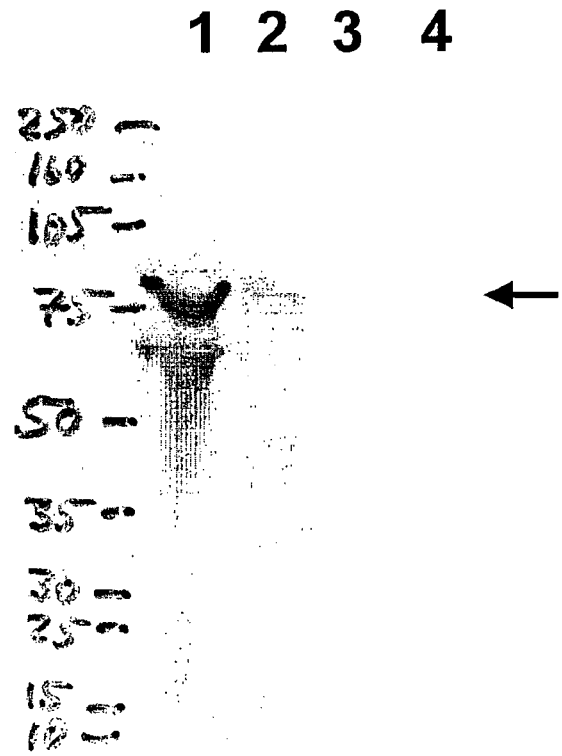
FIG. 10 is a western blot showing gag expression in transfected 293 cells. Lanes 1 to 4 are: (1) gag opt HML-2; (2) gag opt PCAV; (3) gag wt PCAV; (4) mock.
Figure 11A:
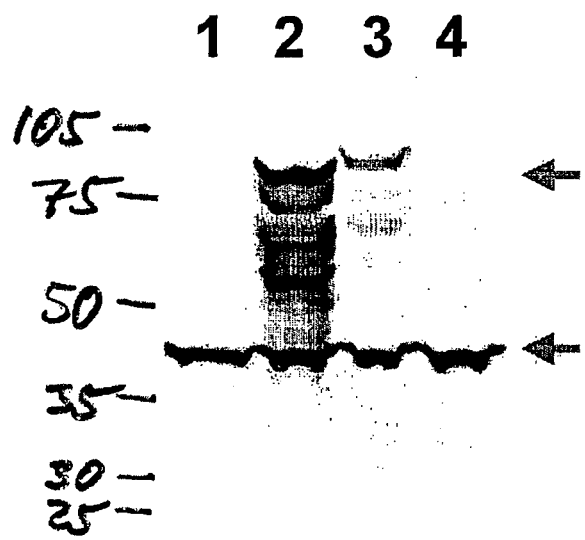
In FIG. 11A the staining antibody was anti-HML-2, but in FIG. 11B it was anti-PCAV. In both 11A and 11B lanes 1 to 4 are: (1) mock; (2) gag opt HML-2; (3) gag opt PCAV; (4) gag wt PCAV. The upper arrow shows the position of gag; the lower arrow shows the β-actin control.
Figure 11B:
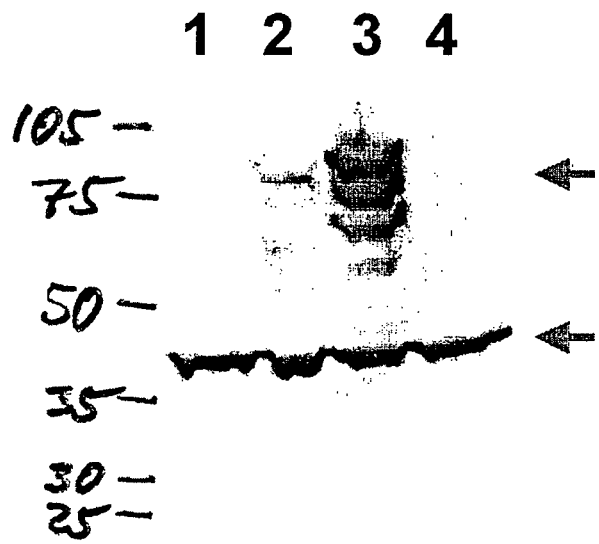
FIG. 11 also shows western blots of transfected 293 cells.

Cells were lysed after 48 hours and analyzed by western blot using pooled mouse antibody against HML2-gag as the primary antibody (1:400), and goat anti-mouse HRP as the secondary antibody (1:20000). FIG. 10 shows that 'gag opt PCAV' (lane 2) expressed much more efficiently than 'gag wt PCAV' (lane 3). Lane 1 ('gag opt HML-2') is more strongly stained than lane 2 ('gag opt PCAV'), but this could be due to the fact that the primary antibody was raised against the homologous HML-2 protein, rather than reflecting a difference in expression efficiency. To address this question, antibodies were also raised against the PCAV product and were used for Western blotting. FIG. 11A shows results using the anti-HML2 as the primary antibody (1:500), and FIG. 11B shows the results with anti-PCAV (1:500). Each antibody stains the homologous protein more strongly than the heterologous protein.

Nucleic Acid Immunization

Vectors of the invention are purified from bacteria and used to immunize mice.

T Cell Responses to PCAV Gag

CB6F1 mice were intramuscularly immunized with pCMVKm2 vectors encoding PCAV gag (FIGS. 4 & 8) and induction of gag-specific CD4+ and CD8+ cells were measured.

Mice received four injections of 50 µg plasmid at week 0, 2, 4 and 6. These plasmids included the wild type gag sequence (SEQ ID 76). Mice were then split into two separate groups for further work.

The first group of three mice received a further 50 µg of plasmid at 25 weeks, but this plasmid included the optimized gag sequence (SEQ ID 77). Eleven days later spleens were harvested and pooled and a single cell suspension was prepared for culture. Spleen cells (1×10⁶ per culture) were cultured overnight at 37° C. in the absence ("unstimulated") or presence ("stimulated") of 1×10⁷ plaque-forming units (pfu) of a recombinant vaccinia which contains the PCAV gag sequence ("rVV-gag", produced by homologous recombination of cloning vector pSC11 [116], followed by plaque purification of recombinant rVVgag). Duplicate stimulated and unstimulated cultures were prepared. The following day Brefeldin A was added to block cytokine secretion and cultures were continued for 2 hours. Cultures were then harvested and stained with fluorescently-labeled monoclonal antibodies for cell surface CD8 and intracellular gamma interferon (IFN-γ). Stained samples were analyzed by flow cytometry and the fraction of CD8+ cells that stained positively for intracellular IFN-γ was determined. Results were as follows:

| Culture condition | Culture #1 | Culture #2 | Average |
|---|---|---|---|
| Unstimulated | 0.10 | 0.14 | 0.12 |
| Stimulated | 1.51 | 1.27 | 1.39 |
| | | Difference | 1.27 |

An average of 1.27% of the pooled splenic CD8+ cells synthesized IFN-γ in response to stimulation with rVV-gag. This demonstrates that the DNA immunization induced CD8+ T cells that specifically recognized and responded to PCAV gag.

The second group of four mice received a further 50 µg of plasmid at 28 weeks, but this plasmid included the optimized gag sequence (SEQ ID 77). Twelve days later spleens were harvested. As a specificity control, a spleen was also obtained from a CB6F1 mouse that had been vaccinated with a pCMV-KM2 vector encoding HML2 env.

Single cell suspensions from individual spleens were prepared for culture. Spleen cells (1×10⁶ per culture) were cultured overnight at 37° C. in the absence of stimulation or in the presence of 1×10⁷ pfu rVV-gag. As a specificity control, additional cultures contained another recombinant vaccinia virus, rVV-HIVgp160env.SF162 ("rVV-HIVenv"—contains full-length env gene from SF162 isolate of HIV-1), which was not expected to cross-react with either gag or env from PCAV.

Duplicate cultures were prepared for each condition. The following day Brefeldin A was added to block cytokine secretion and anti-CD28 antibody was added to co-stimulate CD4 T cells. Cultures were continued for 2 hours and then harvested and stained with fluorescently-labeled monoclonal antibodies for cell surface CD8 and CD4 and intracellular IFN-γ. Stained samples were analyzed by flow cytometry and the fractions of CD8+CD4− and CD4+8− T cells that stained positively for intracellular IFN-γ were determined. Results are shown in the following table, expressed as the % of stained cells in response to stimulation by either PCAV gag or HIV env during spleen culture, after subtraction of the average value seen with cells which were not stimulated during spleen culture:

| Spleen culture stimulation | Vector administered at 28 weeks | | | | |
|---|---|---|---|---|---|
| | PCAV gag | PCAV gag | PCAV gag | PCAV gag | PCAV env |
| | CD8 | | | | |
| PCAV gag | 1.32 | 1.88 | 3.00 | 2.09 | 0.13 |
| HIV env | 0.04 | 0.12 | −0.02 | 0.23 | 0.05 |
| | CD4 | | | | |
| PCAV gag | 0.26 | 0.17 | 0.40 | 0.22 | −0.01 |
| HIV env | 0.01 | −0.02 | −0.03 | 0.01 | −0.02 |

For the 4 mice that had been vaccinated with a vector encoding PCAV gag, therefore, the rVV-gag vector stimulated 1.32% to 3.00% of CD8+ T cells to produce IFN-γ. However, there were few CD8+ T cells (<0.23%) that responded to the irrelevant rVV-HIVgp160env vector. The CD8+ T cell response is thus specific to PCAV gag. Furthermore, the control mouse that was immunized with PCAV env had very few CD8+ T cells (0.13%) which responded to the vaccinia stimulation.

Similarly, vaccination with PCAV gag, but not with PCAV env, induced CD4+ T cells specific for PCAV gag (0.17% to 0.40%).

DNA immunization with vectors encoding PCAV gag thus induces CD8+ and CD4+ T cells that specifically recognize and respond to the PCAV gag antigen.

Figure 12A:
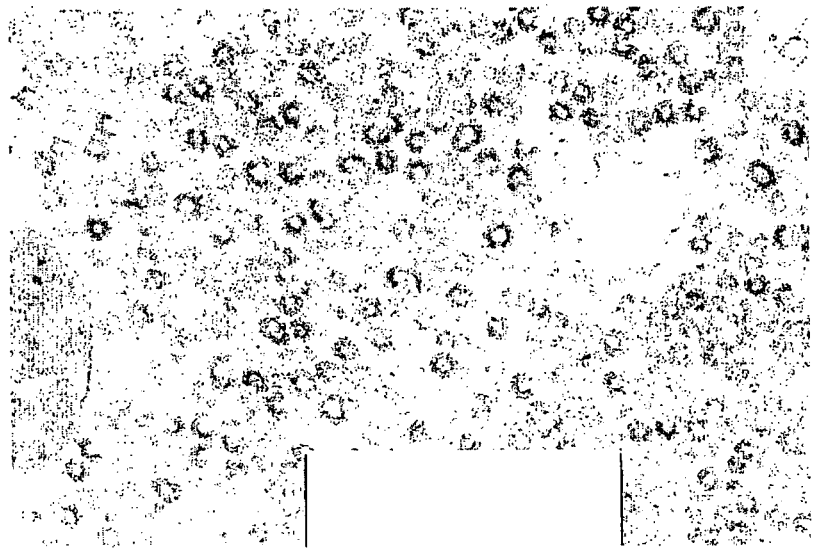
FIG. 12 shows electron microscopy of 293 cells expressing (12A) gag opt PCAV or (12B) gag opt HML-2.
Figure 12B:
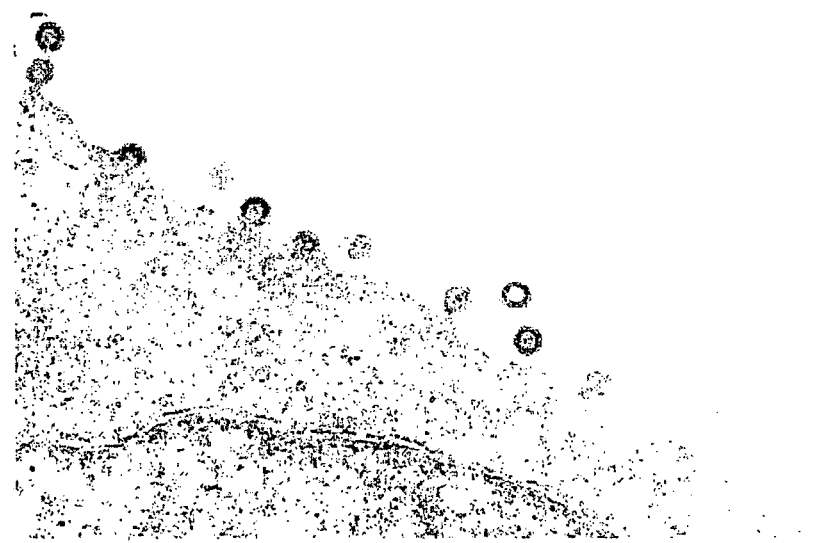

Virus-Like Particles 293 cells were fixed 48 hours after transient transfection with pCMV-gag, either from HML-2 or from PCAV, and inspected by electron microscopy (FIG. 12). VLPs were produced in both cases, but these were mainly intracellular for PCAV and mainly secreted for HML-2.

The assembly of viable VLPs from PCAV and HML-2 indicates that the gag protein has retained its essential activity even though the endogenous virus is "dormant" and might thus be expected to be subject to mutational inactivation.

The above description of preferred embodiments of the invention has been presented by way of illustration and example for purposes of clarity and understanding. It is not intended to be exhaustive or to limit the invention to the precise forms disclosed. It will be readily apparent to those of ordinary skill in the art in light of the teachings of this invention that many changes and modifications may be made thereto without departing from the spirit of the invention. It is intended that the scope of the invention be defined by the appended claims and their equivalents.

SEQUENCE LISTING INDEX

Figure 2:
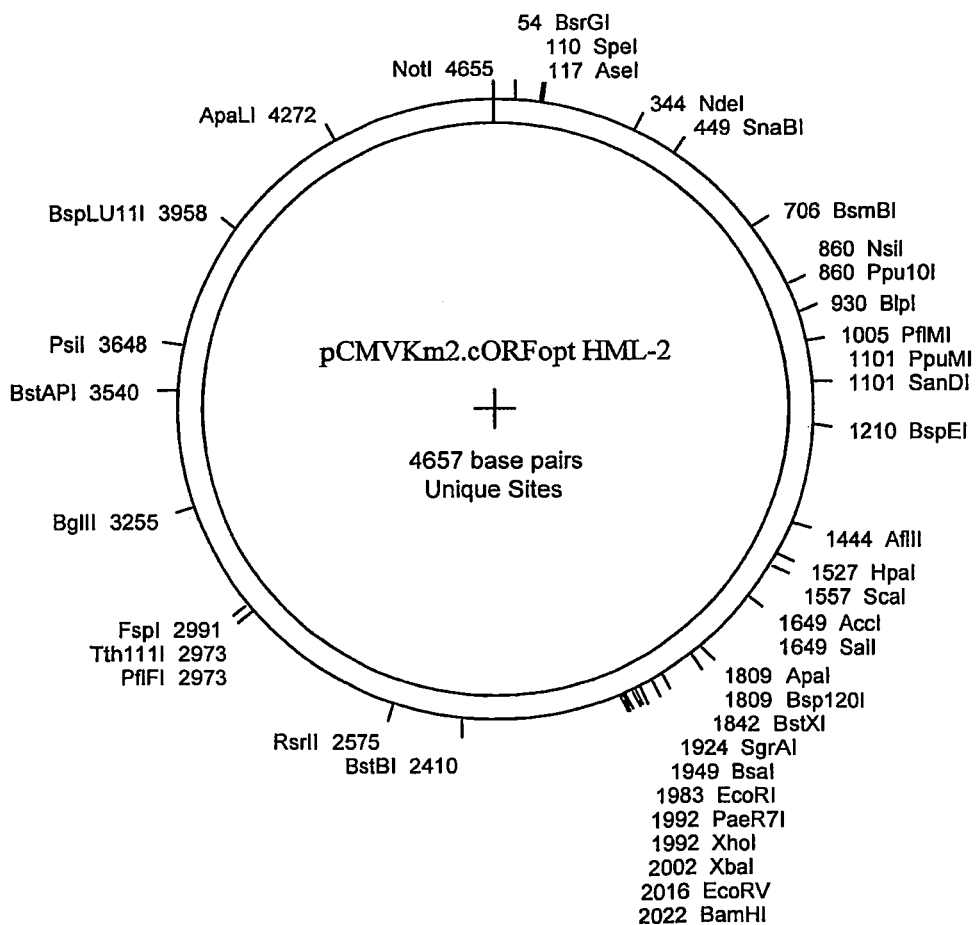
FIGS. 2 to 8 show vectors formed by inserting sequences encoding HML-2 polypeptides into this vector.
Figure 3:
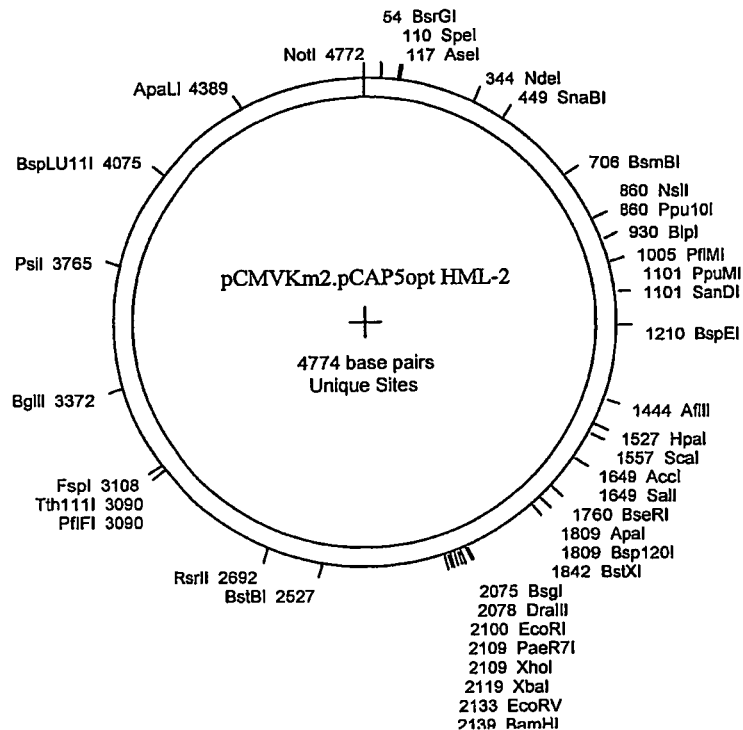
Figure 6:
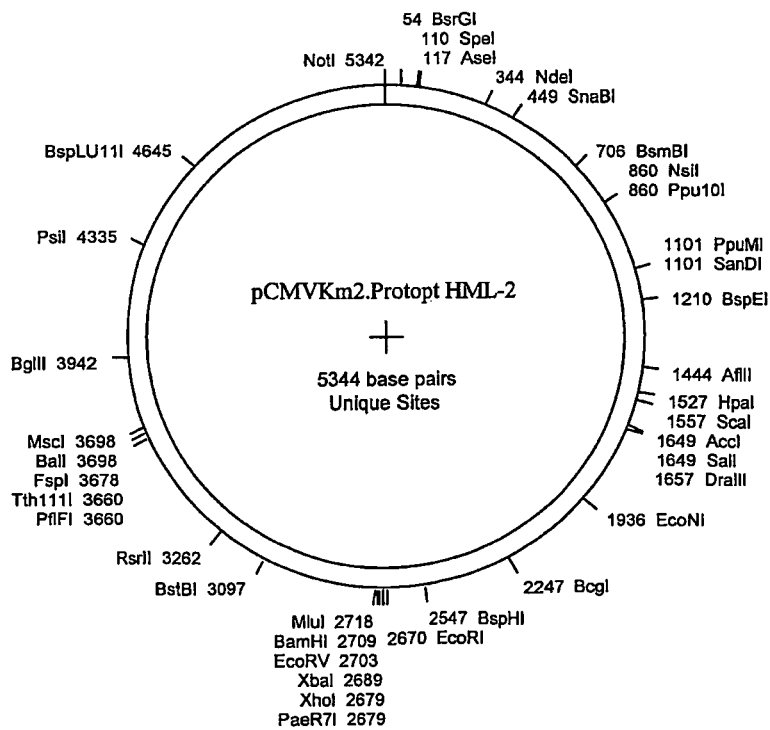
Figure 7:
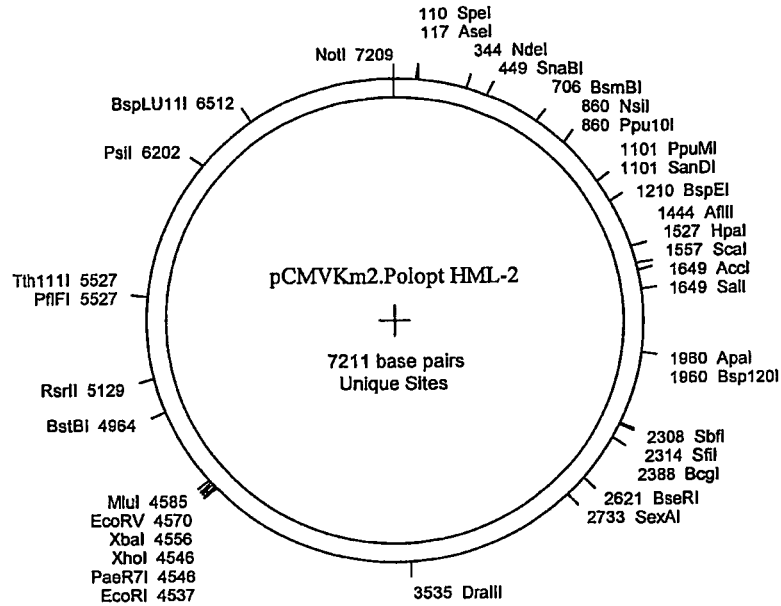

| SEQ ID | DESCRIPTION |
|---|---|
| 1-9 | Gag sequences |
| 10-14 | Prt sequences |
| 15-21 | Pol sequences |
| 22-28 | Env sequences |
| 29-31 | cORF sequences |
| 32-37 | PCAP sequences |
| 38-50 | Splice variants A-M sequences |
| 51 | pCMVKm2.cORFopt HML-2 (FIG. 2) |
| 52 | pCMVKm2.pCAP5opt HML-2 (FIG. 3) |
| 53 | pCMVKm2.gag wt PCAV (FIG. 4) |
| 54 | pCMVKm2.gagopt HML-2 (FIG. 5) |
| 55 | pCMVKm2.Protopt HML-2 (FIG. 6) |
| 56 | pCMVKm2.Polopt HML-2 (FIG. 7) |
| 57-66 | Nucleotide sequences pre- and post-manipulation |
| 67 | Manipulated cORF |
| 68 | Manipulated PCAP5 |
| 69 & 70 | Gag - pre- and post-manipulation |
| 71 & 72 | Prt - pre- and post-manipulation |
| 73 & 74 | Pol - pre- and post-manipulation |
| 75 | PCAV, from the beginning of its first 5' LTR to the end of its fragmented 3' LTR |
| 76 & 77 | PCAV Gag nucleotide sequences - pre-and post manipulation |
| 78 & 79 | PCAV Gag amino acid sequences - pre-and post manipulation |
| 80 | pCMVKm2.gagopt PCAV (FIG. 8) |
| 81 | Wild-type env from HML-2 |
| 82 | Optimized env from HML-2 |
| 83 | Amino acid sequence encoded by SEQ IDs 81 & 82 |

NB:
SEQ IDs 1 to 9 disclosed in reference 1 as SEQ IDs 85, 91, 97, 102, 92, 98, 103, 104 & 146
SEQ IDs 10 to 14 disclosed in reference 1 as SEQ IDs 86, 99, 105, 106 & 147
SEQ IDs 15 to 21 disclosed in reference 1 as SEQ IDs 87, 93, 100, 107, 94, 108 & 148
SEQ IDs 22 to 28 disclosed in reference 1 as SEQ IDs 88, 95, 101, 107, 96, 108 & 149
SEQ IDs 29 to 31 disclosed in reference 1 as SEQ IDs 89, 90 & 109
SEQ IDs 32 to 37 disclosed in reference 1 as SEQ IDs 10, 11, 12, 7, 8 & 9
SEQ IDs 38 to 50 disclosed in reference 1 as SEQ IDs 28-37, 39, 41 & 43
SEQ ID 75 disclosed in reference 3 as SEQ ID 1.

REFERENCES

The Contents of which are Hereby Incorporated in Full by Reference

1. International patent application WO02/46477 (PCT/US01/47824).
2. U.S. patent application Ser. No. 10/016,604 (filed Dec. 7, 2001).
3. International patent application PCT/US02/39136 (filed Dec. 9, 2002).
4. Andersson et al. (1999) *J. Gen. Virol.* 80:255-260.
5. Mayer et al. (1999) *Nat. Genet.* 21 (3), 257-258 (1999)
6. Ono et al., (1986) *J. Virol.* 60:589
7. U.S. Pat. No. 5,858,723
8. Barbulescu et al. (1999) *Curr. Biol.* 9:861-868.
9. Zsiros et al. (1998) *J. Gen. Virol.* 79:61-70.
10. Tönjes et al. (1999) *J. Virol.* 73:9187-9195.
11. Genbank accession number AB047240
12. Paces et al. (2002) *Nucleic Acids Res.* 30:205-206.
13. Reus et al. (2001) *Genomics* 72:314-320.
14. Dunham et al. (1999) *Nature* 402:489-495.
15. Löwer et al. (1996) *Proc. Natl. Acad. Sci USA* 93:5177
16. Boese et al. (2000) *Oncogene* 19:4328-4336.
17. Mueller-Lantzsch et al., AIDS Research and Human Retroviruses 9:343-350 (1993)
18. Berkhout et al. (1999) *J. Virol.* 73:2365-2375.
19. Löwer et al. (1995) *J. Virol.* 69:141-149.
20. Magin et al. (1999) *J. Virol.* 73:9496-9507.
21. Magin-Lachmann (2001) *J Virol.* 75(21):10359-71.
22. International patent application PCT/US02/39344 (filed Dec. 9, 2002).
23. Geysen et al. (1984) *PNAS USA* 81:3998-4002.
24. Carter (1994) *Methods Mol Biol* 36:207-23.
25. Jameson, B A et al., 1988, *CABIOS* 4(1):181-186.
26. Raddrizzani & Hammer (2000) *Brief Bioinform* 1(2):179-89.
27. De Lalla et al. (1999) *J. Immunol.* 163:1725-29.
28. Brusic et al. (1998) *Bioinformatics* 14(2):121-30
29. Meister et al. (1995) *Vaccine* 13(6):581-91.
30. Roberts et al. (1996) *AIDS Res Hum Retroviruses* 12(7): 593-610.
31. Maksyutov & Zagrebelnaya (1993) *Comput Appl Biosci* 9(3):291-7.
32. Feller & de la Cruz (1991) *Nature* 349(6311):720-1.
33. Hopp (1993) *Peptide Research* 6:183-190.
34. Welling et al. (1985) *FEBS Lett.* 188:215-218.
35. Davenport et al. (1995) *Immunogenetics* 42:392-297.
36. U.S. Pat. No. 5,858,723
37. Johnston et al. (2001) *Ann Neurol* 50(4):434-42.
38. Medstrand et al. (1998) *J Virol* 72(12):9782-7.
39. Gennaro (2000) *Remington: The Science and Practice of Pharmacy.* 20th edition, ISBN: 0683306472.
40. WO 93/14778
41. Findeis et al., *Trends Biotechnol.* (1993) 11:202
42. Chiou et al. (1994) *Gene Therapeutics: Methods And Applications Of Direct Gene Transfer.* ed. Wolff
43. Wu et al., *J. Biol. Chem* (1988) 263:621
44. Wu et al., *J. Biol. Chem.* (1994) 269:542
45. Zenke et al., *Proc. Natl. Acad. Sci.* (USA) (1990) 87:3655
46. Wu et al., *J. Biol. Chem.* (1991) 266:338
47. Jolly, *Cancer Gene Therapy* (1994) 1:51
48. Kimura, *Human Gene Therapy* (1994) 5:845
49. Connelly, *Human Gene Therapy* (1995) 1:185
50. Kaplitt, *Nature Genetics* (1994) 6:148
51. WO 90/07936
52. WO 94/03622
53. WO 93/25698
54. WO 93/25234
55. U.S. Pat. No. 5,219,740
56. WO 93/11230
57. WO 93/10218
58. U.S. Pat. No. 4,777,127
59. GB Patent No. 2,200,651
60. EP-A-0 345 242
61. WO 91/02805
62. WO 94/12649
63. WO 93/03769
64. WO 93/19191
65. WO 94/28938
66. WO 95/11984

67. WO 95/00655
68. Curiel, *Hum. Gene Ther.* (1992) 3:147
69. Wu, *J. Biol. Chem.* (1989) 264:16985
70. U.S. Pat. No. 5,814,482
71. WO 95/07994
72. WO 96/17072
73. WO 95/30763
74. WO 97/42338
75. WO 90/11092
76. U.S. Pat. No. 5,580,859
77. U.S. Pat. No. 5,422,120
78. WO 95/13796
79. WO 94/23697
80. WO 91/14445
81. EP 0524968
82. Philip, *Mol. Cell Biol.* (1994) 14:2411
83. Woffendin, *Proc. Natl. Acad. Sci.* (1994) 91:11581
84. U.S. Pat. No. 5,206,152
85. WO 92/11033
86. U.S. Pat. No. 5,149,655
87. WO 92/11033
88. Donnelly et al. (1997) *Annu Rev Immunol* 15:617-648.
89. Strugnell et al. (1997) *Immunol Cell Biol* 75(4):364-369.
90. Robinson & Torres (1997) *Seminars in Immunol* 9:271-283.
91. Brunham et al. (2000) *J Infect Dis* 181 Suppl 3:S538-43.
92. Svanholm et al. (2000) *Scand J Immunol* 51(4):345-53.
93. *DNA Vaccination-Genetic Vaccination* (1998) eds. Koprowski et al. (ISBN 3540633928).
94. *Gene Vaccination:Theory and Practice* (1998) ed. Raz (ISBN 3540644288).
95. WO90/14837
96. *Vaccine Design: subunit and adjuvant approach* (1995) ed. Powell & Newman (ISBN 030644867X).
97. WO00/07621
98. GB-2220221
99. EP-A-0689454
100. EP-A-0835318
101. EP-A-0735898
102. EP-A-0761231
103. WO99/52549
104. WO01/21207
105. WO01/21152
106. WO00/62800
107. WO00/23105
108. WO99/11241
109. WO98/57659
110. WO93/13202.
111. Johnson et al. (1999) *Bioorg Med Chem Lett* 9:2273-2278.
112. International patent application WO00/50078.
113. Singh et al. (2001) *J. Cont. Rele.* 70:267-276.
114. *Current Protocols in Molecular Biology* (F. M. Ausubel et al., eds., 1987) Supplement 30.
115. Smith and Waterman, Adv. Appl. Math. (1981) 2: 482-489.
116. Chakrabarti et al. (1985) *Mol Cell Biol* 5:3403-3409.

```

The invention claimed is:

1. A nucleic acid vector comprising: (i) a promoter; (ii) a sequence encoding a polypeptide from PCAV, said sequence being operably linked to said promoter; and (iii) a selectable marker.

2. The vector of claim 1, further comprising: (iv) an origin of replication; and (v) a transcription terminator downstream of and operably linked to (ii).

3. The vector of claim 2, wherein: (i) & (v) are eukaryotic; and (iii) & (iv) are prokaryotic.

4. The vector of claim 1, wherein the promoter is functional in vivo in a human.

5. The vector of claim 1, wherein the promoter is a viral promoter.

6. The vector of claim 5, wherein the viral promoter is from cytomegalovirus (CMV).

7. The vector of claim 1, comprising transcriptional regulatory sequences in addition to the promoter.

8. The vector of claim 1, wherein the PCAV polypeptide is a gag, prt, pol, env, cORF or PCAP polypeptide.

9. The vector of claim 8, wherein the PCAV polypeptide is a gag polypeptide and has at least 87% identity to SEQ ID NO: 78 or 79.

10. The vector of claim 1, wherein the selectable marker functions in a bacterium.

11. The vector of claim 1, wherein the selectable marker is an antibiotic resistance genes.

12. The vector of claim 1, wherein the vector is a plasmid.

13. The vector of claim 1, wherein the vector comprises an origin of replication.

14. The vector of claim 13, wherein the origin of replication is active in prokaryotes but not in eukaryotes.

15. The vector of claim 1, further comprising a eukaryotic transcriptional terminator sequence downstream of the PCAV-coding sequence.

16. The vector of claim 1, further comprising a multiple cloning site.

17. The vector of claim 1, further comprising an IRES upstream of a second sequence encoding a eukaryotic polypeptide.

18. A pharmaceutical composition comprising the vector of claim 1.

19. A method for raising an immune response, comprising administering an immunogenic dose of the vector of claim 1 to an animal.

20. A method for treating a patient with a prostate tumor, comprising administering to said patient the pharmaceutical composition of claim 18.

21. A virus-like particle (VLP) comprising PCAV gag polypeptides.

22. A method of raising an immune response in an mammal, comprising administering to the mammal the VLP of claim 21, wherein the mammal develops an immune response to PCAV polypeptides.

23. A method for treating a patient with a prostate tumor, comprising administering to said patient the VLP of claim 21, wherein the patient an immune response to PCAV polypeptides.

24. The vector of claim 9, wherein the PCAV polypeptide: (a) comprises SEQ ID NO: 78 or 79; or (b) has at least 90% identity to SEQ ID NO: 78 or 79.

25. The vector of claim 9, wherein the sequence of (ii) comprises: (a) the nucleotide sequence of SEQ ID NO: 77; (b) a polynucleotide sequence that has at least 72% identity to SEQ ID NO: 76; or (c) a fragment of at least 12 nucleotides from SEQ ID NO: 77.

26. The vector of claim 25, wherein the sequence of (ii) comprises: (a) a polynucleotide sequence that has at least 90% identity to SEQ ID NO: 77; or (b) a fragment of at least 20 nucleotides from SEQ ID NO: 77.

27. The vector of claim 25, wherein the vector comprises: (a) the nucleotide sequence of SEQ ID NO: 80; or (b) a polynucleotide sequence that has at least 75% identity to SEQ ID NO: 80.

28. The vector of claim 27, wherein the vector comprises a polynucleotide sequence that has at least 90% identity to SEQ ID NO: 80.

29. The vector of claim 9, wherein the sequence of (ii) comprises the nucleotide sequence of SEQ ID NO: 76, and wherein the vector comprises: (a) the nucleotide sequence of SEQ ID NO: 53; or (b) a polynucleotide sequence with at least 90% identity to SEQ ID NO: 53.

30. A nucleic acid vector comprising: (i) a promoter; (ii) a sequence encoding a polypeptide from a member of the HML-2 subgroup of the HERV-K family of endogenous retroviruses, said sequence being operably linked to said promoter; and (iii) a selectable marker;
wherein the HML-2 polypeptide: (a) has at least 65% identity to one or more of SEQ ID NOS: 5-9, 13, 14, 19-21, 26-28, 32-50 and 69-74; and/or (b) comprises a fragment of at least 7 amino acids from one or more of SEQ ID NOS: 5-9, 13, 14, 19-21, 26-28, 32-50 and 69-74.

31. The vector of claim 30, wherein the HML-2 polypeptide: (a) has at least 90% identity to one or more of SEQ ID NOS: 5-9, 13, 14, 19-21, 26-28, 32-50 and 69-74; and/or (b) comprises a fragment of at least 20 amino acids from one or more of SEQ ID NOS: 5-9, 13, 14, 19-21, 26-28, 32-50 and 69-74.

32. The vector of claim 31, wherein the HML-2 polypeptide comprises one or more of SEQ ID NOS: 5-9, 13, 14, 19-21, 26-28, 32-50 and 69-74.

33. A nucleic acid vector comprising: (i) a promoter; (ii) a sequence encoding a polypeptide from a member of the HML-2 subgroup of the HERV-K family of endogenous retroviruses, said sequence being operably linked to said promoter; and (iii) a selectable marker;
   wherein the vector comprises a polynucleotide sequence that has at least 90% identity to one or more of SEQ ID NOS: 1-4, 10-12, 15-18, 22-25, 51, 52, 54-56, 58-66, 81 and 82.

34. The vector of claim 33, wherein the vector comprises one or more of SEQ ID NOS: 1-4, 10-12, 15-18, 22-25, 51, 52, 54-56, 58-66, 81 and 82.

35. The vector of claim 33, wherein the vector comprises a polynucleotide sequence that has at least 90% identity to one or more of SEQ ID NOS: 51, 52, 54-56, 58, 60, 62, 64, 66 and 82.

36. The vector of claim 35, wherein the vector comprises one or more of SEQ ID NOS: 51, 52, 54-56, 58, 60, 62, 64, 66 and 82.

37. The VLP of claim 21, wherein the PCAV gag polypeptides have at least 87% identity to SEQ ID NO: 78 or 79.

38. The VLP of claim 37, wherein the PCAV gag polypeptides have at least 90% identity to SEQ ID NO: 78 or 79.

39. The VLP of claim 38, wherein the PCAV gag polypeptides comprise SEQ ID NO: 78 or 79.

40. A VLP comprising HML-2 gag polypeptides, wherein the HML-2 gag polypeptides: (a) have at least 90% identity to one or more of SEQ ID NOS: 5, 6, 9, 69 and 70; and/or (b) comprises a fragment of at least 20 amino acids from one or more of SEQ ID NOS: 5, 6, 9, 69 and 70.

41. The VLP of claim 40, wherein the HML-2 gag polypeptides comprise one or more of SEQ ID NOS: 5, 6, 9, 69 and 70.

\* \* \* \* \*

                        SEQUENCE LISTING

<160> NUMBER OF SEQ ID NOS: 83

<210> SEQ ID NO 1
<211> LENGTH: 1998
<212> TYPE: DNA
<213> ORGANISM: Human endogenous retrovirus, K family (HERV-K)

<400> SEQUENCE: 1 atgggcaaa ctaaaagtaa aattaaaagt aaatatgcct cttatctcag ctttattaaa      60
attcttttaa aaagagggg agttaaagta tctacaaaaa atctaatcaa gctatttcaa     120
ataatagaac aattttgccc atggtttcca gaacaaggaa ctttagatct aaaagattgg    180
aaaagaattg gtaaggaact aaaacaagca ggtaggaagg gtaatatcat tccacttaca    240
gtatggaatg attgggccat tattaaagca gctttagaac catttcaaac agaagaagat    300
agcgtttcag tttctgatgc ccctggaagc tgtataatag attgtaatga aaacacaagg    360
aaaaaatccc agaaagaaac ggaaggttta cattgcgaat atgtagcaga gccggtaatg    420
gctcagtcaa cgcaaaatgt tgactataat caattacagg aggtgatata tcctgaaacg    480
ttaaaattag aaggaaaagg tccagaatta gtggggccat cagagtctaa accacgaggc    540
acaagtcctc ttccagcagg tcaggtgcct gtaacattac aacctcaaaa gcaggttaaa    600
gaaaataaga cccaaccgcc agtagcctat caatactggc ctccggctga acttcagtat    660
cggccacccc cagaaagtca gtatggatat ccaggaatgc cccagcacc acagggcagg    720 gcgccatacc ctcagccgcc cactaggaga cttaatccta cggcaccacc tagtagacag    780
ggtagtaaat tacatgaaat tattgataaa tcaagaaagg aaggagatac tgaggcatgg    840
caattcccag taacgttaga accgatgcca cctggagaag gagcccaaga gggagagcct    900
cccacagttg aggccagata caagtctttt tcgataaaaa agctaaaaga tatgaaagag    960
```

```
ggagtaaaac agtatggacc caactcccct tatatgagga cattattaga ttccattgct    1020
catggacata gactcattcc ttatgattgg gagattctgg caaaatcgtc tctctcaccc    1080
tctcaatttt tacaatttaa gacttggtgg attgatgggg tacaagaaca ggtccgaaga    1140
aatagggctg ccaatcctcc agttaacata gatgcagatc aactattagg aataggtcaa    1200
aattggagta ctattagtca acaagcatta atgcaaaatg aggccattga gcaagttaga    1260
gctatctgcc ttagagcctg ggaaaaaatc caagacccag gaagtacctg cccctcattt    1320
aatacagtaa gacaaggttc aaaagagccc tatcctgatt ttgtggcaag gctccaagat    1380
gttgctcaaa agtcaattgc tgatgaaaaa gcccgtaagg tcatagtgga gttgatggca    1440
tatgaaaacg ccaatcctga gtgtcaatca gccattaagc cattaaaagg aaaggttcct    1500
gcaggatcag atgtaatctc agaatatgta aaagcctgtg atggaatcgg aggagctatg    1560
cataaagcta tgcttatggc tcaagcaata acaggagttg ttttaggagg acaagttaga    1620
acatttggaa gaaaatgtta taattgtggt caaattggtc acttaaaaaa gaattgccca    1680
gtcttaaata acagaatat aactattcaa gcaactacaa caggtagaga gccacctgac    1740
ttatgtccaa gatgtaaaaa aggaaaacat tgggctagtc aatgtcgttc taaatttgat    1800
aaaaatgggc aaccattgtc gggaaacgag caaggggcc agcctcaggc cccacaacaa    1860 actgggcat tcccaattca gccatttgtt cctcagggtt ttcagggaca caaccccca    1920 ctgtcccaag tgtttcaggg aataagccag ttaccacaat acaacaattg tccccgcca    1980 caagcggcag tgcagcag                                                 1998

<210> SEQ ID NO 2
<211> LENGTH: 2001
<212> TYPE: DNA
<213> ORGANISM: Human endogenous retrovirus, K family (HERV-K)

<400> SEQUENCE: 2
atggggcaaa ctaaaagtaa aattaaaagt aaatatgcct cttatctcag ctttattaaa      60
attcttttaa aaagagggg agttaaagta tctacaaaaa atctaatcaa gctatttcaa     120
ataatagaac aattttgccc atggtttcca gaacaaggaa ctttagatct aaaagattgg     180
aaaagaattg gtaaggaact aaaacaagca ggtaggaagg gtaatatcat tccacttaca     240
gtatggaatg attgggccat tattaaagca gctttagaac catttcaaac agaagaagat     300
agcgtttcag tttctgatgc ccctggaagc tgtataatag attgtaatga aaacacaagg     360
aaaaaatccc agaaagaaac ggaaggttta cattgcgaat atgtagcaga gccggtaatg     420
gctcagtcaa cgcaaaatgt tgactataat caattacagg aggtgatata tcctgaaacg     480
ttaaaattag aaggaaaagg tccagaatta gtggggccat cagagtctaa accacgaggc     540
acaagtcctc ttccagcagg tcaggtgcct gtaacattac aacctcaaaa gcaggttaaa     600
gaaaataaga cccaaccgcc agtagcctat caatactggc ctccggctga acttcagtat     660
cggccacccc cagaaagtca gtatggatat ccaggaatgc ccccagcacc acagggcagg     720
gcgccatacc ctcagccgcc cactaggaga cttaatccta cggcaccacc tagtagacag     780
ggtagtaaat tacatgaaat tattgataaa tcaagaaagg aaggagatac tgaggcatgg     840
caattcccag taacgttaga accgatgcca cctggagaag agcccaaga ggagagcct     900 cccacagttg aggccagata caagtctttt tcgataaaaa agctgaaaga tatgaaagag     960
ggagtaaaac agtatggacc caactcccct tatatgagga cattattaga ttccattgct    1020
catggacata gactcattcc ttatgattgg gagattctgg caaaatcgtc tctctcaccc    1080
```

```
tctcaattttt tacaatttaa gacttggtgg attgatgggg tacaagaaca ggtccgaaga   1140
aatagggctg ccaatcctcc agttaacata gatgcagatc aactattagg aataggtcaa   1200
aattggagta ctattagtca acaagcatta atgcaaaatg aggccattga gcaagttaga   1260
gctatctgcc ttagagcctg ggaaaaaatc caagacccag gaagtacctg cccctcattt   1320
aatacagtaa gacaaggttc aaaagagccc tatcctgatt ttgtggcaag gctccaagat   1380
gttgctcaaa agtcaattgc tgatgaaaaa gcccgtaagg tcatagtgga gttgatggca   1440
tatgaaaacg ccaatcctga gtgtcaatca gccattaagc cattaaaagg aaaggttcct   1500
gcaggatcag atgtaatctc agaatatgta aaagcctgtg atggaatcgg aggagctatg   1560
tataaagcta tgcttatggc tcaagcaata acaggagttg ttttaggagg acaagttaga   1620
acatttggaa gaaaatgtta taattgtggt caaattggtc acttaaaaaa gaattgccca   1680
gtcttaaata aacagaatat aactattcaa gcaactacaa caggtagaga gccacctgac   1740
ttatgtccaa gatgtaaaaa aggaaaacat tgggctagtc aatgtcgttc taaatttgat   1800
aaaaatgggc aaccattgtc gggaaacgag caaggggcc agcctcaggc cccacaacaa   1860 actgggcat tcccaattca gccatttgtt cctcagggtt ttcagggaca caacccccca   1920
ctgtcccaag tgtttcaggg aataagccag ttaccacaat acaacaattg tccccgcca   1980 caagcggcag tgcagcagta g                                             2001

<210> SEQ ID NO 3
<211> LENGTH: 2004
<212> TYPE: DNA
<213> ORGANISM: Human endogenous retrovirus, K family (HERV-K)

<400> SEQUENCE: 3
atggggcaaa ctaaaagtaa aactaaaagt aaatatgcct cttatctcag ctttattaaa     60
attcttttaa aaagagggggg agttagagta tctacaaaaa atctaatcaa gctatttcaa    120
ataatagaac aattttgccc atggtttcca gaacaaggaa ctttagatct aaaagattgg    180
aaaagaattg gcgaggaact aaaacaagca ggtagaaagg gtaatatcat tccacttaca    240
gtatggaatg attgggccat tattaaagca gctttagaac catttcaaac aaaagaagat    300
agcgtttcag tttctgatgc ccctggaagc tgtgtaatag attgtaatga aagacaggg    360 agaaaatccc agaaagaaac agaaagtttac attgcgaat atgtaacaga gccagtaatg    420
gctcagtcaa cgcaaaatgt tgactataat caattacagg gggtgatata tcctgaaacg    480
ttaaaattag aaggaaaagg tccagaatta gtggggccat cagagtctaa accacgaggg    540
ccaagtcctc ttccagcagg tcaggtgccc gtaacattac aacctcaaac gcaggttaaa    600
gaaaataaga cccaaccgcc agtagcttat caatactggc cgccggctga acttcagtat    660
ctgccacccc cagaaagtca gtatggatat ccaggaatgc ccccagcact acagggcagg    720
gcgccatatc ctcagccgcc cactgtgaga cttaatccta cagcatcacg tagtggacaa    780
ggtggtacac tgcacgcagt cattgatgaa gccagaaaac agggagatct tgaggcatgg    840
cggttcctgg taattttaca actggtacag gccggggaag agactcaagt aggagcgcct    900
gcccgagctg agactagatg tgaacctttc accatgaaaa tgttaaaaga tataaaggaa    960
ggagttaaac aatatggatc caactcccct tatataagaa cattattaga ttccattgct   1020
catggaaata gacttactcc ttatgactgg gaaagtttgg ccaaatcttc cctttcatcc   1080
tctcagtatc tacagtttaa aacctggtgg attgatggag tacaagaaca ggtacgaaaa   1140
aatcaggcta ctaagcccac tgttaatata gacgcagacc aattgttagg aacaggtcca   1200
```

```
aattggagca ccattaacca acaatcagtg atgcagaatg aggctattga acaagtaagg    1260
gctatttgcc tcagggcctg gggaaaaatt caggacccag aacagctttt ccctattaat    1320
tcaattagac aaggctctaa agagccatat cctgactttg tggcaagatt acaagatgct    1380
gctcaaaagt ctattacaga tgacaatgcc cgaaaagtta ttgtagaatt aatggcctat    1440
gaaaatgcaa atccagaatg tcagtcggcc ataaagccat aaaaggaaa agttccagca     1500 ggagttgatg taattacaga atatgtgaag gcttgtgatg ggattggagg agctatgcat    1560
aaggcaatgc taatggctca agcaatgagg gggctcactc taggaggaca agttagaaca    1620
tttgggaaaa aatgttataa ttgtggtcaa atcggtcatc tgaaaaggag ttgcccagtc    1680
ttaaataaac agaatataat aaatcaagct attacagcaa aaaataaaaa gccatctggc    1740
ctgtgtccaa aatgtggaaa aggaaaacat tgggccaatc aatgtcattc taaatttgat    1800
aaagatgggc aaccattgtc gggaaacagg aagaggggcc agcctcaggc cccccaacaa    1860
actggggcat tcccagttca actgtttgtt cctcagggtt ttcaaggaca caacccccta    1920
cagaaaatac caccacttca gggagtcagc caattacaac aatccaacag ctgtcccgcg    1980
ccacagcagg cagcgccaca gtag                                          2004

<210> SEQ ID NO 4
<211> LENGTH: 852
<212> TYPE: DNA
<213> ORGANISM: Human endogenous retrovirus, K family (HERV-K)

<400> SEQUENCE: 4
atggggcaaa ctaaaagtaa aattaaaagt aaatatgcct cttatctcag ctttattaaa      60
attcttttaa aaagaggggg agttaaagta tctacaaaaa atctaatcaa gctatttcaa     120
ataatagaac aattttgccc atggtttcca gaacaaggaa cttcagatct aaaagattgg     180
aaaagaattg gtaaggaact aaaacaagca ggtaggaagg gtaatatcat tccacttaca     240
gtatggaatg attgggccat tattaaagca gctttagaac catttcaaac agaagaagat     300
agcatttcag tttctgatgc ccctggaagc tgtttaatag attgtaatga aaacacaagg     360
aaaaaatccc agaaagaaac cgaaagttta cattgcgaat atgtagcaga gccggtaatg    420
gctcagtcaa cgcaaaatgt tgactataat caattacagg aggtgatata tcctgaaacg    480
ttaaaattag aaggaaaagg tccagaatta atggggccat cagagtctaa ccacgaggc    540 acaagtcctc ttccagcagg tcaggtgctc gtaagattac aacctcaaaa gcaggttaaa    600
gaaaataaga cccaaccgca agtagcctat caatactgcc gctggctgaa cttcagtatc    660
ggccaccccc agaaagtcag tatggatatc caggaatgcc cccagcacca cagggcaggg    720
cgccatacca tcagccgccc actaggagac ttaatcctat ggcaccacct agtagacagg    780
gtagtgaatt acatgaaatt attgataaat caagaaagga aggagatact gaggcatggc    840
aattcccagt aa                                                        852

<210> SEQ ID NO 5
<211> LENGTH: 666
<212> TYPE: PRT
<213> ORGANISM: Human endogenous retrovirus, K family (HERV-K)

<400> SEQUENCE: 5

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30
```

```
Lys Asn Leu Ile Lys Leu Phe Gln Ile Ile Glu Gln Phe Cys Pro Trp
            35                  40                  45

Phe Pro Glu Gln Gly Thr Leu Asp Leu Lys Asp Trp Lys Arg Ile Gly
 50                  55                  60

Lys Glu Leu Lys Gln Ala Gly Arg Lys Gly Asn Ile Ile Pro Leu Thr
 65                  70                  75                  80

Val Trp Asn Asp Trp Ala Ile Ile Lys Ala Ala Leu Glu Pro Phe Gln
                 85                  90                  95

Thr Glu Glu Asp Ser Val Ser Val Ser Asp Ala Pro Gly Ser Cys Ile
            100                 105                 110

Ile Asp Cys Asn Glu Asn Thr Arg Lys Lys Ser Gln Lys Glu Thr Glu
            115                 120                 125

Gly Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Ala Gly Gln Val Pro Val Thr
            180                 185                 190

Leu Gln Pro Gln Lys Gln Val Lys Glu Asn Lys Thr Gln Pro Pro Val
    195                 200                 205

Ala Tyr Gln Tyr Trp Pro Pro Ala Glu Leu Gln Tyr Arg Pro Pro Pro
    210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
            245                 250                 255

Pro Ser Arg Gln Gly Ser Lys Leu His Glu Ile Ile Asp Lys Ser Arg
            260                 265                 270

Lys Glu Gly Asp Thr Glu Ala Trp Gln Phe Pro Val Thr Leu Glu Pro
    275                 280                 285

Met Pro Pro Gly Glu Gly Ala Gln Glu Gly Glu Pro Pro Thr Val Glu
    290                 295                 300

Ala Arg Tyr Lys Ser Phe Ser Ile Lys Lys Leu Lys Asp Met Lys Glu
305                 310                 315                 320

Gly Val Lys Gln Tyr Gly Pro Asn Ser Pro Tyr Met Arg Thr Leu Leu
            325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
    355                 360                 365

Trp Trp Ile Asp Gly Val Gln Glu Val Arg Arg Asn Arg Ala Ala
    370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
    435                 440                 445

Glu Pro Tyr Pro Asp Phe Val Ala Arg Leu Gln Asp Val Ala Gln Lys
```

```
                 450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
                485                 490                 495

Gly Lys Val Pro Ala Gly Ser Asp Val Ile Ser Glu Tyr Val Lys Ala
                500                 505                 510

Cys Asp Gly Ile Gly Gly Ala Met Tyr Lys Ala Met Leu Met Ala Gln
                515                 520                 525

Ala Ile Thr Gly Val Val Leu Gly Gly Gln Val Arg Thr Phe Gly Arg
                530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
                565                 570                 575

Glu Pro Pro Asp Leu Cys Pro Arg Cys Lys Lys Gly Lys His Trp Ala
                580                 585                 590

Ser Gln Cys Arg Ser Lys Phe Asp Lys Asn Gly Gln Pro Leu Ser Gly
                595                 600                 605

Asn Glu Gln Arg Gly Gln Pro Gln Ala Pro Gln Gln Thr Gly Ala Phe
                610                 615                 620

Pro Ile Gln Pro Phe Val Pro Gln Gly Phe Gln Gly Gln Gln Pro Pro
625                 630                 635                 640

Leu Ser Gln Val Phe Gln Gly Ile Ser Gln Leu Pro Gln Tyr Asn Asn
                645                 650                 655

Cys Pro Pro Pro Gln Ala Ala Val Gln Gln
                660                 665

<210> SEQ ID NO 6
<211> LENGTH: 667
<212> TYPE: PRT
<213> ORGANISM: Human endogenous retrovirus, K family (HERV-K)

<400> SEQUENCE: 6

Met Gly Gln Thr Lys Ser Lys Thr Lys Ser Lys Tyr Ala Ser Tyr Leu
1               5                   10                  15

Ser Phe Ile Lys Ile Leu Leu Lys Arg Gly Gly Val Arg Val Ser Thr
                20                  25                  30

Lys Asn Leu Ile Lys Leu Phe Gln Ile Ile Glu Gln Phe Cys Pro Trp
            35                  40                  45

Phe Pro Glu Gln Gly Thr Leu Asp Leu Lys Asp Trp Lys Arg Ile Gly
    50                  55                  60

Glu Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Lys Glu Asp Ser Val Ser Val Ser Asp Ala Pro Gly Ser Cys Val
            100                 105                 110

Ile Asp Cys Asn Glu Lys Thr Gly Arg Lys Ser Gln Lys Glu Thr Glu
        115                 120                 125

Ser Leu His Cys Glu Tyr Val Thr Glu Pro Val Met Ala Gln Ser Thr
    130                 135                 140

Gln Asn Val Asp Tyr Asn Gln Leu Gln Gly Val Ile Tyr Pro Glu Thr
145                 150                 155                 160

Leu Lys Leu Glu Gly Lys Gly Pro Glu Leu Val Gly Pro Ser Glu Ser
```

-continued

```
                165                 170                 175
Lys Pro Arg Gly Pro Ser Pro Leu Pro Ala Gly Gln Val Pro Val Thr
            180                 185                 190

Leu Gln Pro Gln Thr Gln Val Lys Glu Asn Lys Thr Gln Pro Pro Val
        195                 200                 205

Ala Tyr Gln Tyr Trp Pro Pro Ala Glu Leu Gln Tyr Leu Pro Pro Pro
    210                 215                 220

Glu Ser Gln Tyr Gly Tyr Pro Gly Met Pro Pro Ala Leu Gln Gly Arg
225                 230                 235                 240

Ala Pro Tyr Pro Gln Pro Pro Thr Val Arg Leu Asn Pro Thr Ala Ser
            245                 250                 255

Arg Ser Gly Gln Gly Gly Thr Leu His Ala Val Ile Asp Glu Ala Arg
        260                 265                 270

Lys Gln Gly Asp Leu Glu Ala Trp Arg Phe Leu Val Ile Leu Gln Leu
    275                 280                 285

Val Gln Ala Gly Glu Glu Thr Gln Val Gly Ala Pro Ala Arg Ala Glu
290                 295                 300

Thr Arg Cys Glu Pro Phe Thr Met Lys Met Leu Lys Asp Ile Lys Glu
305                 310                 315                 320

Gly Val Lys Gln Tyr Gly Ser Asn Ser Pro Tyr Ile Arg Thr Leu Leu
            325                 330                 335

Asp Ser Ile Ala His Gly Asn Arg Leu Thr Pro Tyr Asp Trp Glu Ser
        340                 345                 350

Leu Ala Lys Ser Ser Leu Ser Ser Gln Tyr Leu Gln Phe Lys Thr
    355                 360                 365

Trp Trp Ile Asp Gly Val Gln Glu Gln Val Arg Lys Asn Gln Ala Thr
370                 375                 380

Lys Pro Thr Val Asn Ile Asp Ala Asp Gln Leu Leu Gly Thr Gly Pro
385                 390                 395                 400

Asn Trp Ser Thr Ile Asn Gln Gln Ser Val Met Gln Asn Glu Ala Ile
            405                 410                 415

Glu Gln Val Arg Ala Ile Cys Leu Arg Ala Trp Gly Lys Ile Gln Asp
        420                 425                 430

Pro Gly Thr Ala Phe Pro Ile Asn Ser Ile Arg Gln Gly Ser Lys Glu
    435                 440                 445

Pro Tyr Pro Asp Phe Val Ala Arg Leu Gln Asp Ala Ala Gln Lys Ser
    450                 455                 460

Ile Thr Asp Asp Asn Ala Arg Lys Val Ile Val Glu Leu Met Ala Tyr
465                 470                 475                 480

Glu Asn Ala Asn Pro Glu Cys Gln Ser Ala Ile Lys Pro Leu Lys Gly
            485                 490                 495

Lys Val Pro Ala Gly Val Asp Val Ile Thr Glu Tyr Val Lys Ala Cys
        500                 505                 510

Asp Gly Ile Gly Gly Ala Met His Lys Ala Met Leu Met Ala Gln Ala
    515                 520                 525

Met Arg Gly Leu Thr Leu Gly Gly Gln Val Arg Thr Phe Gly Lys Lys
530                 535                 540

Cys Tyr Asn Cys Gly Gln Ile Gly His Leu Arg Ser Cys Pro Val
545                 550                 555                 560

Leu Asn Lys Gln Asn Ile Ile Asn Gln Ala Ile Thr Ala Lys Asn Lys
            565                 570                 575

Lys Pro Ser Gly Leu Cys Pro Lys Cys Gly Lys Gly His Trp Ala
        580                 585                 590
```

```
Asn Gln Cys His Ser Lys Phe Asp Lys Asp Gly Gln Pro Leu Ser Gly
            595                 600                 605

Asn Arg Lys Arg Gly Gln Pro Gln Ala Pro Gln Gln Thr Gly Ala Phe
    610                 615                 620

Pro Val Gln Leu Phe Val Pro Gln Gly Phe Gln Gly Gln Gln Pro Leu
625                 630                 635                 640

Gln Lys Ile Pro Pro Leu Gln Gly Val Ser Gln Leu Gln Gln Ser Asn
                645                 650                 655

Ser Cys Pro Ala Pro Gln Gln Ala Ala Pro Gln
            660                 665

<210> SEQ ID NO 7
<211> LENGTH: 283
<212> TYPE: PRT
<213> ORGANISM: Human endogenous retrovirus, K family (HERV-K)

<400> SEQUENCE: 7

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Ser Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Ile Ser Val Ser Asp Ala Pro Gly Ser Cys Leu
            100                 105                 110

Ile Asp Cys Asn Glu Asn Thr Arg Lys Lys Ser Gln Lys Glu Thr Glu
        115                 120                 125

Ser Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Met Gly Pro Ser Glu Ser
                165                 170                 175

Lys Pro Arg Gly Thr Ser Pro Leu Pro Ala Gly Gln Val Leu Val Arg
            180                 185                 190

Leu Gln Pro Gln Lys Gln Val Lys Glu Asn Lys Thr Gln Pro Gln Val
        195                 200                 205

Ala Tyr Gln Tyr Cys Arg Trp Leu Asn Phe Ser Ile Gly His Pro Gln
    210                 215                 220

Lys Val Ser Met Asp Ile Gln Glu Cys Pro Gln His His Arg Ala Gly
225                 230                 235                 240

Arg His Thr Ile Ser Arg Pro Leu Gly Asp Leu Ile Leu Trp His His
                245                 250                 255

Leu Val Asp Arg Val Val Asn Tyr Met Lys Leu Leu Ile Asn Gln Glu
            260                 265                 270

Arg Lys Glu Ile Leu Arg His Gly Asn Ser Gln
        275                 280

<210> SEQ ID NO 8
<211> LENGTH: 434
```

-continued

```
<212> TYPE: PRT
<213> ORGANISM: Human endogenous retrovirus, K family (HERV-K)

<400> SEQUENCE: 8

Met Pro Pro Ala Pro Gln Gly Arg Ala Pro Tyr His Gln Pro Pro Thr
1               5                   10                  15

Arg Arg Leu Asn Pro Met Ala Pro Ser Arg Gln Gly Ser Glu Leu
            20                  25                  30

His Glu Ile Ile Asp Lys Ser Arg Lys Glu Gly Asp Thr Glu Ala Trp
        35                  40                  45

Gln Phe Pro Val Thr Leu Glu Pro Met Pro Pro Gly Glu Gly Ala Gln
    50                  55                  60

Glu Gly Glu Pro Pro Thr Val Glu Ala Arg Tyr Lys Ser Phe Ser Ile
65                  70                  75                  80

Lys Met Leu Lys Asp Met Lys Glu Gly Val Lys Gln Tyr Gly Pro Asn
                85                  90                  95

Ser Pro Tyr Met Arg Thr Leu Leu Asp Ser Ile Ala Tyr Gly His Arg
            100                 105                 110

Leu Ile Pro Tyr Asp Trp Glu Ile Leu Ala Lys Ser Ser Leu Ser Pro
        115                 120                 125

Ser Gln Phe Leu Gln Phe Lys Thr Trp Trp Ile Asp Gly Val Gln Glu
    130                 135                 140

Gln Val Arg Arg Asn Arg Ala Ala Asn Pro Pro Val Asn Ile Asp Ala
145                 150                 155                 160

Asp Gln Leu Leu Gly Ile Gly Gln Asn Trp Ser Thr Ile Ser Gln Gln
                165                 170                 175

Ala Leu Met Gln Asn Glu Ala Ile Glu Gln Val Arg Ala Ile Cys Leu
            180                 185                 190

Arg Ala Trp Glu Lys Ile Gln Asp Pro Gly Ser Thr Cys Pro Ser Phe
        195                 200                 205

Asn Thr Val Arg Gln Gly Ser Lys Glu Pro Tyr Pro Asp Phe Val Ala
    210                 215                 220

Arg Leu Gln Asp Val Ala Gln Lys Ser Ile Ala Asp Glu Lys Ala Gly
225                 230                 235                 240

Lys Val Ile Val Glu Leu Met Ala Tyr Glu Asn Ala Asn Pro Glu Cys
                245                 250                 255

Gln Ser Ala Ile Lys Pro Leu Lys Gly Lys Val Pro Ala Gly Ser Asp
            260                 265                 270

Val Ile Ser Glu Tyr Val Lys Ala Cys Asp Gly Ile Gly Gly Ala Met
        275                 280                 285

His Lys Ala Met Leu Met Ala Gln Ala Ile Thr Gly Val Val Leu Gly
    290                 295                 300

Gly Gln Val Arg Thr Phe Gly Gly Lys Cys Tyr Asn Cys Gly Gln Ile
305                 310                 315                 320

Gly His Leu Lys Lys Asn Cys Pro Val Leu Asn Lys Gln Asn Ile Thr
                325                 330                 335

Ile Gln Ala Thr Thr Thr Gly Arg Glu Pro Pro Asp Leu Cys Pro Arg
            340                 345                 350

Cys Lys Lys Gly Lys His Trp Ala Ser Gln Cys Arg Ser Lys Phe Asp
        355                 360                 365

Lys Asn Gly Gln Pro Leu Ser Gly Asn Glu Gln Arg Gly Gln Pro Gln
    370                 375                 380

Ala Pro Gln Gln Thr Gly Ala Phe Pro Ile Gln Pro Phe Val Pro Gln
385                 390                 395                 400
```

-continued

```
Gly Phe Gln Gly Gln Gln Pro Pro Leu Ser Gln Val Phe Gln Gly Ile
                405                 410                 415

Ser Gln Leu Pro Gln Tyr Asn Asn Cys Pro Ser Pro Gln Ala Ala Val
            420                 425                 430

Gln Gln

<210> SEQ ID NO 9
<211> LENGTH: 666
<212> TYPE: PRT
<213> ORGANISM: Human endogenous retrovirus, K family (HERV-K)

<400> SEQUENCE: 9

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

Phe Pro Glu Gln Gly Thr Leu Asp Leu Lys Asp Trp Lys Arg Ile Gly
    50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Val Ser Val Ser Asp Ala Pro Gly Ser Cys Ile
            100                 105                 110

Ile Asp Cys Asn Glu Asn Thr Gly Lys Lys Ser Gln Lys Glu Thr Glu
        115                 120                 125

Gly Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
        195                 200                 205

Ala Tyr Gln Tyr Trp Pro Pro Ala Glu Leu Gln Tyr Arg Pro Pro Pro
    210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Gln Gly Ser Lys Leu His Glu Ile Ile Asp Lys Ser Arg
            260                 265                 270

Lys Glu Gly Asp Thr Glu Ala Trp Gln Phe Pro Val Thr Leu Glu Pro
        275                 280                 285

Met Pro Pro Gly Glu Gly Ala Gln Glu Gly Glu Pro Pro Thr Val Glu
    290                 295                 300

Ala Arg Tyr Lys Ser Phe Ser Ile Lys Lys Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
```

|     |     |     |     | 340 |     |     |     | 345 |     |     |     | 350 |     |     |
|---|---|---|---|---|---|---|---|---|---|---|---|---|---|---|

Gln Ala Lys Ser Ser Leu Ser Pro Ser Gln Phe Leu Gln Phe Lys Thr
                355                 360                 365
Trp Trp Ile Asp Gly Val Gln Glu Gln Val Arg Arg Asn Arg Ala Ala
            370                 375                 380
Asn Pro Pro Val Asn Ile Asp Ala Asp Gln Leu Leu Gly Ile Gly Gln
385                 390                 395                 400
Asn Trp Ser Thr Ile Ser Gln Gln Ala Leu Met Gln Asn Glu Ala Ile
                405                 410                 415
Glu Gln Val Arg Ala Ile Cys Leu Arg Ala Trp Glu Lys Ile Gln Asp
            420                 425                 430
Pro Gly Ser Thr Cys Pro Ser Phe Asn Thr Val Arg Gln Gly Ser Lys
            435                 440                 445
Glu Pro Tyr Pro Asp Phe Val Ala Arg Leu Gln Asp Val Ala Gln Lys
            450                 455                 460
Ser Ile Ala Asp Glu Lys Ala Arg Lys Val Ile Val Glu Leu Met Ala
465                 470                 475                 480
Tyr Glu Asn Ala Asn Pro Glu Cys Gln Ser Ala Ile Lys Pro Leu Lys
                485                 490                 495
Gly Lys Val Pro Ala Gly Ser Asp Val Ile Ser Glu Tyr Val Lys Ala
            500                 505                 510
Cys Asp Gly Ile Gly Gly Ala Met His Lys Ala Met Leu Met Ala Gln
            515                 520                 525
Ala Ile Thr Gly Val Val Leu Gly Gly Gln Val Arg Thr Phe Gly Arg
            530                 535                 540
Lys Cys Tyr Asn Cys Gly Gln Ile Gly His Leu Lys Lys Asn Cys Pro
545                 550                 555                 560
Val Leu Asn Lys Gln Asn Ile Thr Ile Gln Ala Thr Thr Thr Gly Arg
                565                 570                 575
Glu Pro Pro Asp Leu Cys Pro Arg Cys Lys Lys Gly Lys His Trp Ala
            580                 585                 590
Ser Gln Cys Arg Ser Lys Phe Asp Lys Asn Gly Gln Pro Leu Ser Gly
            595                 600                 605
Asn Glu Gln Arg Gly Gln Pro Gln Ala Pro Gln Gln Thr Gly Ala Phe
            610                 615                 620
Pro Ile Gln Pro Phe Val Pro Gln Gly Phe Gln Gly Gln Gln Pro Pro
625                 630                 635                 640
Leu Ser Gln Val Phe Gln Gly Ile Ser Gln Leu Pro Gln Tyr Asn Asn
                645                 650                 655
Cys Pro Pro Pro Gln Ala Ala Val Gln Gln
            660                 665

<210> SEQ ID NO 10
<211> LENGTH: 1000
<212> TYPE: DNA
<213> ORGANISM: Human endogenous retrovirus, K family (HERV-K)

<400> SEQUENCE: 10
atgggcaacc attgtcggga acgagcaaa ggggccagcc tcaggcccca caacaaactg      60
gggcattccc aattcagcca tttgttcctc agggttttca gggacaacaa ccccactgt     120 cccaagtgtt tcagggaata agccagttac cacaatacaa caattgtccc ccgccacaag    180
cggcagtgca gcagtagatt tatgtactat acaagcagtc tctctgcttc caggggagcc    240
cccacaaaaa accccacag gggtatatgg acccctgcct aaggggactg taggactaat    300

-continued

```
cttgggacga tcaagtctaa atctaaaagg agttcaaatt catactagtg tggttgattc      360
agactataaa ggcgaaattc aattggttat tagctcttca attccttgga gtgccagtcc      420
aagagacagg attgctcaat tattactcct gccatacatt aagggtggaa atagtgaaat      480
aaaaagaata ggagggcttg gaagcactga tccaacagga aaggctgcat attgggcaag      540
tcaggtctca gagaacagac ctgtgtgtaa ggccattatt caaggaaaac agtttgaagg      600
gttggtagac actggagcag atgtctctat cattgctttta aatcagtggc caaaaaattg     660
gcctaaacaa aaggctgtta caggacttgt cggcataggc acagcctcag aagtgtatca      720
aagtacggag attttacatt gcttagggcc agataatcaa gaaagtactg ttcagccaat      780
gattacttca attcctctta atctgtgggg tcgagattta ttacaacaat ggggtgcgga      840
aatcaccatg cccgctccat catatagccc cacgagtcaa aaaatcatga ccaagatggg      900
atatatacca ggaaagggac tagggaaaaa tgaagatggc attaaaattc cagttgaggc      960
taaaataaat caagaaagag aaggaatagg gaatccttgc                           1000

<210> SEQ ID NO 11
<211> LENGTH: 1004
<212> TYPE: DNA
<213> ORGANISM: Human endogenous retrovirus, K family (HERV-K)

<400> SEQUENCE: 11
atgggcaacc attgtcggga acaggaaga ggggccagcc tcaggccccc caacaaactg       60
gggcattccc agttcaactg tttgttcctc agggttttca aggacaacaa cccctacaga      120
aaataccacc acttcaggga gtcagccaat tacaacaatc aacagctgt cccgcgccac       180 agcaggcagc gccacagtag atttatgttc cacccaaatg gtctctttac tccctggaga      240 gccccccacaa aagattccta gaggggtata tggcccgctg ccagaaggga gggtaggcct    300
tattttaggg agatcaagtc taaatttgaa gggagtccaa attcatactg gggtaattta     360
ttcagattat aaaggggggaa ttcagttagt gatcagctcc actgttccct ggagtgccaa    420
tccaggtgat agaattgctc aattactgct tttgccttat gttaaaattg gggaaaacaa     480
aacgaaaaga acaggagggt ttggaagtac caaccctgca ggaaaagcca cttattgggc    540
taatcaggtc tcagaggata gacccgtgtg tacagtcact attcagggaa agagtttgaa     600
ggattagtgg atacccaggc tgatgtttct atcatcggca taggcaccgc ctcagaagtg     660
tatcaaagtg ccatgatttt acattgtcta ggatctgata atcaagaaag tacggttcag     720
cctatgatca cttctattcc aatcaattta tggggccgag acttgttaca acaatggcat    780
gcagagatta ctatcccagc ctccctatac agccccagga atcaaaaaat catgactaaa     840
atgggatagc tccctaaaaa gggactagga agaatgaag atggcattaa agtcccaact     900
gaggctgaaa aaaatcaaaa aagaaaagg ataggggcat cctttttaga agcggtcact      960
gtagagcctc caaaacccat tccattaatt tgggggggaaa aaa                     1004

<210> SEQ ID NO 12
<211> LENGTH: 279
<212> TYPE: DNA
<213> ORGANISM: Human endogenous retrovirus, K family (HERV-K)

<400> SEQUENCE: 12
atggagattt tacattgctt agggccagat aatcaagaaa gtactgttca gccaatgatt       60
acttcaattc ctcttaatct gtggggtcga gatttattac aacaatgggg tgcggaaatc      120
accatgcccg ctccattata tagccccacg agtcaaaaaa tcatgaccaa gatgggatat      180
```

```
ataccaggaa agggactagg gaaaaatgaa gatggcatta aagttccagt tgaggctaaa        240
ataaatcaag aaagagaagg aatagggtat ccttttttag                             279
```

<210> SEQ ID NO 13
<211> LENGTH: 92
<212> TYPE: PRT
<213> ORGANISM: Human endogenous retrovirus, K family (HERV-K)

<400> SEQUENCE: 13

```
Met Glu Ile Leu His Cys Leu Gly Pro Asp Asn Gln Glu Ser Thr Val
1               5                   10                  15

Gln Pro Met Ile Thr Ser Ile Pro Leu Asn Leu Trp Gly Arg Asp Leu
            20                  25                  30

Leu Gln Gln Trp Gly Ala Glu Ile Thr Met Pro Ala Pro Leu Tyr Ser
        35                  40                  45

Pro Thr Ser Gln Lys Ile Met Thr Lys Met Gly Tyr Ile Pro Gly Lys
    50                  55                  60

Gly Leu Gly Lys Asn Glu Asp Gly Ile Lys Val Pro Val Glu Ala Lys
65                  70                  75                  80

Ile Asn Gln Glu Arg Glu Gly Ile Gly Tyr Pro Phe
                85                  90
```

<210> SEQ ID NO 14
<211> LENGTH: 333
<212> TYPE: PRT
<213> ORGANISM: Human endogenous retrovirus, K family (HERV-K)

<400> SEQUENCE: 14

```
Trp Ala Thr Ile Val Gly Lys Arg Ala Lys Gly Pro Ala Ser Gly Pro
1               5                   10                  15

Thr Thr Asn Trp Gly Ile Pro Asn Ser Ala Ile Cys Ser Ser Gly Phe
            20                  25                  30

Ser Gly Thr Thr Thr Pro Thr Val Pro Ser Val Ser Gly Asn Lys Pro
        35                  40                  45

Val Thr Thr Ile Gln Gln Leu Ser Pro Ala Thr Ser Gly Ser Ala Ala
    50                  55                  60

Val Asp Leu Cys Thr Ile Gln Ala Val Ser Leu Leu Pro Gly Glu Pro
65                  70                  75                  80

Pro Gln Lys Thr Pro Thr Gly Val Tyr Gly Pro Leu Pro Lys Gly Thr
                85                  90                  95

Val Gly Leu Ile Leu Gly Arg Ser Ser Leu Asn Leu Lys Gly Val Gln
            100                 105                 110

Ile His Thr Ser Val Val Asp Ser Asp Tyr Lys Gly Glu Ile Gln Leu
        115                 120                 125

Val Ile Ser Ser Ser Ile Pro Trp Ser Ala Ser Pro Arg Asp Arg Ile
    130                 135                 140

Ala Gln Leu Leu Leu Leu Pro Tyr Ile Lys Gly Gly Asn Ser Glu Ile
145                 150                 155                 160

Lys Arg Ile Gly Gly Leu Gly Ser Thr Asp Pro Thr Gly Lys Ala Ala
                165                 170                 175

Tyr Trp Ala Ser Gln Val Ser Glu Asn Arg Pro Val Cys Lys Ala Ile
            180                 185                 190

Ile Gln Gly Lys Gln Phe Glu Gly Leu Val Asp Thr Gly Ala Asp Val
        195                 200                 205

Ser Ile Ile Ala Leu Asn Gln Trp Pro Lys Asn Trp Pro Lys Gln Lys
    210                 215                 220
```

```
Ala Val Thr Gly Leu Val Gly Ile Gly Thr Ala Ser Glu Val Tyr Gln
225                 230                 235                 240

Ser Thr Glu Ile Leu His Cys Leu Gly Pro Asp Asn Gln Glu Ser Thr
            245                 250                 255

Val Gln Pro Met Ile Thr Ser Ile Pro Leu Asn Leu Trp Gly Arg Asp
        260                 265                 270

Leu Leu Gln Gln Trp Gly Ala Glu Ile Thr Met Pro Ala Pro Ser Tyr
    275                 280                 285

Ser Pro Thr Ser Gln Lys Ile Met Thr Lys Met Gly Tyr Ile Pro Gly
290                 295                 300

Lys Gly Leu Gly Lys Asn Glu Asp Gly Ile Lys Ile Pro Val Glu Ala
305                 310                 315                 320

Lys Ile Asn Gln Glu Arg Glu Gly Ile Gly Asn Pro Cys
                325                 330

<210> SEQ ID NO 15
<211> LENGTH: 2896
<212> TYPE: DNA
<213> ORGANISM: Human endogenous retrovirus, K family (HERV-K)

<400> SEQUENCE: 15
atggcattaa aattccagtt gaggctaaaa taaatcaaga aagagaagga atagggaatc      60
cttgctaggg gcggccactg tagagcctcc taaacccata ccattaactt ggaaaacaga    120
aaaaccagtg tgggtaaatc agtggccgct accaaaacaa aaactggagg ctttacattt    180
attagcaaat gaacagttag aaaagggtca tattgagcct tcgttctcac cttggaattc    240
tcctgtgttt gtaattcaga agaaatcagg caaatggcgt atgttaactg acttaagggc    300
tgtaaacgcc gtaattcaac ccatggggcc tctccaaccc gggttgccct ctccggccat    360
gatcccaaaa gattggcctt aattataat tgatctaaag gattgctttt ttaccatccc    420
tctggcagag caggattgcg aaaaatttgc ctttactata ccagccataa ataataaaga    480
accagccacc aggtttcagt ggaaagtgtt acctcaggga atgcttaata gtccaactat    540
ttgtcagact tttgtaggtc gagctcttca accagttaga gaaagttttt cagactgtta    600
tattattcat tgtattgatg atattttatg tgctgcagaa acgaaagata attaattga    660 ctgttataca tttctgcaag cagaggttgc caatgctgga ctggcaatag catctgataa    720
gatccaaacc tctactcctt ttcattattt agggatgcag atagaaaata gaaaaattaa    780
gccacaaaaa atagaaataa gaaagacac attaaaaaca ctaaatgatt ttcaaaaatt    840
actaggagat attaattgga ttcggccaac tctaggcatt cctacttatg ccatgtcaaa    900
tttgttctct atcttaagag gagactcaga cttaaatagt aaaagaatgt taacccccaga    960 ggcaacaaaa gaaattaaat tagtggaaga aaaaattcag tcagcgcaaa taaatagaat   1020
agatccctta gccccactcc aacttttgat ttttgccact gcacattctc aacaggcat   1080 cattattcaa aatactgatc ttgtggagtg gtcattcctt cctcacagta cagttaagac   1140
ttttacattg tacttggatc aaatagctac attaatcggt cagacaagat tacgaataat   1200 aaaaattatgt gggaatgacc cagacaaaat agttgtccct ttaaccaagg aacaagttag   1260
acaagccttt atcaattctg gtgcatggaa gattggtctt gctaattttg tgggaattat   1320
tgataatcat tacccaaaaa caaagatctt ccagttctta aaattgacta cttggattct   1380
acctaaaatt accagacgtg aaccctttaga aaatgctcta acagtattta ctgatggttc   1440
cagcaatgga aaagcagctt acacaggacc gaaagaacga gtaatcaaaa ctccatatca   1500
atcggctcaa agagcagagt tggttgcagt cattacagtg ttacaagatt ttgaccaacc   1560
```

```
tatcaatatt atatcagatt ctgcatatgt agtacaggct acaagggatg ttgagacagc   1620
tctaattaaa tatagcatgg atgatcagtt aaaccagcta ttcaatttat tacaacaaac   1680
tgtaagaaaa agaaatttcc cattttatat tacacatatt cgagcacaca ctaatttacc   1740
agggcctttg actaaagcaa atgaacaagc tgacttactg gtatcatctg cactcataaa   1800
agcacaagaa cttcatgctt tgactcatgt aaatgcagca ggattaaaaa acaaatttga   1860
tgtcacatgg aaacaggcaa agatattgt acaacattgc acccagtgtc aagtcttaca    1920
cctgcccact caagaggcag gagttaatcc cagaggtctg tgtcctaatg cattatggca   1980
aatggatgtc acgcatgtac cttcatttgg aagattatca tatgttcacg taacagttga   2040
tacttattca catttcatat gggcaacttg ccaaacagga gaaagtactt cccatgttaa   2100
aaaacattta ttgtcttgtt ttgctgtaat gggagttcca gaaaaaatca aaactgacaa   2160
tggaccagga tattgtagta aagctttcca aaaattctta agtcagtgga aaatttcaca   2220
tacaacagga attccttata attcccaagg acaggccata gttgaaagaa ctaatagaac   2280
actcaaaact caattagtta aacaaaagaa aggggagac agtaaggagt gtaccactcc    2340
tcagatgcaa cttaatctag cactctatac tttaaatttt ttaaacattt atagaaatca   2400
gactactact tctgcagaac aacatcttac tggtaaaaag aacagcccac atgaaggaaa   2460
actaatttgg tggaaagata taaaaataa gacatgggaa ataggaaagg tgataacgtg    2520
ggggagaggt tttgcttgtg tttcaccagg agaaaatcag cttcctgttt ggatacccac   2580
tagacatttg aagttctaca atgaacccat cagagatgca aagaaaagca cctccgcgga   2640
gacggagaca tcgcaatcga gcaccgttga ctcacaagat gaacaaaatg gtgacgtcag   2700
aagaacagat gaagttgcca tccaccaaga aggcagagcc gccaacttgg gcacaactaa   2760
agaagctgac gcagttagct acaaaatatc tagagaacac aaaggtgaca caaaccccag   2820
agagtatgct gcttgcagcc ttgatgattg tatcaatggt ggtaagtctc cctatgcctg   2880
caggagcagc tgcagc                                                   2896

<210> SEQ ID NO 16
<211> LENGTH: 2619
<212> TYPE: DNA
<213> ORGANISM: Human endogenous retrovirus, K family (HERV-K)

<400> SEQUENCE: 16
atgttaactg acttaagggc tgtaaacgcc gtaattcaac ccatggggcc tctccaaccc     60
gggttgccct ctccggccat gatcccaaaa gattggcctt taattataat tgatctaaag   120
gattgctttt ttaccatccc tctggcgagg caggattgcg aaaaatttgc ctttactata   180
ccagccataa ataataaaga accagccacc aggtttcagt ggaaagtgtt acctcaggga   240
atgcttaata gtccaactat ttgtcagact tttgtaggtc gagctcttca accagttaga   300
gaaaagtttt cagactgtta tattattcat tgtattgatg atatttttatg tgctgcagaa   360 acgaaagata aattaattga ctgttataca tttctgcaag cagaggttgc caatgctgga   420
ctggcaatag catctgataa gatccaaacc tctactcctt ttcattattt agggatgcag   480
atagaaaata gaaaaattaa gccacaaaaa atagaaataa gaaagacac attaaaaaca    540 ctaaatgatt ttcaaaaatt actaggagat attaattgga ttcggccaac tctaggcatt   600
cctacttatg ccatgtcaaa tttgttctct atcttaagag gagactcaga cttaaatagt   660
aaaagaatgt aaccccagaa ggcaacaaaa gaaattaaat tagtggaaga aaaaattcag   720
tcagcgcaaa taaatagaat agatccctta gccccactcc aacttttgat ttttgccact   780
```

```
gcacattctc caacaggcat cattattcaa aatactgatc ttgtggagtg gtcattcctt    840
cctcacagta cagttaagac ttttacattg tacttggatc aaatagctac attaatcggt    900
cagacaagat tacgaataat aaaattatgt gggaatgacc cagacaaaat agttgtccct    960
ttaaccaagg aacaagttag acaagccttt atcaattctg gtgcatggaa gattggtctt   1020
gctaattttg tgggaattat tgataatcat tacccaaaaa caaagatctt ccagttctta   1080
aaattgacta cttggattct acctaaaatt accagacgtg aacctttaga aaatgctcta   1140
acagtattta ctgatggttc cagcaatgga aaagcagctt acacaggacc gaaagaacga   1200
gtaatcaaaa ctccatatca atcggctcaa agagcagagt tggttgcagt cattacagtg   1260
ttacaagatt ttgaccaacc tatcaatatt atatcagatt ctgcatatgt agtacaggct   1320
acaagggatg ttgagacagc tctaattaaa tatagcatgg atgatcagtt aaaccagcta   1380
ttcaatttat tacaacaaac tgtaagaaaa agaaatttcc cattttatat tacacatatt   1440
cgagcacaca ctaatttacc agggccttg actaaagcaa atgaacaagc tgacttactg   1500
gtatcatctg cactcataaa agcacaagaa cttcatgctt tgactcatgt aaatgcagca   1560
ggattaaaaa acaaatttga tgtcacatgg aaacaggcaa agatattgt acaacattgc   1620 acccagtgtc aagtcttaca cctgcccact caagaggcag gagttaatcc cagaggtctg   1680
tgtcctaatg cattatggca aatggatgtc acgcatgtac cttcatttgg aagattatca   1740
tatgttcacg taacagttga tacttattca catttcatat gggcaacttg ccaaacagga   1800
gaaagtactt cccatgttaa aaaacattta ttgtcttgtt ttgctgtaat gggagttcca   1860
gaaaaaatca aaactgacaa tggaccagga tattgtagta agctttccaa aaattctta    1920 agtcagtgga aaatttcaca tacaacagga attccttata attcccaagg acaggccata   1980
gttgaaagaa ctaatagaac actcaaaact caattagtta acaaaaaga aggggagac    2040 agtaaggagt gtaccactcc tcagatgcaa cttaatctag cactctatac tttaaatttt   2100
ttaaacattt atagaaatca gactactact tctgcagaac aacatcttac tggtaaaaag   2160
aacagcccac atgaaggaaa actaatttgg tggaaagata gtaaaaataa gacatgggaa   2220 ataggaggg tgataacgtg ggggagaggt tttgcttgtg tttcaccagg agaaaatcag   2280
cttcctgttt ggatacccac tagacatttg aagttctaca atgaacccat cagagatgca   2340
aagaaaagca cctccgcgga gacggagaca tcgcaatcga gcaccgttga ctcacaagat   2400
gaacaaaatg gtgacgtcag aagaacagat gaagttgcca tccaccaaga aggcagagcc   2460
gccaacttgg gcacaactaa agaagctgac gcagttagct acaaaatatc tagagaacac   2520
aaaggtgaca caaaccccag agagtatgct gcttgcagcc ttgatgattg tatcaatggt   2580
ggtaagtctc cctatgcctg caggagcagc tgcagctaa                         2619

<210> SEQ ID NO 17
<211> LENGTH: 2671
<212> TYPE: DNA
<213> ORGANISM: Human endogenous retrovirus, K family (HERV-K)

<400> SEQUENCE: 17
atggcattaa agtcccaact gaggctgaaa aaaatcaaaa aagaaaagg aatagggcat     60 ccttttaga agcggtcact gtagagcctc caaaacccat tccattaatt tggggggaaa    120 aaaaaactg tatggtaaat cagtagccgc ttccaaaaca aaaactggag gctttacact    180
tattagcaaa gaaacagtta gaaaaaggac atattgagcc ttcattttcg ccttggaatt    240
ctcctgtttg taattcagaa aaaatccggc agatggcgta tgctaactga cttaagagcc    300
```

-continued

```
attaatgcca taattcaacc catgggggct ctcccatccc ggttgccctc tccagccatg    360
gtcccctttα attataattg atctgaagga ttgcttttt accattcctc tggcaaaaga    420
ggattttgaa aaatttgctt ttactatacc agcctaaata ataaagaacc agccaccagg    480
tttcagtgga aagtattgcc tcagggaatg cttaataatt caactatttg tcagactttc    540
atagctcaag ctctgcaacc agttagagac aagttttcag actgttatat cgttcattat    600
gttgatattt tgtgtgctgc agaaacgaga gacaaattaa ttgaccgtta cacatttctc    660
agacagaggt tgccaacgcg ggactgacaa tagcatctga taagattcaa acctctcctc    720
ctttccatta cttgggaatg caggtagagg aaaggaaaat taaaccacaa aaaatagaaa    780
taagaaaaga cacattaaaa acattaaatg agtttcaaaa gttggtagga gatactaatt    840
ggattcggag atattaattg gatttggcca actctaggca ttcctactta tgccatgtca    900
attttgttct ctttcttaag aggggacttg gaattaaata gtgaagaat gttacctcca     960
gaggcaacta aagaaattaa attaattgaa gaaaaaaatt cggtcagcac aagtaaaatag   1020
gatcacttgg ccccactcca aattttgatt tttggtactg cacattctct aacagccatc   1080
attgttcaaa acacagatct tgtggattgg tccttccttc ctcatagtac aattaagact   1140
tttacattgt acttggatca aatggctaca ttaattggtc agggaagatt acgaataata   1200
acattgtgtg gaaatgaccc agataaaatc actgttcctt tcaacaagca acaagttaga   1260
caagcctta tcagttctgg tgcatggcag attggtcttg ctaattttct gggaattatt    1320
gataatcatt acccaaaaac aaaaatcttc cagttcttaa aattgactac ttggattcta   1380
cctaaaatta ccagacgtga acctttagaa aatgctctaa cagtatttac tgatggttcc   1440
agcaatggaa aagcggctta cacagggccg aaagaacgag taatcaaaac tccgtatcaa   1500
tcagctcaaa gagcagagtt ggttgcagtc attacagtgt tacaagattt tgaccaacct   1560
atcaatatta tatcagattc tgcatatgta gtacaggcta caagggatgt tgagacagct   1620
ctaattaaat atagcacgga cgatcattta aaccagctat tcaatttatt acaacaaact   1680
gtaagaaaaa gaaatttccc attttatatt actcatattc gagcacacac taatttacca   1740
gggcctttga ctaaagcaaa tgaacaagct gacttactgg tatcatctgc attcataaaa   1800
gcacaagaac ttcttgcttt gactcatgta aatgcagcag gattaaaaaa caaatttgat   1860
gtcacatgga aacaggcaaa agatattgta caacattgca cccagtgtca agtcttacac   1920
ctgtccactc aagaggcagg agttaatccc agaggtctgt gtcctaatgc gttatggcaa   1980
atggatggca cgcatgttcc ttcatttgga agattatcat atgttcatgt aacagttgat   2040
acttattcac atttcatatg ggcaacttgc caaacaggag aaagtacttc ccatgttaaa   2100
aaacattat tatcttgttt tgctgtaatg ggagttccag aaaaaatcaa aactgacaat   2160
ggaccaggat attgtagtaa agcttttccaa aaattcttaa gtcagtggaa aatttcacat   2220
acaacaggaa ttccttataa ttcccaagga caggccatag ttgaaagaac taatagaaca   2280
ctcaaaactc aattagttaa acaaaaagaa gggggagaca gtaaggagtg taccactcct   2340
cagatgcaac ttaatctagc actctatact ttaaattttt taaacattta tagaaatcag   2400
actactactt ctgcaaaaca acatcttact ggtaaaaagc acagcccaca tgaaggaaaa   2460
ctaattggt ggaaagataa taaaaataag acatgggaaa tagggaaggt gataacgtgg    2520
gggagaggtt tgcttgtgt ttcaccagga gaaaatcagc ttcctgtttg atacccact    2580
agacattga agttctacaa tgaacccatc ggagatgcaa agaaagggc ctccacagag     2640
atggtaaccc cagtcacatg gatggataat c                                  2671
```

<210> SEQ ID NO 18
<211> LENGTH: 4086
<212> TYPE: DNA
<213> ORGANISM: Human endogenous retrovirus, K family (HERV-K)

<400> SEQUENCE: 18

```
atggggcctc tccaacccgg gttgccctct ccggccatga tcccaaaaga ttggccttta      60
attataattg atctaaagga ttgcttttt accatccctc tggcagagca ggattgtgaa     120
aaatttgcct ttactatacc agccataaat aataaagaac cagccaccag gtttcagtgg     180
aaagtgttac ctcagggaat gcttaatagt ccaactattt gtcagacttt tgtaggtcga     240
gctcttcaac cagtgagaga aaagttttca gactgttata ttattcatta tattgatgat     300
attttatgtg ctgcagaaac gaaagataaa ttaattgact gttatacatt tctgcaagca     360
gaggttgcca atgctggact ggcaatagca tccgataaga tccaaacctc tactcctttt     420
cattatttag ggatgcagat agaaataga aaaattaagc cacaaaaaat agaaataaga     480
aaagacacat taaaaacact aaatgatttt caaaaattac taggagatat taattggatt     540
cggccaactc taggcattcc tactatgcc atgtcaaatt tgttctctat cttaaggaga     600
gactcagact taaatagtca agaatatta accccagagg caacaaaaga aattaaatta     660
gtggaagaaa aaattcagtc agcgcaaata aatagaaatg atcccttagc cccactccaa     720
cttttgattt tgccactgc acattctcca acaggcatca ttattcaaaa tactgatctt     780
gtggagtggt cattccttcc tcacagtaca gttaagactt ttacattgta cttggatcaa     840
atagctacat taatcggtca gacaagatta cgaataacaa aattatgtgg aaatgaccca     900
gacaaaatag ttgtcccttt aaccaaggaa caagttagac aagcctttat caattctggt     960
gcatggcaga ttggtcttgc taattttgtg ggacttattg ataatcatta cccaaaaaca    1020
aagatcttcc agttcttaaa attgactact tggattctac ctaaaattac cagacgtgaa    1080
ccctttagaaa atgctctaac agtatttact gatggttcca gcaatggaaa agcagcttac    1140
acagggccga agaacgagt aatcaaaact ccatatcaat cggctcaaag agacgagttg    1200
gttgcagtca ttacagtgtt acaagatttt gaccaaccta tcaatattat atcagattct    1260
gcatatgtag tacaggctac aagggatgtt gagacagctc taattaaata tagcatggat    1320
gatcagttaa ccagctatt caatttatta caacaaactg taagaaaaag aaatttccca    1380
ttttatatta cttatattcg agcacacact aatttaccag ggcctttgac taaagcaaat    1440
gaacaagctg acttactggt atcatctgca ctcataaaag cacaagaact tcatgctttg    1500
actcatgtaa atgcagcagg attaaaaaac aaatttgatg tcacatggaa acaggcaaaa    1560
gatattgtac aacattgcac ccagtgtcaa gtcttacacc tgcccactca agaggcagga    1620
gttaatccca gagtctgtg tcctaatgca ttatggcaaa tggatgtcac gcatgtacct    1680
tcatttggaa gattatcata tgttcatgta acagttgata cttattcaca tttcatatgg    1740
gcaacttgcc aaacaggaga agtacttcc catgttaaaa acatttatt gtcttgtttt    1800
gctgtaatgg gagttccaga aaaatcaaa actgacaatg gaccaggata ttgtagtaaa    1860
gcttttccaaa aattcttaag tcagtggaaa atttcacata aacaggaat tccttataat    1920
tcccaaggac aggccatagt tgaaagaact aatagaacac tcaaaactca attagttaaa    1980
caaaaagaag ggggagacag taaggagtgt accactcctc agatgcaact taatctagca    2040
ctctatactt taaatttttt aaacatttat agaaatcaga ctactacttc tgcagaacaa    2100
catcttactg gtaaaagaa cagcccacat gaaggaaaac taatttggtg gaaagataat    2160
```

-continued

```
aaaaataaga catgggaaat agggaaggtg ataacgtggg ggagaggttt tgcttgtgtt    2220
tcaccaggag aaaatcagct tcctgtttgg ttacccacta gacatttgaa gttctacaat    2280
gaacccatcg gagatgcaaa gaaaagggcc tccacggaga tggtaacacc agtcacatgg    2340
atggataatc ctatagaagt atatgttaat gatagtatat gggtacctgg ccccatagat    2400
gatcgctgcc ctgccaaacc tgaggaagaa gggatgatga taaatatttc cattgggtat    2460
cgttatcctc ctatttgcct agggagagca ccaggatgtt taatgcctgc agtccaaaat    2520
tggttggtag aagtacctac tgtcagtccc atcagtagat tcacttatca catggtaagc    2580
gggatgtcac tcaggccacg ggtaaattat ttacaagact tttcttatca aagatcatta    2640
aaatttagac ctaaagggaa accttgcccc aaggaaattc ccaaagaatc aaaaaataca    2700
gaagttttag tttgggaaga atgtgtgcc aatagtgcgg tgatattata aacaatgaa     2760
tttggaacta ttatagattg ggcacctcga ggtcaattct accacaattg ctcaggacaa    2820
actcagtcgt gtccaagtgc acaagtgagt ccagctgttg atagcgactt aacagaaagt    2880
ttagacaaac ataagcataa aaaattgcag tctttctacc cttgggaatg gggagaaaaa    2940
ggaatctcta ccccaagacc aaaaatagta agtcctgttt ctggtcctga acatccagaa    3000
ttatggaggc ttactgtggc ctcacaccac attagaattt ggtctggaaa tcaaacttta    3060
gaaacaagag attgtaagcc attttatact gtcgacctaa attccagtct aacagttcct    3120
ttacaaagtt gcgtaaagcc cccttatatg ctagttgtag gaaatatagt tattaaacca    3180
gactcccaga ctataacctg tgaaaattgt agattgctta cttgcattga ttcaactttt    3240
aattggcaac accgtattct gctggtgaga gcaagagagg gcgtgtggat ccctgtgtcc    3300
atggaccgac cgtgggaggc ctcaccatcc gtccatattt tgactgaagt attaaaaggt    3360
gttttaaaata gatccaaaag attcattttt actttaattg cagtgattat gggattaatt    3420
gcagtcacag ctacggctgc tgtagcagga gttgcattgc actcttctgt tcagtcagta    3480
aactttgtta atgattggca aaagaattct acaagattgt ggaattcaca atctagtatt    3540
gatcaaaaat tggcaaatca aattaatgat cttagacaaa ctgtcatttg atgggagac    3600
agactcatga gcttagaaca tcgtttccag ttacaatgtg actggaatac gtcagatttt    3660
tgtattacac cccaaattta taatgagtct gagcatcact gggacatggt tagacgccat    3720
ctacagggaa gagaagataa tctcactta gacatttcca aattaaaaga acaaattttc    3780
gaagcatcaa aagcccattt aaatttggtg ccaggaactg aggcaattgc aggagttgct    3840
gatggcctcg caaatcttaa ccctgtcact tgggttaaga ccattggaag tacatcgatt    3900
ataaatctca tattaatcct tgtgtgcctg ttttgtctgt tgttagtctg caggtgtacc    3960
caacagctcc gaagagacag cgaccatcga gaacgggcca tgatgacgat ggcggttttg    4020
tcgaaaagaa aaggggggaa atgtggggaaa agcaagagag atcaaattgt tactgtgtct    4080
gtgtag                                                              4086
```

<210> SEQ ID NO 19
<211> LENGTH: 872
<212> TYPE: PRT
<213> ORGANISM: Human endogenous retrovirus, K family (HERV-K)

<400> SEQUENCE: 19

```
Met Leu Thr Asp Leu Arg Ala Val Asn Ala Val Ile Gln Pro Met Gly
1               5                   10                  15

Pro Leu Gln Pro Gly Leu Pro Ser Pro Ala Met Ile Pro Lys Asp Trp
            20                  25                  30
```

```
Pro Leu Ile Ile Ile Asp Leu Lys Asp Cys Phe Phe Thr Ile Pro Leu
            35                  40                  45

Ala Glu Gln Asp Cys Glu Lys Phe Ala Phe Thr Ile Pro Ala Ile Asn
 50                  55                  60

Asn Lys Glu Pro Ala Thr Arg Phe Gln Trp Lys Val Leu Pro Gln Gly
 65                  70                  75                  80

Met Leu Asn Ser Pro Thr Ile Cys Gln Thr Phe Val Gly Arg Ala Leu
                 85                  90                  95

Gln Pro Val Arg Glu Lys Phe Ser Asp Cys Tyr Ile Ile His Cys Ile
                100                 105                 110

Asp Asp Ile Leu Cys Ala Ala Glu Thr Lys Asp Lys Leu Ile Asp Cys
                115                 120                 125

Tyr Thr Phe Leu Gln Ala Glu Val Ala Asn Ala Gly Leu Ala Ile Ala
        130                 135                 140

Ser Asp Lys Ile Gln Thr Ser Thr Pro Phe His Tyr Leu Gly Met Gln
145                 150                 155                 160

Ile Glu Asn Arg Lys Ile Lys Pro Gln Lys Ile Glu Ile Arg Lys Asp
                165                 170                 175

Thr Leu Lys Thr Leu Asn Asp Phe Gln Lys Leu Leu Gly Asp Ile Asn
            180                 185                 190

Trp Ile Arg Pro Thr Leu Gly Ile Pro Thr Tyr Ala Met Ser Asn Leu
        195                 200                 205

Phe Ser Ile Leu Arg Gly Asp Ser Asp Leu Asn Ser Lys Arg Met Leu
    210                 215                 220

Thr Pro Glu Ala Thr Lys Glu Ile Lys Leu Val Glu Glu Lys Ile Gln
225                 230                 235                 240

Ser Ala Gln Ile Asn Arg Ile Asp Pro Leu Ala Pro Leu Gln Leu Leu
                245                 250                 255

Ile Phe Ala Thr Ala His Ser Pro Thr Gly Ile Ile Ile Gln Asn Thr
                260                 265                 270

Asp Leu Val Glu Trp Ser Phe Leu Pro His Ser Thr Val Lys Thr Phe
            275                 280                 285

Thr Leu Tyr Leu Asp Gln Ile Ala Thr Leu Ile Gly Gln Thr Arg Leu
        290                 295                 300

Arg Ile Ile Lys Leu Cys Gly Asn Asp Pro Asp Lys Ile Val Val Pro
305                 310                 315                 320

Leu Thr Lys Glu Gln Val Arg Gln Ala Phe Ile Asn Ser Gly Ala Trp
                325                 330                 335

Lys Ile Gly Leu Ala Asn Phe Val Gly Ile Ile Asp Asn His Tyr Pro
                340                 345                 350

Lys Thr Lys Ile Phe Gln Phe Leu Lys Leu Thr Thr Trp Ile Leu Pro
            355                 360                 365

Lys Ile Thr Arg Arg Glu Pro Leu Glu Asn Ala Leu Thr Val Phe Thr
        370                 375                 380

Asp Gly Ser Ser Asn Gly Lys Ala Ala Tyr Thr Gly Pro Lys Glu Arg
385                 390                 395                 400

Val Ile Lys Thr Pro Tyr Gln Ser Ala Gln Arg Ala Glu Leu Val Ala
                405                 410                 415

Val Ile Thr Val Leu Gln Asp Phe Asp Gln Pro Ile Asn Ile Ile Ser
                420                 425                 430

Asp Ser Ala Tyr Val Val Gln Ala Thr Arg Asp Val Glu Thr Ala Leu
            435                 440                 445

Ile Lys Tyr Ser Met Asp Asp Gln Leu Asn Gln Leu Phe Asn Leu Leu
```

-continued

```
            450                 455                 460
Gln Gln Thr Val Arg Lys Arg Asn Phe Pro Phe Tyr Ile Thr His Ile
465                 470                 475                 480

Arg Ala His Thr Asn Leu Pro Gly Pro Leu Thr Lys Ala Asn Glu Gln
                485                 490                 495

Ala Asp Leu Leu Val Ser Ser Ala Leu Ile Lys Ala Gln Glu Leu His
                500                 505                 510

Ala Leu Thr His Val Asn Ala Ala Gly Leu Lys Asn Lys Phe Asp Val
                515                 520                 525

Thr Trp Lys Gln Ala Lys Asp Ile Val Gln His Cys Thr Gln Cys Gln
                530                 535                 540

Val Leu His Leu Pro Thr Gln Glu Ala Gly Val Asn Pro Arg Gly Leu
545                 550                 555                 560

Cys Pro Asn Ala Leu Trp Gln Met Asp Val Thr His Val Pro Ser Phe
                565                 570                 575

Gly Arg Leu Ser Tyr Val His Val Thr Val Asp Thr Tyr Ser His Phe
                580                 585                 590

Ile Trp Ala Thr Cys Gln Thr Gly Glu Ser Thr Ser His Val Lys Lys
                595                 600                 605

His Leu Leu Ser Cys Phe Ala Val Met Gly Val Pro Glu Lys Ile Lys
                610                 615                 620

Thr Asp Asn Gly Pro Gly Tyr Cys Ser Lys Ala Phe Gln Lys Phe Leu
625                 630                 635                 640

Ser Gln Trp Lys Ile Ser His Thr Thr Gly Ile Pro Tyr Asn Ser Gln
                645                 650                 655

Gly Gln Ala Ile Val Glu Arg Thr Asn Arg Thr Leu Lys Thr Gln Leu
                660                 665                 670

Val Lys Gln Lys Glu Gly Gly Asp Ser Lys Glu Cys Thr Thr Pro Gln
                675                 680                 685

Met Gln Leu Asn Leu Ala Leu Tyr Thr Leu Asn Phe Leu Asn Ile Tyr
                690                 695                 700

Arg Asn Gln Thr Thr Thr Ser Ala Glu Gln His Leu Thr Gly Lys Lys
705                 710                 715                 720

Asn Ser Pro His Glu Gly Lys Leu Ile Trp Trp Lys Asp Ser Lys Asn
                725                 730                 735

Lys Thr Trp Glu Ile Gly Lys Val Ile Thr Trp Gly Arg Gly Phe Ala
                740                 745                 750

Cys Val Ser Pro Gly Glu Asn Gln Leu Pro Val Trp Ile Pro Thr Arg
                755                 760                 765

His Leu Lys Phe Tyr Asn Glu Pro Ile Arg Asp Ala Lys Lys Ser Thr
                770                 775                 780

Ser Ala Glu Thr Glu Thr Ser Gln Ser Ser Thr Val Asp Ser Gln Asp
785                 790                 795                 800

Glu Gln Asn Gly Asp Val Arg Arg Thr Asp Glu Val Ala Ile His Gln
                805                 810                 815

Glu Gly Arg Ala Ala Asn Leu Gly Thr Thr Lys Glu Ala Asp Ala Val
                820                 825                 830

Ser Tyr Lys Ile Ser Arg Glu His Lys Gly Asp Thr Asn Pro Arg Glu
                835                 840                 845

Tyr Ala Ala Cys Ser Leu Asp Asp Cys Ile Asn Gly Gly Lys Ser Pro
                850                 855                 860

Tyr Ala Cys Arg Ser Ser Cys Ser
865                 870
```

```
<210> SEQ ID NO 20
<211> LENGTH: 1361
<212> TYPE: PRT
<213> ORGANISM: Human endogenous retrovirus, K family (HERV-K)
<220> FEATURE:
<221> NAME/KEY: SITE
<222> LOCATION: 917
<223> OTHER INFORMATION: Xaa is any amino acid

<400> SEQUENCE: 20
```

| | | | | | | | | | | | | | | | |
|---|---|---|---|---|---|---|---|---|---|---|---|---|---|---|---|
| Met | Gly | Pro | Leu | Gln | Pro | Gly | Leu | Pro | Ser | Pro | Ala | Met | Ile | Pro | Lys |
| 1 | | | | 5 | | | | | 10 | | | | | 15 | |
| Asp | Trp | Pro | Leu | Ile | Ile | Ile | Asp | Leu | Lys | Asp | Cys | Phe | Phe | Thr | Ile |
| | | | 20 | | | | | 25 | | | | | 30 | | |
| Pro | Leu | Ala | Glu | Gln | Asp | Cys | Glu | Lys | Phe | Ala | Phe | Thr | Ile | Pro | Ala |
| | | 35 | | | | | 40 | | | | | 45 | | | |
| Ile | Asn | Asn | Lys | Glu | Pro | Ala | Thr | Arg | Phe | Gln | Trp | Lys | Val | Leu | Pro |
| 50 | | | | | 55 | | | | | 60 | | | | | |
| Gln | Gly | Met | Leu | Asn | Ser | Pro | Thr | Ile | Cys | Gln | Thr | Phe | Val | Gly | Arg |
| 65 | | | | 70 | | | | | 75 | | | | | 80 | |
| Ala | Leu | Gln | Pro | Val | Arg | Glu | Lys | Phe | Ser | Asp | Cys | Tyr | Ile | Ile | His |
| | | | | 85 | | | | | 90 | | | | | 95 | |
| Tyr | Ile | Asp | Asp | Ile | Leu | Cys | Ala | Ala | Glu | Thr | Lys | Asp | Lys | Leu | Ile |
| | | | 100 | | | | | 105 | | | | | 110 | | |
| Asp | Cys | Tyr | Thr | Phe | Leu | Gln | Ala | Glu | Val | Ala | Asn | Ala | Gly | Leu | Ala |
| | | 115 | | | | | 120 | | | | | 125 | | | |
| Ile | Ala | Ser | Asp | Lys | Ile | Gln | Thr | Ser | Thr | Pro | Phe | His | Tyr | Leu | Gly |
| 130 | | | | | 135 | | | | | 140 | | | | | |
| Met | Gln | Ile | Glu | Asn | Arg | Lys | Ile | Lys | Pro | Gln | Lys | Ile | Glu | Ile | Arg |
| 145 | | | | 150 | | | | | 155 | | | | | 160 | |
| Lys | Asp | Thr | Leu | Lys | Thr | Leu | Asn | Asp | Phe | Gln | Lys | Leu | Leu | Gly | Asp |
| | | | | 165 | | | | | 170 | | | | | 175 | |
| Ile | Asn | Trp | Ile | Arg | Pro | Thr | Leu | Gly | Ile | Pro | Thr | Tyr | Ala | Met | Ser |
| | | | 180 | | | | | 185 | | | | | 190 | | |
| Asn | Leu | Phe | Ser | Ile | Leu | Arg | Gly | Asp | Ser | Asp | Leu | Asn | Ser | Gln | Arg |
| | | 195 | | | | | 200 | | | | | 205 | | | |
| Ile | Leu | Thr | Pro | Glu | Ala | Thr | Lys | Glu | Ile | Lys | Leu | Val | Glu | Glu | Lys |
| 210 | | | | | 215 | | | | | 220 | | | | | |
| Ile | Gln | Ser | Ala | Gln | Ile | Asn | Arg | Ile | Asp | Pro | Leu | Ala | Pro | Leu | Gln |
| 225 | | | | 230 | | | | | 235 | | | | | 240 | |
| Leu | Leu | Ile | Phe | Ala | Thr | Ala | His | Ser | Pro | Thr | Gly | Ile | Ile | Ile | Gln |
| | | | | 245 | | | | | 250 | | | | | 255 | |
| Asn | Thr | Asp | Leu | Val | Glu | Trp | Ser | Phe | Leu | Pro | His | Ser | Thr | Val | Lys |
| | | | 260 | | | | | 265 | | | | | 270 | | |
| Thr | Phe | Thr | Leu | Tyr | Leu | Asp | Gln | Ile | Ala | Thr | Leu | Ile | Gly | Gln | Thr |
| | | 275 | | | | | 280 | | | | | 285 | | | |
| Arg | Leu | Arg | Ile | Thr | Lys | Leu | Cys | Gly | Asn | Asp | Pro | Asp | Lys | Ile | Val |
| | 290 | | | | | 295 | | | | | 300 | | | | |
| Val | Pro | Leu | Thr | Lys | Glu | Gln | Val | Arg | Gln | Ala | Phe | Ile | Asn | Ser | Gly |
| 305 | | | | | 310 | | | | | 315 | | | | | 320 |
| Ala | Trp | Gln | Ile | Gly | Leu | Ala | Asn | Phe | Val | Gly | Leu | Ile | Asp | Asn | His |
| | | | | 325 | | | | | 330 | | | | | 335 | |
| Tyr | Pro | Lys | Thr | Lys | Ile | Phe | Gln | Phe | Leu | Lys | Leu | Thr | Thr | Trp | Ile |
| | | | 340 | | | | | 345 | | | | | 350 | | |
| Leu | Pro | Lys | Ile | Thr | Arg | Arg | Glu | Pro | Leu | Glu | Asn | Ala | Leu | Thr | Val |
| | | 355 | | | | | 360 | | | | | 365 | | | |

-continued

```
Phe Thr Asp Gly Ser Ser Asn Gly Lys Ala Ala Tyr Thr Gly Pro Lys
    370                 375                 380

Glu Arg Val Ile Lys Thr Pro Tyr Gln Ser Ala Gln Arg Asp Glu Leu
385                 390                 395                 400

Val Ala Val Ile Thr Val Leu Gln Asp Phe Asp Gln Pro Ile Asn Ile
                405                 410                 415

Ile Ser Asp Ser Ala Tyr Val Val Gln Ala Thr Arg Asp Val Glu Thr
                420                 425                 430

Ala Leu Ile Lys Tyr Ser Met Asp Asp Gln Leu Asn Gln Leu Phe Asn
                435                 440                 445

Leu Leu Gln Gln Thr Val Arg Lys Arg Asn Phe Pro Phe Tyr Ile Thr
    450                 455                 460

Tyr Ile Arg Ala His Thr Asn Leu Pro Gly Pro Leu Thr Lys Ala Asn
465                 470                 475                 480

Glu Gln Ala Asp Leu Leu Val Ser Ser Ala Leu Ile Lys Ala Gln Glu
                485                 490                 495

Leu His Ala Leu Thr His Val Asn Ala Ala Gly Leu Lys Asn Lys Phe
                500                 505                 510

Asp Val Thr Trp Lys Gln Ala Lys Asp Ile Val Gln His Cys Thr Gln
                515                 520                 525

Cys Gln Val Leu His Leu Pro Thr Gln Glu Ala Gly Val Asn Pro Arg
    530                 535                 540

Gly Leu Cys Pro Asn Ala Leu Trp Gln Met Asp Val Thr His Val Pro
545                 550                 555                 560

Ser Phe Gly Arg Leu Ser Tyr Val His Val Thr Val Asp Thr Tyr Ser
                565                 570                 575

His Phe Ile Trp Ala Thr Cys Gln Thr Gly Glu Ser Thr Ser His Val
                580                 585                 590

Lys Lys His Leu Leu Ser Cys Phe Ala Val Met Gly Val Pro Glu Lys
            595                 600                 605

Ile Lys Thr Asp Asn Gly Pro Gly Tyr Cys Ser Lys Ala Phe Gln Lys
    610                 615                 620

Phe Leu Ser Gln Trp Lys Ile Ser His Thr Thr Gly Ile Pro Tyr Asn
625                 630                 635                 640

Ser Gln Gly Gln Ala Ile Val Glu Arg Thr Asn Arg Thr Leu Lys Thr
                645                 650                 655

Gln Leu Val Lys Gln Lys Glu Gly Gly Asp Ser Lys Glu Cys Thr Thr
                660                 665                 670

Pro Gln Met Gln Leu Asn Leu Ala Leu Tyr Thr Leu Asn Phe Leu Asn
                675                 680                 685

Ile Tyr Arg Asn Gln Thr Thr Thr Ser Ala Glu Gln His Leu Thr Gly
    690                 695                 700

Lys Lys Asn Ser Pro His Glu Gly Lys Leu Ile Trp Trp Lys Asp Asn
705                 710                 715                 720

Lys Asn Lys Thr Trp Glu Ile Gly Lys Val Ile Thr Trp Gly Arg Gly
                725                 730                 735

Phe Ala Cys Val Ser Pro Gly Glu Asn Gln Leu Pro Val Trp Leu Pro
                740                 745                 750

Thr Arg His Leu Lys Phe Tyr Asn Glu Pro Ile Gly Asp Ala Lys Lys
            755                 760                 765

Arg Ala Ser Thr Glu Met Val Thr Pro Val Thr Trp Met Asp Asn Pro
    770                 775                 780

Ile Glu Val Tyr Val Asn Asp Ser Ile Trp Val Pro Gly Pro Ile Asp
```

```
785                 790                 795                 800
Asp Arg Cys Pro Ala Lys Pro Glu Glu Gly Met Met Ile Asn Ile
            805                 810                 815

Ser Ile Gly Tyr Arg Tyr Pro Ile Cys Leu Gly Arg Ala Pro Gly
            820                 825                 830

Cys Leu Met Pro Ala Val Gln Asn Trp Leu Val Glu Val Pro Thr Val
            835                 840                 845

Ser Pro Ile Ser Arg Phe Thr Tyr His Met Val Ser Gly Met Ser Leu
850                 855                 860

Arg Pro Arg Val Asn Tyr Leu Gln Asp Phe Ser Tyr Gln Arg Ser Leu
865                 870                 875                 880

Lys Phe Arg Pro Lys Gly Lys Pro Cys Pro Lys Glu Ile Pro Lys Glu
            885                 890                 895

Ser Lys Asn Thr Glu Val Leu Val Trp Glu Glu Cys Val Ala Asn Ser
            900                 905                 910

Ala Val Ile Leu Xaa Asn Asn Glu Phe Gly Thr Ile Ile Asp Trp Ala
            915                 920                 925

Pro Arg Gly Gln Phe Tyr His Asn Cys Ser Gly Gln Thr Gln Ser Cys
            930                 935                 940

Pro Ser Ala Gln Val Ser Pro Ala Val Asp Ser Asp Leu Thr Glu Ser
945                 950                 955                 960

Leu Asp Lys His Lys His Lys Lys Leu Gln Ser Phe Tyr Pro Trp Glu
            965                 970                 975

Trp Gly Glu Lys Gly Ile Ser Thr Pro Arg Pro Lys Ile Val Ser Pro
            980                 985                 990

Val Ser Gly Pro Glu His Pro Glu Leu Trp Arg Leu Thr Val Ala Ser
            995                 1000                1005

His His Ile Arg Ile Trp Ser Gly Asn Gln Thr Leu Glu Thr Arg Asp
            1010                1015                1020

Cys Lys Pro Phe Tyr Thr Val Asp Leu Asn Ser Ser Leu Thr Val Pro
1025                1030                1035                1040

Leu Gln Ser Cys Val Lys Pro Pro Tyr Met Leu Val Val Gly Asn Ile
            1045                1050                1055

Val Ile Lys Pro Asp Ser Gln Thr Ile Thr Cys Glu Asn Cys Arg Leu
            1060                1065                1070

Leu Thr Cys Ile Asp Ser Thr Phe Asn Trp Gln His Arg Ile Leu Leu
            1075                1080                1085

Val Arg Ala Arg Glu Gly Val Trp Ile Pro Val Ser Met Asp Arg Pro
            1090                1095                1100

Trp Glu Ala Ser Pro Ser Val His Ile Leu Thr Glu Val Leu Lys Gly
1105                1110                1115                1120

Val Leu Asn Arg Ser Lys Arg Phe Ile Phe Thr Leu Ile Ala Val Ile
            1125                1130                1135

Met Gly Leu Ile Ala Val Thr Ala Thr Ala Ala Val Ala Gly Val Ala
            1140                1145                1150

Leu His Ser Ser Val Gln Ser Val Asn Phe Val Asn Asp Trp Gln Lys
            1155                1160                1165

Asn Ser Thr Arg Leu Trp Asn Ser Gln Ser Ser Ile Asp Gln Lys Leu
            1170                1175                1180

Ala Asn Gln Ile Asn Asp Leu Arg Gln Thr Val Ile Trp Met Gly Asp
            1185                1190                1195                1200

Arg Leu Met Ser Leu Glu His Arg Phe Gln Leu Gln Cys Asp Trp Asn
            1205                1210                1215
```

-continued

Thr Ser Asp Phe Cys Ile Thr Pro Gln Ile Tyr Asn Glu Ser Glu His
                1220                1225                1230

His Trp Asp Met Val Arg Arg His Leu Gln Gly Arg Glu Asp Asn Leu
        1235                1240                1245

Thr Leu Asp Ile Ser Lys Leu Lys Glu Gln Ile Phe Glu Ala Ser Lys
        1250                1255                1260

Ala His Leu Asn Leu Val Pro Gly Thr Glu Ala Ile Ala Gly Val Ala
1265                1270                1275                1280

Asp Gly Leu Ala Asn Leu Asn Pro Val Thr Trp Val Lys Thr Ile Gly
                1285                1290                1295

Ser Thr Ser Ile Ile Asn Leu Ile Leu Ile Leu Val Cys Leu Phe Cys
                1300                1305                1310

Leu Leu Leu Val Cys Arg Cys Thr Gln Gln Leu Arg Arg Asp Ser Asp
        1315                1320                1325

His Arg Glu Arg Ala Met Met Thr Met Ala Val Leu Ser Lys Arg Lys
        1330                1335                1340

Gly Gly Asn Val Gly Lys Ser Lys Arg Asp Gln Ile Val Thr Val Ser
1345                1350                1355                1360

Val

<210> SEQ ID NO 21
<211> LENGTH: 956
<212> TYPE: PRT
<213> ORGANISM: Human endogenous retrovirus, K family (HERV-K)

<400> SEQUENCE: 21

Asn Lys Ser Arg Lys Arg Arg Asn Arg Glu Ser Leu Leu Gly Ala Ala
1               5                   10                  15

Thr Val Glu Pro Pro Lys Pro Ile Pro Leu Thr Trp Lys Thr Glu Lys
                20                  25                  30

Pro Val Trp Val Asn Gln Trp Pro Leu Pro Lys Gln Lys Leu Glu Ala
        35                  40                  45

Leu His Leu Leu Ala Asn Glu Gln Leu Glu Lys Gly His Ile Glu Pro
    50                  55                  60

Ser Phe Ser Pro Trp Asn Ser Pro Val Phe Val Ile Gln Lys Lys Ser
65              70                  75                  80

Gly Lys Trp Arg Met Leu Thr Asp Leu Arg Ala Val Asn Ala Val Ile
                85                  90                  95

Gln Pro Met Gly Pro Leu Gln Pro Gly Leu Pro Ser Pro Ala Met Ile
            100                 105                 110

Pro Lys Asp Trp Pro Leu Ile Ile Ile Asp Leu Lys Asp Cys Phe Phe
        115                 120                 125

Thr Ile Pro Leu Ala Glu Gln Asp Cys Glu Lys Phe Ala Phe Thr Ile
    130                 135                 140

Pro Ala Ile Asn Asn Lys Glu Pro Ala Thr Arg Phe Gln Trp Lys Val
145                 150                 155                 160

Leu Pro Gln Gly Met Leu Asn Ser Pro Thr Ile Cys Gln Thr Phe Val
                165                 170                 175

Gly Arg Ala Leu Gln Pro Val Arg Glu Lys Phe Ser Asp Cys Tyr Ile
            180                 185                 190

Ile His Cys Ile Asp Asp Ile Leu Cys Ala Ala Glu Thr Lys Asp Lys
        195                 200                 205

Leu Ile Asp Cys Tyr Thr Phe Leu Gln Ala Glu Val Ala Asn Ala Gly
    210                 215                 220

Leu Ala Ile Ala Ser Asp Lys Ile Gln Thr Ser Thr Pro Phe His Tyr

```
            225                 230                 235                 240
Leu Gly Met Gln Ile Glu Asn Arg Lys Ile Lys Pro Gln Lys Ile Glu
                245                 250                 255

Ile Arg Lys Asp Thr Leu Lys Thr Leu Asn Asp Phe Gln Lys Leu Leu
                260                 265                 270

Gly Asp Ile Asn Trp Ile Arg Pro Thr Leu Gly Ile Pro Thr Tyr Ala
                275                 280                 285

Met Ser Asn Leu Phe Ser Ile Leu Arg Gly Asp Ser Asp Leu Asn Ser
            290                 295                 300

Lys Arg Met Leu Thr Pro Glu Ala Thr Lys Glu Ile Lys Leu Val Glu
305                 310                 315                 320

Glu Lys Ile Gln Ser Ala Gln Ile Asn Arg Ile Asp Pro Leu Ala Pro
                325                 330                 335

Leu Gln Leu Leu Ile Phe Ala Thr Ala His Ser Pro Thr Gly Ile Ile
                340                 345                 350

Ile Gln Asn Thr Asp Leu Val Glu Trp Ser Phe Leu Pro His Ser Thr
                355                 360                 365

Val Lys Thr Phe Thr Leu Tyr Leu Asp Gln Ile Ala Thr Leu Ile Gly
            370                 375                 380

Gln Thr Arg Leu Arg Ile Ile Lys Leu Cys Gly Asn Asp Pro Asp Lys
385                 390                 395                 400

Ile Val Val Pro Leu Thr Lys Glu Gln Val Arg Gln Ala Phe Ile Asn
                405                 410                 415

Ser Gly Ala Trp Lys Ile Gly Leu Ala Asn Phe Val Gly Ile Ile Asp
                420                 425                 430

Asn His Tyr Pro Lys Thr Lys Ile Phe Gln Phe Leu Lys Leu Thr Thr
                435                 440                 445

Trp Ile Leu Pro Lys Ile Thr Arg Arg Glu Pro Leu Glu Asn Ala Leu
            450                 455                 460

Thr Val Phe Thr Asp Gly Ser Ser Asn Gly Lys Ala Ala Tyr Thr Gly
465                 470                 475                 480

Pro Lys Glu Arg Val Ile Lys Thr Pro Tyr Gln Ser Ala Gln Arg Ala
                485                 490                 495

Glu Leu Val Ala Val Ile Thr Val Leu Gln Asp Phe Asp Gln Pro Ile
                500                 505                 510

Asn Ile Ile Ser Asp Ser Ala Tyr Val Val Gln Ala Thr Arg Asp Val
                515                 520                 525

Glu Thr Ala Leu Ile Lys Tyr Ser Met Asp Asp Gln Leu Asn Gln Leu
            530                 535                 540

Phe Asn Leu Leu Gln Gln Thr Val Arg Lys Arg Asn Phe Pro Phe Tyr
545                 550                 555                 560

Ile Thr His Ile Arg Ala His Thr Asn Leu Pro Gly Pro Leu Thr Lys
                565                 570                 575

Ala Asn Glu Gln Ala Asp Leu Leu Val Ser Ser Ala Leu Ile Lys Ala
                580                 585                 590

Gln Glu Leu His Ala Leu Thr His Val Asn Ala Gly Leu Lys Asn
                595                 600                 605

Lys Phe Asp Val Thr Trp Lys Gln Ala Lys Asp Ile Val Gln His Cys
            610                 615                 620

Thr Gln Cys Gln Val Leu His Leu Pro Thr Gln Glu Ala Gly Val Asn
625                 630                 635                 640

Pro Arg Gly Leu Cys Pro Asn Ala Leu Trp Gln Met Asp Val Thr His
                645                 650                 655
```

Val Pro Ser Phe Gly Arg Leu Ser Tyr Val His Val Thr Val Asp Thr
            660                 665                 670

Tyr Ser His Phe Ile Trp Ala Thr Cys Gln Thr Gly Glu Ser Thr Ser
        675                 680                 685

His Val Lys Lys His Leu Leu Ser Cys Phe Ala Val Met Gly Val Pro
    690                 695                 700

Glu Lys Ile Lys Thr Asp Asn Gly Pro Gly Tyr Cys Ser Lys Ala Phe
705                 710                 715                 720

Gln Lys Phe Leu Ser Gln Trp Lys Ile Ser His Thr Gly Ile Pro
            725                 730                 735

Tyr Asn Ser Gln Gly Gln Ala Ile Val Glu Arg Thr Asn Arg Thr Leu
            740                 745                 750

Lys Thr Gln Leu Val Lys Gln Lys Glu Gly Gly Asp Ser Lys Glu Cys
        755                 760                 765

Thr Thr Pro Gln Met Gln Leu Asn Leu Ala Leu Tyr Thr Leu Asn Phe
        770                 775                 780

Leu Asn Ile Tyr Arg Asn Gln Thr Thr Thr Ser Ala Glu Gln His Leu
785                 790                 795                 800

Thr Gly Lys Lys Asn Ser Pro His Glu Gly Lys Leu Ile Trp Trp Lys
            805                 810                 815

Asp Asn Lys Asn Lys Thr Trp Glu Ile Gly Lys Val Ile Thr Trp Gly
            820                 825                 830

Arg Gly Phe Ala Cys Val Ser Pro Gly Glu Asn Gln Leu Pro Val Trp
        835                 840                 845

Ile Pro Thr Arg His Leu Lys Phe Tyr Asn Glu Pro Ile Arg Asp Ala
        850                 855                 860

Lys Lys Ser Thr Ser Ala Glu Thr Glu Thr Ser Gln Ser Ser Thr Val
865                 870                 875                 880

Asp Ser Gln Asp Glu Gln Asn Gly Asp Val Arg Arg Thr Asp Glu Val
            885                 890                 895

Ala Ile His Gln Glu Gly Arg Ala Ala Asn Leu Gly Thr Thr Lys Glu
        900                 905                 910

Ala Asp Ala Val Ser Tyr Lys Ile Ser Arg Glu His Lys Gly Asp Thr
        915                 920                 925

Asn Pro Arg Glu Tyr Ala Ala Cys Ser Leu Asp Asp Cys Ile Asn Gly
        930                 935                 940

Gly Lys Ser Pro Tyr Ala Cys Arg Ser Ser Cys Ser
945                 950                 955

<210> SEQ ID NO 22
<211> LENGTH: 2000
<212> TYPE: DNA
<213> ORGANISM: Human endogenous retrovirus, K family (HERV-K)

<400> SEQUENCE: 22
atgaacccat cagagatgca agaaaagca cctccgcgga cggagaca tcgcaatcga     60 gcaccgttga ctcacaagat gaacaaaatg gtgacgtcag aagaacagat gaagttgcca   120
tccaccaaga aggcagagcc gccaacttgg cacaactaa agaagctgac gcagttagct    180
acaaaatatc tagagaacac aaaggtgaca caaaccccag agagtatgct gcttgcagcc   240
ttgatgattg tatcaatggt ggtaagtctc cctatgcctg caggagcagc tgcagctaac   300
tatacctact gggcctatgt gcctttcccg cccttaattc gggcagtcac atggatggat   360
aatcctacag aagtatatgt taatgatagt gtatgggtac ctggccccat agatgatcgc   420
tgccctgcca aacctgagga agaagggatg atgataaata tttccattgg gtatcattat   480

```
cctcctattt gcctagggag agcaccagga tgtttaatgc ctgcagtcca aaattggttg      540
gtagaagtac ctactgtcag tcccatctgt agattcactt atcacatggt aagcgggatg      600
tcactcaggc cacgggtaaa ttatttacaa gactttcctt atcaaagatc attaaaattt      660
agacctaaag ggaaaccttg ccccaaggaa attcccaaag aatcaaaaaa tacagaagtt      720
ttagtttggg aagaatgtgt ggccaatagt gcggtgatat tacaaaacaa tgaattcgga      780
actattatag attgggcacc tcgaggtcaa ttctaccaca attgctcagg acaaactcag      840
tcgtgtccaa gtgcacaagt gagtccagct gttgatagcg acttaacaga agtttagac       900 aaacataagc ataaaaaatt gcagtctttc tacccttggg aatggggaga aaaaggaatc      960
tctaccccaa gaccaaaaat agtaagtcct gtttctggtc ctgaacatcc agaattatgg     1020
aggcttactg tggcctcaca ccacattaga atttggtctg gaaatcaaac tttagaaaca     1080
agagatcgta agccatttta tactattgac ctgaattcca gtctaacagt tcctttacaa     1140
agttgcgtaa agccccctta tatgctagtt gtaggaaata tagttattaa accagactcc     1200
cagactataa cctgtgaaaa ttgtagattg cttacttgca ttgattcaac ttttaattgg     1260
caacaccgta ttctgctggt gagagcaaga gagggcgtgt ggatccctgt gtccatggac     1320
cgaccgtggg aggcctcgcc atccgtccat attttgactg aagtattaaa aggtgtttta     1380
aatagatcca aaagattcat ttttacttta attgcagtga ttatgggatt aattgcagtc     1440
acagctacgg ctgctgtagc aggagttgca ttgcactctt ctgttcagtc agtaaacttt     1500
gttaatgatt ggcaaaaaaa ttctacaaga ttgtggaatt cacaatctag tattgatcaa     1560
aaattggcaa atcaaattaa tgatcttaga caaactgtca tttggatggg agacagactc     1620
atgagcttag aacatcgttt ccagttacaa tgtgactgga atacgtcaga ttttgtatt      1680 acaccccaaa tttataatga gtctgagcat cactgggaca tggttagacg ccatctacag     1740
ggaagagaag ataatctcac tttagacatt tccaaattaa agaacaaat tttcgaagca      1800 tcaaaagccc atttaaattt ggtgccagga actgaggcaa ttgcaggagt tgctgatggc     1860
ctcgcaaatc ttaaccctgt cacttgggtt aagaccattg gaagtactac gattataaat     1920
ctcatattaa tccttgtgtg cctgttttgt ctgttgttag tctgcaggtg tacccaacag     1980
ctccgaagag acagcgacca                                                 2000
```

<210> SEQ ID NO 23
<211> LENGTH: 2085
<212> TYPE: DNA
<213> ORGANISM: Human endogenous retrovirus, K family (HERV-K)

<400> SEQUENCE: 23

```
atgcaaagaa aagcacctcc gcggagacgg agacatcgca atcgagcacc gttgactcac       60
aagatgaaca aaatggtgac gtcagaagaa cagatgaagt tgccatccac caagaaggca      120
gagccgccaa cttgggcaca actaaagaag ctgacgcagt tagctacaaa atatctagag      180
aacacaaagg tgcacaaaac cccagagagt atgctgcttg cagccttgat gattgtatca      240
atggtggtaa gtctccctat gcctgcagga gcagctgcag ctaactatac ctactgggcc      300
tatgtgcctt tcccgccctt aattcgggca gtcacatgga tggataatcc tacagaagta      360
tatgttaatg atagtgtatg ggtacctggc cccatagatg atcgctgccc tgccaaacct      420
gaggaagaag ggatgatgat aaatattttcc attgggtatc attatcctcc tatttgccta     480
gggagagcac caggatgttt aatgcctgca gtccaaaatt ggttggtaga agtacctact      540
gtcagtccca tctgtagatt cacttatcac atggtaagcg ggatgtcact caggccacgg      600
```

```
gtaaattatt tacaagactt ttcttatcaa agatcattaa aatttagacc taaagggaaa      660
ccttgcccca aggaaattcc caaagaatca aaaaatacag aagttttagt ttgggaagaa      720
tgtgtggcca atagtgcggt gatattacaa aacaatgaat tcggaactat tatagattgg     780
gcacctcgag gtcaattcta ccacaattgc tcaggacaaa ctcagtcgtg tcaaagtgca     840
caagtgagtc cagctgttga tagcgactta acagaaagtt tagacaaaca taagcataaa     900
aaattgcagt ctttctaccc ttgggaatgg ggagaaaaag gaatctctac cccaagacca     960
aaaatagtaa gtcctgtttc tggtcctgaa catccagaat tatggaggct tactgtggcc    1020
tcacaccaca ttagaatttg gtctggaaat caaactttag aaacaagaga tcgtaagcca    1080
ttttatacta ttgacctgaa ttccagtcta acagttcctt tacaaagttg cgtaaagccc    1140
ccttatatgc tagttgtagg aaatatagtt attaaaccag actcccagac tataacctgt    1200
gaaaattgta gattgcttac ttgcattgat tcaactttta attggcaaca ccgtattctg    1260
ctggtgagag caagagaggg cgtgtggatc cctgtgtcca tggaccgacc gtgggaggcc    1320
tcgccatccg tccatatttt gactgaagta ttaaaaggtg ttttaaatag atccaaaaga    1380
ttcatttttg ctttaattgc agtgattatg ggattaattg cagtcacagc tacggctgct    1440
gtagcaggag ttgcattgca ctcttctgtt cagtcagtaa actttgttaa tgattggcaa    1500
aaaaattcta caagattgtg gaattcacaa tctagtattg atcaaaaatt ggcaaatcaa    1560
attaatgatc ttagacaaac tgtcatttgg atgggagaca gactcatgag cttagaacat    1620
cgtttccagt tacaatgtga ctggaatacg tcagatttttt gtattacacc ccaaatttat    1680
aatgagtctg agcatcactg ggacatggtt agacgccatc tacagggaag agaagataat    1740
ctcactttag acatttccaa attaaaagaa caaattttcg aagcatcaaa agcccattta    1800
aatttggtgc aggaactgaa ggcaattgca ggagttgctg atggcctcgc aaatcttaac    1860
cctgtcactt gggttaagac cattggaagt actacgatta taaatctcat attaatcctt    1920
gtgtgcctgt tttgtctgtt gttagtctgc aggtgtaccc aacagctccg aagagacagc    1980
gaccatcgag aacgggccat gatgacgatg gcggttttgt cgaaaagaaa agggggaaat    2040
gtggggaaaa gcaagagaga tcagattgtt actgtgtctg tgtag                    2085

<210> SEQ ID NO 24
<211> LENGTH: 1665
<212> TYPE: DNA
<213> ORGANISM: Human endogenous retrovirus, K family (HERV-K)

<400> SEQUENCE: 24
gtcacatgga tggataatcc tatagaagta tatgttaatg atagtgtatg ggtacctggc       60
cccacagatg atcgctgccc tgccaaacct gaggaagaag ggatgatgat aaatatttcc     120
attgtgtatc gttatcctcc tatttgccta gggagagcac caggatgttt aatgcctgca     180
gtccaaaatt ggttggtaga agtacctact gtcagtccta acagtagatt cacttatcac     240
atggtaagcg ggatgtcact caggccacgg gtaaattatt tacaagactt ttcttatcaa     300
agatcattaa aatttagacc taaagggaaa ccttgcccca aggaaattcc caaagaatca     360
aaaaatacag aagttttagt ttgggaagaa tgtgtggcca atagtgcggt gatattacaa     420
aacaatgaat tcggaactat tatagattgg gcacctcgag gtcaattcta ccacaattgc     480
tcaggacaaa ctcagtcgtg tccaagtgca caagtgagtc cagctgttga tagcgactta     540
acagaaagtc tagacaaaca taagcataaa aaattacagt ctttctaccc ttgggaatgg     600
ggagaaaaag gaatctctac cccaagacca gaataataa gtcctgtttc tggtcctgaa     660
```

| | |
|---|---|
| catccagaat tatggaggct ttggcctgac accacattag aatttggtct ggaaatcaaa | 720 |
| ctttagaaac aagagatcgt aagccatttt atactatcga cctaaattcc agtctaacgg | 780 |
| ttcctttaca aagttgcgta aagccctctt atatgctagt tgtaggaaat atagttatta | 840 |
| aaccagactc ccaaactata acctgtgaaa attgtagatt gtttacttgc attgattcaa | 900 |
| cttttaattg gcggcaccgt attctgctgg tgagagcaag agagggcgtg tggatctctg | 960 |
| tgtccgtgga ctgaccgtgg gaggcctcgc catccatcca tattttgact gaagtattaa | 1020 |
| aagacatttt aaatagatcc aaaagattca ttttttacctt aattgcagtg attatgggat | 1080 |
| taattgcagt cacagctacg gctgctgtgg caggagttgc attgcactct tctgttcagt | 1140 |
| cggtaaactt tgttaatgat tggcaaaaga attctacaag attgtggaat tcacaatcta | 1200 |
| gtattgatca aaaattggca aatcaaatta atgatcttag acaaactgtc atttggatgg | 1260 |
| gagacagact catgagctta gaacattgtt ccagttaca gtgtgactgg aatacgtcag | 1320 |
| attttttgtat tacaccccaa atttataatg agtctgagca tcactgggac atggttagac | 1380 |
| gccatctaca gggaagagaa gataatctca ctttagacat ttccaaatta aaataacaaa | 1440 |
| ttttcgaagc atcaaaagcc catttaaatt tgatgccagg aactgaggca attgcaggag | 1500 |
| ttgctgatgg cctcgcaaat cttaaccctg tcacttgggt taagaccatc ggaagtacta | 1560 |
| tgattataaa tctcatatta atccttgtgt gcctgttttg tctgttgtta gtctgcaggt | 1620 |
| gtacccaaca gctccgaaga gacagcgacc atcgagaacg ggcca | 1665 |

<210> SEQ ID NO 25
<211> LENGTH: 4086
<212> TYPE: DNA
<213> ORGANISM: Human endogenous retrovirus, K family (HERV-K)

<400> SEQUENCE: 25

| | |
|---|---|
| atggggcctc tccaacccgg gttgccctct ccggccatga tcccaaaaga ttggccttta | 60 |
| attataattg atctaaagga ttgcttttttt accatccctc tggcagagca ggattgtgaa | 120 |
| aaatttgcct ttactatacc agccataaat aataaagaac cagccaccag gtttcagtgg | 180 |
| aaagtgttac ctcagggaat gcttaatagt ccaactatt gtcagacttt tgtaggtcga | 240 |
| gctcttcaac cagtgagaga aaagttttca gactgttata ttattcatta tattgatgat | 300 |
| atttttatgtg ctgcagaaac gaaagataaa ttaattgact gttatacatt tctgcaagca | 360 |
| gaggttgcca atgctggact ggcaatagca tccgataaga tccaaacctc tactcctttt | 420 |
| cattatttag ggatgcagat agaaaataga aaaattaagc cacaaaaaat agaaataaga | 480 |
| aaagacacat taaaaacact aaatgatttt caaaaattac taggagatat taattggatt | 540 |
| cggccaactc taggcattcc tactatgcc atgtcaaatt tgttctctat cttaagagga | 600 |
| gactcagact taaatagtca aagaatatta accccagagg caacaaaaga attaaatta | 660 |
| gtggaagaaa aaattcagtc agcgcaaata aatagaatag atcccttagc cccactccaa | 720 |
| cttttgattt tgccactgc acattctcca acaggcatca ttattcaaaa tactgatctt | 780 |
| gtggagtggt cattccttcc tcacagtaca gttaagactt ttacattgta cttggatcaa | 840 |
| atagctacat taatcggtca gacaagatta cgaataacaa aattatgtgg aaatgaccca | 900 |
| gacaaaatag ttgtcccttt aaccaaggaa caagttagac aagcctttat caattctggt | 960 |
| gcatggcaga ttggtcttgc taattttgtg ggacttattg ataatcatta cccaaaaaca | 1020 |
| aagatcttcc agttccttaaa attgactact tggattctac ctaaaattac cagacgtgaa | 1080 |
| cctttagaaa atgctctaac agtatttact gatggttcca gcaatggaaa agcagcttac | 1140 |

```
acagggccga aagaacgagt aatcaaaact ccatatcaat cggctcaaag agacgagttg   1200
gttgcagtca ttacagtgtt acaagatttt gaccaaccta tcaatattat atcagattct   1260
gcatatgtag tacaggctac aagggatgtt gagacagctc taattaaata tagcatggat   1320
gatcagttaa accagctatt caatttatta caacaaactg taagaaaaag aaatttccca   1380
ttttatatta cttatattcg agcacacact aatttaccag ggcctttgac taaagcaaat   1440
gaacaagctg acttactggt atcatctgca ctcataaaag cacaagaact tcatgctttg   1500
actcatgtaa atgcagcagg attaaaaaac aaatttgatg tcacatggaa acaggcaaaa   1560
gatattgtac aacattgcac ccagtgtcaa gtcttacacc tgcccactca agaggcagga   1620
gttaatccca gaggtctgtg tcctaatgca ttatggcaaa tggatgtcac gcatgtacct   1680
tcatttggaa gattatcata tgttcatgta acagttgata cttattcaca tttcatatgg   1740
gcaacttgcc aaacaggaga aagtacttcc catgttaaaa aacattttatt gtcttgtttt   1800 gctgtaatgg gagttccaga aaaaatcaaa actgacaatg gaccaggata ttgtagtaaa   1860
gctttccaaa aattcttaag tcagtggaaa atttcacata caacaggaat tccttataat   1920
tcccaaggac aggccatagt tgaaagaact aatagaacac tcaaaactca attagttaaa   1980 caaaagaag ggggagacag taaggagtgt accactcctc agatgcaact taatctagca   2040
ctctatactt taaattttt aaacatttat agaaatcaga ctactactc tgcagaacaa   2100 catcttactg gtaaaaagaa cagcccacat gaaggaaaac taatttggtg gaaagataat   2160
aaaaataaga catgggaaat agggaaggtg ataacgtggg ggagaggttt tgcttgtgtt   2220
tcaccaggag aaaatcagct tcctgtttgg ttacccacta gacatttgaa gttctacaat   2280
gaacccatcg gagatgcaaa gaaaagggcc tccacggaga tggtaacacc agtcacatgg   2340
atggataatc ctatagaagt atatgttaat gatagtatat gggtacctgg ccccatagat   2400
gatcgctgcc ctgccaaacc tgaggaagaa gggatgatga taaatatttc cattgggtat   2460
cgttatcctc ctatttgcct agggagagca ccaggatgtt taatgcctgc agtccaaaat   2520
tggttggtag aagtacctac tgtcagtccc atcagtagat tcacttatca catggtaagc   2580
gggatgtcac tcaggccacg ggtaaattat ttacaagact tttcttatca aagatcatta   2640
aaatttagac ctaaagggaa accttgcccc aaggaaattc ccaaagaatc aaaaaataca   2700
gaagttttag tttgggaaga atgtgtggcc aatagtgcgg tgatattata aaacaatgaa   2760
tttggaacta ttatagattg ggcacctcga ggtcaattct accacaattg ctcaggacaa   2820
actcagtcgt gtccaagtgc acaagtgagt ccagctgttg atagcgactt aacagaaagt   2880
ttagacaaac ataagcataa aaaattgcag tctttctacc cttgggaatg gggagaaaaa   2940
ggaatctcta ccccaagacc aaaaatagta agtcctgttt ctggtcctga acatccagaa   3000
ttatggaggc ttactgtggc ctcacaccac attagaattt ggtctggaaa tcaaacttta   3060
gaaacaagag attgtaagcc attttatact gtcgacctaa attccagtct aacagttcct   3120
ttacaaagtt gcgtaaagcc cccttatatg ctagttgtag gaaatatagt tattaaacca   3180
gactcccaga ctataacctg tgaaaattgt agattgctta cttgcattga ttcaactttt   3240
aattggcaac accgtattct gctggtgaga gcaagagagg gcgtgtggat ccctgtgtcc   3300
atggaccgac cgtgggaggc ctcaccatcc gtccatattt tgactgaagt attaaaaggt   3360
gttttaaata gatccaaaag attcattttt actttaattg cagtgattat gggattaatt   3420
gcagtcacag ctacggctgc tgtagcagga gttgcattgc actcttctgt tcagtcagta   3480
aactttgtta atgattggca aaagaattct acaagattgt ggaattcaca atctagtatt   3540
```

```
gatcaaaaat tggcaaatca aattaatgat cttagacaaa ctgtcatttg gatgggagac   3600
agactcatga gcttagaaca tcgtttccag ttacaatgtg actggaatac gtcagatttt   3660
tgtattacac cccaaattta taatgagtct gagcatcact gggacatggt tagacgccat   3720
ctacagggaa gagaagataa tctcacttta gacatttcca aattaaaaga acaaattttc   3780
gaagcatcaa aagcccattt aaatttggtg ccaggaactg aggcaattgc aggagttgct   3840
gatggcctcg caaatcttaa ccctgtcact tgggttaaga ccattggaag tacatcgatt   3900
ataaatctca tattaatcct tgtgtgcctg ttttgtctgt tgttagtctg caggtgtacc   3960
caacagctcc gaagagacag cgaccatcga gaacgggcca tgatgacgat ggcggttttg   4020
tcgaaaagaa aaggggaaa tgtggggaaa agcaagagag atcaaattgt tactgtgtct   4080
gtgtag                                                             4086
```

<210> SEQ ID NO 26
<211> LENGTH: 694
<212> TYPE: PRT
<213> ORGANISM: Human endogenous retrovirus, K family (HERV-K)

<400> SEQUENCE: 26

```
Met Gln Arg Lys Ala Pro Pro Arg Arg Arg His Arg Asn Arg Ala
1               5                   10                  15

Pro Leu Thr His Lys Met Asn Lys Met Val Thr Ser Glu Glu Gln Met
                20                  25                  30

Lys Leu Pro Ser Thr Lys Lys Ala Glu Pro Pro Thr Trp Ala Gln Leu
                35                  40                  45

Lys Lys Leu Thr Gln Leu Ala Thr Lys Tyr Leu Glu Asn Thr Lys Val
                50                  55                  60

Thr Gln Thr Pro Glu Ser Met Leu Leu Ala Ala Leu Met Ile Val Ser
65                  70                  75                  80

Met Val Val Ser Leu Pro Met Pro Ala Gly Ala Ala Ala Ala Asn Tyr
                85                  90                  95

Thr Tyr Trp Ala Tyr Val Pro Phe Pro Pro Leu Ile Arg Ala Val Thr
                100                 105                 110

Trp Met Asp Asn Pro Thr Glu Val Tyr Val Asn Asp Ser Val Trp Val
                115                 120                 125

Pro Gly Pro Ile Asp Asp Arg Cys Pro Ala Lys Pro Glu Glu Glu Gly
                130                 135                 140

Met Met Ile Asn Ile Ser Ile Gly Tyr His Tyr Pro Pro Ile Cys Leu
145                 150                 155                 160

Gly Arg Ala Pro Gly Cys Leu Met Pro Ala Val Gln Asn Trp Leu Val
                165                 170                 175

Glu Val Pro Thr Val Ser Pro Ile Cys Arg Phe Thr Tyr His Met Val
                180                 185                 190

Ser Gly Met Ser Leu Arg Pro Arg Val Asn Tyr Leu Gln Asp Phe Ser
                195                 200                 205

Tyr Gln Arg Ser Leu Lys Phe Arg Pro Lys Gly Lys Pro Cys Pro Lys
                210                 215                 220

Glu Ile Pro Lys Glu Ser Lys Asn Thr Glu Val Leu Val Trp Glu Glu
225                 230                 235                 240

Cys Val Ala Asn Ser Ala Val Ile Leu Gln Asn Asn Glu Phe Gly Thr
                245                 250                 255

Ile Ile Asp Trp Ala Pro Arg Gly Gln Phe Tyr His Asn Cys Ser Gly
                260                 265                 270
```

```
Gln Thr Gln Ser Cys Gln Ser Ala Gln Val Ser Pro Ala Val Asp Ser
        275                 280                 285

Asp Leu Thr Glu Ser Leu Asp Lys His Lys His Lys Lys Leu Gln Ser
    290                 295                 300

Phe Tyr Pro Trp Glu Trp Gly Glu Lys Gly Ile Ser Thr Pro Arg Pro
305                 310                 315                 320

Lys Ile Val Ser Pro Val Ser Gly Pro Glu His Pro Glu Leu Trp Arg
                325                 330                 335

Leu Thr Val Ala Ser His His Ile Arg Ile Trp Ser Gly Asn Gln Thr
                340                 345                 350

Leu Glu Thr Arg Asp Arg Lys Pro Phe Tyr Thr Ile Asp Leu Asn Ser
        355                 360                 365

Ser Leu Thr Val Pro Leu Gln Ser Cys Val Lys Pro Pro Tyr Met Leu
    370                 375                 380

Val Val Gly Asn Ile Val Ile Lys Pro Asp Ser Gln Thr Ile Thr Cys
385                 390                 395                 400

Glu Asn Cys Arg Leu Leu Thr Cys Ile Asp Ser Thr Phe Asn Trp Gln
                405                 410                 415

His Arg Ile Leu Leu Val Arg Ala Arg Glu Gly Val Trp Ile Pro Val
                420                 425                 430

Ser Met Asp Arg Pro Trp Glu Ala Ser Pro Ser Val His Ile Leu Thr
                435                 440                 445

Glu Val Leu Lys Gly Val Leu Asn Arg Ser Lys Arg Phe Ile Phe Thr
    450                 455                 460

Leu Ile Ala Val Ile Met Gly Leu Ile Ala Val Thr Ala Thr Ala Ala
465                 470                 475                 480

Val Ala Gly Val Ala Leu His Ser Ser Val Gln Ser Val Asn Phe Val
                485                 490                 495

Asn Asp Trp Gln Lys Asn Ser Thr Arg Leu Trp Asn Ser Gln Ser Ser
                500                 505                 510

Ile Asp Gln Lys Leu Ala Asn Gln Ile Asn Asp Leu Arg Gln Thr Val
        515                 520                 525

Ile Trp Met Gly Asp Arg Leu Met Ser Leu Glu His Arg Phe Gln Leu
    530                 535                 540

Gln Cys Asp Trp Asn Thr Ser Asp Phe Cys Ile Thr Pro Gln Ile Tyr
545                 550                 555                 560

Asn Glu Ser Glu His His Trp Asp Met Val Arg Arg His Leu Gln Gly
                565                 570                 575

Arg Glu Asp Asn Leu Thr Leu Asp Ile Ser Lys Leu Lys Glu Gln Ile
                580                 585                 590

Phe Glu Ala Ser Lys Ala His Leu Asn Leu Val Pro Gly Thr Glu Ala
    595                 600                 605

Ile Ala Gly Val Ala Asp Gly Leu Ala Asn Leu Asn Pro Val Thr Trp
610                 615                 620

Val Lys Thr Ile Gly Ser Thr Thr Ile Ile Asn Leu Ile Leu Ile Leu
625                 630                 635                 640

Val Cys Leu Phe Cys Leu Leu Leu Val Cys Arg Cys Thr Gln Gln Leu
                645                 650                 655

Arg Arg Asp Ser Asp His Arg Glu Arg Ala Met Met Thr Met Ala Val
                660                 665                 670

Leu Ser Lys Arg Lys Gly Gly Asn Val Gly Lys Ser Lys Arg Asp Gln
    675                 680                 685

Ile Val Thr Val Ser Val
        690
```

<210> SEQ ID NO 27
<211> LENGTH: 1361
<212> TYPE: PRT
<213> ORGANISM: Human endogenous retrovirus, K family (HERV-K)
<220> FEATURE:
<221> NAME/KEY: SITE
<222> LOCATION: 917
<223> OTHER INFORMATION: Xaa is any amino acid

<400> SEQUENCE: 27

```
Met Gly Pro Leu Gln Pro Gly Leu Pro Ser Pro Ala Met Ile Pro Lys
1               5                   10                  15

Asp Trp Pro Leu Ile Ile Ile Asp Leu Lys Asp Cys Phe Phe Thr Ile
            20                  25                  30

Pro Leu Ala Glu Gln Asp Cys Glu Lys Phe Ala Phe Thr Ile Pro Ala
        35                  40                  45

Ile Asn Asn Lys Glu Pro Ala Thr Arg Phe Gln Trp Lys Val Leu Pro
50                  55                  60

Gln Gly Met Leu Asn Ser Pro Thr Ile Cys Gln Thr Phe Val Gly Arg
65                  70                  75                  80

Ala Leu Gln Pro Val Arg Glu Lys Phe Ser Asp Cys Tyr Ile Ile His
                85                  90                  95

Tyr Ile Asp Asp Ile Leu Cys Ala Ala Glu Thr Lys Asp Lys Leu Ile
            100                 105                 110

Asp Cys Tyr Thr Phe Leu Gln Ala Glu Val Ala Asn Ala Gly Leu Ala
        115                 120                 125

Ile Ala Ser Asp Lys Ile Gln Thr Ser Thr Pro Phe His Tyr Leu Gly
130                 135                 140

Met Gln Ile Glu Asn Arg Lys Ile Lys Pro Gln Lys Ile Glu Ile Arg
145                 150                 155                 160

Lys Asp Thr Leu Lys Thr Leu Asn Asp Phe Gln Lys Leu Leu Gly Asp
                165                 170                 175

Ile Asn Trp Ile Arg Pro Thr Leu Gly Ile Pro Thr Tyr Ala Met Ser
            180                 185                 190

Asn Leu Phe Ser Ile Leu Arg Gly Asp Ser Asp Leu Asn Ser Gln Arg
        195                 200                 205

Ile Leu Thr Pro Glu Ala Thr Lys Glu Ile Lys Leu Val Glu Glu Lys
210                 215                 220

Ile Gln Ser Ala Gln Ile Asn Arg Ile Asp Pro Leu Ala Pro Leu Gln
225                 230                 235                 240

Leu Leu Ile Phe Ala Thr Ala His Ser Pro Thr Gly Ile Ile Ile Gln
                245                 250                 255

Asn Thr Asp Leu Val Glu Trp Ser Phe Leu Pro His Ser Thr Val Lys
            260                 265                 270

Thr Phe Thr Leu Tyr Leu Asp Gln Ile Ala Thr Leu Ile Gly Gln Thr
        275                 280                 285

Arg Leu Arg Ile Thr Lys Leu Cys Gly Asn Asp Pro Asp Lys Ile Val
290                 295                 300

Val Pro Leu Thr Lys Glu Gln Val Arg Gln Ala Phe Ile Asn Ser Gly
305                 310                 315                 320

Ala Trp Gln Ile Gly Leu Ala Asn Phe Val Gly Leu Ile Asp Asn His
                325                 330                 335

Tyr Pro Lys Thr Lys Ile Phe Gln Phe Leu Lys Leu Thr Thr Trp Ile
            340                 345                 350

Leu Pro Lys Ile Thr Arg Arg Glu Pro Leu Glu Asn Ala Leu Thr Val
```

```
                355                 360                 365
Phe Thr Asp Gly Ser Ser Asn Gly Lys Ala Ala Tyr Thr Gly Pro Lys
370                 375                 380

Glu Arg Val Ile Lys Thr Pro Tyr Gln Ser Ala Gln Arg Asp Glu Leu
385                 390                 395                 400

Val Ala Val Ile Thr Val Leu Gln Asp Phe Asp Gln Pro Ile Asn Ile
                405                 410                 415

Ile Ser Asp Ser Ala Tyr Val Val Gln Ala Thr Arg Asp Val Glu Thr
                420                 425                 430

Ala Leu Ile Lys Tyr Ser Met Asp Asp Gln Leu Asn Gln Leu Phe Asn
                435                 440                 445

Leu Leu Gln Gln Thr Val Arg Lys Arg Asn Phe Pro Phe Tyr Ile Thr
450                 455                 460

Tyr Ile Arg Ala His Thr Asn Leu Pro Gly Pro Leu Thr Lys Ala Asn
465                 470                 475                 480

Glu Gln Ala Asp Leu Leu Val Ser Ser Ala Leu Ile Lys Ala Gln Glu
                485                 490                 495

Leu His Ala Leu Thr His Val Asn Ala Ala Gly Leu Lys Asn Lys Phe
                500                 505                 510

Asp Val Thr Trp Lys Gln Ala Lys Asp Ile Val Gln His Cys Thr Gln
                515                 520                 525

Cys Gln Val Leu His Leu Pro Thr Gln Glu Ala Gly Val Asn Pro Arg
530                 535                 540

Gly Leu Cys Pro Asn Ala Leu Trp Gln Met Asp Val Thr His Val Pro
545                 550                 555                 560

Ser Phe Gly Arg Leu Ser Tyr Val His Val Thr Val Asp Thr Tyr Ser
                565                 570                 575

His Phe Ile Trp Ala Thr Cys Gln Thr Gly Glu Ser Thr Ser His Val
                580                 585                 590

Lys Lys His Leu Leu Ser Cys Phe Ala Val Met Gly Val Pro Glu Lys
                595                 600                 605

Ile Lys Thr Asp Asn Gly Pro Gly Tyr Cys Ser Lys Ala Phe Gln Lys
610                 615                 620

Phe Leu Ser Gln Trp Lys Ile Ser His Thr Thr Gly Ile Pro Tyr Asn
625                 630                 635                 640

Ser Gln Gly Gln Ala Ile Val Glu Arg Thr Asn Arg Thr Leu Lys Thr
                645                 650                 655

Gln Leu Val Lys Gln Lys Glu Gly Gly Asp Ser Lys Glu Cys Thr Thr
                660                 665                 670

Pro Gln Met Gln Leu Asn Leu Ala Leu Tyr Thr Leu Asn Phe Leu Asn
                675                 680                 685

Ile Tyr Arg Asn Gln Thr Thr Thr Ser Ala Glu Gln His Leu Thr Gly
690                 695                 700

Lys Lys Asn Ser Pro His Glu Gly Lys Leu Ile Trp Trp Lys Asp Asn
705                 710                 715                 720

Lys Asn Lys Thr Trp Glu Ile Gly Lys Val Ile Thr Trp Gly Arg Gly
                725                 730                 735

Phe Ala Cys Val Ser Pro Gly Glu Asn Gln Leu Pro Val Trp Leu Pro
                740                 745                 750

Thr Arg His Leu Lys Phe Tyr Asn Glu Pro Ile Gly Asp Ala Lys Lys
                755                 760                 765

Arg Ala Ser Thr Glu Met Val Thr Pro Val Thr Trp Met Asp Asn Pro
770                 775                 780
```

```
Ile Glu Val Tyr Val Asn Asp Ser Ile Trp Val Pro Gly Pro Ile Asp
785                 790                 795                 800

Asp Arg Cys Pro Ala Lys Pro Glu Glu Gly Met Met Ile Asn Ile
            805                 810                 815

Ser Ile Gly Tyr Arg Tyr Pro Pro Ile Cys Leu Gly Arg Ala Pro Gly
                820                 825                 830

Cys Leu Met Pro Ala Val Gln Asn Trp Leu Val Glu Val Pro Thr Val
        835                 840                 845

Ser Pro Ile Ser Arg Phe Thr Tyr His Met Val Ser Gly Met Ser Leu
    850                 855                 860

Arg Pro Arg Val Asn Tyr Leu Gln Asp Phe Ser Tyr Gln Arg Ser Leu
865                 870                 875                 880

Lys Phe Arg Pro Lys Gly Lys Pro Cys Pro Lys Glu Ile Pro Lys Glu
                885                 890                 895

Ser Lys Asn Thr Glu Val Leu Val Trp Glu Glu Cys Val Ala Asn Ser
            900                 905                 910

Ala Val Ile Leu Xaa Asn Asn Glu Phe Gly Thr Ile Asp Trp Ala
        915                 920                 925

Pro Arg Gly Gln Phe Tyr His Asn Cys Ser Gly Gln Thr Gln Ser Cys
    930                 935                 940

Pro Ser Ala Gln Val Ser Pro Ala Val Asp Ser Asp Leu Thr Glu Ser
945                 950                 955                 960

Leu Asp Lys His Lys His Lys Lys Leu Gln Ser Phe Tyr Pro Trp Glu
                965                 970                 975

Trp Gly Glu Lys Gly Ile Ser Thr Pro Arg Pro Lys Ile Val Ser Pro
            980                 985                 990

Val Ser Gly Pro Glu His Pro Glu Leu Trp Arg Leu Thr Val Ala Ser
        995                 1000                1005

His His Ile Arg Ile Trp Ser Gly Asn Gln Thr Leu Glu Thr Arg Asp
    1010                1015                1020

Cys Lys Pro Phe Tyr Thr Val Asp Leu Asn Ser Ser Leu Thr Val Pro
1025                1030                1035                1040

Leu Gln Ser Cys Val Lys Pro Pro Tyr Met Leu Val Val Gly Asn Ile
                1045                1050                1055

Val Ile Lys Pro Asp Ser Gln Thr Ile Thr Cys Glu Asn Cys Arg Leu
            1060                1065                1070

Leu Thr Cys Ile Asp Ser Thr Phe Asn Trp Gln His Arg Ile Leu Leu
        1075                1080                1085

Val Arg Ala Arg Glu Gly Val Trp Ile Pro Val Ser Met Asp Arg Pro
    1090                1095                1100

Trp Glu Ala Ser Pro Ser Val His Ile Leu Thr Glu Val Leu Lys Gly
1105                1110                1115                1120

Val Leu Asn Arg Ser Lys Arg Phe Ile Phe Thr Leu Ile Ala Val Ile
                1125                1130                1135

Met Gly Leu Ile Ala Val Thr Ala Thr Ala Ala Val Ala Gly Val Ala
            1140                1145                1150

Leu His Ser Ser Val Gln Ser Val Asn Phe Val Asn Asp Trp Gln Lys
        1155                1160                1165

Asn Ser Thr Arg Leu Trp Asn Ser Gln Ser Ser Ile Asp Gln Lys Leu
    1170                1175                1180

Ala Asn Gln Ile Asn Asp Leu Arg Gln Thr Val Ile Trp Met Gly Asp
1185                1190                1195                1200

Arg Leu Met Ser Leu Glu His Arg Phe Gln Leu Gln Cys Asp Trp Asn
                1205                1210                1215
```

```
Thr Ser Asp Phe Cys Ile Thr Pro Gln Ile Tyr Asn Glu Ser Glu His
        1220                1225                1230

His Trp Asp Met Val Arg Arg His Leu Gln Gly Arg Glu Asp Asn Leu
        1235                1240                1245

Thr Leu Asp Ile Ser Lys Leu Lys Glu Gln Ile Phe Glu Ala Ser Lys
        1250                1255                1260

Ala His Leu Asn Leu Val Pro Gly Thr Glu Ala Ile Ala Gly Val Ala
1265                1270                1275                1280

Asp Gly Leu Ala Asn Leu Asn Pro Val Thr Trp Val Lys Thr Ile Gly
                1285                1290                1295

Ser Thr Ser Ile Ile Asn Leu Ile Leu Ile Leu Val Cys Leu Phe Cys
                1300                1305                1310

Leu Leu Leu Val Cys Arg Cys Thr Gln Gln Leu Arg Arg Asp Ser Asp
            1315                1320                1325

His Arg Glu Arg Ala Met Met Thr Met Ala Val Leu Ser Lys Arg Lys
        1330                1335                1340

Gly Gly Asn Val Gly Lys Ser Lys Arg Asp Gln Ile Val Thr Val Ser
1345                1350                1355                1360

Val

<210> SEQ ID NO 28
<211> LENGTH: 699
<212> TYPE: PRT
<213> ORGANISM: Human endogenous retrovirus, K family (HERV-K)

<400> SEQUENCE: 28

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
        50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Thr Glu Val Tyr Val Asn
        115                 120                 125

Asp Ser Val Trp Val Pro Gly Pro Ile Asp Asp Arg Cys Pro Ala Lys
    130                 135                 140

Pro Glu Glu Glu Gly Met Met Ile Asn Ile Ser Ile Gly Tyr His Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Cys Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220
```

```
Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
            245                 250                 255

Asn Glu Phe Gly Thr Ile Ile Asp Trp Ala Pro Arg Gly Gln Phe Tyr
        260                 265                 270

His Asn Cys Ser Gly Gln Thr Gln Ser Cys Pro Ser Ala Gln Val Ser
    275                 280                 285

Pro Ala Val Asp Ser Asp Leu Thr Glu Ser Leu Asp Lys His Lys His
290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Val Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Ile Asp Leu Asn Ser Ser Leu Thr Val Pro Leu Gln Ser Cys Val Lys
370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
        435                 440                 445

Val His Ile Leu Thr Glu Val Leu Lys Gly Val Leu Asn Arg Ser Lys
    450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
                485                 490                 495

Ser Val Asn Phe Val Asn Asp Trp Gln Lys Asn Ser Thr Arg Leu Trp
            500                 505                 510

Asn Ser Gln Ser Ser Ile Asp Gln Lys Leu Ala Asn Gln Ile Asn Asp
        515                 520                 525

Leu Arg Gln Thr Val Ile Trp Met Gly Asp Arg Leu Met Ser Leu Glu
530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
                565                 570                 575

Arg His Leu Gln Gly Arg Glu Asp Asn Leu Thr Leu Asp Ile Ser Lys
            580                 585                 590

Leu Lys Glu Gln Ile Phe Glu Ala Ser Lys Ala His Leu Asn Leu Val
        595                 600                 605

Pro Gly Thr Glu Ala Ile Ala Gly Val Ala Asp Gly Leu Ala Asn Leu
610                 615                 620

Asn Pro Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Cys Arg
                645                 650                 655
```

```
Cys Thr Gln Gln Leu Arg Arg Asp Ser Asp His Arg Glu Arg Ala Met
            660                 665                 670
Met Thr Met Ala Val Leu Ser Lys Arg Lys Gly Gly Asn Val Gly Lys
        675                 680                 685
Ser Lys Arg Asp Gln Ile Val Thr Val Ser Val
        690                 695
```

```
<210> SEQ ID NO 29
<211> LENGTH: 294
<212> TYPE: DNA
<213> ORGANISM: Human endogenous retrovirus, K family (HERV-K)

<400> SEQUENCE: 29
agttctacaa tgaacccatc agagatgcaa agaaaagcac ctccgcggag acggagacat      60
cgcaatcgag caccgttgac tcacaagatg aacaaaatgg tgacgtcaga agaacagatg     120
aagttgccat ccaccaagaa ggcagagccg ccaacttggg cacaactaaa gaagctgacg     180
cagttagcta caaatatct agagaacaca aaggtgacac aaaccccaga gagtatgctg     240
cttgcagcct tgatgattgt atcaatggtg gtaagtctcc ctatgcctgc agga           294

<210> SEQ ID NO 30
<211> LENGTH: 57
<212> TYPE: DNA
<213> ORGANISM: Human endogenous retrovirus, K family (HERV-K)

<400> SEQUENCE: 30
tctgcaggtg tacccaacag ctccgaagag acagcgacca tcgagaacgg gccatga        57

<210> SEQ ID NO 31
<211> LENGTH: 105
<212> TYPE: PRT
<213> ORGANISM: Human endogenous retrovirus, K family (HERV-K)

<400> SEQUENCE: 31

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Gly Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Ser Ala Gly Val Pro Asn Ser Ser Glu
                85                  90                  95

Glu Thr Ala Thr Ile Glu Asn Gly Pro
            100                 105

<210> SEQ ID NO 32
<211> LENGTH: 86
<212> TYPE: PRT
<213> ORGANISM: Human endogenous retrovirus, K family (HERV-K)

<400> SEQUENCE: 32

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30
```

```
Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
 50                  55                  60

Glu Asn Thr Lys Ser Ala Gly Val Pro Asn Ser Ser Glu Glu Thr Ala
 65                  70                  75                  80

Thr Ile Glu Asn Gly Pro
                85

<210> SEQ ID NO 33
<211> LENGTH: 74
<212> TYPE: PRT
<213> ORGANISM: Human endogenous retrovirus, K family (HERV-K)

<400> SEQUENCE: 33

Met Asn Pro Ser Glu Met Gln Arg Lys Gly Pro Pro Gln Arg Cys Leu
 1               5                  10                  15

Gln Val Tyr Pro Thr Ala Pro Lys Arg Gln Arg Pro Ser Arg Thr Gly
            20                  25                  30

His Asp Asp Gly Gly Phe Val Glu Lys Lys Arg Gly Lys Cys Gly
            35                  40                  45

Glu Lys Gln Glu Arg Ser Asp Cys Tyr Cys Val Cys Val Glu Arg Ser
 50                  55                  60

Arg His Arg Arg Leu His Phe Val Leu Tyr
 65                  70

<210> SEQ ID NO 34
<211> LENGTH: 79
<212> TYPE: PRT
<213> ORGANISM: Human endogenous retrovirus, K family (HERV-K)

<400> SEQUENCE: 34

Met Asn Ser Leu Glu Met Gln Arg Lys Val Trp Arg Trp Arg His Pro
 1               5                  10                  15

Asn Arg Leu Ala Ser Leu Gln Val Tyr Pro Ala Ala Pro Lys Arg Gln
            20                  25                  30

Gln Pro Ala Arg Met Gly His Ser Asp Asp Gly Gly Phe Val Lys Lys
            35                  40                  45

Lys Arg Gly Gly Tyr Val Arg Lys Arg Glu Ile Arg Leu Ser Leu Cys
 50                  55                  60

Leu Cys Arg Lys Gly Arg His Lys Lys Leu His Phe Val Leu Tyr
 65                  70                  75

<210> SEQ ID NO 35
<211> LENGTH: 129
<212> TYPE: PRT
<213> ORGANISM: Human endogenous retrovirus, K family (HERV-K)

<400> SEQUENCE: 35

Met Asn Pro Ser Glu Met Gln Arg Lys Ala Pro Pro Arg Arg Arg Arg
 1               5                  10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
 50                  55                  60

Glu Asn Thr Lys Val Ile Leu Gln Val Tyr Pro Thr Ala Pro Lys Arg
```

```
                65                  70                  75                  80
Gln Arg Pro Ser Arg Thr Gly His Asp Asp Gly Gly Phe Val Glu
                    85                  90                  95
Lys Lys Arg Gly Lys Cys Gly Glu Lys Gln Glu Arg Ser Asp Cys Tyr
                    100                 105                 110
Cys Val Cys Val Glu Arg Ser Arg His Arg Arg Leu His Phe Val Leu
                    115                 120                 125
Tyr

<210> SEQ ID NO 36
<211> LENGTH: 125
<212> TYPE: PRT
<213> ORGANISM: Human endogenous retrovirus, K family (HERV-K)

<400> SEQUENCE: 36

Met Asn Pro Ser Glu Met Gln Arg Lys Ala Pro Pro Arg Arg Arg Arg
1               5                   10                  15
His Arg Asn Arg Ala Pro Leu Thr His Lys Met Asn Lys Met Val Thr
                    20                  25                  30
Ser Glu Glu Gln Met Lys Leu Pro Ser Thr Lys Lys Ala Glu Pro Pro
                    35                  40                  45
Thr Trp Ala Gln Leu Lys Lys Leu Thr Gln Leu Ala Thr Lys Tyr Leu
                    50                  55                  60
Glu Asn Thr Lys Val Tyr Pro Thr Ala Pro Lys Arg Gln Arg Pro Ser
65                  70                  75                  80
Arg Thr Gly His Asp Asp Gly Gly Phe Val Glu Lys Lys Arg Gly
                    85                  90                  95
Lys Cys Gly Glu Lys Gln Glu Arg Ser Asp Cys Tyr Cys Val Cys Val
                    100                 105                 110
Glu Arg Ser Arg His Arg Arg Leu His Phe Val Leu Tyr
                    115                 120                 125

<210> SEQ ID NO 37
<211> LENGTH: 144
<212> TYPE: PRT
<213> ORGANISM: Human endogenous retrovirus, K family (HERV-K)

<400> SEQUENCE: 37

Met Asn Pro Ser Glu Met Gln Arg Lys Ala Pro Pro Arg Arg Arg Arg
1               5                   10                  15
His Arg Asn Arg Ala Pro Leu Thr His Lys Met Asn Lys Met Val Thr
                    20                  25                  30
Ser Glu Glu Gln Met Lys Leu Pro Ser Thr Lys Lys Ala Glu Pro Pro
                    35                  40                  45
Thr Trp Ala Gln Leu Lys Lys Leu Thr Gln Leu Ala Thr Lys Tyr Leu
                    50                  55                  60
Glu Asn Thr Lys Val Thr Gln Thr Pro Glu Ser Met Leu Leu Ala Ala
65                  70                  75                  80
Leu Met Ile Val Ser Met Val Val Tyr Pro Thr Ala Pro Lys Arg Gln
                    85                  90                  95
Arg Pro Ser Arg Thr Gly His Asp Asp Gly Gly Phe Val Glu Lys
                    100                 105                 110
Lys Arg Gly Lys Cys Gly Glu Lys Gln Glu Arg Ser Asp Cys Tyr Cys
                    115                 120                 125
Val Cys Val Glu Arg Ser Arg His Arg Arg Leu His Phe Val Leu Tyr
                    130                 135                 140
```

-continued

<210> SEQ ID NO 38
<211> LENGTH: 74
<212> TYPE: PRT
<213> ORGANISM: Human endogenous retrovirus, K family (HERV-K)

<400> SEQUENCE: 38

Met Asn Pro Ser Glu Met Gln Arg Lys Gly Pro Pro Gln Arg Cys Leu
1               5                   10                  15

Gln Val Tyr Pro Thr Ala Pro Lys Arg Gln Arg Pro Ser Arg Thr Gly
            20                  25                  30

His Asp Asp Asp Gly Gly Phe Val Glu Lys Lys Arg Gly Lys Cys Gly
        35                  40                  45

Glu Lys Gln Glu Arg Ser Asp Cys Tyr Cys Val Cys Val Glu Arg Ser
    50                  55                  60

Arg His Arg Arg Leu His Phe Val Leu Tyr
65                  70

<210> SEQ ID NO 39
<211> LENGTH: 74
<212> TYPE: PRT
<213> ORGANISM: Human endogenous retrovirus, K family (HERV-K)

<400> SEQUENCE: 39

Met Asn Pro Ser Glu Met Gln Arg Lys Gly Pro Pro Gln Arg Cys Leu
1               5                   10                  15

Gln Val Tyr Pro Thr Ala Pro Lys Arg Gln Arg Pro Ser Arg Thr Gly
            20                  25                  30

His Asp Asp Asp Gly Gly Phe Val Glu Lys Lys Arg Gly Lys Cys Gly
        35                  40                  45

Glu Lys Gln Glu Arg Ser Asp Cys Tyr Cys Val Cys Val Glu Arg Ser
    50                  55                  60

Arg His Arg Arg Leu His Phe Val Leu Tyr
65                  70

<210> SEQ ID NO 40
<211> LENGTH: 44
<212> TYPE: PRT
<213> ORGANISM: Human endogenous retrovirus, K family (HERV-K)

<400> SEQUENCE: 40

Met Glu Tyr Lys Asn Arg His Leu Lys Phe Tyr Asn Glu Pro Ile Gly
1               5                   10                  15

Asp Ala Lys Lys Arg Ala Ser Thr Glu Met Ser Ala Gly Val Pro Asn
            20                  25                  30

Ser Ser Glu Glu Thr Ala Thr Ile Glu Asn Gly Pro
        35                  40

<210> SEQ ID NO 41
<211> LENGTH: 74
<212> TYPE: PRT
<213> ORGANISM: Human endogenous retrovirus, K family (HERV-K)

<400> SEQUENCE: 41

Met Asn Pro Ser Glu Met Gln Arg Lys Gly Pro Pro Gln Arg Cys Leu
1               5                   10                  15

Gln Val Tyr Pro Thr Ala Pro Lys Arg Gln Arg Pro Ser Arg Thr Gly
            20                  25                  30

His Asp Asp Asp Gly Gly Phe Val Glu Lys Lys Arg Gly Lys Cys Gly
        35                  40                  45

Glu Lys Gln Glu Arg Ser Asp Cys Tyr Cys Val Cys Val Glu Arg Ser
50                  55                  60

Arg His Arg Arg Leu His Phe Val Leu Tyr
65                  70

<210> SEQ ID NO 42
<211> LENGTH: 86
<212> TYPE: PRT
<213> ORGANISM: Human endogenous retrovirus, K family (HERV-K)

<400> SEQUENCE: 42

Met Asn Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
        50                  55                  60

Glu Asn Thr Lys Ser Ala Gly Val Pro Asn Ser Ser Glu Glu Thr Ala
65                  70                  75                  80

Thr Ile Glu Asn Gly Pro
                85

<210> SEQ ID NO 43
<211> LENGTH: 105
<212> TYPE: PRT
<213> ORGANISM: Human endogenous retrovirus, K family (HERV-K)

<400> SEQUENCE: 43

Met Asn Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
        50                  55                  60

Glu Asn Thr Lys Val Thr Gln Thr Pro Glu Ser Met Leu Leu Ala Ala
65                  70                  75                  80

Leu Met Ile Val Ser Met Val Ser Ala Gly Val Pro Asn Ser Ser Glu
                85                  90                  95

Glu Thr Ala Thr Ile Glu Asn Gly Pro
            100                 105

<210> SEQ ID NO 44
<211> LENGTH: 127
<212> TYPE: PRT
<213> ORGANISM: Human endogenous retrovirus, K family (HERV-K)

<400> SEQUENCE: 44

Met Val Thr Pro Val Thr Trp Met Asp Asn Pro Ile Glu Val Tyr Val
1               5                   10                  15

Asn Asp Ser Val Trp Val Pro Gly Pro Thr Asp Asp Arg Cys Pro Ala
                20                  25                  30

Lys Pro Glu Glu Glu Gly Met Met Ile Asn Ile Ser Ile Val Tyr Arg
            35                  40                  45

Tyr Pro Pro Ile Cys Leu Gly Arg Ala Pro Gly Cys Leu Met Pro Ala
        50                  55                  60

```
Val Gln Asn Cys Leu Gln Val Tyr Pro Thr Ala Pro Lys Arg Gln Arg
 65                  70                  75                  80

Pro Ser Arg Thr Gly His Asp Asp Gly Gly Phe Val Glu Lys Lys
                 85                  90                  95

Arg Gly Lys Cys Gly Glu Lys Gln Glu Arg Ser Asp Cys Tyr Cys Val
            100                 105                 110

Cys Val Glu Arg Ser Arg His Arg Arg Leu His Phe Val Leu Tyr
        115                 120                 125
```

<210> SEQ ID NO 45
<211> LENGTH: 105
<212> TYPE: PRT
<213> ORGANISM: Human endogenous retrovirus, K family (HERV-K)

<400> SEQUENCE: 45

```
Met Val Thr Pro Val Thr Trp Met Asp Asn Pro Ile Glu Val Tyr Val
 1               5                  10                  15

Asn Asp Ser Glu Trp Val Pro Gly Pro Thr Asp Asp Arg Cys Pro Ala
                20                  25                  30

Lys Pro Glu Glu Glu Gly Met Met Ile Asn Ile Ser Ile Gly Leu Gln
            35                  40                  45

Val Tyr Pro Thr Ala Pro Lys Arg Gln Arg Pro Ser Arg Thr Gly His
        50                  55                  60

Asp Asp Gly Gly Phe Val Glu Lys Lys Arg Gly Lys Cys Gly Glu
 65                 70                  75                  80

Lys Gln Glu Arg Ser Asp Cys Tyr Cys Val Cys Val Glu Arg Ser Arg
                85                  90                  95

His Arg Arg Leu His Phe Val Met Cys
            100                 105
```

<210> SEQ ID NO 46
<211> LENGTH: 79
<212> TYPE: PRT
<213> ORGANISM: Human endogenous retrovirus, K family (HERV-K)

<400> SEQUENCE: 46

```
Met Asn Ser Leu Glu Met Gln Arg Lys Val Trp Arg Trp Arg His Pro
 1               5                  10                  15

Asn Arg Leu Ala Ser Leu Gln Val Tyr Pro Ala Ala Pro Lys Arg Gln
                20                  25                  30

Gln Pro Ala Arg Met Gly His Ser Asp Asp Gly Gly Phe Val Lys Lys
            35                  40                  45

Lys Arg Gly Gly Tyr Val Arg Lys Arg Glu Ile Arg Leu Ser Leu Cys
        50                  55                  60

Leu Cys Arg Lys Gly Arg His Lys Lys Leu His Phe Asp Leu Tyr
 65                 70                  75
```

<210> SEQ ID NO 47
<211> LENGTH: 214
<212> TYPE: PRT
<213> ORGANISM: Human endogenous retrovirus, K family (HERV-K)

<400> SEQUENCE: 47

```
Met Asn Ser Leu Glu Met Gln Arg Lys Ala Pro Pro Arg Arg Arg
 1               5                  10                  15

His Arg Asn Arg Ala Pro Leu Thr His Lys Met Asn Lys Met Val Thr
                20                  25                  30

Ser Glu Glu Gln Met Lys Leu Ser Ser Thr Lys Lys Ala Glu Pro Pro
```

```
                    35                  40                  45
Thr Trp Ala Gln Leu Lys Lys Leu Thr Gln Leu Ala Thr Lys Tyr Leu
 50                  55                  60

Glu Asn Thr Lys Val Thr Gln Thr Pro Glu Ser Met Leu Leu Ala Ala
 65                  70                  75                  80

Leu Met Ile Val Ser Met Val Ser Leu Pro Met Pro Ala Gly Ala
                     85                  90                  95

Ala Ala Ala Asn Tyr Thr Tyr Trp Ala Tyr Val Pro Phe Pro Pro Leu
                100                 105                 110

Ile Arg Ala Val Thr Trp Met Asp Asn Pro Thr Glu Val Tyr Val Asn
                115                 120                 125

Asp Ser Val Trp Val Pro Gly Pro Ile Asp Asp Arg Cys Pro Ala Lys
                130                 135                 140

Pro Glu Glu Glu Gly Met Met Ile Asn Ile Ser Ile Gly Tyr His Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Cys Arg Phe
                180                 185                 190

Thr Tyr His Met Ser Ala Gly Val Pro Asn Ser Ser Glu Glu Thr Ala
                195                 200                 205

Thr Ile Glu Asn Gly Pro
    210

<210> SEQ ID NO 48
<211> LENGTH: 129
<212> TYPE: PRT
<213> ORGANISM: Human endogenous retrovirus, K family (HERV-K)

<400> SEQUENCE: 48

Met Asn Pro Ser Glu Met Gln Arg Lys Ala Pro Pro Arg Arg Arg Arg
 1               5                  10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
                35                  40                  45

Thr Trp Ala Gln Leu Lys Lys Leu Thr Gln Leu Ala Thr Lys Tyr Leu
 50                  55                  60

Glu Asn Thr Lys Val Thr Leu Gln Val Tyr Pro Thr Ala Pro Lys Arg
 65                  70                  75                  80

Gln Arg Pro Ser Arg Thr Gly His Asp Asp Asp Gly Gly Phe Val Glu
                 85                  90                  95

Lys Lys Arg Gly Lys Cys Gly Glu Lys Gln Glu Arg Ser Asp Cys Tyr
                100                 105                 110

Cys Val Cys Val Glu Arg Ser Arg His Arg Arg Leu His Phe Val Met
                115                 120                 125

Tyr

<210> SEQ ID NO 49
<211> LENGTH: 125
<212> TYPE: PRT
<213> ORGANISM: Human endogenous retrovirus, K family (HERV-K)

<400> SEQUENCE: 49

Met Asn Pro Ser Glu Met Gln Arg Lys Ala Pro Pro Arg Arg Arg Arg
 1               5                  10                  15
```

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
 50                  55                  60

Glu Asn Thr Lys Val Tyr Pro Thr Ala Pro Lys Arg Gln Arg Pro Ser
65                  70                  75                  80

Arg Thr Gly His Asp Asp Gly Gly Phe Val Glu Lys Lys Arg Gly
                85                  90                  95

Lys Cys Gly Glu Lys Gln Glu Ser Asp Cys Tyr Cys Val Cys Val
            100                 105                 110

Glu Arg Ser Arg His Arg Arg Leu His Phe Val Met Tyr
        115                 120                 125

<210> SEQ ID NO 50
<211> LENGTH: 145
<212> TYPE: PRT
<213> ORGANISM: Human endogenous retrovirus, K family (HERV-K)
<220> FEATURE:
<221> NAME/KEY: SITE
<222> LOCATION: 64
<223> OTHER INFORMATION: Xaa is any amino acid

<400> SEQUENCE: 50

Met Asn Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Xaa
 50                  55                  60

Leu Glu Asn Thr Lys Val Thr Gln Thr Pro Glu Ser Met Leu Leu Ala
65                  70                  75                  80

Ala Leu Met Ile Val Ser Met Val Val Tyr Pro Thr Ala Pro Lys Arg
            85                  90                  95

Gln Arg Pro Ser Arg Thr Gly His Asp Asp Gly Gly Phe Val Glu
        100                 105                 110

Lys Lys Arg Gly Lys Cys Gly Glu Lys Gln Glu Arg Ser Asp Cys Tyr
    115                 120                 125

Cys Val Cys Val Glu Arg Ser Arg His Arg Arg Leu His Phe Val Met
130                 135                 140

Tyr
145

<210> SEQ ID NO 51
<211> LENGTH: 4657
<212> TYPE: DNA
<213> ORGANISM: Artificial Sequence
<220> FEATURE:
<223> OTHER INFORMATION: pCMVKm2.cORFopt HML-2 vector

<400> SEQUENCE: 51
gccgcggaat tcgactcta ggccattgca tacgttgtat ctatatcata atatgtacat      60
ttatattggc tcatgtccaa tatgaccgcc atgttgacat tgattattga ctagttatta   120
atagtaatca attacggggt cattagttca tagcccatat atggagttcc gcgttacata   180
acttacggta aatggcccgc ctggctgacc gcccaacgac ccccgcccat tgacgtcaat   240

```
aatgacgtat gttcccatag taacgccaat agggactttc cattgacgtc aatgggtgga    300
gtatttacgg taaactgccc acttggcagt acatcaagtg tatcatatgc caagtccgcc    360
ccctattgac gtcaatgacg gtaaatggcc cgcctggcat tatgcccagt acatgacctt    420
acgggacttt cctacttggc agtacatcta cgtattagtc atcgctatta ccatggtgat    480
gcggttttgg cagtacacca atgggcgtgg atagcggttt gactcacggg gatttccaag    540
tctccacccc attgacgtca atgggagttt gttttggcac caaaatcaac gggactttcc    600
aaaatgtcgt aataacccg ccccgttgac gcaaatgggc ggtaggcgtg tacggtggga    660
ggtctatata agcagagctc gtttagtgaa ccgtcagatc gcctggagac gccatccacg    720
ctgttttgac ctccatagaa gacaccggga ccgatccagc ctccgcggcc gggaacggtg    780
cattggaacg cggattcccc gtgccaagag tgacgtaagt accgcctata gactctatag    840
gcacacccct ttggctctta tgcatgctat actgttttg cttggggcc tatacacccc    900 cgcttcctta tgctataggt gatggtatag cttagcctat aggtgtgggt tattgaccat    960
tattgaccac tcccctattg gtgacgatac tttccattac taatccataa catggctctt   1020
tgccacaact atctctattg ctatatgcc aatactctgt ccttcagaga ctgacacgga    1080
ctctgtattt ttacaggatg gggtcccatt tattatttac aaattcacat atacaacaac   1140
gccgtccccc gtgcccgcag ttttattaa acatagcgtg gatctccac gcgaatctcg   1200 ggtacgtgtt ccggacatgg gctcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccgtcgt cgacgccacc atgaacccca gcagatgca   1680 gcgcaaggcc ccccccgcc gccgccgcca ccgcaaccgc gccccctga cccacaagat   1740 gaacaagatg gtgaccagcg aggagcagat gaagctgccc agcaccaaga aggccgagcc   1800
ccccacctgg gccagctga agaagctgac ccagctggcc accaagtacc tggagaacac   1860
caaggtgacc cagacccccg agagcatgct gctggccgcc ctgatgatcg tgagcatggt   1920
gagcgccggc gtgcccaaca gcagcgagga gaccgccacc atcgagaacg ccccgctta   1980 aagaattcag actcgagcaa gtctagaaag ccatggatat cggatccact acgcgttaga   2040
gctcgctgat cagcctcgac tgtgccttct agttgccagc catctgttgt ttgccctcc   2100 cccgtgcctt ccttgaccct ggaaggtgcc actcccactg tccttcccta ataaaatgag   2160
gaaattgcat cgcattgtct gagtaggtgt cattctattc tggggggtgg ggtggggcag   2220
gacagcaagg gggaggattg ggaagacaat agcaggggggg tggcgaaga actccagcat   2280 gagatccccg cgctggagga tcatccagcc ggcgtcccgg aaaacgattc cgaagcccaa   2340
cctttcatag aaggcggcgg tggaatcgaa atctcgtgat ggcaggttgg gcgtcgcttg   2400
gtcggtcatt tcgaacccca gagtcccgct cagaagaact cgtcaagaag gcgatagaag   2460
gcgatgcgct gcgaatcggg agcggcgata ccgtaaagca cgaggaagcg gtcagcccat   2520
tcgccgccaa gctcttcagc aatatcacgg gtagccaacg ctatgtcctg atagcggtcc   2580
gccacaccca gccggccaca gtcgatgaat ccagaaaagc ggccattttc caccatgata   2640
```

```
ttcggcaagc aggcatcgcc atgggtcacg acgagatcct cgccgtcggg catgcgcgcc    2700
ttgagcctgg cgaacagttc ggctggcgcg agccctgat gctcttcgtc cagatcatcc     2760
tgatcgacaa gaccggcttc catccgagta cgtgctcgct cgatgcgatg tttcgcttgg    2820
tggtcgaatg ggcaggtagc cggatcaagc gtatgcagcc gccgcattgc atcagccatg   2880
atggatactt tctcggcagg agcaaggtga gatgacagga gatcctgccc cggcacttcg    2940
cccaatagca gccagtccct tcccgcttca gtgacaacgt cgagcacagc tgcgcaagga    3000
acgcccgtcg tggccagcca cgatagccgc gctgcctcgt cctgcagttc attcagggca    3060
ccggacaggt cggtcttgac aaaaagaacc gggcgcccct gcgctgacag ccggaacacg    3120
gcggcatcag agcagccgat tgtctgttgt gcccagtcat agccgaatag cctctccacc    3180
caagcggccg gagaacctgc gtgcaatcca tcttgttcaa tcatgcgaaa cgatcctcat    3240
cctgtctctt gatcagatct tgatccctg cgccatcaga tccttggcgg caagaaagcc     3300
atccagttta ctttgcaggg cttcccaacc ttaccagagg gcgccccagc tggcaattcc    3360
ggttcgcttg ctgtccataa aaccgcccag tctagctatc gccatgtaag cccactgcaa    3420
gctacctgct ttctctttgc gcttgcgttt tcccttgtcc agatagccca gtagctgaca    3480
ttcatccggg gtcagcaccg tttctgcgga ctggctttct acgtgttccg cttcctttag    3540
cagcccttgc gccctgagtg cttgcggcag cgtgaagcta attcatggtt aaattttgt    3600
taaatcagct cattttttaa ccaataggcc gaaatcggca aaatcccttta taaatcaaaa   3660
gaatagcccg agatagggtt gagtgttgtt ccagtttgga acaagagtcc actattaaag    3720
aacgtggact ccaacgtcaa agggcgaaaa accgtctatc agggcgatgg ccggatcagc    3780
ttatgcggtg tgaaataccg cacagatgcg taaggagaaa ataccgcatc aggcgctctt    3840
ccgcttcctc gctcactgac tcgctgcgct cggtcgttcg gctgcggcga gcggtatcag    3900
ctcactcaaa ggcggtaata cggttatcca cagaatcagg ggataacgca ggaaagaaca    3960
tgtgagcaaa aggccagcaa aaggccagga accgtaaaaa ggccgcgttg ctggcgtttt    4020
tccataggct ccgcccccct gacgagcatc acaaaaatcg acgctcaagt cagaggtggc    4080
gaaacccgac aggactataa agataccagg cgtttccccc tggaagctcc ctcgtgcgct    4140
ctcctgttcc gaccctgccg cttaccggat acctgtccgc ctttctccct tcgggaagcg    4200
tggcgctttc tcatagctca cgctgtaggt atctcagttc ggtgtaggtc gttcgctcca    4260
agctgggctg tgtgcacgaa ccccccgttc agcccgaccg ctgcgcctta tccggtaact    4320
atcgtcttga gtccaacccg gtaagacacg acttatcgcc actggcagca gccactggta    4380
acaggattag cagagcgagg tatgtaggcg gtgctacaga gttcttgaag tggtggccta    4440
actacggcta cactagaagg acagtatttg gtatctgcgc tctgctgaag ccagttacct    4500
tcggaaaaag agttggtagc tcttgatccg gcaaacaaac caccgctggt agcggtggtt    4560
tttttgtttg caagcagcag attacgcgca gaaaaaaagg atctcaagaa gatcctttga    4620
tcttttctac tgaacggtga tccccaccgg aattgcg                             4657
```

<210> SEQ ID NO 52  
<211> LENGTH: 4774  
<212> TYPE: DNA  
<213> ORGANISM: Artificial Sequence  
<220> FEATURE:  
<223> OTHER INFORMATION: pCMVKm2.pCAP5opt HML-2 vector

<400> SEQUENCE: 52

```
gccgcggaat tcgactcta ggccattgca tacgttgtat ctatatcata atatgtacat      60
```

```
ttatattggc tcatgtccaa tatgaccgcc atgttgacat tgattattga ctagttatta   120
atagtaatca attacggggt cattagttca tagcccatat atggagttcc gcgttacata   180
acttacggta aatggcccgc ctggctgacc gcccaacgac ccccgcccat tgacgtcaat   240
aatgacgtat gttcccatag taacgccaat agggactttc cattgacgtc aatgggtgga   300
gtatttacgg taaactgccc acttggcagt acatcaagtg tatcatatgc caagtccgcc   360
ccctattgac gtcaatgacg gtaaatggcc cgcctggcat tatgcccagt acatgacctt   420
acgggacttt cctacttggc agtacatcta cgtattagtc atcgctatta ccatggtgat   480
gcggttttgg cagtacacca atgggcgtgg atagcggttt gactcacggg gatttccaag   540
tctccacccc attgacgtca atgggagttt gttttggcac caaaatcaac gggactttcc   600
aaaatgtcgt aataacccccg ccccgttgac gcaaatgggc ggtaggcgtg tacggtggga   660
ggtctatata agcagagctc gtttagtgaa ccgtcagatc gcctggagac gccatccacg   720
ctgttttgac ctccatagaa gacaccggga ccgatccagc ctccgcggcc gggaacggtg   780
cattggaacg cggattcccc gtgccaagag tgacgtaagt accgcctata gactctatag   840
gcacacccct ttggctctta tgcatgctat actgttttttg gcttgggggcc tatacacccc   900 cgcttcctta tgctataggt gatggtatag cttagcctat aggtgtgggt tattgaccat   960
tattgaccac tcccctattg gtgacgatac tttccattac taatccataa catggctctt  1020
tgccacaact atctctattg gctatatgcc aatactctgt ccttcagaga ctgacacgga  1080
ctctgtattt ttacaggatg gggtcccatt tattatttac aaattcacat atacaacaac  1140
gccgtccccc gtgcccgcag ttttttattaa acatagcgtg ggatctccac gcgaatctcg  1200
ggtacgtgtt ccggacatgg gctcttctcc ggtagcggcg gagcttccac atccgagccc  1260
tggtcccatg cctccagcgg ctcatggtcg ctcggcagct ccttgctcct aacagtggag  1320
gccagactta ggcacagcac aatgcccacc accaccagtg tgccgcacaa ggccgtggcg  1380
gtagggtatg tgtctgaaaa tgagctcgga gattgggctc gcaccgctga cgcagatgga  1440
agacttaagg cagcggcaga agaagatgca ggcagctgag ttgttgtatt ctgataagag  1500
tcagaggtaa ctcccgttgc ggtgctgtta acggtggagg gcagtgtagt ctgagcagta  1560
ctcgttgctg ccgcgcgcgc caccagacat aatagctgac agactaacag actgttcctt  1620
tccatgggtc ttttctgcag tcaccgtcgt cgacgccacc atgaacccca gcgagatgca  1680
gcgcaaggcc cccccccgcc gccgccgcca ccgcaaccgc gcccccctga cccacaagat  1740
gaacaagatg gtgaccagcg aggagcagat gaagctgccc agcaccaaga aggccgagcc  1800 ccccaccctgg gccagctga agaagctgac ccagctggcc accaagtacc tggagaacac  1860
caaggtgacc cagacccccg agagcatgct gctggccgcc ctgatgatcg tgagcatggt  1920
ggtgtacccc accgccccca gcgccagcg ccccagccgc accggccacg acgacgacgg  1980
cggcttcgtg gagaagaagc gcggcaagtg cggcgagaag caggagcgca gcgactgcta  2040
ctgcgtgtgc gtggagcgca gccgccaccg ccgcctgcac ttcgtgctgt acgcttaaag  2100
aattcagact cgagcaagtc tagaaagcca tggatatcgg atccactacg cgttagagct  2160
cgctgatcag cctcgactgt gccttctagt tgccagccat ctgttgtttg ccctccccc  2220 gtgccttcct tgaccctgga aggtgccact cccactgtcc tttcctaata aaatgaggaa  2280
attgcatcgc attgtctgag taggtgtcat tctattctgg ggggtggggt ggggcaggac  2340
agcaaggggg aggattggga agacaatagc agggggggtgg gcgaagaact ccagcatgag  2400
atccccgcgc tggaggatca tccagccggc gtcccggaaa acgattccga agcccaacct  2460
```

```
ttcatagaag gcggcggtgg aatcgaaatc tcgtgatggc aggttgggcg tcgcttggtc   2520
ggtcatttcg aaccccagag tcccgctcag aagaactcgt caagaaggcg atagaaggcg   2580
atgcgctgcg aatcgggagc ggcgataccg taaagcacga ggaagcggtc agcccattcg   2640
ccgccaagct cttcagcaat atcacgggta gccaacgcta tgtcctgata gcggtccgcc   2700
acacccagcc ggccacagtc gatgaatcca aaaagcggc cattttccac catgatattc    2760
ggcaagcagg catcgccatg ggtcacgacg agatcctcgc cgtcgggcat gcgcgccttg   2820
agcctggcga acagttcggc tggcgcgagc ccctgatgct cttcgtccag atcatcctga   2880
tcgacaagac cggcttccat ccgagtacgt gctcgctcga tgcgatgttt cgcttggtgg   2940
tcgaatgggc aggtagccgg atcaagcgta tgcagccgcc gcattgcatc agccatgatg   3000
gatactttct cggcaggagc aaggtgagat gacaggagat cctgccccgg cacttcgccc   3060
aatagcagcc agtcccttcc cgcttcagtg acaacgtcga gcacagctgc gcaaggaacg   3120
cccgtcgtgg ccagccacga tagccgcgct gcctcgtcct gcagttcatt cagggcaccg   3180
gacaggtcgg tcttgacaaa aagaaccggg cgcccctgcg ctgacagccg gaacacggcg   3240
gcatcagagc agccgattgt ctgttgtgcc cagtcatagc cgaatagcct ctccacccaa   3300
gcggccggag aacctgcgtg caatccatct tgttcaatca tgcgaaacga tcctcatcct   3360
gtctcttgat cagatcttga tccctgcgc catcagatcc ttggcggcaa gaaagccatc    3420
cagtttactt tgcagggctt cccaaccta ccagagggcg cccagctgg caattccggt      3480 tcgcttgctg tccataaaac cgcccagtct agctatcgcc atgtaagccc actgcaagct   3540
acctgctttc tctttgcgct tgcgttttcc cttgtccaga tagcccagta gctgacattc   3600
atccggggtc agcaccgttt ctgcggactg gcttttctacg tgttccgctt cctttagcag  3660
cccttgcgcc ctgagtgctt gcggcagcgt gaagctaatt catggttaaa ttttttgttaa  3720 atcagctcat tttttaacca ataggccgaa atcggcaaaa tcccttataa atcaaaagaa    3780
tagcccgaga tagggttgag tgttgttcca gtttggaaca agagtccact attaaagaac   3840
gtggactcca acgtcaaagg gcgaaaaacc gtctatcagg gcgatggccg gatcagctta   3900
tgcggtgtga ataccgcac agatgcgtaa ggagaaaata ccgcatcagg cgctcttccg     3960
cttcctcgct cactgactcg ctgcgctcgg tcgttcggct gcggcgagcg gtatcagctc   4020
actcaaaggc ggtaatacgg ttatccacag aatcagggga taacgcagga agaacatgt     4080 gagcaaaagg ccagcaaaag gccaggaacc gtaaaaaggc cgcgttgctg gcgtttttcc   4140
ataggctccg ccccctgac gagcatcaca aaatcgacg ctcaagtcag aggtggcgaa      4200
acccgacagg actataaaga taccaggcgt ttccccctgg aagctccctc gtgcgctctc   4260
ctgttccgac cctgccgctt accggatacc tgtccgcctt tctcccttcg ggaagcgtgg   4320
cgctttctca tagctcacgc tgtaggtatc tcagttcggt gtaggtcgtt cgctccaagc   4380
tgggctgtgt gcacgaaccc cccgttcagc ccgaccgctg cgccttatcc ggtaactatc   4440
gtcttgagtc aacccggta agacacgact tatcgccact ggcagcagcc actggtaaca    4500
ggattagcag agcgaggtat gtaggcggtg ctacagagtt cttgaagtgg tggcctaact   4560
acggctacac tagaaggaca gtatttggta tctgcgctct gctgaagcca gttaccttcg   4620
gaaaaagagt tggtagctct tgatccggca acaaaccac cgctggtagc ggtggttttt    4680
ttgtttgcaa gcagcagatt acgcgcagaa aaaaggatc tcaagaagat cctttgatct    4740
tttctactga acggtgatcc ccaccggaat tgcg                              4774
```

<210> SEQ ID NO 53
<211> LENGTH: 6483
<212> TYPE: DNA
<213> ORGANISM: Artificial Sequence
<220> FEATURE:
<223> OTHER INFORMATION: pCMVKm2.gag wt PCAV vector

<400> SEQUENCE: 53

```
gccgcggaat tcgactcta ggccattgca tacgttgtat ctatatcata atatgtacat      60
ttatattggc tcatgtccaa tatgaccgcc atgttgacat tgattattga ctagttatta    120
atagtaatca attacggggt cattagttca tagcccatat atggagttcc gcgttacata   180
acttacggta aatggcccgc ctggctgacc gcccaacgac ccccgcccat tgacgtcaat   240
aatgacgtat gttcccatag taacgccaat agggactttc cattgacgtc aatgggtgga   300
gtatttacgg taaactgccc acttggcagt acatcaagtg tatcatatgc caagtccgcc   360
ccctattgac gtcaatgacg gtaaatggcc cgcctggcat tatgcccagt acatgacctt   420
acgggacttt cctacttggc agtacatcta cgtattagtc atcgctatta ccatggtgat   480
gcggttttgg cagtacacca atgggcgtgg atagcggttt gactcacggg gatttccaag   540
tctccacccc attgacgtca atgggagttt gttttggcac caaaatcaac gggactttcc   600
aaaatgtcgt aataaccccg ccccgttgac gcaaatgggc ggtaggcgtg tacggtggga   660
ggtctatata agcagagctc gtttagtgaa ccgtcagatc gcctggagac gccatccacg   720
ctgttttgac ctccatagaa gacaccggga ccgatccagc ctccgcggcc gggaacggtg   780
cattggaacg cggattcccc gtgccaagag tgacgtaagt accgcctata gactctatag   840
gcacacccct ttggctctta tgcatgctat actgttttg gcttggggcc tatacacccc   900
cgcttcctta tgctataggt gatggtatag cttagcctat aggtgtgggt tattgaccat   960
tattgaccac tcccctattg gtgacgatac tttccattac taatccataa catggctctt  1020
tgccacaact atctctattg gctatatgcc aatactctgt ccttcagaga ctgacacgga  1080
ctctgtattt ttacaggatg gggtcccatt tattatttac aaattcacat atacaacaac  1140
gccgtccccc gtgcccgcag tttttattaa acatagcgtg gatctccac gcgaatctcg  1200
ggtacgtgtt ccggacatgg gctcttctcc ggtagcggcg gagcttccac atccgagccc  1260
tggtcccatg cctccagcgg ctcatggtcg ctcggcagct ccttgctcct aacagtggag  1320
gccagactta ggcacagcac aatgcccacc accaccagtg tgccgcacaa ggccgtggcg  1380
gtagggtatg tgtctgaaaa tgagctcgga gattgggctc gcaccgctga cgcagatgga  1440
agacttaagg cagcggcaga agaagatgca ggcagctgag ttgttgtatt ctgataagag  1500
tcagaggtaa ctcccgttgc ggtgctgtta acggtggagg gcagtgtagt ctgagcagta  1560
ctcgttgctg ccgcgcgcgc caccagacat aatagctgac agactaacag actgttcctt  1620
tccatgggtc ttttctgcag tcaccgtcgt cgacgccacc atgggcaaa ctgaaagtaa  1680
atatgcctct tatctcagct ttattaaaat tcttttaaga agaggggag ttagagcttc  1740
tacagaaaat ctaattacgc tatttcaaac aatagaacaa ttctgcccat ggtttccaga  1800
acagggaact ttagatctaa aagattggga aaaaattggc aaagaattaa aacaagcaaa  1860
tagggaaggt aaaatcatcc cacttacagt atggaatgat tgggccatta ttaaagcaac  1920
tttagaacca tttcaaacag agaagatat tgtttcagtt tctgatgccc ctaaaagctg  1980
tgtaacagat tgtgaagaag aggcagggac agaatcccag caaggaacgg aaagttcaca  2040
ttgtaaaatat gtagcagagt ctgtaatggc tcagtcaacg caaaatgttg actacagtca  2100
attacaggag ataatatacc ctgaatcatc aaaattgggg gaaggaggtc cagaatcatt  2160
```

```
ggggccatca gagcctaaac cacgatcgcc atcaactcct cctcccgtgg ttcagatgcc    2220
tgtaacatta caacctcaaa cgcaggttag acaagcacaa accccaagag aaaatcaagt    2280
agaaagggac agagtctcta tcccggcaat gccaactcag atacagtatc cacaatatca    2340
gccggtagaa aataagaccc aaccgctggt agtttatcaa taccggctgc caaccgagct    2400
tcagtatcgg cctccttcag aggttcaata cagacctcaa gcggtgtgtc ctgtgccaaa    2460
tagcacggca ccataccagc aacccacagc gatggcgtct aattcaccag caacacagga    2520
cgcggcgctg tatcctcagc cgcccactgt gagacttaat cctacagcat cacgtagtgg    2580
acagggtggt gcactgcatg cagtcattga tgaagccaga aaacagggcg atcttgaggc    2640
atggcggttc ctggtaattt tacaactggt acaggccggg gaagagactc aagtaggagc    2700
gcctgcccga gctgagacta gatgtgaacc tttcaccatg aaaatgttaa aagatataaa    2760
ggaaggagtt aaacaatatg gatccaactc cccttatata agaacattat tagattccat    2820
tgctcatgga aatagactta ctccttatga ctgggaaatt ttggccaaat cttccctttc    2880
atcctctcag tatctacagt ttaaaacctg gtggattgat ggagtacaag aacaggtacg    2940
aaaaaatcag gctactaagc ccactgttaa tatagacgca gaccaattgt taggaacagg    3000
tccaaattgg agcaccatta accaacaatc agtgatgcag aatgaggcta ttgaacaagt    3060
aagggctatt tgcctcaggg cctggggaaa aattcaggac ccaggaacag ctttccctat    3120
taattcaatt agacaaggct ctaaagagcc atatcctgac tttgtggcaa gattacaaga    3180
tgctgctcaa aagtctatta cagatgacaa tgcccgaaaa gttattgtag aattaatggc    3240
ctatgaaaat gcaaatccag aatgtcagtc ggccataaag ccattaaaag gaaaagttcc    3300
agcaggagtt gatgtaatta cagaatatgt gaaggcttgt gatgggattg gaggagctat    3360
gcataaggca atgctaatgg ctcaagcaat gagggggctc actctaggag acaagttag    3420
aacatttggg aaaaaatgtt ataattgtgg tcaaatcggt catctgaaaa ggagttgccc    3480
agtcttaaat aaacagaata taataaatca agctattaca gcaaaaaata aaaagccatc    3540
tggcctgtgt ccaaaatgtg aaaaggaaa acattgggcc aatcaatgtc attctaaatt    3600
tgataaggat gggcaaccat tgtcgggaaa caggaagagg ggccagcctc aggcccccca    3660
acaaactggg gcattcccag ttcaactgtt tgttcctcag ggttttcaag acaacaacc    3720
cctacagaaa ataccaccac ttcagggagt cagccaatta caacaatcca acagctgtcc    3780
cgcgccacag caggcagcac cgcagtaaga attcagactc gagcaagtct agaaagccat    3840
ggatatcgga tccactacgc gttagagctc gctgatcagc ctcgactgtg ccttctagtt    3900
gccagccatc tgttgtttgc ccctcccccg tgccttcctt gaccctggaa ggtgccactc    3960
ccactgtcct ttcctaataa aatgaggaaa ttgcatcgca ttgtctgagt aggtgtcatt    4020
ctattctggg gggtggggtg gggcaggaca gcaaggggga ggattgggaa gacaatagca    4080
ggggggtggg cgaagaactc cagcatgaga tccccgcgct ggaggatcat ccagccggcg    4140
tcccggaaaa cgattccgaa gcccaacctt tcatagaagg cggcggtgga atcgaaatct    4200
cgtgatggca ggttgggcgt cgcttggtcg gtcatttcga accccagagt cccgctcaga    4260
agaactcgtc aagaaggcga tagaaggcga tgcgctgcga atcgggagcg gcgataccgt    4320
aaagcacgag gaagcggtca gcccattcgc cgccaagctc ttcagcaata tcacgggtag    4380
ccaacgctat gtcctgatag cggtccgcca cacccagccg gccacagtcg atgaatccag    4440
aaaagcggcc attttccacc atgatattcg gcaagcaggc atcgccatgg gtcacgacga    4500
gatcctcgcc gtcgggcatg cgcgccttga gcctggcgaa cagttcggct ggcgcgagcc    4560
```

```
cctgatgctc ttcgtccaga tcatcctgat cgacaagacc ggcttccatc cgagtacgtg      4620
ctcgctcgat gcgatgtttc gcttggtggt cgaatgggca ggtagccgga tcaagcgtat      4680
gcagccgccg cattgcatca gccatgatgg atactttctc ggcaggagca aggtgagatg      4740
acaggagatc ctgccccggc acttcgccca atagcagcca gtcccttccc gcttcagtga      4800
caacgtcgag cacagctgcg caaggaacgc ccgtcgtggc cagccacgat agccgcgctg      4860
cctcgtcctg cagttcattc agggcaccgg acaggtcggt cttgacaaaa agaaccgggc      4920
gcccctgcgc tgacagccgg aacacggcgg catcagagca gccgattgtc tgttgtgccc      4980
agtcatagcc gaatagcctc tccacccaag cggccggaga acctgcgtgc aatccatctt      5040
gttcaatcat gcgaaacgat cctcatcctg tctcttgatc agatcttgat cccctgcgcc      5100
atcagatcct tggcggcaag aaagccatcc agtttacttt gcagggcttc ccaaccttac      5160
cagagggcgc cccagctggc aattccggtt cgcttgctgt ccataaaacc gcccagtcta      5220
gctatcgcca tgtaagccca ctgcaagcta cctgctttct ctttgcgctt gcgttttccc      5280
ttgtccagat agcccagtag ctgacattca tccggggtca gcaccgtttc tgcggactgg      5340 cttttctacgt gttccgcttc ctttagcagc ccttgcgccc tgagtgcttg cggcagcgtg      5400
aagctaattc atggttaaat ttttgttaaa tcagctcatt ttttaaccaa taggccgaaa      5460
tcggcaaaat cccttataaa tcaaaagaat agcccgagat agggttgagt gttgttccag      5520
tttggaacaa gagtccacta ttaaagaacg tggactccaa cgtcaaaggg cgaaaaaccg      5580
tctatcaggg cgatggccgg atcagcttat gcggtgtgaa ataccgcaca gatgcgtaag      5640
gagaaaatac cgcatcaggc gctcttccgc ttcctcgctc actgactcgc tgcgctcggt      5700
cgttcggctg cggcgagcgg tatcagctca ctcaaaggcg gtaatacggt tatccacaga      5760
atcaggggat aacgcaggaa agaacatgtg agcaaaaggc cagcaaaagg ccaggaaccg      5820
taaaaaggcc gcgttgctgg cgttttttcca taggctccgc cccctgacg agcatcacaa      5880 aaatcgacgc tcaagtcaga ggtggcgaaa cccgacagga ctataaagat accaggcgtt      5940
tccccctgga agctccctcg tgcgctctcc tgttccgacc ctgccgctta ccggatacct      6000
gtccgccttt ctcccttcgg gaagcgtggc gctttctcat agctcacgct gtaggtatct      6060
cagttcggtg taggtcgttc gctccaagct gggctgtgtg cacgaacccc ccgttcagcc      6120
cgaccgctgc gccttatccg gtaactatcg tcttgagtcc aacccggtaa gacacgactt      6180
atcgccactg gcagcagcca ctggtaacag gattagcaga gcgaggtatg taggcggtgc      6240
tacagagttc ttgaagtggt ggcctaacta cggctacact agaaggacag tatttggtat      6300
ctgcgctctg ctgaagccag ttaccttcgg aaaaagagtt ggtagctctt gatccggcaa      6360
acaaaccacc gctggtagcg gtggtttttt tgtttgcaag cagcagatta cgcgcagaaa      6420
aaaaggatct caagaagatc ctttgatctt ttctactgaa cggtgatccc caccggaatt      6480
gcg                                                                    6483
```

<210> SEQ ID NO 54
<211> LENGTH: 6340
<212> TYPE: DNA
<213> ORGANISM: Artificial Sequence
<220> FEATURE:
<223> OTHER INFORMATION: pCMVKm2.gagopt HML-2 vector

<400> SEQUENCE: 54

```
gccgcggaat tcgactcta ggccattgca tacgttgtat ctatatcata atatgtacat        60
ttatattggc tcatgtccaa tatgaccgcc atgttgacat tgattattga ctagttatta      120
```

```
atagtaatca attacggggt cattagttca tagcccatat atggagttcc gcgttacata      180
acttacggta aatggcccgc ctggctgacc gcccaacgac ccccgcccat tgacgtcaat      240
aatgacgtat gttcccatag taacgccaat agggactttc cattgacgtc aatgggtgga      300
gtatttacgg taaactgccc acttggcagt acatcaagtg tatcatatgc caagtccgcc      360
ccctattgac gtcaatgacg gtaaatggcc cgcctggcat tatgcccagt acatgacctt      420
acgggacttt cctacttggc agtacatcta cgtattagtc atcgctatta ccatggtgat      480
gcggttttgg cagtacacca atgggcgtgg atagcggttt gactcacggg gatttccaag      540
tctccacccc attgacgtca atgggagttt gttttggcac caaaatcaac gggactttcc      600
aaaatgtcgt aataacccg ccccgttgac gcaaatgggc ggtaggcgtg tacggtggga      660
ggtctatata agcagagctc gtttagtgaa ccgtcagatc gcctggagac gccatccacg      720
ctgttttgac ctccatagaa gacaccggga ccgatccagc ctccgcggcc gggaacggtg      780
cattggaacg cggattcccc gtgccaagag tgacgtaagt accgcctata gactctatag      840
gcacacccct ttggctctta tgcatgctat actgttttg gcttgggggcc tatacacccc     900
cgcttcctta tgctataggt gatggtatag cttagcctat aggtgtgggt tattgaccat      960
tattgaccac tcccctattg gtgacgatac tttccattac taatccataa catggctctt     1020
tgccacaact atctctattg gctatatgcc aatactctgt ccttcagaga ctgacacgga     1080
ctctgtattt ttacaggatg ggtcccatt tattatttac aaattcacat atacaacaac      1140
gccgtccccc gtgcccgcag tttttattaa acatagcgtg gatctccac gcgaatctcg      1200
ggtacgtgtt ccggacatgg gctcttctcc ggtagcggcg gagcttccac atccgagccc     1260
tggtcccatg cctccagcgg ctcatggtcg ctcggcagct ccttgctcct aacagtggag     1320
gccagactta ggcacagcac aatgcccacc accaccagtg tgccgcacaa ggccgtggcg     1380
gtagggtatg tgtctgaaaa tgagctcgga gattgggctc gcaccgctga cgcagatgga     1440
agacttaagg cagcggcaga agaagatgca ggcagctgag ttgttgtatt ctgataagag     1500
tcagaggtaa ctcccgttgc ggtgctgtta acggtggagg gcagtgtagt ctgagcagta     1560
ctcgttgctg ccgcgcgcgc caccagacat aatagctgac agactaacag actgttcctt     1620
tccatgggtc ttttctgcag tcaccgtcgt cgacgccacc atgggccaga ccaagagcaa     1680
gatcaagagc aagtacgcca gctacctgag cttcatcaag atcctgctga gcgcggcgg     1740
cgtgaaggtg agcaccaaga acctgatcaa gctgttccag atcatcgagc agttctgccc     1800
ctggttcccc gagcagggca ccctggacct gaaggactgg aagcgcatcg gcaaggagct     1860
gaagcaggcc ggccgcaagg gcaacatcat ccccctgacc gtgtggaacg actgggccat     1920
catcaaggcc gccctggagc ccttccagac cgaggaggac agcgtgagcg tgagcgacgc     1980
ccccggcagc tgcatcatcg actgcaacga gaacacccgc aagaagagcc agaaggagac     2040
cgagggcctg cactgcgagt acgtggccga gcccgtgatg gcccagagca cccagaacgt     2100
ggactacaac cagctgcagg aggtgatcta ccccgagacc ctgaagctgg agggcaaggg     2160
ccccgagctg gtgggcccca gcgagagcaa gcccgcggc accagccccc tgcccgccgg     2220
ccaggtgccc gtgaccctgc agccccagaa gcaggtgaag gagaacaaga cccagccccc     2280
cgtggcctac cagtactggc cccccgccga gctgcagtac cgcccccccc ccgagagcca     2340
gtacggctac cccggcatgc cccccgcccc ccagggccgc gccccctacc cccagccccc     2400
cacccgccgc ctgaacccca ccgcccccc cagccgccag ggcagcaagc tgcacgagat     2460
catcgacaag agccgcaagg agggcgacac cgaggcctgg cagttccccg tgaccctgga     2520
```

```
gcccatgccc cccggcgagg gcgcccagga gggcgagccc ccaccgtgg aggcccgcta    2580 caagagcttc agcatcaaga agctgaagga catgaaggag ggcgtgaagc agtacggccc    2640
caacagcccc tacatgcgca ccctgctgga cagcatcgcc cacggccacc gcctgatccc    2700
ctacgactgg gagatcctgg ccaagagcag cctgagcccc agccagttcc tgcagttcaa    2760
gacctggtgg atcgacggcg tgcaggagca ggtgcgccgc aaccgcgccg ccaaccccccc   2820 cgtgaacatc gacgccgacc agctgctggg catcggccag aactggagca ccatcagcca    2880
gcaggccctg atgcagaacg aggccatcga gcaggtgcgc gccatctgcc tgcgcgcctg    2940
ggagaagatc caggaccccg gcagcacctg ccccagcttc aacaccgtgc gccagggcag    3000
caaggagccc tacccgact tcgtggcccg cctgcaggac gtggcccaga gagcatcgc     3060 cgacgagaag gcccgcaagg tgatcgtgga gctgatggcc tacgagaacg ccaacccga    3120 gtgccagagc gccatcaagc ccctgaaggg caaggtgccc gccggcagcg acgtgatcag    3180
cgagtacgtg aaggcctgcg acggcatcgg cggcgccatg cacaaggcca tgctgatggc    3240
ccaggccatc accggcgtgg tgctgggcgg ccaggtgcgc accttcggcc gcaagtgcta    3300
caactgcggc cagatcggcc acctgaagaa gaactgcccc gtgctgaaca gcagaacat    3360 caccatccag gccaccacca ccggccgcga gccccccgac ctgtgccccc gctgcaagaa    3420
gggcaagcac tgggccagcc agtgccgcag caagttcgac aagaacggcc agcccctgag    3480
cggcaacgag cagcgcggcc agcccaggc ccccagcag accggcgcct tccccatcca     3540
gcccttcgtg cccagggct tccagggca gcagccccc ctgagccagg tgttccaggg      3600
catcagccag ctgccccagt acaacaactg ccccccccc caggccgccg tgcagcaggc    3660
ttaaagaatt cagactcgag caagtctaga aagccatgga tatcggatcc actacgcgtt    3720
agagctcgct gatcagcctc gactgtgcct tctagttgcc agccatctgt tgtttgcccc    3780
tcccccgtgc cttccttgac cctggaaggt gccactccca ctgtccttc ctaataaaat    3840 gaggaaattg catcgcattg tctgagtagg tgtcattcta ttctgggggg tggggtgggg    3900
caggacagca agggggagga ttgggaagac aatagcaggg gggtgggcga agaactccag    3960
catgagatcc ccgcgctgga ggatcatcca gccggcgtcc cggaaaacga ttccgaagcc    4020 caaccttca tagaaggcgg cggtggaatc gaaatctcgt gatggcaggt tgggcgtcgc     4080
ttggtcggtc atttcgaacc ccagagtccc gctcagaaga actcgtcaag aaggcgatag    4140
aaggcgatgc gctgcgaatc gggagcggcg ataccgtaaa gcacgaggaa gcggtcagcc    4200
cattcgccgc caagctcttc agcaatatca cgggtagcca acgctatgtc ctgatagcgg    4260
tccgccacac ccagccggcc acagtcgatg aatccagaaa agcggccatt ttccaccatg    4320
atattcggca agcaggcatc gccatgggtc acgacgagat cctcgccgtc gggcatgcgc    4380
gccttgagcc tggcgaacag ttcggctggc gcgagcccct gatgctcttc gtccagatca    4440
tcctgatcga caagaccggc ttccatccga gtacgtgctc gctcgatgcg atgtttcgct    4500
tggtggtcga atgggcaggt agccggatca agcgtatgca gccgccgcat tgcatcagcc    4560
atgatggata ctttctcggc aggagcaagg tgagatgaca ggagatcctg ccccggcact    4620
tcgcccaata gcagccagtc ccttcccgct tcagtgacaa cgtcgagcac agctgcgcaa    4680
ggaacgcccg tcgtggccag ccacgatagc cgcgctgcct cgtcctgcag ttcattcagg    4740
gcaccggaca ggtcggtctt gacaaaaaga accgggcgcc cctgcgctga cagccggaac    4800
acggcggcat cagagcagcc gattgtctgt tgtgcccagt catagccgaa tagcctctcc    4860
acccaagcgg ccggagaacc tgcgtgcaat ccatcttgtt caatcatgcg aaacgatcct    4920
```

```
catcctgtct cttgatcaga tcttgatccc ctgcgccatc agatccttgg cggcaagaaa      4980
gccatccagt ttactttgca gggcttccca accttaccag agggcgcccc agctggcaat      5040
tccggttcgc ttgctgtcca taaaaccgcc cagtctagct atcgccatgt aagcccactg      5100
caagctacct gctttctctt tgcgcttgcg ttttcccttg tccagatagc ccagtagctg      5160
acattcatcc ggggtcagca ccgtttctgc ggactggctt tctacgtgtt ccgcttcctt      5220
tagcagccct tgcgccctga gtgcttgcgg cagcgtgaag ctaattcatg gttaaatttt      5280
tgttaaatca gctcattttt taaccaatag gccgaaatcg gcaaaatccc ttataaatca      5340
aaagaatagc ccgagatagg gttgagtgtt gttccagttt ggaacaagag tccactatta      5400
aagaacgtgg actccaacgt caaagggcga aaaccgtctc atcagggcga tggccggatc      5460
agcttatgcg gtgtgaaata ccgcacagat gcgtaaggag aaaataccgc atcaggcgct      5520
cttccgcttc ctcgctcact gactcgctgc gctcggtcgt tcggctgcgg cgagcggtat      5580
cagctcactc aaaggcggta atacggttat ccacagaatc aggggataac gcaggaaaga      5640
acatgtgagc aaaaggccag caaaaggcca ggaaccgtaa aaaggccgcg ttgctggcgt      5700
ttttccatag gctccgcccc cctgacgagc atcacaaaaa tcgacgctca agtcagaggt      5760
ggcgaaaccc gacaggacta taaagatacc aggcgtttcc ccctggaagc tccctcgtgc      5820
gctctcctgt tccgaccctg ccgcttaccg gatacctgtc cgcctttctc ccttcgggaa      5880
gcgtggcgct ttctcatagc tcacgctgta ggtatctcag ttcggtgtag gtcgttcgct      5940
ccaagctggg ctgtgtgcac gaaccccccg ttcagcccga ccgctgcgcc ttatccggta      6000
actatcgtct tgagtccaac ccggtaagac acgacttatc gccactggca gcagccactg      6060
gtaacaggat tagcagagcg aggtatgtag cggtgctac agagttcttg aagtggtggc      6120
ctaactacgg ctacactaga aggacagtat ttggtatctg cgctctgctg aagccagtta      6180
ccttcggaaa aagagttggt agctcttgat ccggcaaaca aaccaccgct ggtagcggtg      6240
gtttttttgt ttgcaagcag cagattacgc gcagaaaaaa aggatctcaa gaagatcctt      6300
tgatcttttc tactgaacgg tgatccccac cggaattgcg                            6340
```

<210> SEQ ID NO 55
<211> LENGTH: 5344
<212> TYPE: DNA
<213> ORGANISM: Artificial Sequence
<220> FEATURE:
<223> OTHER INFORMATION: pCMVKm2.Protopt HML-2 vector

<400> SEQUENCE: 55

```
gccgcggaat tcgactcta ggccattgca tacgttgtat ctatatcata atatgtacat       60
ttatattggc tcatgtccaa tatgaccgcc atgttgacat tgattattga ctagttatta      120
atagtaatca attacggggt cattagttca tagcccatat atggagttcc gcgttacata      180
acttacggta aatggcccgc ctggctgacc gcccaacgac ccccgcccat tgacgtcaat      240
aatgacgtat gttcccatag taacgccaat agggactttc cattgacgtc aatgggtgga      300
gtatttacgg taaactgccc acttggcagt acatcaagtg tatcatatgc caagtccgcc      360
ccctattgac gtcaatgacg gtaaatggcc cgcctggcat tatgcccagt acatgacctt      420
acgggacttt cctacttggc agtacatcta cgtattagtc atcgctatta ccatggtgat      480
gcggttttgg cagtacacca atgggcgtgg atagcggttt gactcacggg gatttccaag      540
tctccacccc attgacgtca atgggagttt gttttggcac caaaatcaac gggactttcc      600
aaaatgtcgt aataaccccg ccccgttgac gcaaatgggc ggtaggcgtg tacggtggga      660
```

```
ggtctatata agcagagctc gtttagtgaa ccgtcagatc gcctggagac gccatccacg    720
ctgttttgac ctccatagaa gacaccggga ccgatccagc ctccgcggcc gggaacggtg    780
cattggaacg cggattcccc gtgccaagag tgacgtaagt accgcctata gactctatag    840
gcacacccct ttggctctta tgcatgctat actgtttttg gcttggggcc tatacacccc    900
cgcttcctta tgctataggt gatggtatag cttagcctat aggtgtgggt tattgaccat    960
tattgaccac tccectattg gtgacgatac tttccattac taatccataa catggctctt   1020
tgccacaact atctctattg gctatatgcc aatactctgt ccttcagaga ctgacacgga   1080
ctctgtattt ttacaggatg gggtcccatt tattatttac aaattcacat atacaacaac   1140
gccgtccccc gtgccgcag tttttattaa acatagcgtg ggatctccac gcgaatctcg    1200
ggtacgtgtt ccggacatgg gctcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtt gccgcacaa ggccgtggcg    1380 gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccgtcgt cgacgccacc atgtgggcca ccatcgtggg   1680
caagcgcgcc aagggccccg ccagcggccc caccaccaac tggggcatcc caacagcgc    1740 catctgcagc agcggcttca gcggcaccac caccccacc gtgcccagcg tgagcggcaa   1800
caagcccgtg accaccatcc agcagctgag ccccgccacc agcggcagcg ccgccgtgga   1860
cctgtgcacc atccaggccg tgagcctgct gccggcgag ccccccaga agaccccac     1920 cggcgtgtac ggccccctgc ccaagggcac cgtgggcctg atcctgggcc gcagcagcct   1980
gaacctgaag ggcgtgcaga tccacaccag cgtggtggac agcgactaca agggcgagat   2040
ccagctggta tcagcagca gcatcccctg gagcgccagc cccgcgacc gcatcgccca     2100 gctgctgctg ctgccctaca tcaagggcgg caacagcgag atcaagcgca tcggcggcct   2160
gggcagcacc gaccccaccg gcaaggccgc ctactgggcc agccaggtga gcgagaaccg   2220
ccccgtgtgc aaggccatca tccagggcaa gcagttcgag ggcctggtgg acaccggcgc   2280
cgacgtgagc atcatcgccc tgaaccagtg gcccaagaac tggcccaagc agaaggccgt   2340
gaccggcctg gtgggcatcg gcaccgccag cgaggtgtac cagagcaccg agatcctgca   2400
ctgcctgggc cccgacaacc aggagagcac cgtgcagccc atgatcacca gcatccccct   2460
gaacctgtgg ggccgcgacc tgctgcagca gtggggcgcc gagatcacca tgcccgcccc   2520
cagctacagc cccaccagcc agaagatcat gaccaagatg ggctacatcc ccggcaaggg   2580
cctgggcaag aacgaggacg gcatcaagat ccccgtggag gccaagatca accaggagcg   2640
cgagggcatc ggcaacccct gcgcttaaag aattcagact cgagcaagtc tagaaagcca   2700
tggatatcgg atccactacg cgttagagct cgctgatcag cctcgactgt gccttctagt   2760
tgccagccat ctgttgtttg cccctccccc gtgccttcct tgaccctgga aggtgccact   2820
cccactgtcc tttcctaata aaatgaggaa attgcatcgc attgtctgag taggtgtcat   2880
tctattctgg ggggtggggt ggggcaggac agcaagggg aggattggga agacaatagc    2940
agggggggtg gcgaagaact ccagcatgag atccccgcgc tggaggatca tccagccggc   3000
gtcccggaaa acgattccga agcccaacct ttcatagaag gcggcggtgg aatcgaaatc   3060
```

```
tcgtgatggc aggttgggcg tcgcttggtc ggtcatttcg aacccagag tcccgctcag    3120
aagaactcgt caagaaggcg atagaaggcg atgcgctgcg aatcgggagc ggcgataccg    3180
taaagcacga ggaagcggtc agcccattcg ccgccaagct cttcagcaat atcacgggta    3240
gccaacgcta tgtcctgata gcggtccgcc acacccagcc ggccacagtc gatgaatcca    3300
gaaaagcggc catttttccac catgatattc ggcaagcagg catcgccatg ggtcacgacg    3360
agatcctcgc cgtcgggcat gcgcgccttg agcctggcga acagttcggc tggcgcgagc    3420
ccctgatgct cttcgtccag atcatcctga tcgacaagac cggcttccat ccgagtacgt    3480
gctcgctcga tgcgatgttt cgcttggtgg tcgaatgggc aggtagccgg atcaagcgta    3540
tgcagccgcc gcattgcatc agccatgatg gatactttct cggcaggagc aaggtgagat    3600
gacaggagat cctgccccgg cacttcgccc aatagcagcc agtcccttcc cgcttcagtg    3660
acaacgtcga gcacagctgc gcaaggaacg cccgtcgtgg ccagccacga tagccgcgct    3720
gcctcgtcct gcagttcatt cagggcaccg gacaggtcgg tcttgacaaa agaaccggg     3780
cgcccctgcg ctgacagccg gaacacggcg gcatcagagc agccgattgt ctgttgtgcc    3840
cagtcatagc cgaatagcct ctccacccaa gcggccggaa aacctgcgtg caatccatct    3900
tgttcaatca tgcgaaacga tcctcatcct gtctcttgat cagatcttga tccctgcgc    3960
catcagatcc ttggcggcaa gaaagccatc cagtttactt tgcagggctt cccaaccttta    4020
ccagagggcg ccccagctgg caattccggt tcgcttgctg tccataaaac cgcccagtct    4080
agctatcgcc atgtaagccc actgcaagct acctgctttc tctttgcgct tgcgttttcc    4140
cttgtccaga tagcccagta gctgacattc atccggggtc agcaccgttt ctgcggactg    4200
gctttctacg tgttccgctt cctttagcag cccttgcgcc ctgagtgctt gcggcagcgt    4260
gaagctaatt catggttaaa ttttttgttaa atcagctcat tttttaacca ataggccgaa    4320
atcggcaaaa tcccttataa atcaaaagaa tagcccgaga tagggttgag tgttgttcca    4380
gtttggaaca agagtccact attaagaac gtggactcca acgtcaaagg gcgaaaaacc    4440
gtctatcagg gcgatggccg gatcagctta tgccgtgtga ataccgcac agatgcgtaa    4500
ggagaaaata ccgcatcagg cgctcttccg cttcctcgct cactgactcg ctgcgctcgg    4560
tcgttcggct gcggcgagcg gtatcagctc actcaaaggc ggtaatacgg ttatccacag    4620
aatcagggga taacgcagga aagaacatgt gagcaaaagg ccagcaaaag gccaggaacc    4680
gtaaaaaggc cgcgttgctg gcgtttttcc ataggctccg ccccctgac gagcatcaca    4740
aaaatcgacg ctcaagtcag aggtggcgaa acccgacagg actataaaga taccaggcgt    4800
ttccccctgg aagctccctc gtgcgctctc ctgttccgac cctgccgctt accggatacc    4860
tgtccgcctt tctcccttcg ggaagcgtgg cgctttctca tagctcacgc tgtaggtatc    4920
tcagttcggt gtaggtcgtt cgctccaagc tgggctgtgt gcacgaaccc cccgttcagc    4980
ccgaccgctg cgccttatcc ggtaactatc gtcttgagtc aacccggta agacacgact    5040
tatcgccact ggcagcagcc actggtaaca ggattagcag agcgaggtat gtaggcggtg    5100
ctacagagtt cttgaagtgg tggcctaact acggctacac tagaaggaca gtatttggta    5160
tctgcgctct gctgaagcca gttaccttcg gaaaaagagt tggtagctct tgatccggca    5220
aacaaaccac cgctggtagc ggtggttttt tgtttgcaa gcagcagatt acgcgcagaa    5280
aaaaaggatc tcaagaagat cctttgatct tttctactga acggtgatcc ccaccggaat    5340
tgcg                                                                5344
```

<210> SEQ ID NO 56
<211> LENGTH: 7211
<212> TYPE: DNA
<213> ORGANISM: Artificial Sequence
<220> FEATURE:
<223> OTHER INFORMATION: pCMVKm2.Polopt HML-2 vector

<400> SEQUENCE: 56

```
gccgcggaat tcgactcta ggccattgca tacgttgtat ctatatcata atatgtacat      60
ttatattggc tcatgtccaa tatgaccgcc atgttgacat tgattattga ctagttatta    120
atagtaatca attacggggt cattagttca tagcccatat atggagttcc gcgttacata    180
acttacggta aatggcccgc ctggctgacc gcccaacgac ccccgcccat tgacgtcaat    240
aatgacgtat gttcccatag taacgccaat agggactttc cattgacgtc aatgggtgga    300
gtatttacgg taaactgccc acttggcagt acatcaagtg tatcatatgc caagtccgcc    360
ccctattgac gtcaatgacg gtaaatggcc cgcctggcat tatgcccagt acatgacctt    420
acgggacttt cctacttggc agtacatcta cgtattagtc atcgctatta ccatggtgat    480
gcggttttgg cagtacacca atgggcgtgg atagcggttt gactcacggg gatttccaag    540
tctccacccc attgacgtca atgggagttt gttttggcac caaaatcaac gggactttcc    600
aaaatgtcgt aataaccccg ccccgttgac gcaaatgggc ggtaggcgtg tacggtggga    660
ggtctatata agcagagctc gtttagtgaa ccgtcagatc gcctggagac gccatccacg    720
ctgttttgac ctccatagaa gacaccggga ccgatccagc ctccgcggcc gggaacggtg    780
cattggaacg cggattcccc gtgccaagag tgacgtaagt accgcctata gactctatag    840
gcacacccct ttggctctta tgcatgctat actgttttg gcttggggcc tatacacccc    900
cgcttcctta tgctataggt gatggtatag cttagcctat aggtgtgggt tattgaccat    960
tattgaccac tcccctattg gtgacgatac tttccattac taatccataa catggctctt   1020
tgccacaact atctctattg ctatatgcc aatactctgt ccttcagaga ctgacacgga   1080
ctctgtatt ttacaggatg gggtcccatt tattatttac aaattcacat atacaacaac   1140
gccgtccccc gtgcccgcag tttttattaa acatagcgtg gatctccac gcgaatctcg    1200
ggtacgtgtt ccggacatgg gctcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccgtcgt cgacgccacc atgaacaaga gccgcaagcg   1680
ccgcaaccgc gagagcctgc tgggcgccgc caccgtggag cccccaagc ccatcccct   1740
gacctggaag accgagaagc ccgtgtgggt gaaccagtgg cccctgccca agcagaagct   1800
ggaggccctg cacctgctgg ccaacgagca gctggagaag ggccacatcg agcccagctt   1860
cagcccctgg aacagccccg tgttcgtgat ccagaagaag agcggcaagt ggcgcatgct   1920
gaccgacctg cgcgccgtga acgccgtgat ccagccatg ggccccctgc agcccggcct   1980
gcccagccc gccatgatcc caaggactg gccctgatc atcatcgacc tgaaggactg   2040
cttcttcacc atcccctgg ccgagcagga ctgcgagaag ttcgccttca ccatcccgc   2100
catcaacaac aaggagcccg ccacccgctt ccagtggaag gtgctgcccc agggcatgct   2160
```

```
gaacagcccc accatctgcc agaccttcgt gggccgcgcc ctgcagcccg tgcgcgagaa    2220
gttcagcgac tgctacatca tccactgcat cgacgacatc ctgtgcgccg ccgagaccaa    2280
ggacaagctg atcgactgct acaccttcct gcaggccgag gtggccaacg ccggcctggc    2340
catcgccagc gacaagatcc agaccagcac ccccttccac tacctgggca tgcagatcga    2400
gaaccgcaag atcaagcccc agaagatcga gatccgcaag gacaccctga agaccctgaa    2460
cgacttccag aagctgctgg gcgacatcaa ctggatccgc cccaccctgg gcatccccac    2520
ctacgccatg agcaacctgt tcagcatcct gcgcggcgac agcgacctga cagcaagcg     2580 catgctgacc cccgaggcca ccaaggagat caagctggtg gaggagaaga tccagagcgc    2640
ccagatcaac cgcatcgacc ccctggcccc cctgcagctg ctgatcttcg ccaccgccca    2700
cagccccacc ggcatcatca tccagaacac cgacctggtg gagtggagct tcctgcccca    2760
cagcaccgtg aagaccttca ccctgtacct ggaccagatc gccaccctga tcggccagac    2820
ccgcctgcgc atcatcaagc tgtgcggcaa cgaccccgac aagatcgtgg tgcccctgac    2880
caaggagcag gtgcgccagg ccttcatcaa cagcggcgcc tggaagatcg gcctggccaa    2940
cttcgtgggc atcatcgaca ccactaccc  caagaccaag atcttccagt tcctgaagct    3000
gaccacctgg atcctgccca agatcacccg ccgcgagccc ctggagaacg ccctgaccgt    3060
gttcaccgac ggcagcagca acggcaaggc cgcctacacc ggccccaagg agcgcgtgat    3120 caagacccc  taccagagcg cccagcgcgc cgagctggtg gccgtgatca ccgtgctgca    3180
ggacttcgac cagcccatca acatcatcag cgacagcgcc tacgtggtgc aggccacccg    3240
cgacgtggag accgccctga tcaagtacag catggacgac cagctgaacc agctgttcaa    3300
cctgctgcag cagaccgtgc gcaagcgcaa cttccccttc tacatcaccc acatccgcgc    3360
ccacaccaac ctgcccggcc ccctgaccaa ggccaacgag caggccgacc tgctggtgag    3420
cagcgccctg atcaaggccc aggagctgca cgccctgacc cacgtgaacg ccgccggcct    3480
gaagaacaag ttcgacgtga cctggaagca ggccaaggac atcgtgcagc actgcaccca    3540
gtgccaggtg ctgcacctgc cacccagga ggccggcgtg aaccccgcg  gcctgtgccc     3600 caacgccctg tggcagatgg acgtgaccca cgtgcccagc ttcggccgcc tgagctacgt    3660
gcacgtgacc gtggacacct acagccactt catctgggcc acctgccaga ccggcgagag    3720
caccagccac gtgaagaagc acctgctgag ctgcttcgcc gtgatgggcg tgcccgagaa    3780
gatcaagacc gacaacggcc ccggctactg cagcaaggcc ttccagaagt tcctgagcca    3840
gtggaagatc agccacacca ccggcatccc ctacaacagc cagggccagg ccatcgtgga    3900
gcgcaccaac cgcaccctga agacccagct ggtgaagcag aaggagggcg gcgacagcaa    3960
ggagtgcacc accccccaga tgcagctgaa cctggccctg tacaccctga acttcctgaa    4020
catctaccgc aaccagacca ccaccagcgc cgagcagcac ctgaccggca agaagaacag    4080
cccccacgag ggcaagctga tctggtggaa ggacaacaag aacaagacct gggagatcgg    4140
caaggtgatc acctgggccc gcggcttcgc ctgcgtgagc cccggcgaga ccagctgcc     4200 cgtgtggatc cccacccgcc acctgaagtt ctacaacgag cccatccgcg acgccaagaa    4260
gagcaccagc gccgagaccg agaccagcca gagcagcacc gtggacagcc aggacgagca    4320
gaacggcgac gtgcgccgca ccgacgaggt ggccatccac caggagggcc gcgccgccaa    4380
cctgggcacc accaaggagg ccgacgccgt gagctacaag atcagccgcg agcacaaggg    4440
cgacaccaac ccccgcgagt acgccgcctg cagcctggac gactgcatca acggcggcaa    4500
gagcccctac gcctgccgca gcagctgcag cttaaagaat tcagactcga gcaagtctag    4560
```

```
aaagccatgg atatcggatc cactacgcgt tagagctcgc tgatcagcct cgactgtgcc    4620
ttctagttgc cagccatctg ttgtttgccc ctccccgtg ccttccttga ccctggaagg    4680
tgccactccc actgtccttt cctaataaaa tgaggaaatt gcatcgcatt gtctgagtag    4740
gtgtcattct attctggggg gtggggtggg gcaggacagc aaggggagg attgggaaga     4800 caatagcagg ggggtgggcg aagaactcca gcatgagatc cccgcgctgg aggatcatcc    4860
agccggcgtc ccggaaaacg attccgaagc ccaaccttc atagaaggcg gcggtggaat     4920
cgaaatctcg tgatggcagg ttgggcgtcg cttggtcggt catttcgaac cccagagtcc    4980
cgctcagaag aactcgtcaa gaaggcgata gaaggcgatg cgctgcgaat cgggagcggc    5040
gataccgtaa agcacgagga gcggtcagc ccattcgccg ccaagctctt cagcaatatc     5100
acgggtagcc aacgctatgt cctgatagcg gtccgccaca cccagccggc cacagtcgat    5160
gaatccagaa aagcggccat tttccaccat gatattcggc aagcaggcat cgccatgggt    5220
cacgacgaga tcctcgccgt cgggcatgcg cgccttgagc ctggcgaaca gttcggctgg    5280
cgcgagcccc tgatgctctt cgtccagatc atcctgatcg acaagaccgg cttccatccg    5340
agtacgtgct cgctcgatgc gatgtttcgc ttggtggtcg aatgggcagg tagccggatc    5400
aagcgtatgc agccgccgca ttgcatcagc catgatggat actttctcgg caggagcaag    5460
gtgagatgac aggagatcct gccccggcac ttcgcccaat agcagccagt cccttcccgc    5520
ttcagtgaca acgtcgagca cagctgcgca aggaacgccc gtcgtggcca gccacgatag    5580
ccgcgctgcc tcgtcctgca gttcattcag ggcaccggac aggtcggtct tgacaaaaag    5640
aaccgggcgc ccctgcgctg acagccggaa cacggcggca tcagagcagc cgattgtctg    5700
ttgtgcccag tcatagccga atagcctctc cacccaagcg gccggagaac ctgcgtgcaa    5760
tccatcttgt tcaatcatgc gaaacgatcc tcatcctgtc tcttgatcag atcttgatcc    5820
cctgcgccat cagatccttg gcggcaagaa agccatccag tttactttgc agggcttccc    5880
aaccttacca gagggcgccc cagctggcaa ttccggttcg cttgctgtcc ataaaaccgc    5940
ccagtctagc tatcgccatg taagcccact gcaagctacc tgctttctct ttgcgcttgc    6000
gttttccctt gtccagatag cccagtagct gacattcatc cggggtcagc accgtttctg    6060
cggactggct ttctacgtgt tccgcttcct ttagcagccc ttgcgccctg agtgcttgcg    6120
gcagcgtgaa gctaattcat ggttaaattt ttgttaaatc agctcatttt ttaaccaata    6180
ggccgaaatc ggcaaaatcc cttataaatc aaaagaatag cccgagatag ggttgagtgt    6240
tgttccagtt tggaacaaga gtccactatt aaagaacgtg gactccaacg tcaaagggcg    6300
aaaaaccgtc tatcagggcg atggcccgat cagcttatgc ggtgtgaaat accgcacaga    6360
tgcgtaagga gaaaataccg catcaggcgc tcttccgctt cctcgctcac tgactcgctg    6420
cgctcggtcg ttcggctgcg gcgagcggta tcagctcact caaaggcggt aatacggtta    6480
tccacagaat caggggataa cgcaggaaag aacatgtgag caaaaggcca gcaaaaggcc    6540
aggaaccgta aaaaggccgc gttgctggcg ttttccata ggctccgccc ccctgacgag     6600
catcacaaaa atcgacgctc aagtcagagg tggcgaaacc cgacaggact ataaagatac    6660
caggcgtttc ccctggaag ctccctcgtg cgctctcctg ttccgaccct gccgcttacc     6720
ggatacctgt ccgcctttct cccttcggga agcgtggcgc tttctcatag ctcacgctgt    6780
aggtatctca gttcggtgta ggtcgttcgc tccaagctgg gctgtgtgca cgaaccccc     6840 gttcagcccg accgctgcgc cttatccggt aactatcgtc ttgagtccaa cccggtaaga    6900
cacgacttat cgccactggc agcagccact ggtaacagga ttagcagagc gaggtatgta    6960
```

```
ggcggtgcta cagagttctt gaagtggtgg cctaactacg gctacactag aaggacagta    7020
tttggtatct gcgctctgct gaagccagtt accttcggaa aaagagttgg tagctcttga    7080
tccggcaaac aaaccaccgc tggtagcggt ggttttttg tttgcaagca gcagattacg     7140
cgcagaaaaa aaggatctca agaagatcct ttgatctttt ctactgaacg gtgatcccca    7200
ccggaattgc g                                                         7211

<210> SEQ ID NO 57
<211> LENGTH: 318
<212> TYPE: DNA
<213> ORGANISM: Human endogenous retrovirus, K family (HERV-K)

<400> SEQUENCE: 57
atgaacccat cagagatgca agaaaagca cctccgcgga gacggagaca tcgcaatcga      60
gcaccgttga ctcacaagat gaacaaaatg gtgacgtcag aagaacagat gaagttgcca    120
tccaccaaga aggcagagcc gccaacttgg cacaactaa agaagctgac gcagttagct     180
acaaaatatc tagagaacac aaaggtgaca caaaccccag agagtatgct gcttgcagcc    240
ttgatgattg tatcaatggt gtctgcaggt gtacccaaca gctccgaaga gacagcgacc    300
atcgagaacg ggccatga                                                  318

<210> SEQ ID NO 58
<211> LENGTH: 321
<212> TYPE: DNA
<213> ORGANISM: Artificial Sequence
<220> FEATURE:
<223> OTHER INFORMATION: Modified cORF sequence

<400> SEQUENCE: 58
atgaacccca gcgagatgca gcgcaaggcc ccccccgcc gccgccgcca ccgcaaccgc       60
gcccccctga cccacaagat gaacaagatg gtgaccagcg aggagcagat gaagctgccc    120
agcaccaaga aggccgagcc ccccaccttgg gcccagctga agaagctgac ccagctggcc   180
accaagtacc tggagaacac caaggtgacc cagaccccg agagcatgct gctggccgcc    240
ctgatgatcg tgagcatggt gagcgccggc gtgcccaaca gcagcgagga gaccgccacc   300
atcgagaacg gccccgctta a                                              321

<210> SEQ ID NO 59
<211> LENGTH: 435
<212> TYPE: DNA
<213> ORGANISM: Human endogenous retrovirus, K family (HERV-K)

<400> SEQUENCE: 59
atgaacccat cggagatgca agaaaagca cctccgcgga gacggagaca tcgcaatcga      60
gcaccgttga ctcacaagat gaacaaaatg gtgacgtcag aagaacagat gaagttgcca    120
tccaccaaga aggcagagcc gccaacttgg cacaactaa agaagctgac gcagttagct     180
acaaaatatc tagagaacac aaaggtgaca caaaccccag agagtatgct gcttgcagcc    240
ttgatgattg tatcaatggt ggtgtaccca acagctccga agacagcg accatcgaga     300 acgggccatg atgacgatgg cggttttgtc gaaagaaaa ggggaaatg tggggaaaag      360 caagagagat cagattgtta ctgtgtctgt gtagaaagaa gtagacatag gagactccat    420
tttgttctgt actaa                                                     435

<210> SEQ ID NO 60
<211> LENGTH: 438
```

<212> TYPE: DNA
<213> ORGANISM: Artificial Sequence
<220> FEATURE:
<223> OTHER INFORMATION: Modified PCAP5 sequence

<400> SEQUENCE: 60

| | | | | | | |
|---|---|---|---|---|---|---|
| atgaacccca | gcgagatgca | gcgcaaggcc | cccccccgcc | gccgccgcca | ccgcaaccgc | 60 |
| gcccccctga | cccacaagat | gaacaagatg | gtgaccagcg | aggagcagat | gaagctgccc | 120 |
| agcaccaaga | aggccgagcc | ccccacctgg | gcccagctga | agaagctgac | ccagctggcc | 180 |
| accaagtacc | tggagaacac | caaggtgacc | cagaccccccg | agagcatgct | gctggccgcc | 240 |
| ctgatgatcg | tgagcatggt | ggtgtacccc | accgccccca | agcgccagcg | ccccagccgc | 300 |
| accggccacg | acgacgacgg | cggcttcgtg | gagaagaagc | gcggcaagtg | cggcgagaag | 360 |
| caggagcgca | gcgactgcta | ctgcgtgtgc | gtggagcgca | gccgccaccg | ccgcctgcac | 420 |
| ttcgtgctgt | acgcttaa | | | | | 438 |

<210> SEQ ID NO 61
<211> LENGTH: 2001
<212> TYPE: DNA
<213> ORGANISM: Human endogenous retrovirus, K family (HERV-K)

<400> SEQUENCE: 61

| | | | | | | |
|---|---|---|---|---|---|---|
| atggggcaaa | ctaaaagtaa | aattaaaagt | aaatatgcct | cttatctcag | ctttattaaa | 60 |
| attcttttaa | aaagaggggg | agttaaagta | tctacaaaaa | atctaatcaa | gctatttcaa | 120 |
| ataatagaac | aattttgccc | atggtttcca | gaacaaggaa | ctttagatct | aaaagattgg | 180 |
| aaaagaattg | gtaaggaact | aaaacaagca | ggtaggaagg | gtaatatcat | tccacttaca | 240 |
| gtatggaatg | attgggccat | tattaaagca | gctttagaac | catttcaaac | agaagaagat | 300 |
| agcgtttcag | tttctgatgc | ccctggaagc | tgtataatag | attgtaatga | aaacacaagg | 360 |
| aaaaaatccc | agaaagaaac | ggaaggttta | cattgcgaat | atgtagcaga | gccggtaatg | 420 |
| gctcagtcaa | cgcaaaatgt | tgactataat | caattacagg | aggtgatata | tcctgaaacg | 480 |
| ttaaaattag | aaggaaaagg | tccagaatta | gtggggccat | cagagtctaa | accacgaggc | 540 |
| acaagtcctc | ttccagcagg | tcaggtgcct | gtaacattac | aacctcaaaa | gcaggttaaa | 600 |
| gaaaataaga | cccaaccgcc | agtagccata | caatactggc | ctccggctga | acttcagtat | 660 |
| cggccaccccc | cagaaagtca | gtatggatat | ccaggaatgc | ccccagcacc | acagggcagg | 720 |
| gcgccatacc | ctcagccgcc | cactaggaga | cttaatccta | cggcaccacc | tagtagacag | 780 |
| ggtagtaaat | tacatgaaat | tattgataaa | tcaagaaagg | aaggagatac | tgaggcatgg | 840 |
| caattcccag | taacgttaga | accgatgcca | cctggagaag | gagcccaaga | gggagagcct | 900 |
| cccacagttg | aggccagata | caagtctttt | tcgataaaaa | agctaaaaga | tatgaaagag | 960 |
| ggagtaaaaac | agtatggacc | caactcccct | tatatgagga | cattattaga | ttccattgct | 1020 |
| catggacata | gactcattcc | ttatgattgg | gagattctgg | caaaatcgtc | tctctcaccc | 1080 |
| tctcaatttt | tacaatttaa | gacttggtgg | attgatgggg | tacaagaaca | ggtccgaaga | 1140 |
| aatagggctg | ccaatcctcc | agttaacata | gatgcagatc | aactattagg | aataggtcaa | 1200 |
| aattggagta | ctattagtca | acaagcatta | atgcaaaatg | aggccattga | gcaagttaga | 1260 |
| gctatctgcc | ttagagcctg | ggaaaaaatc | caagacccag | aagtacctg | ccctcattt | 1320 |
| aatacagtaa | gacaaggttc | aaaagagccc | tatcctgatt | ttgtggcaag | gctccaagat | 1380 |
| gttgctcaaa | agtcaattgc | tgatgaaaaa | gcccgtaagg | tcatagtgga | gttgatggca | 1440 |
| tatgaaaacg | ccaatcctga | gtgtcaatca | gccattaagc | cattaaaagg | aaaggttcct | 1500 |

```
gcaggatcag atgtaatctc agaatatgta aaagcctgtg atggaatcgg aggagctatg    1560
cataaagcta tgcttatggc tcaagcaata acaggagttg ttttaggagg acaagttaga    1620
acatttggaa gaaaatgtta taattgtggt caaattggtc acttaaaaaa gaattgccca    1680
gtcttaaata aacagaatat aactattcaa gcaactacaa caggtagaga gccacctgac    1740
ttatgtccaa gatgtaaaaa aggaaaacat tgggctagtc aatgtcgttc taaatttgat    1800
aaaaatgggc aaccattgtc gggaaacgag caaaggggcc agcctcaggc cccacaacaa    1860 actgggcat  tcccaattca gccatttgtt cctcagggtt ttcagggaca acaaccccca    1920
ctgtcccaag tgtttcaggg aataagccag ttaccacaat acaacaattg tccccgcca     1980 caagcggcag tgcagcagta g                                              2001

<210> SEQ ID NO 62
<211> LENGTH: 2004
<212> TYPE: DNA
<213> ORGANISM: Artificial Sequence
<220> FEATURE:
<223> OTHER INFORMATION: Modified gag sequence

<400> SEQUENCE: 62
atgggccaga ccaagagcaa gatcaagagc aagtacgcca gctacctgag cttcatcaag      60
atcctgctga gcgcggcgg  cgtgaaggtg agcaccaaga acctgatcaa gctgttccag     120
atcatcgagc agttctgccc ctggttcccc gagcagggca ccctggacct gaaggactgg     180
aagcgcatcg gcaaggagct gaagcaggcc ggccgcaagg gcaacatcat ccccctgacc     240
gtgtggaacg actgggccat catcaaggcc gccctggagc ccttccagac cgaggaggac     300
agcgtgagcg tgagcgacgc ccccggcagc tgcatcatcg actgcaacga gaacacccgc     360
aagaagagcc agaaggagac cgagggcctg cactgcgagt acgtggccga gccgtgatg      420 gcccagagca cccagaacgt ggactacaac cagctgcagg aggtgatcta ccccgagacc     480
ctgaagctgg agggcaaggg ccccgagctg gtgggcccca gcgagagcaa gccccgcggc     540 accagcccc  tgcccgccgg ccaggtgccc gtgaccctgc agcccagaa  gcaggtgaag     600 gagaacaaga cccagcccc  cgtggcctac cagtactggc ccccgccga  gctgcagtac     660 cgcccccccc ccgagagcca gtacggctac cccggcatgc ccccgcccc  ccagggccgc     720 gcccctacc  cccagccccc cacccgccgc ctgaacccca ccgccccccc cagccgccag     780
ggcagcaagc tgcacgagat catcgacaag agccgcaagg agggcgacac cgaggcctgg     840
cagttccccg tgaccctgga gcccatgccc ccggcgagg  gcgcccagga gggcgagccc     900
cccaccgtgg aggcccgcta caagagcttc agcatcaaga gctgaagga  catgaaggag     960 ggcgtgaagc agtacggccc caacagcccc tacatgcgca ccctgctgga cagcatcgcc    1020
cacggccacc gcctgatccc ctacgactgg gagatcctgg ccaagagcag cctgagcccc    1080
agccagttcc tgcagttcaa gacctggtgg atcgacggcg tgcaggagca ggtgcgccgc    1140
aaccgcgccg ccaacccccc cgtgaacatc gacgccgacc agctgctggg catcggccag    1200
aactggagca ccatcagcca gcaggccctg atgcagaacg aggccatcga gcaggtgcgc    1260
gccatctgcc tgcgcgccct ggagaagatc caggacccg  gcagcacctg ccccagcttc    1320
aacaccgtgc gccagggcag caaggagccc taccccgact cgtggcccg  cctgcaggac    1380 gtggcccaga gagcatcgc  cgacgagaag gccgcaagg  tgatcgtgga gctgatggcc    1440
tacgagaacg ccaaccccga gtgccagagc gccatcaagc ccctgaaggg caaggtgccc    1500
gccggcagcg acgtgatcag cgagtacgtg aaggcctgcg acggcatcgg cggcgccatg    1560
```

| | |
|---|---|
| cacaaggcca tgctgatggc ccaggccatc accggcgtgg tgctgggcgg ccaggtgcgc | 1620 |
| accttcggcc gcaagtgcta caactgcggc cagatcggcc acctgaagaa gaactgcccc | 1680 |
| gtgctgaaca agcagaacat caccatccag gccaccacca ccggccgcga gcccccgac | 1740 |
| ctgtgccccc gctgcaagaa gggcaagcac tgggccagcc agtgccgcag caagttcgac | 1800 |
| aagaacggcc agcccctgag cggcaacgag cagcgcggcc agcccaggc cccccagcag | 1860 |
| accggcgcct tccccatcca gcccttcgtg ccccagggct ccagggcca gcagcccccc | 1920 |
| ctgagccagg tgttccaggg catcagccag ctgccccagt acaacaactg ccccccccc | 1980 |
| caggccgccg tgcagcaggc ttaa | 2004 |

<210> SEQ ID NO 63
<211> LENGTH: 1005
<212> TYPE: DNA
<213> ORGANISM: Human endogenous retrovirus, K family (HERV-K)

<400> SEQUENCE: 63

| | |
|---|---|
| atgtgggcaa ccattgtcgg gaaacgagca aaggggccag cctcaggccc cacaacaaac | 60 |
| tggggcattc ccaattcagc catttgttcc tcagggtttt cagggacaac aaccccact | 120 |
| gtcccaagtg tttcagggaa taagccagtt accacaatac aacaattgtc ccccgccaca | 180 |
| agcggcagtg cagcagtaga tttatgtact atacaagcca tctctctgct tccaggggag | 240 |
| cccccacaaa aaaccccac agggggtatat ggaccctgc ctaaggggac tgtaggacta | 300 |
| atcttgggac gatcaagtct aaatctaaaa ggagttcaaa ttcatactag tgtggttgat | 360 |
| tcagactata aaggcgaaat tcaattggtt attagctctt caattccttg gagtgccagt | 420 |
| ccaagagaca ggattgctca attattactc ctgccataca ttaagggtgg aaatagtgaa | 480 |
| ataaaagaa taggagggct tggaagcact gatccaacag gaaaggctgc atattgggca | 540 |
| agtcaggtct cagagaacag acctgtgtgt aaggccatta ttcaaggaaa acagtttgaa | 600 |
| gggttggtag acactggagc agatgtctct atcattgctt taaatcagtg gccaaaaaat | 660 |
| tggcctaaac aaaaggctgt tacaggactt gtcggcatag gcacagcctc agaagtgtat | 720 |
| caaagtacgg agattttaca ttgcttaggg ccagataatc aagaaagtac tgttcagcca | 780 |
| atgattactt caattcctct taatctgtgg ggtcgagatt tattacaaca atggggtgcg | 840 |
| gaaatcacca tgcccgctcc atcatatagc cccacgagtc aaaaaatcat gaccaagatg | 900 |
| ggatatatac caggaaaggg actagggaaa aatgaagatg cattaaaat tccagttgag | 960 |
| gctaaaataa atcaagaaag agaaggaata gggaatcctt gctag | 1005 |

<210> SEQ ID NO 64
<211> LENGTH: 1008
<212> TYPE: DNA
<213> ORGANISM: Artificial Sequence
<220> FEATURE:
<223> OTHER INFORMATION: Modified Prt sequence

<400> SEQUENCE: 64

| | |
|---|---|
| atgtgggcca ccatcgtggg caagcgcgcc aagggccccg ccagcggccc caccaccaac | 60 |
| tggggcatcc ccaacagcgc catctgcagc agcggcttca gcggcaccac cacccccacc | 120 |
| gtgcccagcg tgagcggcaa caagcccgtg accaccatcc agcagctgag ccccgccacc | 180 |
| agcggcagcg ccgccgtgga cctgtgcacc atccaggccg tgagcctgct gccggcgag | 240 |
| ccccccaga agaccccac cggcgtgtac ggccccctgc ccaagggcac cgtgggcctg | 300 |
| atcctgggcc gcagcagcct gaacctgaag ggcgtgcaga tccacaccag cgtggtggac | 360 |

```
agcgactaca agggcgagat ccagctggtg atcagcagca gcatcccctg gagcgccagc    420
ccccgcgacc gcatcgccca gctgctgctg ctgccctaca tcaagggcgg caacagcgag    480
atcaagcgca tcggcggcct gggcagcacc gaccccaccg gcaaggccgc ctactgggcc    540
agccaggtga gcgagaaccg ccccgtgtgc aaggccatca tccagggcaa gcagttcgag    600
ggcctggtgg acaccggcgc cgacgtgagc atcatcgccc tgaaccagtg gcccaagaac    660
tggcccaagc agaaggccgt gaccggcctg gtgggcatcg gcaccgccag cgaggtgtac    720
cagagcaccg atcctgca ctgcctgggc cccgacaacc aggagagcac cgtgcagccc      780
atgatcacca gcatcccccct gaacctgtgg gccgcgacc tgctgcagca gtggggcgcc    840
gagatcacca tgcccgcccc cagctacagc cccaccagcc agaagatcat gaccaagatg    900
ggctacatcc ccggcaaggg cctgggcaag aacgaggacg gcatcaagat ccccgtggag    960
gccaagatca accaggagcg cgagggcatc ggcaacccct gcgcttaa                1008

<210> SEQ ID NO 65
<211> LENGTH: 2874
<212> TYPE: DNA
<213> ORGANISM: Human endogenous retrovirus, K family (HERV-K)

<400> SEQUENCE: 65
atgaataaat caagaaagag aaggaatagg gaatccttgc taggggcggc cactgtagag     60
cctcctaaac ccataccatt aacttggaaa acagaaaaac cagtgtgggt aaatcagtgg    120
ccgctaccaa aacaaaaact ggaggcttta catttattag caaatgaaca gttagaaaag    180
ggtcatattg agccttcgtt ctcaccttgg aattctcctg tgtttgtaat tcagaagaaa    240
tcaggcaaat ggcgtatgtt aactgactta agggctgtaa acgccgtaat tcaacccatg    300
gggcctctcc aacccgggtt gccctctccg gccatgatcc caaaagattg gcctttaatt    360
ataattgatc taaaggattg cttttttacc atccctctgg cagagcagga ttgcgaaaaa    420
tttgccttta ctataccagc cataaataat aaagaaccag ccaccaggtt tcagtggaaa    480
gtgttacctc agggaatgct taatagtcca actatttgtc agacttttgt aggtcgagct    540
cttcaaccag ttagagaaaa gttttcagac tgttatatta ttcattgtat tgatgatatt    600 ttatgtctg cagaaacgaa agataaatta attgactgtt atacatttct gcaagcagag     660
gttgccaatg ctggactggc aatagcatct gataagatcc aaacctctac tccttttcat    720
tatttaggga tgcagataga aaatagaaaa attaagccac aaaaaatag aataagaaaa     780 gacacattaa aaacactaaa tgattttcaa aaattactag gagatattaa ttggattcgg    840
ccaactctag gcattcctac ttatgccatg tcaaatttgt tctctatctt aagaggagac    900
tcagacttaa atagtaaaag aatgttaacc ccagaggcaa caaagaaaat taaattagtg    960
gaagaaaaaa ttcagtcagc gcaaataaat agaatagatc ccttagcccc actccaactt   1020
ttgatttttg ccactgcaca ttctccaaca ggcatcatta ttcaaaatac tgatcttgtg   1080
gagtggtcat tccttcctca cagtacagtt aagacttta cattgtactt ggatcaaata   1140
gctacattaa tcggtcagac aagattacga ataataaaat tatgtgggaa tgacccagac   1200
aaaatagttg tcccttttaac caaggaacaa gttagacaag cctttatcaa ttctggtgca   1260
tggaagattg gtcttgctaa ttttgtggga attattgata tcattacccc aaaaacaaag   1320
atcttccagt tcttaaaatt gactacttgg attctaccta aaattaccag acgtgaacct   1380
ttagaaaatg ctctaacagt atttactgat ggttccagca atggaaagc agcttacaca     1440 ggaccgaaag aacgagtaat caaaactcca tatcaatcgg ctcaaagagc agagttggtt   1500
```

```
gcagtcatta cagtgttaca agattttgac caacctatca atattatatc agattctgca    1560
tatgtagtac aggctacaag ggatgttgag acagctctaa ttaaatatag catggatgat    1620
cagttaaacc agctattcaa tttattacaa caaactgtaa gaaaagaaa tttcccattt     1680 tatattacac atattcgagc acacactaat ttaccagggc ctttgactaa agcaaatgaa    1740
caagctgact tactggtatc atctgcactc ataaaagcac aagaacttca tgctttgact    1800
catgtaaatg cagcaggatt aaaaaacaaa tttgatgtca catggaaaca ggcaaaagat    1860
attgtacaac attgcaccca gtgtcaagtc ttacacctgc ccactcaaga ggcaggagtt    1920
aatcccagag gtctgtgtcc taatgcatta tggcaaatgg atgtcacgca tgtaccttca    1980
tttggaagat tatcatatgt tcacgtaaca gttgatactt attcacattt catatgggca    2040
acttgccaaa caggagaaag tacttcccat gttaaaaaac atttattgtc ttgttttgct    2100
gtaatgggag ttccagaaaa aatcaaaact gacaatggac caggatattg tagtaaagct    2160
ttccaaaaat tcttaagtca gtggaaaatt tcacatacaa caggaattcc ttataattcc    2220
caaggacagg ccatagttga agaactaat agaacactca aaactcaatt agttaaacaa     2280
aaagaagggg gagacagtaa ggagtgtacc actcctcaga tgcaacttaa tctagcactc    2340
tatactttaa attttttaaa cattatagaa atcagacta ctacttctgc agaacaacat     2400
cttactggta aaaagaacag cccacatgaa ggaaaactaa tttggtggaa agataataaa    2460
aataagacat gggaaatagg gaaggtgata acgtggggga gaggttttgc ttgtgtttca    2520
ccaggagaaa atcagcttcc tgtttggata cccactagac atttgaagtt ctacaatgaa    2580
cccatcagag atgcaaagaa aagcacctcc gcggagacgg agacatcgca atcgagcacc    2640
gttgactcac aagatgaaca aaatggtgac gtcagaagaa cagatgaagt tgccatccac    2700
caagaaggca gagccgccaa cttgggcaca actaagaag ctgacgcagt tagctacaaa     2760
atatctagag aacacaaagg tgacacaaac cccagagagt atgctgcttg cagccttgat    2820
gattgtatca atggtggtaa gtctccctat gcctgcagga gcagctgcag ctaa          2874

<210> SEQ ID NO 66
<211> LENGTH: 2877
<212> TYPE: DNA
<213> ORGANISM: Artificial Sequence
<220> FEATURE:
<223> OTHER INFORMATION: Modified pol sequence

<400> SEQUENCE: 66
atgaacaaga gccgcaagcg ccgcaaccgc gagagcctgc tgggcgccgc caccgtggag      60
ccccccaagc ccatcccccct gacctggaag accgagaagc ccgtgtgggt gaaccagtgg    120 ccctgccca gcagaagct ggaggccctg cacctgctgg ccaacgagca gctggagaag       180
ggccacatcg agcccagctt cagccctgg aacagccccg tgttcgtgat ccagaagaag      240
agcggcaagt ggcgcatgct gaccgacctg cgcgccgtga acgccgtgat ccagcccatg     300 ggcccctgc agccggcct gcccagcccc gccatgatcc caaggactg gcccctgatc         360 atcatcgacc tgaaggactg cttcttcacc atccccctgg ccgagcagga ctgcgagaag      420
ttcgccttca ccatccccgc catcaacaac aaggagcccg ccacccgctt ccagtggaag      480
gtgctgcccc agggcatgct gaacagcccc accatctgcc agaccttcgt gggccgcgcc      540
ctgcagcccg tgcgcgagaa gttcagcgac tgctacatca tccactgcat cgacgacatc      600
ctgtgcgccg ccgagaccaa ggacaagctg atcgactgct acaccttcct gcaggccgag      660
gtggccaacg ccggcctggc catcgccagc gacaagatcc agaccagcac cccttccac       720
```

```
tacctgggca tgcagatcga gaaccgcaag atcaagcccc agaagatcga gatccgcaag    780
gacaccctga agaccctgaa cgacttccag aagctgctgg gcgacatcaa ctggatccgc    840
cccaccctgg gcatcccgac ctacgccatg agcaacctgt tcagcatcct gcgcggcgac    900
agcgacctga acagcaagcg catgctgacc cccgaggcca ccaaggagat caagctggtg    960
gaggagaaga tccagagcgc ccagatcaac cgcatcgacc ccctggcccc cctgcagctg    1020
ctgatcttcg ccaccgccca gcccaccc ggcatcatca tccagaacac cgacctggtg     1080
gagtggagct tcctgcccca cagcaccgtg aagaccttca ccctgtacct ggaccagatc    1140
gccaccctga tcggccagac ccgcctgcgc atcatcaagc tgtgcggcaa cgaccccgac    1200
aagatcgtgg tgcccctgac caaggagcag gtgcgccagg ccttcatcaa cagcggcgcc    1260
tggaagatcg gcctggccaa cttcgtgggc atcatcgaca accactaccc caagaccaag    1320
atcttccagt tcctgaagct gaccacctgg atcctgccca agatcacccg ccgcgagccc    1380
ctggagaacg ccctgaccgt gttcaccgac ggcagcagca cggcaaggc cgcctacacc     1440
ggccccaagg agcgcgtgat caagaccccc taccagagcg cccagcgcgc cgagctggtg    1500
gccgtgatca ccgtgctgca ggacttcgac cagcccatca acatcatcag cgacagcgcc    1560
tacgtggtgc aggccacccg cgacgtggag accgccctga tcaagtacag catggacgac    1620
cagctgaacc agctgttcaa cctgctgcag cagaccgtgc gcaagcgcaa cttccccttc    1680
tacatcaccc acatccgcgc ccacaccaac ctgcccggcc ccctgaccaa ggccaacgag    1740
caggccgacc tgctggtgag cagcgccctg atcaaggccc aggagctgca cgccctgacc    1800
cacgtgaacg ccgccggcct gaagaacaag ttcgacgtga cctggaagca ggccaaggac    1860
atcgtgcagc actgcacccca gtgccaggtg ctgcacctgc ccacccagga ggccggcgtg    1920
aaccccgcg gcctgtgccc caacgccctg tggcagatgg acgtgaccca cgtgcccagc    1980
ttcggccgc tgagctacgt gcacgtgacc gtggacacct acagccactt catctgggcc    2040
acctgccaga ccggcgagag caccagccac gtgaagaagc acctgctgag ctgcttcgcc    2100
gtgatgggcg tgcccgagaa gatcaagacc gacaacggcc ccggctactg cagcaaggcc    2160
ttccagaagt tcctgagcca gtggaagatc agccacacca ccggcatccc ctacaacagc    2220
cagggccagg ccatcgtgga gcgcaccaac cgcacccctg agacccagct ggtgaagcag    2280
aaggagggcg gcgacagcaa ggagtgcacc accccccaga tgcagctgaa cctggccctg    2340
tacaccctga acttcctgaa catctaccgc aaccagacca ccaccagcgc cgagcagcac    2400
ctgaccggca agaagaacag cccccacgag ggcaagctga tctggtggaa ggacaacaag    2460
aacaagacct gggagatcgg caaggtgatc acctggggcc gcggcttcgc ctgcgtgagc    2520
cccggcgaga ccagctgcc cgtgtggatc cccacccgcc acctgaagtt ctacaacgag    2580
cccatccgcg acgccaagaa gagcaccagc gccgagaccg agaccagcca gagcagcacc    2640
gtggacagcc aggacgagca gaacggcgac gtgcgccgca ccgacgaggt ggccatccac    2700
caggagggcc gcgccgccaa cctgggcacc accaaggagg ccgacgccgt gagctacaag    2760
atcagccgcg agcacaaggg cgacaccaac ccccgcgagt acgccgcctg cagcctggac    2820
gactgcatca acggcggcaa gagcccctac gcctgccgca gcagctgcag cgcttaa       2877
```

<210> SEQ ID NO 67
<211> LENGTH: 106
<212> TYPE: PRT
<213> ORGANISM: Artificial Sequence
<220> FEATURE:
<223> OTHER INFORMATION: Manipulated cORF

<400> SEQUENCE: 67

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Ser Ala Gly Val Pro Asn Ser Ser Glu
                85                  90                  95

Glu Thr Ala Thr Ile Glu Asn Gly Pro Ala
            100                 105

<210> SEQ ID NO 68
<211> LENGTH: 145
<212> TYPE: PRT
<213> ORGANISM: Artificial Sequence
<220> FEATURE:
<223> OTHER INFORMATION: Manipulated PCAP5

<400> SEQUENCE: 68

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Tyr Pro Thr Ala Pro Lys Arg Gln
                85                  90                  95

Arg Pro Ser Arg Thr Gly His Asp Asp Gly Gly Phe Val Glu Lys
            100                 105                 110

Lys Arg Gly Lys Cys Gly Glu Lys Gln Glu Arg Ser Asp Cys Tyr Cys
        115                 120                 125

Val Cys Val Glu Arg Ser Arg His Arg Arg Leu His Phe Val Leu Tyr
    130                 135                 140

Ala
145

<210> SEQ ID NO 69
<211> LENGTH: 666
<212> TYPE: PRT
<213> ORGANISM: Human endogenous retrovirus, K family (HERV-K)

<400> SEQUENCE: 69

Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Gly Val Lys Val Ser Thr
            20                  25                  30

Lys Asn Leu Ile Lys Leu Phe Gln Ile Ile Glu Gln Phe Cys Pro Trp
        35                  40                  45

```
Phe Pro Glu Gln Gly Thr Leu Asp Leu Lys Asp Trp Lys Arg Ile Gly
         50                  55                  60

Lys Glu Leu Lys Gln Ala Gly Arg Lys Gly Asn Ile Ile Pro Leu Thr
 65                  70                  75                  80

Val Trp Asn Asp Trp Ala Ile Ile Lys Ala Ala Leu Glu Pro Phe Gln
                 85                  90                  95

Thr Glu Glu Asp Ser Val Ser Val Ser Asp Ala Pro Gly Ser Cys Ile
            100                 105                 110

Ile Asp Cys Asn Glu Asn Thr Arg Lys Lys Ser Gln Lys Glu Thr Glu
        115                 120                 125

Gly Leu His Cys Glu Tyr Val Ala Glu Pro Val Met Ala Gln Ser Thr
    130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
        195                 200                 205

Ala Tyr Gln Tyr Trp Pro Pro Ala Glu Leu Gln Tyr Arg Pro Pro Pro
    210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Gln Gly Ser Lys Leu His Glu Ile Ile Asp Lys Ser Arg
            260                 265                 270

Lys Glu Gly Asp Thr Glu Ala Trp Gln Phe Pro Val Thr Leu Glu Pro
        275                 280                 285

Met Pro Pro Gly Glu Gly Ala Gln Glu Gly Glu Pro Pro Thr Val Glu
    290                 295                 300

Ala Arg Tyr Lys Ser Phe Ser Ile Lys Lys Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
        355                 360                 365

Trp Trp Ile Asp Gly Val Gln Glu Gln Val Arg Arg Asn Arg Ala Ala
    370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
                405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
        435                 440                 445

Glu Pro Tyr Pro Asp Phe Val Ala Arg Leu Gln Asp Val Ala Gln Lys
    450                 455                 460

Ser Ile Ala Asp Glu Lys Ala Arg Lys Val Ile Val Glu Leu Met Ala
```

```
                465                 470                 475                 480
Tyr Glu Asn Ala Asn Pro Glu Cys Gln Ser Ala Ile Lys Pro Leu Lys
                    485                 490                 495
Gly Lys Val Pro Ala Gly Ser Asp Val Ile Ser Glu Tyr Val Lys Ala
                500                 505                 510
Cys Asp Gly Ile Gly Gly Ala Met His Lys Ala Met Leu Met Ala Gln
            515                 520                 525
Ala Ile Thr Gly Val Val Leu Gly Gly Gln Val Arg Thr Phe Gly Arg
        530                 535                 540
Lys Cys Tyr Asn Cys Gly Gln Ile Gly His Leu Lys Lys Asn Cys Pro
545                 550                 555                 560
Val Leu Asn Lys Gln Asn Ile Thr Ile Gln Ala Thr Thr Gly Arg
                565                 570                 575
Glu Pro Pro Asp Leu Cys Pro Arg Cys Lys Lys Gly Lys His Trp Ala
                580                 585                 590
Ser Gln Cys Arg Ser Lys Phe Asp Lys Asn Gly Gln Pro Leu Ser Gly
            595                 600                 605
Asn Glu Gln Arg Gly Gln Pro Gln Ala Pro Gln Gln Thr Gly Ala Phe
        610                 615                 620
Pro Ile Gln Pro Phe Val Pro Gln Gly Phe Gln Gly Gln Pro Pro
625                 630                 635                 640
Leu Ser Gln Val Phe Gln Gly Ile Ser Gln Leu Pro Gln Tyr Asn Asn
                645                 650                 655
Cys Pro Pro Pro Gln Ala Ala Val Gln Gln
            660                 665

<210> SEQ ID NO 70
<211> LENGTH: 667
<212> TYPE: PRT
<213> ORGANISM: Artificial Sequence
<220> FEATURE:
<223> OTHER INFORMATION: Manipulated Gag

<400> SEQUENCE: 70

Met Gly Gln Thr Lys Ser Lys Ile Lys Ser Lys Tyr Ala Ser Tyr Leu
1               5                   10                  15
Ser Phe Ile Lys Ile Leu Leu Lys Arg Gly Gly Val Lys Val Ser Thr
            20                  25                  30
Lys Asn Leu Ile Lys Leu Phe Gln Ile Ile Glu Gln Phe Cys Pro Trp
        35                  40                  45
Phe Pro Glu Gln Gly Thr Leu Asp Leu Lys Asp Trp Lys Arg Ile Gly
    50                  55                  60
Lys Glu Leu Lys Gln Ala Gly Arg Lys Gly Asn Ile Ile Pro Leu Thr
65                  70                  75                  80
Val Trp Asn Asp Trp Ala Ile Ile Lys Ala Ala Leu Glu Pro Phe Gln
                85                  90                  95
Thr Glu Glu Asp Ser Val Ser Val Ser Asp Ala Pro Gly Ser Cys Ile
            100                 105                 110
Ile Asp Cys Asn Glu Asn Thr Arg Lys Lys Ser Gln Lys Glu Thr Glu
        115                 120                 125
Gly Leu His Cys Glu Tyr Val Ala Glu Pro Val Met Ala Gln Ser Thr
    130                 135                 140
Gln Asn Val Asp Tyr Asn Gln Leu Gln Glu Val Ile Tyr Pro Glu Thr
145                 150                 155                 160
Leu Lys Leu Glu Gly Lys Gly Pro Glu Leu Val Gly Pro Ser Glu Ser
                165                 170                 175
```

```
Lys Pro Arg Gly Thr Ser Pro Leu Pro Ala Gly Gln Val Pro Val Thr
            180                 185                 190

Leu Gln Pro Gln Lys Gln Val Lys Glu Asn Lys Thr Gln Pro Pro Val
            195                 200                 205

Ala Tyr Gln Tyr Trp Pro Pro Ala Glu Leu Gln Tyr Arg Pro Pro Pro
            210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
            245                 250                 255

Pro Ser Arg Gln Gly Ser Lys Leu His Glu Ile Ile Asp Lys Ser Arg
            260                 265                 270

Lys Glu Gly Asp Thr Glu Ala Trp Gln Phe Pro Val Thr Leu Glu Pro
            275                 280                 285

Met Pro Pro Gly Glu Gly Ala Gln Glu Gly Glu Pro Pro Thr Val Glu
            290                 295                 300

Ala Arg Tyr Lys Ser Phe Ser Ile Lys Lys Leu Lys Asp Met Lys Glu
305                 310                 315                 320

Gly Val Lys Gln Tyr Gly Pro Asn Ser Pro Tyr Met Arg Thr Leu Leu
            325                 330                 335

Asp Ser Ile Ala His Gly His Arg Leu Ile Pro Tyr Asp Trp Glu Ile
            340                 345                 350

Leu Ala Lys Ser Ser Leu Ser Pro Ser Gln Phe Leu Gln Phe Lys Thr
            355                 360                 365

Trp Trp Ile Asp Gly Val Gln Glu Gln Val Arg Arg Asn Arg Ala Ala
            370                 375                 380

Asn Pro Pro Val Asn Ile Asp Ala Asp Gln Leu Leu Gly Ile Gly Gln
385                 390                 395                 400

Asn Trp Ser Thr Ile Ser Gln Gln Ala Leu Met Gln Asn Glu Ala Ile
            405                 410                 415

Glu Gln Val Arg Ala Ile Cys Leu Arg Ala Trp Glu Lys Ile Gln Asp
            420                 425                 430

Pro Gly Ser Thr Cys Pro Ser Phe Asn Thr Val Arg Gln Gly Ser Lys
            435                 440                 445

Glu Pro Tyr Pro Asp Phe Val Ala Arg Leu Gln Asp Val Ala Gln Lys
            450                 455                 460

Ser Ile Ala Asp Glu Lys Ala Arg Lys Val Ile Val Glu Leu Met Ala
465                 470                 475                 480

Tyr Glu Asn Ala Asn Pro Glu Cys Gln Ser Ala Ile Lys Pro Leu Lys
            485                 490                 495

Gly Lys Val Pro Ala Gly Ser Asp Val Ile Ser Glu Tyr Val Lys Ala
            500                 505                 510

Cys Asp Gly Ile Gly Gly Ala Met His Lys Ala Met Leu Met Ala Gln
            515                 520                 525

Ala Ile Thr Gly Val Val Leu Gly Gly Gln Val Arg Thr Phe Gly Arg
            530                 535                 540

Lys Cys Tyr Asn Cys Gly Gln Ile Gly His Leu Lys Lys Asn Cys Pro
545                 550                 555                 560

Val Leu Asn Lys Gln Asn Ile Thr Ile Gln Ala Thr Thr Thr Gly Arg
            565                 570                 575

Glu Pro Pro Asp Leu Cys Pro Arg Cys Lys Lys Gly Lys His Trp Ala
            580                 585                 590

Ser Gln Cys Arg Ser Lys Phe Asp Lys Asn Gly Gln Pro Leu Ser Gly
```

-continued

```
                595                 600                 605
Asn Glu Gln Arg Gly Gln Pro Gln Ala Pro Gln Thr Gly Ala Phe
            610                 615                 620

Pro Ile Gln Pro Phe Val Pro Gln Gly Phe Gln Gly Gln Pro Pro
625                 630                 635                 640

Leu Ser Gln Val Phe Gln Gly Ile Ser Gln Leu Pro Gln Tyr Asn Asn
                645                 650                 655

Cys Pro Pro Gln Ala Ala Val Gln Gln Ala
            660                 665

<210> SEQ ID NO 71
<211> LENGTH: 334
<212> TYPE: PRT
<213> ORGANISM: Human endogenous retrovirus, K family (HERV-K)

<400> SEQUENCE: 71

Met Trp Ala Thr Ile Val Gly Lys Arg Ala Lys Gly Pro Ala Ser Gly
1               5                   10                  15

Pro Thr Thr Asn Trp Gly Ile Pro Asn Ser Ala Ile Cys Ser Ser Gly
                20                  25                  30

Phe Ser Gly Thr Thr Thr Pro Thr Val Pro Ser Val Ser Gly Asn Lys
            35                  40                  45

Pro Val Thr Thr Ile Gln Gln Leu Ser Pro Ala Thr Ser Gly Ser Ala
50                  55                  60

Ala Val Asp Leu Cys Thr Ile Gln Ala Val Ser Leu Leu Pro Gly Glu
65                  70                  75                  80

Pro Pro Gln Lys Thr Pro Thr Gly Val Tyr Gly Pro Leu Pro Lys Gly
                85                  90                  95

Thr Val Gly Leu Ile Leu Gly Arg Ser Ser Leu Asn Leu Lys Gly Val
            100                 105                 110

Gln Ile His Thr Ser Val Val Asp Ser Asp Tyr Lys Gly Glu Ile Gln
        115                 120                 125

Leu Val Ile Ser Ser Ser Ile Pro Trp Ser Ala Ser Pro Arg Asp Arg
130                 135                 140

Ile Ala Gln Leu Leu Leu Leu Pro Tyr Ile Lys Gly Gly Asn Ser Glu
145                 150                 155                 160

Ile Lys Arg Ile Gly Gly Leu Gly Ser Thr Asp Pro Thr Gly Lys Ala
                165                 170                 175

Ala Tyr Trp Ala Ser Gln Val Ser Glu Asn Arg Pro Val Cys Lys Ala
            180                 185                 190

Ile Ile Gln Gly Lys Gln Phe Glu Gly Leu Val Asp Thr Gly Ala Asp
        195                 200                 205

Val Ser Ile Ile Ala Leu Asn Gln Trp Pro Lys Asn Trp Pro Lys Gln
210                 215                 220

Lys Ala Val Thr Gly Leu Val Gly Ile Gly Thr Ala Ser Glu Val Tyr
225                 230                 235                 240

Gln Ser Thr Glu Ile Leu His Cys Leu Gly Pro Asp Asn Gln Glu Ser
                245                 250                 255

Thr Val Gln Pro Met Ile Thr Ser Ile Pro Leu Asn Leu Trp Gly Arg
            260                 265                 270

Asp Leu Leu Gln Gln Trp Gly Ala Glu Ile Thr Met Pro Ala Pro Ser
        275                 280                 285

Tyr Ser Pro Thr Ser Gln Lys Ile Met Thr Lys Met Gly Tyr Ile Pro
290                 295                 300

Gly Lys Gly Leu Gly Lys Asn Glu Asp Gly Ile Lys Ile Pro Val Glu
```

```
                305                 310                 315                 320
Ala Lys Ile Asn Gln Glu Arg Glu Gly Ile Gly Asn Pro Cys
                325                 330

<210> SEQ ID NO 72
<211> LENGTH: 335
<212> TYPE: PRT
<213> ORGANISM: Artificial Sequence
<220> FEATURE:
<223> OTHER INFORMATION: Manipulated Prt

<400> SEQUENCE: 72

Met Trp Ala Thr Ile Val Gly Lys Arg Ala Lys Gly Pro Ala Ser Gly
1               5                   10                  15

Pro Thr Thr Asn Trp Gly Ile Pro Asn Ser Ala Ile Cys Ser Ser Gly
                20                  25                  30

Phe Ser Gly Thr Thr Thr Pro Thr Val Pro Ser Val Ser Gly Asn Lys
            35                  40                  45

Pro Val Thr Thr Ile Gln Gln Leu Ser Pro Ala Thr Ser Gly Ser Ala
    50                  55                  60

Ala Val Asp Leu Cys Thr Ile Gln Ala Val Ser Leu Leu Pro Gly Glu
65                  70                  75                  80

Pro Pro Gln Lys Thr Pro Thr Gly Val Tyr Gly Pro Leu Pro Lys Gly
                85                  90                  95

Thr Val Gly Leu Ile Leu Gly Arg Ser Ser Leu Asn Leu Lys Gly Val
                100                 105                 110

Gln Ile His Thr Ser Val Val Asp Ser Asp Tyr Lys Gly Glu Ile Gln
            115                 120                 125

Leu Val Ile Ser Ser Ser Ile Pro Trp Ser Ala Ser Pro Arg Asp Arg
130                 135                 140

Ile Ala Gln Leu Leu Leu Pro Tyr Ile Lys Gly Gly Asn Ser Glu
145                 150                 155                 160

Ile Lys Arg Ile Gly Gly Leu Gly Ser Thr Asp Pro Thr Gly Lys Ala
                165                 170                 175

Ala Tyr Trp Ala Ser Gln Val Ser Glu Asn Arg Pro Val Cys Lys Ala
            180                 185                 190

Ile Ile Gln Gly Lys Gln Phe Glu Gly Leu Val Asp Thr Gly Ala Asp
        195                 200                 205

Val Ser Ile Ile Ala Leu Asn Gln Trp Pro Lys Asn Trp Pro Lys Gln
    210                 215                 220

Lys Ala Val Thr Gly Leu Val Gly Ile Gly Thr Ala Ser Glu Val Tyr
225                 230                 235                 240

Gln Ser Thr Glu Ile Leu His Cys Leu Gly Pro Asp Asn Gln Glu Ser
                245                 250                 255

Thr Val Gln Pro Met Ile Thr Ser Ile Pro Leu Asn Leu Trp Gly Arg
            260                 265                 270

Asp Leu Leu Gln Gln Trp Gly Ala Glu Ile Thr Met Pro Ala Pro Ser
        275                 280                 285

Tyr Ser Pro Thr Ser Gln Lys Ile Met Thr Lys Met Gly Tyr Ile Pro
    290                 295                 300

Gly Lys Gly Leu Gly Lys Asn Glu Asp Gly Ile Lys Ile Pro Val Glu
305                 310                 315                 320

Ala Lys Ile Asn Gln Glu Arg Glu Gly Ile Gly Asn Pro Cys Ala
                325                 330                 335

<210> SEQ ID NO 73
```

-continued

<211> LENGTH: 957
<212> TYPE: PRT
<213> ORGANISM: Human endogenous retrovirus, K family (HERV-K)

<400> SEQUENCE: 73

```
Met Asn Lys Ser Arg Lys Arg Asn Arg Glu Ser Leu Leu Gly Ala
1               5                   10                  15

Ala Thr Val Glu Pro Pro Lys Pro Ile Pro Leu Thr Trp Lys Thr Glu
            20                  25                  30

Lys Pro Val Trp Val Asn Gln Trp Pro Leu Pro Lys Gln Lys Leu Glu
                35                  40                  45

Ala Leu His Leu Leu Ala Asn Glu Gln Leu Glu Lys Gly His Ile Glu
        50                  55                  60

Pro Ser Phe Ser Pro Trp Asn Ser Pro Val Phe Val Ile Gln Lys Lys
65                  70                  75                  80

Ser Gly Lys Trp Arg Met Leu Thr Asp Leu Arg Ala Val Asn Ala Val
                85                  90                  95

Ile Gln Pro Met Gly Pro Leu Gln Pro Gly Leu Pro Ser Pro Ala Met
            100                 105                 110

Ile Pro Lys Asp Trp Pro Leu Ile Ile Ile Asp Leu Lys Asp Cys Phe
        115                 120                 125

Phe Thr Ile Pro Leu Ala Glu Gln Asp Cys Glu Lys Phe Ala Phe Thr
130                 135                 140

Ile Pro Ala Ile Asn Asn Lys Glu Pro Ala Thr Arg Phe Gln Trp Lys
145                 150                 155                 160

Val Leu Pro Gln Gly Met Leu Asn Ser Pro Thr Ile Cys Gln Thr Phe
                165                 170                 175

Val Gly Arg Ala Leu Gln Pro Val Arg Glu Lys Phe Ser Asp Cys Tyr
            180                 185                 190

Ile Ile His Cys Ile Asp Asp Ile Leu Cys Ala Ala Glu Thr Lys Asp
        195                 200                 205

Lys Leu Ile Asp Cys Tyr Thr Phe Leu Gln Ala Glu Val Ala Asn Ala
    210                 215                 220

Gly Leu Ala Ile Ala Ser Asp Lys Ile Gln Thr Ser Thr Pro Phe His
225                 230                 235                 240

Tyr Leu Gly Met Gln Ile Glu Asn Arg Lys Ile Lys Pro Gln Lys Ile
                245                 250                 255

Glu Ile Arg Lys Asp Thr Leu Lys Thr Leu Asn Asp Phe Gln Lys Leu
            260                 265                 270

Leu Gly Asp Ile Asn Trp Ile Arg Pro Thr Leu Gly Ile Pro Thr Tyr
        275                 280                 285

Ala Met Ser Asn Leu Phe Ser Ile Leu Arg Gly Asp Ser Asp Leu Asn
    290                 295                 300

Ser Lys Arg Met Leu Thr Pro Glu Ala Thr Lys Glu Ile Lys Leu Val
305                 310                 315                 320

Glu Glu Lys Ile Gln Ser Ala Gln Ile Asn Arg Ile Asp Pro Leu Ala
                325                 330                 335

Pro Leu Gln Leu Leu Ile Phe Ala Thr Ala His Ser Pro Thr Gly Ile
            340                 345                 350

Ile Ile Gln Asn Thr Asp Leu Val Glu Trp Ser Phe Leu Pro His Ser
        355                 360                 365

Thr Val Lys Thr Phe Thr Leu Tyr Leu Asp Gln Ile Ala Thr Leu Ile
    370                 375                 380

Gly Gln Thr Arg Leu Arg Ile Ile Lys Leu Cys Gly Asn Asp Pro Asp
385                 390                 395                 400
```

```
Lys Ile Val Val Pro Leu Thr Lys Glu Gln Val Arg Gln Ala Phe Ile
                405                 410                 415

Asn Ser Gly Ala Trp Lys Ile Gly Leu Ala Asn Phe Val Gly Ile Ile
                420                 425                 430

Asp Asn His Tyr Pro Lys Thr Lys Ile Phe Gln Phe Leu Lys Leu Thr
                435                 440                 445

Thr Trp Ile Leu Pro Lys Ile Thr Arg Arg Glu Pro Leu Glu Asn Ala
            450                 455                 460

Leu Thr Val Phe Thr Asp Gly Ser Ser Asn Gly Lys Ala Ala Tyr Thr
465                 470                 475                 480

Gly Pro Lys Glu Arg Val Ile Lys Thr Pro Tyr Gln Ser Ala Gln Arg
                485                 490                 495

Ala Glu Leu Val Ala Val Ile Thr Val Leu Gln Asp Phe Asp Gln Pro
                500                 505                 510

Ile Asn Ile Ile Ser Asp Ser Ala Tyr Val Val Gln Ala Thr Arg Asp
                515                 520                 525

Val Glu Thr Ala Leu Ile Lys Tyr Ser Met Asp Asp Gln Leu Asn Gln
            530                 535                 540

Leu Phe Asn Leu Leu Gln Gln Thr Val Arg Lys Arg Asn Phe Pro Phe
545                 550                 555                 560

Tyr Ile Thr His Ile Arg Ala His Thr Asn Leu Pro Gly Pro Leu Thr
                565                 570                 575

Lys Ala Asn Glu Gln Ala Asp Leu Leu Val Ser Ser Ala Leu Ile Lys
                580                 585                 590

Ala Gln Glu Leu His Ala Leu Thr His Val Asn Ala Ala Gly Leu Lys
            595                 600                 605

Asn Lys Phe Asp Val Thr Trp Lys Gln Ala Lys Asp Ile Val Gln His
            610                 615                 620

Cys Thr Gln Cys Gln Val Leu His Leu Pro Thr Gln Glu Ala Gly Val
625                 630                 635                 640

Asn Pro Arg Gly Leu Cys Pro Asn Ala Leu Trp Gln Met Asp Val Thr
                645                 650                 655

His Val Pro Ser Phe Gly Arg Leu Ser Tyr Val His Val Thr Val Asp
                660                 665                 670

Thr Tyr Ser His Phe Ile Trp Ala Thr Cys Gln Thr Gly Glu Ser Thr
            675                 680                 685

Ser His Val Lys Lys His Leu Leu Ser Cys Phe Ala Val Met Gly Val
        690                 695                 700

Pro Glu Lys Ile Lys Thr Asp Asn Gly Pro Gly Tyr Cys Ser Lys Ala
705                 710                 715                 720

Phe Gln Lys Phe Leu Ser Gln Trp Lys Ile Ser His Thr Thr Gly Ile
                725                 730                 735

Pro Tyr Asn Ser Gln Gly Gln Ala Ile Val Glu Arg Thr Asn Arg Thr
            740                 745                 750

Leu Lys Thr Gln Leu Val Lys Gln Lys Glu Gly Gly Asp Ser Lys Glu
                755                 760                 765

Cys Thr Thr Pro Gln Met Gln Leu Asn Leu Ala Leu Tyr Thr Leu Asn
770                 775                 780

Phe Leu Asn Ile Tyr Arg Asn Gln Thr Thr Thr Ser Ala Glu Gln His
785                 790                 795                 800

Leu Thr Gly Lys Lys Asn Ser Pro His Glu Gly Lys Leu Ile Trp Trp
            805                 810                 815

Lys Asp Asn Lys Asn Lys Thr Trp Glu Ile Gly Lys Val Ile Thr Trp
```

```
                   820                 825                 830

Gly Arg Gly Phe Ala Cys Val Ser Pro Gly Glu Asn Gln Leu Pro Val
            835                 840                 845

Trp Ile Pro Thr Arg His Leu Lys Phe Tyr Asn Glu Pro Ile Arg Asp
850                 855                 860

Ala Lys Lys Ser Thr Ser Ala Glu Thr Glu Thr Ser Gln Ser Ser Thr
865                 870                 875                 880

Val Asp Ser Gln Asp Glu Gln Asn Gly Asp Val Arg Arg Thr Asp Glu
            885                 890                 895

Val Ala Ile His Gln Glu Gly Arg Ala Ala Asn Leu Gly Thr Thr Lys
            900                 905                 910

Glu Ala Asp Ala Val Ser Tyr Lys Ile Ser Arg Glu His Lys Gly Asp
            915                 920                 925

Thr Asn Pro Arg Glu Tyr Ala Ala Cys Ser Leu Asp Asp Cys Ile Asn
            930                 935                 940

Gly Gly Lys Ser Pro Tyr Ala Cys Arg Ser Ser Cys Ser
945                 950                 955

<210> SEQ ID NO 74
<211> LENGTH: 958
<212> TYPE: PRT
<213> ORGANISM: Artificial Sequence
<220> FEATURE:
<223> OTHER INFORMATION: Manipulated Pol

<400> SEQUENCE: 74

Met Asn Lys Ser Arg Lys Arg Asn Arg Glu Ser Leu Leu Gly Ala
1               5                   10                  15

Ala Thr Val Glu Pro Pro Lys Pro Ile Pro Leu Thr Trp Lys Thr Glu
                20                  25                  30

Lys Pro Val Trp Val Asn Gln Trp Pro Leu Pro Lys Gln Lys Leu Glu
            35                  40                  45

Ala Leu His Leu Leu Ala Asn Glu Gln Leu Glu Lys Gly His Ile Glu
        50                  55                  60

Pro Ser Phe Ser Pro Trp Asn Ser Pro Val Phe Val Ile Gln Lys Lys
65                  70                  75                  80

Ser Gly Lys Trp Arg Met Leu Thr Asp Leu Arg Ala Val Asn Ala Val
                85                  90                  95

Ile Gln Pro Met Gly Pro Leu Gln Pro Gly Leu Pro Ser Pro Ala Met
            100                 105                 110

Ile Pro Lys Asp Trp Pro Leu Ile Ile Ile Asp Leu Lys Asp Cys Phe
        115                 120                 125

Phe Thr Ile Pro Leu Ala Glu Gln Asp Cys Glu Lys Phe Ala Phe Thr
    130                 135                 140

Ile Pro Ala Ile Asn Asn Lys Glu Pro Ala Thr Arg Phe Gln Trp Lys
145                 150                 155                 160

Val Leu Pro Gln Gly Met Leu Asn Ser Pro Thr Ile Cys Gln Thr Phe
                165                 170                 175

Val Gly Arg Ala Leu Gln Pro Val Arg Glu Lys Phe Ser Asp Cys Tyr
            180                 185                 190

Ile Ile His Cys Ile Asp Asp Ile Leu Cys Ala Ala Glu Thr Lys Asp
        195                 200                 205

Lys Leu Ile Asp Cys Tyr Thr Phe Leu Gln Ala Glu Val Ala Asn Ala
    210                 215                 220

Gly Leu Ala Ile Ala Ser Asp Lys Ile Gln Thr Ser Thr Pro Phe His
225                 230                 235                 240
```

```
Tyr Leu Gly Met Gln Ile Glu Asn Arg Lys Ile Lys Pro Gln Lys Ile
            245                 250                 255

Glu Ile Arg Lys Asp Thr Leu Lys Thr Leu Asn Asp Phe Gln Lys Leu
        260                 265                 270

Leu Gly Asp Ile Asn Trp Ile Arg Pro Thr Leu Gly Ile Pro Thr Tyr
            275                 280                 285

Ala Met Ser Asn Leu Phe Ser Ile Leu Arg Gly Asp Ser Asp Leu Asn
        290                 295                 300

Ser Lys Arg Met Leu Thr Pro Glu Ala Thr Lys Glu Ile Lys Leu Val
305                 310                 315                 320

Glu Glu Lys Ile Gln Ser Ala Gln Ile Asn Arg Ile Asp Pro Leu Ala
            325                 330                 335

Pro Leu Gln Leu Leu Ile Phe Ala Thr Ala His Ser Pro Thr Gly Ile
            340                 345                 350

Ile Ile Gln Asn Thr Asp Leu Val Glu Trp Ser Phe Leu Pro His Ser
            355                 360                 365

Thr Val Lys Thr Phe Thr Leu Tyr Leu Asp Gln Ile Ala Thr Leu Ile
            370                 375                 380

Gly Gln Thr Arg Leu Arg Ile Ile Lys Leu Cys Gly Asn Asp Pro Asp
385                 390                 395                 400

Lys Ile Val Val Pro Leu Thr Lys Glu Gln Val Arg Gln Ala Phe Ile
            405                 410                 415

Asn Ser Gly Ala Trp Lys Ile Gly Leu Ala Asn Phe Val Gly Ile Ile
            420                 425                 430

Asp Asn His Tyr Pro Lys Thr Lys Ile Phe Gln Phe Leu Lys Leu Thr
            435                 440                 445

Thr Trp Ile Leu Pro Lys Ile Thr Arg Arg Glu Pro Leu Glu Asn Ala
            450                 455                 460

Leu Thr Val Phe Thr Asp Gly Ser Ser Asn Gly Lys Ala Ala Tyr Thr
465                 470                 475                 480

Gly Pro Lys Glu Arg Val Ile Lys Thr Pro Tyr Gln Ser Ala Gln Arg
            485                 490                 495

Ala Glu Leu Val Ala Val Ile Thr Val Leu Gln Asp Phe Asp Gln Pro
            500                 505                 510

Ile Asn Ile Ile Ser Asp Ser Ala Tyr Val Val Gln Ala Thr Arg Asp
            515                 520                 525

Val Glu Thr Ala Leu Ile Lys Tyr Ser Met Asp Asp Gln Leu Asn Gln
            530                 535                 540

Leu Phe Asn Leu Leu Gln Gln Thr Val Arg Lys Arg Asn Phe Pro Phe
545                 550                 555                 560

Tyr Ile Thr His Ile Arg Ala His Thr Asn Leu Pro Gly Pro Leu Thr
            565                 570                 575

Lys Ala Asn Glu Gln Ala Asp Leu Leu Val Ser Ser Ala Leu Ile Lys
            580                 585                 590

Ala Gln Glu Leu His Ala Leu Thr His Val Asn Ala Ala Gly Leu Lys
            595                 600                 605

Asn Lys Phe Asp Val Thr Trp Lys Gln Ala Lys Asp Ile Val Gln His
            610                 615                 620

Cys Thr Gln Cys Gln Val Leu His Leu Pro Thr Gln Glu Ala Gly Val
625                 630                 635                 640

Asn Pro Arg Gly Leu Cys Pro Asn Ala Leu Trp Gln Met Asp Val Thr
            645                 650                 655

His Val Pro Ser Phe Gly Arg Leu Ser Tyr Val His Val Thr Val Asp
```

```
                    660             665             670
Thr Tyr Ser His Phe Ile Trp Ala Thr Cys Gln Thr Gly Glu Ser Thr
            675             680             685
Ser His Val Lys Lys His Leu Leu Ser Cys Phe Ala Val Met Gly Val
            690             695             700
Pro Glu Lys Ile Lys Thr Asp Asn Gly Pro Gly Tyr Cys Ser Lys Ala
705             710             715             720
Phe Gln Lys Phe Leu Ser Gln Trp Lys Ile Ser His Thr Thr Gly Ile
            725             730             735
Pro Tyr Asn Ser Gln Gly Gln Ala Ile Val Glu Arg Thr Asn Arg Thr
            740             745             750
Leu Lys Thr Gln Leu Val Lys Gln Lys Glu Gly Gly Asp Ser Lys Glu
            755             760             765
Cys Thr Thr Pro Gln Met Gln Leu Asn Leu Ala Leu Tyr Thr Leu Asn
            770             775             780
Phe Leu Asn Ile Tyr Arg Asn Gln Thr Thr Thr Ser Ala Glu Gln His
785             790             795             800
Leu Thr Gly Lys Lys Asn Ser Pro His Glu Gly Lys Leu Ile Trp Trp
            805             810             815
Lys Asp Asn Lys Asn Lys Thr Trp Glu Ile Gly Lys Val Ile Thr Trp
            820             825             830
Gly Arg Gly Phe Ala Cys Val Ser Pro Gly Glu Asn Gln Leu Pro Val
            835             840             845
Trp Ile Pro Thr Arg His Leu Lys Phe Tyr Asn Glu Pro Ile Arg Asp
            850             855             860
Ala Lys Lys Ser Thr Ser Ala Glu Thr Glu Thr Ser Gln Ser Ser Thr
865             870             875             880
Val Asp Ser Gln Asp Glu Gln Asn Gly Asp Val Arg Arg Thr Asp Glu
            885             890             895
Val Ala Ile His Gln Glu Gly Arg Ala Ala Asn Leu Gly Thr Thr Lys
            900             905             910
Glu Ala Asp Ala Val Ser Tyr Lys Ile Ser Arg Glu His Lys Gly Asp
            915             920             925
Thr Asn Pro Arg Glu Tyr Ala Ala Cys Ser Leu Asp Asp Cys Ile Asn
            930             935             940
Gly Gly Lys Ser Pro Tyr Ala Cys Arg Ser Ser Cys Ser Ala
945             950             955

<210> SEQ ID NO 75
<211> LENGTH: 12366
<212> TYPE: DNA
<213> ORGANISM: Human endogenous retrovirus, K family (HERV-K), located
      at 22q11.2

<400> SEQUENCE: 75 tgtgggaaa  agaaagagag  atcagactgt  tactgtgtct  atgtagaaag  aaatagacat    60
aagagactcc  attttgttct  gtactaagaa  aaattcttct  gctttgagat  gctgttaatc   120
tgtaacccta  gccccaaccc  tgtgctcaca  gaaacaggtg  ctgtgttgac  tcaaggttta   180
atggattcag  ggctgtgcag  gatgtgcttt  gttaaacaaa  tgcttgaagg  cagcaagctt   240
gttaagagtc  atcaccactc  cctaatctca  agtaagcagg  acacaaaaca  ctgcggaagg   300
ccgcagggac  ctctgcctag  gaaagccagg  tgttgtccaa  ggtttctccc  catgtgacag   360
tctgaaatat  ggcctcttgg  gaagggaaag  acctgactgt  ccctggccc   gacacccgta   420 aagggtctgt  gctgaggatt  agtaaaagag  gaaggaaggc  ctctttgcag  ttgagataag   480
```

```
aggaaggcat ctgtctcctg ctcatccctg ggcaatggaa tgtcttggtg taaagcctga    540
ttgtatatgc catctactga gataggagaa aactgcctta gggctggagg tgggacatgc    600
tggcggcaat actgctcttt aaggcattga gatgtttatg tatatgcaca tcaaaagcac    660 agcactttt tctttacctt gtttatgatg cagagacatt tgttcacatg ttttcctgct    720
ggccctctcc ccactattac cctattgtcc tgccacatcc ccctctccga gatggtagag    780
ataatgatca ataaatactg agggaactca gagaccggtg cggcgcgggt cctccatatg    840
ctgagcgccg gtcccctggg cccacttttc tttctctata ctttgtctct gttgtctttc    900
ttttctcaag tctctcgttc cacctgagga gaaatgccca cagctgtgga ggcgcaggcc    960
actccatctg gtgcccaacg tggatgcttt tctctagggt gaagggactc tcgagtgtgg   1020
tcattgagga caagtcaacg agagattccc gagtacgtct acagtgagcc ttgtggtaag   1080
cttgggcgct cggaagaagc cagggttaat ggggcaaact aaaagtaaag tctctcattc   1140
cacctgatga gaaacaccca gaggtgtgga ggggcaggcc accccttcag ggtagggtcc   1200
cctccatgca gaccatagag cacaggtgtg ccccaaagag gagcagagag aaggagggag   1260
agggcccacg agagacttgg aaatgaatgg caggatttta ggcgctggac ttgggttcgg   1320
ggcacctggc cttccttgt gtatttctcc tactgtctgc ctaactattt aatacaataa   1380
aagaaaacca gccctggtt cttgtggtgt ttccaccctc ccgggtcccc gctggctgcc   1440
tggcttcctc ccgcagctcc tgctgtgtgt gtatgtgtgt gtgtgtgcac atctgtgggg   1500
cgtatgtgtg ttcgtctttg taattgaggc tgcagagtgg agagagcagg ggttttctct   1560
ggggacccag agagaaggag gcgttttcac cacagccgaa cagggcagga ccccagcacc   1620
cgggacccag cgggactttg ccaaggggat ggacctggct gggccacgcg gctgtttgtg   1680
tagggaaaag aaagagagat cacactgtta ctgtgtctat gtagaaaagg aagacataaa   1740
ctccattttg agctgtacta agaaaaatta ttttgccttg acctgctgtt aacctgtaac   1800
tgtagcccca accctgtgct caaagaaaca tgtgctgtat ggaatcaagg tttaagggat   1860
caagggctgt acaggatgtg ccttgttaac aatgtgttta caggcagtat gcttggtaaa   1920
agtcatcgcc attctccatt ctccattaat caggggcacg atgcactgcg gaaagccaca   1980
gggacctctg cccgagaaag cctgggtatt gtccaaggct tccccccact gagacagcct   2040
gagatacggc ctcgtgggaa gggaaagacc tgaccgtccc ccagcccgac acccgtaaag   2100
ggtctgtgct gaggaggatt agtaaaaggg gaaggcctct tgcagttgag ataagaggaa   2160
ggcctccgtc tcctgcatgt ccttgggaat ggaatgtctt ggtgtaaaac ccgatagtac   2220
attccttcta ttctgagaga agaaaaccac cctgtggctg gaggtgagat atgctagcgg   2280
caatgctgct ctgttactct tgctacact gagatgtttg ggtggagaga agcataaatc   2340
tggcctatgt gcacatctgg gcacagaacc tccccttgaa cttgtgacac agattccttt   2400
gttcacatgt tttcctgctg accttctccc cactatcgcc ctgttctccc accgcattcc   2460
ccttgctgag atagtgaaaa tagtaatctg tagataccaa gggaactcag agaccatggc   2520
cggtgcacat cctccgtacg ctgagcgctg gtcccctggg cccattgttc tttctctata   2580 cttgtctct gtgtcttatt tcttccctca gtctctcatc cctcctgacg agaaataccc   2640
acaggtgtgg aggggctggc ccccttcatc tgatgcccaa tgtgggtgcc tttctctagg   2700
gtgaaggtac tctacagtgt ggtcattgag gacaagttga cgagagagtc ccaagtacgt   2760
ccacggtcag ccttgcggta agcttgtgtg cttagaggaa cccagggtaa cgatgggca   2820 aactgaaagt aaatatgcct cttatctcag ctttattaaa attcttttaa gaagagggg   2880
```

```
agttagagct tctacagaaa atctaattac gctatttcaa acaatagaac aattctgccc   2940 atggttttcca gaacagggaa ctttagatct aaaagattgg gaaaaaattg gcaaagaatt   3000
aaaacaagca aatagggaag gtaaaatcat cccacttaca gtatggaatg attgggccat   3060
tattaaagca actttagaac catttcaaac aggagaagat attgtttcag tttctgatgc   3120
ccctaaaagc tgtgtaacag attgtgaaga gaggcaggg acagaatccc agcaaggaac   3180
ggaaagttca cattgtaaat atgtagcaga gtctgtaatg gctcagtcaa cgcaaaatgt   3240
tgactacagt caattacagg agataatata ccctgaatca tcaaaattgg gggaaggagg   3300
tccagaatca ttggggccat cagagcctaa accacgatcg ccatcaactc ctcctcccgt   3360
ggttcagatg cctgtaacat acaacctca acgcaggtt agacaagcac aaaccccaag   3420
agaaaatcaa gtagaaaggg acagagtctc tatcccggca atgccaactc agatacagta   3480
tccacaatat cagccggtag aaaataagac ccaaccgctg gtagtttatc aataccggct   3540
gccaaccgag cttcagtatc ggcctccttc agaggttcaa tacagacctc aagcggtgtg   3600
tcctgtgcca aatagcacgg caccatacca gcaacccaca gcgatggcgt ctaattcacc   3660
agcaacacag gacgcggcgc tgtatcctca gccgcccact gtgagactta atcctacagc   3720
atcacgtagt ggacagggtg gtgcactgca tgcagtcatt gatgaagcca gaaaacaggg   3780
cgatcttgag gcatggcggt tcctggtaat tttacaactg gtacaggccg gggaagagac   3840
tcaagtagga gcgcctgccc gagctgagac tagatgtgaa cctttcacca tgaaaatgtt   3900
aaaagatata aaggaaggag ttaaacaata tggatccaac tcccttata taagaacatt   3960 attagattcc attgctcatg gaaatagact tactccttat gactgggaaa ttttggccaa   4020
atcttccctt tcatcctctc agtatctaca gtttaaaacc tggtggattg atggagtaca   4080
agaacaggta cgaaaaaatc aggctactaa gcccactgtt aatatagacg cagaccaatt   4140
gttaggaaca ggtccaaatt ggagcaccat taaccaacaa tcagtgatgc agaatgaggc   4200
tattgaacaa gtaagggcta tttgcctcag ggcctgggga aaaattcagg acccaggaac   4260 agcttttccct attaattcaa ttagacaagg ctctaaagag ccatatcctg actttgtggc   4320
aagattacaa gatgctgctc aaaagtctat tacagatgac aatgcccgaa aagttattgt   4380
agaattaatg gcctatgaaa atgcaaatcc agaatgtcag tcggccataa agccattaaa   4440
aggaaaagtt ccagcaggag ttgatgtaat tacagaatat gtgaaggctt gtgatgggat   4500
tggaggagct atgcataagg caatgctaat ggctcaagca atgaggggc tcactctagg   4560 aggacaagtt agaacatttg ggaaaaatg ttataattgt ggtcaaatcg gtcatctgaa   4620
aaggagttgc ccaggcttaa ataaacagaa tataataaat caagctatta cagcaaaaaa   4680
taaaaagcca tctggcctgt gtccaaaatg tggaaaagca aaacattggg ccaatcaatg   4740
tcattctaaa tttgataaag atgggcaacc attgtctgga acaggaaga ggggccagcc   4800 tcaggccccc caacaaactg gggcattccc agttaaactg tttgttcctc agggttttca   4860
aggacaacaa cccctacaga aaataccacc acttcaggga gtcagccaat tacaacaatc   4920
caacagctgt cccgcgccac agcaggcagc accgcagtag atttatgttc cacccaaatg   4980 gtcttttttac tccctggaaa gccccacaa aagattccta gagggtata tggcccgctg   5040 ccagaaggga gggtaggcct ttgagggaga tcaagtctaa atttgaaggg agtccaaatt   5100
catactgggg taatttattc agattataaa gggggaattc agttagtgat cagctccact   5160
gttccccgga gtgccaatcc aggtgataga attgctcaat tactgctttt gccttatgtt   5220
aaaattgggg aaaacaaaaa ggaaagaaca ggagggtttg gaagtaccaa ccctgcagga   5280
```

```
aaagctgctt attgggctaa tcaggtctca gaggatagac ccgtgtgtac agtcactatt    5340
cagggaaaga gtttgaagga ttagtggata cccaggctga tgtttctgtc atcggcatag    5400
gtactgcctc agaagtgtat caaagtgcca tgattttaca ttgtccagga tctgataatc    5460
aagaaagtac ggttcagcct gtgatcactt cattccaatc aatttatggg gccgagactt    5520
gttacaacaa tggcatgcag agattactat cccagcctcc ctatacagcc ccaggaataa    5580
aaaaatcatg actaaaatgg gatagctccc taaaaaggga ctaggaaaga agtcccaatt    5640
gaggctgaaa aaaatcaaaa aagaaaagga atagggcatc cttttttagga gcggtcactg    5700 tagagcctcc aaaacccatt ccattaactt gggggaaaaa aaaacaactg tatggtaaat    5760
cagcagcgct tccaaaacaa aaactggagg ctttacattt attagcaaag aaacaattag    5820
aaaaaggaca ttgagccttc attttcgcct tggaattctg tttgtaattc agaaaaaatc    5880
cggcagatgg cgtataatgc cgtaattcaa cccatggggg ctctcccacc ccggttgccc    5940
tctccagcca tggtcccctt taattataat tgatctgaag gattgctttt ttaccattcc    6000
tctggcaaaa caggattttg aaaaatttgc ttttaccaca ccagcctaaa taataaagaa    6060
ccagccacca ggtttcagtg gaaagtattg cctcagggaa tgcttaatag ttcaactatt    6120
tgtcagctca agctctgcaa ccagttagag acaagttttc agactgttac atcgttcact    6180
atgttgatat tttgtgtgct gcagaaacga gagacaaatt aattgaccgt tacacatttc    6240
tgcagacaga ggttgccaac gcgggactga caataacatc tgataagatt caaacctcta    6300
ctcctttccg ttacttggga atgcaggtag aggaaaggaa aattaaacca caaaaaatag    6360
aaataagaaa agacacatta aaagcattaa atgagtttca aaagttgcta ggagatacta    6420
attggatttg gagatattaa ttggatttgg ccaactctag gcattcctac ttatgccatg    6480
tcaaatttgt tctctttctt aagaggggac tcggaattaa atagtgaaag aacgttaact    6540
ccagaggcaa ctaaagaaat taaattaatt gaagaaaaaa ttcggtcagc acaagtaaat    6600
agaatagatc acttggcccc actccaaatt ttgattttttg ctactgcaca ttccctaaca    6660
ggcatcattg ttcaaaatac agatcttgtg gagtggtcct tccttcctca cagtacaatt    6720 aagacttttta cattgtactt ggatcaaatg gctacattaa ttggtcaggg aagattatga    6780
ataataacat tgtgtggaaa tgacccagat aaaatcactg ttcctttcaa caagcaacag    6840
gttagacaag cctttatcaa ttctggtgca tggcagattg gtcttgccga ttttgtggga    6900
attattgaca atcgttaccc caaaacaaaa atcttccagt ttttaaaatt gactacttgg    6960
attttaccta agttaccaa acataagcct ttaaaaaatg ctctggcagt gtttactgat    7020
ggttccagca atggaaaagt ggcttacacc gggccaaaag aatgagtcat caaaactcag    7080
tatcacttga ctcaaagagc agagttggtt gccgtcatta cagtgttaac aagattttaa    7140
tcagtctatt aacattgtat cagattctgc atatgtagta caggctacaa aggatattga    7200
gagagcccta atcaaataca ttatggatga tcagttaaac ccgctgttta atttgttaca    7260
acaaaatgta agaaaagaa atttcccatt ttatattact catattcgag cacacactaa    7320
tttaccaggg cctttaacta aagcaaatga acaagctgac ttgctagtat catctgcatt    7380
catggaagca caagaacttc atgccttgac tcatgtaaat gcaataggat taaaaaataa    7440
atttgatatc acatggaaac agacaaaaaa tattgtacaa cattgcaccc agtgtcagat    7500
tctacacctg gccactcagg aggcaagagt taatcccaga ggtctatgtc ctaatgtgtt    7560
atggcaaatg gatgtcatgc acgtaccttc atttggaaaa ttgtcatttg tccatgtgac    7620
agttgatact tattcacatt tcatatgggc aacctgccag acaggagaaa gtacttccca    7680
```

```
tgttaaaaga catttattat cttgttttcc tgtcatggga gttccagaaa aagttaaaac   7740
agacaatggg ccaggttact gtagtaaagc agttcaaaaa ttcttaaatc agtggaaaat   7800
tacacataca ataggaattc tctataattc ccaaggacag gccataattg aaagaactaa   7860
tagaacactc aaagctcaat tggttaaaca aaaaaaagga aaagacagga gtataacact   7920
ccccagatgc aacttaatct agcactctat actttaaatg ttttaaacat ttatagaaat   7980
cagaccacta cctctgcaga acaacatctt actggtaaaa ggaacagccc acatgaagga   8040
aaactgattt ggtggaaaga taataaaaat aaaacatggg aaatggggaa ggtgataacg   8100
tgggggagag gttttgcttg tgtttcacca ggagaaaatc agcttcctgt ttggataccc   8160
actagacatt taaagttcta caatgaactc actggagatg caagaaaaag tgtggagatg   8220
gagacacccc aatcgactcg ccaggtaaac aaaatggtga tatcagaaga acagaaaaag   8280
ttgccttcca tcaaggaagc agagttgcca atataggcac aattaaagaa gctgacacag   8340
ttagctaaaa aaaaaagcct agagaataca aaggtgacac caactccaga gaatatgctg   8400
cttgcagctc tgatgattgt atcaacggtg gtaagtcttc ccaagtctgc aggagcagct   8460
gcagctaatt atacttactg ggcctatgtg ccttcccac ccttaattcg ggcagttaca   8520
tagatggata atcctattga agtagatgtt aataatagtg catgggtgcc tggccccaca   8580
gatgactgtt gccctgccca acctgaagaa ggaatgatga tgaatatttc cattgggtat   8640
ccttatcctc ctgtttgcct agggaaggca ccaggatgct taatgcctac aacccaaaat   8700
tggttggtag aagtacctac agtcagtgct accagtagat ttacttatca catggtaagt   8760
ggaatgtcac agataaataa tttacaggac ccttcttatc aaagatcatt acaatgtagg   8820
cctaagggga aggcttgccc caaggaaatt cccaaagaat caaaaagccc agaagtctta   8880
gtctgcggag aatgtgtggc tgatactgca gtgtagtaca aaacaatgaa ttttgaacta   8940
tgatagactg ggtcccttga ggccaattat atcataactg tacaggccag actcattcat   9000
gttcacaggc cccatccatc tggcccatta atccagccta tgacggtgat gtaactgaaa   9060
ggctggacca ggtttataga aggttagaat cactctgtcc aaggaaatgg ggtgaaaagg   9120
gaatttcatc accttgacca aagttagtcc tgttactggt cctgaacatc cagaattagg   9180
aagcttactg tggcctcaca ccacattaga atttgttctg gaaatcaagc tataggaaca   9240
agagatcgta agtcatatta tactatcaac ctaaattcca gtctgacaat tcctttgcaa   9300
aattgtgtaa aactccctta tattgctagt tgtaggaaaa acatagttat taaacctgat   9360
tcccaaacca taatctgtga aaattgtgga atgtttactt gcattgattt gacttttaat   9420
tggcagcacc gtattctact aggaagagca agagagggtg tgtggatcct tgtgtccatg   9480
gaccgaccat gggaggcttc gctatccatc catattttaa cggaagtatt aaaaggaatt   9540
ctaactagat ccaaaagatt cattttttact ttgatggcag tgattatggg cctcattgca   9600
gtcacagcta ctgctgcggc tgctggaatt gctttacact cctctgttca aactgcagaa   9660
tacgtaaatg attggcaaaa gaattcctca aaattgtgga attctcagat ccaaatagat   9720
caaaaattgg caaaccaaat taatgatctt agacaaactg tcatttggat gggagaggct   9780
catgagcttg gaatatcttt ttcagttacg atgtgactgg aatacatcag attttttgtgt   9840 tacaccacaa gcctataatg agtctgagca tcactggac atggttagat gccatctgca   9900
aggaggagaa gataatctta ctttagacat ttcaaaatta aaagaatttt ttttttctttt   9960 gagacagagt ctcgctctgt cgcccaggct ggagtgcagt ggcgtgatct cagctcactg  10020
caagttccgc ctcctgggtt tacaccattc tcctgcctca gcctcccaag tagttgggac  10080
```

```
tacaggagcc caccaccatg cctggctaat ttttttggg ttttaatag agatggagtt    10140
tcaccgtgtt agccaggatg gtctcgatct cctgaccttg tgatctgccc accttggcct    10200
cccaaagtgc tgggattaca gtcgtgagcc accgtgccca gccaagaaaa aattttgag    10260
gcatcaaaag cccatttaaa tttggtgcca ggaacggaga caatcgtgaa agctgctgat    10320
agcctcacaa atcttaagcc agtcacttgg gttaaaagca tcagaagttt cactattgta    10380
aatttcatat taatccttgt atgcctgttc tgtctgttgt tagtctacag gtgtatccag    10440
cagctccaaa gagacagcaa ccagcaagaa tgggccatag tgacgatggt ggttttgtca    10500
aaagaaaag gggggatat gtaaggaaaa gagagatcag actttcactg tgtctatgta    10560
gaaaggaag acataagaaa ctccattttg atctgtacta agaaaaattg ttttgccttg    10620
agatgctgtt aatctgtaac tttagcccca accctgtgct cacggaaaca tgtgctgtaa    10680
ggtttaaggg atctagggct gtgcaggatg taccttgtta acaatatgtt tgcaggcagt    10740
atgtttggta aaagtcatcg ccattctcca ttctcgatta accaggggct caatgcactg    10800
tggaaagcca caggaacctc tgcccaagaa agcctggctg ttgtgggaag tcaggaccc    10860
cgaatggagg gaccagctgg tgctgcatca ggaaacataa attgtgaaga tttcttggac    10920
atttatcagt ttccaaaatt aatactttta taatttctta cacctgtctt actttaatct    10980
cttaatcctg ttatctttgt aagctgagga tatacgtcac ctcaggacca ctattgtaca    11040
aattgattgt aaaacatgtt cacatgtgtt tgaacaatat gaaatcagtg caccttgaaa    11100
atgaacagaa taacagtgat tttagggaac aaaggaagac aaccataagg tctgactgcc    11160
tgaggggtcg ggcaaaaagc catattttc ttcttgcaga gagcctataa atggacgtgc    11220
aagtaggaga gatattgcta aattcttttc ctagcaagga atataatact aagaccctag    11280
ggaaagaatt gcattcctgg ggggaggtct ataaacggcc gctctgggag tgtctgtcct    11340
atgtggttga gataaggact gagatacgcc ctggtctcct gcagtaccct caggcttact    11400
aggattggga aaccccagtc ctggtaaatt tgaggtcagg ccggttcttt gctctgaacc    11460
ctgttttctg ttaagatgtt tatcaagaca atacatgcac cgctgaacat agacccttat    11520
caggagtttc tgattttgct ctggtcctgt ttcttcagaa gcatgtcatc tttgctctgc    11580
cttctgccct ttgaagcatg tgatctttgt gacctactcc ctgttcatac ccccctcccc    11640
ttttaaaatc cctaataaaa acttgctggt tttgtggctc aggggggcat catggaccta    11700
ccaatacgtg atgtcacccc cggtggccca gctgtaaaat tcctttcttt atactcttat    11760
ttctcagacc agctgacact tagggaaaat agaaagaacc tatgttgaaa tattggaggc    11820
gggttcccc gatacctggg tattgtccaa ggtttccttt gctgaggagg attagtaaaa    11880
ggaatgcctc catctcctgc atgtccctgg gaacagaatg ttcccaccaa ccaccctgtg    11940
gctggaggcg ggatatgctg gcagcaatgc tgctctatta ctctttgcta cactgagatg    12000
tttgggtgga gagaagcata aatctggcct atgtgcacat ctgggcacag caccttcctt    12060
tgaacttatt tgtgacacag attccttgc tcacgttttc ctgttgactt tctcaccact    12120
caccctattc tcctgtggca ttcgccttgc ggagatagtg aaaatagtaa taaatactga    12180
gggaactcag actgagggaa ctcagactgg gcagaccggg gccagtgtgg gtcctccata    12240
tgctgagcgc cggttccctg ggcccactgt tcttttctcta tactttgtct ctgtgcctta    12300
ttttctcagt ctctcattcc acctgatgag aaatacccac aggtgtggag gggctggccc    12360
ccttca                                                               12366
```

<210> SEQ ID NO 76
<211> LENGTH: 2148
<212> TYPE: DNA
<213> ORGANISM: Human endogenous retrovirus, K family (HERV-K)

<400> SEQUENCE: 76

```
atggggcaaa ctgaaagtaa atatgcctct tatctcagct ttattaaaat tcttttaaga      60
agaggggag  ttagagcttc tacagaaaat ctaattacgc tatttcaaac aatagaacaa     120
ttctgcccat ggtttccaga acagggaact ttagatctaa aagattggga aaaaattggc     180
aaagaattaa acaagcaaa  tagggaaggt aaaatcatcc cacttacagt atggaatgat     240
tgggccatta ttaaagcaac tttagaacca tttcaaacag agaagatat  tgtttcagtt     300
tctgatgccc ctaaaagctg tgtaacagat tgtgaagaag aggcagggac agaatcccag     360
caaggaacgg aaagttcaca ttgtaaatat gtagcagagt ctgtaatggc tcagtcaacg     420
caaaatgttg actacagtca attacaggag ataatatacc tgaatcatc  aaaattgggg     480
gaaggaggtc cagaatcatt ggggccatca gagcctaaac cacgatcgcc atcaactcct     540
cctcccgtgg ttcagatgcc tgtaacatta caacctcaaa cgcaggttag acaagcacaa     600
accccaagag aaaatcaagt agaaagggac agagtctcta tcccggcaat gccaactcag     660
atacagtatc cacaatatca gccggtagaa aataagaccc aaccgctggt agtttatcaa     720
taccggctgc caaccgagct tcagtatcgg cctccttcag aggttcaata cagacctcaa     780
gcggtgtgtc ctgtgccaaa tagcacggca ccataccagc aacccacagc gatggcgtct     840
aattcaccag caacacagga cgcggcgctg tatcctcagc cgcccactgt gagacttaat     900
cctacagcat cacgtagtgg acagggtggt gcactgcatg cagtcattga tgaagccaga     960
aaacagggcg atcttgaggc atggcggttc ctggtaattt tacaactggt acaggccggg    1020
gaagagactc aagtaggagc gcctgcccga gctgagacta gatgtgaacc tttcaccatg    1080
aaaatgttaa aagatataaa ggaaggagtt aaacaatatg gatccaactc cccttatata    1140
agaacattat tagattccat tgctcatgga aatagactta ctccttatga ctgggaaatt    1200
ttggccaaat cttcccttc  atcctctcag tatctacagt ttaaaacctg gtggattgat    1260
ggagtacaag aacaggtacg aaaaaatcag gctactaagc ccactgttaa tatagacgca    1320
gaccaattgt taggaacagg tccaaattgg agcaccatta accaacaatc agtgatgcag    1380
aatgaggcta ttgaacaagt aagggctatt tgcctcaggg cctggggaaa aattcaggac    1440
ccaggaacag ctttccctat taattcaatt agacaaggct ctaaagagcc atatcctgac    1500
tttgtggcaa gattacaaga tgctgctcaa aagtctatta cagatgacaa tgcccgaaaa    1560
gttattgtag aattaatggc ctatgaaaat gcaaatccag aatgtcagtc ggccataaag    1620
ccattaaaag gaaaagttcc agcaggagtt gatgtaatta cagaatatgt gaaggcttgt    1680
gatgggattg gaggagctat gcataaggca atgctaatgg ctcaagcaat gaggggctc    1740
actctaggag gacaagttag aacatttggg aaaaaatgtt ataattgtgg tcaaatcggt    1800
catctgaaaa ggagttgccc agtcttaaat aaacagaata taataaatca agctattaca    1860
gcaaaaaata aaaagccatc tggcctgtgt ccaaaatgtg aaaaggaaa  acattgggcc    1920
aatcaatgtc attctaaatt tgataaggat gggcaaccat tgtcgggaaa caggaagagg    1980
ggccagcctc aggcccccca acaaactggg gcattcccaa ttcaactgtt tgttcctcag    2040
ggttttcaag acaacaaacc cctacagaaa ataccaccac ttcagggagt cagccaatta    2100
caacaatcca acagctgtcc cgcgccacag caggcagcac cgcagtaa              2148
```

```
<210> SEQ ID NO 77
<211> LENGTH: 2151
<212> TYPE: DNA
<213> ORGANISM: Artificial Sequence
<220> FEATURE:
<223> OTHER INFORMATION: Manipulated Gag

<400> SEQUENCE: 77
atgggccaga ccgagagcaa gtacgccagc tacctgagct tcatcaagat cctgctgcgc      60
cgcggcggcg tgcgcgccag caccgagaac ctgatcaccc tgttccagac catcgagcag     120
ttctgcccct ggttccccga gcagggcacc ctggacctga aggactggga agatcggc       180
aaggagctga agcaggccaa ccgcgagggc aagatcatcc ccctgaccgt gtggaacgac     240
tgggccatca tcaaggccac cctggagccc ttccagaccg cgaggacat cgtgagcgtg      300
agcgacgccc ccaagagctg cgtgaccgac tgcgaggagg aggccggcac cgagagccag     360
cagggcaccg agagcagcca ctgcaagtac gtggccgaga gcgtgatggc ccagagcacc     420
cagaacgtgg actacagcca gctgcaggag atcatctacc cgagagcag caagctgggc     480
gagggcggcc ccgagagcct gggccccagc gagcccaagc ccgcagccc cagcacccccc    540
cccccgtgg tgcagatgcc cgtgaccctg agccccaga cccaggtgcg ccaggccag        600
acccccgcg agaaccaggt ggagcgcgac cgcgtgagca tccccgccat gcccacccag     660
atccagtacc ccagtacca gcccgtggag aacaagaccc agccctggt ggtgtaccag       720
taccgcctgc caccgagct gcagtaccgc cccccagcg aggtgcagta ccgccccag       780
gccgtgtgcc ccgtgcccaa cagcaccgcc cctaccagc agcccaccgc catggccagc     840
aacagccccg ccacccagga cgccgccctg tacccccagc ccccaccgt gcgcctgaac     900
cccaccgcca gccgcagcgg ccagggcggc gccctgcacg ccgtgatcga cgaggcccgc    960
aagcagggcg acctggaggc ctggcgcttc ctggtgatcc tgcagctggt gcaggccggc   1020
gaggagaccc aggtgggcgc ccccgcccgc gccgagaccc gctgcgagcc cttcaccatg    1080
aagatgctga aggacatcaa ggagggcgtg aagcagtacg gcagcaacag cccctacatc    1140
cgcacccctgc tggacagcat cgcccacggc aaccgcctga cccccctacga ctgggagatc   1200
ctggccaaga gcagcctgag cagcagccag tacctgcagt tcaagacctg gtggatcgac   1260
ggcgtgcagg agcaggtgcg caagaaccag gccaccaagc ccaccgtgaa catcgacgcc   1320
gaccagctgc tgggcaccgg ccccaactgg agcaccatca accagcagag cgtgatgcag   1380
aacgaggcca tcgagcaggt gcgcgccatc tgcctgcgcg cctggggcaa gatccaggac   1440
cccggcaccg ccttccccat caacagcatc cgccagggca gcaaggagcc tacccccgac   1500
ttcgtggccc gcctgcagga cgccgcccag aagagcatca ccgacgacaa cgcccgcaag   1560
gtgatcgtgg agctgatggc ctacgagaac gccaaccccg agtgccagag cgccatcaag   1620
cccctgaagg gcaaggtgcc cgccggcgtg gacgtgatca ccgagtacgt gaaggcctgc   1680
gacggcatcg gcggcgccat gcacaaggcc atgctgatgg cccaggccat cgcgcggcctg   1740
acccctggggcg gccaggtgcg caccttcggc aagaagtgct acaactgcgg ccagatcggc   1800
cacctgaagc gcagctgccc cgtgctgaac aagcagaaca tcatcaacca ggccatcacc   1860
gccaagaaca gaagccccag cggcctgtgc cccaagtgcg gcaagggcaa gcactgggcc   1920
aaccagtgcc acagcaagtt cgacaaggac ggccagcccc tgagcggcaa ccgcaagcgc   1980
ggccagcccc aggcccccca gcagaccggc gccttccccg tgcagctgtt cgtgccccag   2040
ggcttccagg ccagcagcc cctgcagaag atccccccc tgcagggcgt gagccagctg   2100
cagcagagca acagctgccc cgcccccag caggccgccc ccaggcttaa             2151
```

<210> SEQ ID NO 78
<211> LENGTH: 715
<212> TYPE: PRT
<213> ORGANISM: Human endogenous retrovirus, K family (HERV-K)

<400> SEQUENCE: 78

```
Met Gly Gln Thr Glu Ser Lys Tyr Ala Ser Tyr Leu Ser Phe Ile Lys
1               5                   10                  15

Ile Leu Leu Arg Arg Gly Val Arg Ala Ser Thr Glu Asn Leu Ile
            20                  25                  30

Thr Leu Phe Gln Thr Ile Glu Gln Phe Cys Pro Trp Phe Pro Glu Gln
            35                  40                  45

Gly Thr Leu Asp Leu Lys Asp Trp Glu Lys Ile Gly Lys Glu Leu Lys
    50                  55                  60

Gln Ala Asn Arg Glu Gly Lys Ile Ile Pro Leu Thr Val Trp Asn Asp
65                  70                  75                  80

Trp Ala Ile Ile Lys Ala Thr Leu Glu Pro Phe Gln Thr Gly Glu Asp
                85                  90                  95

Ile Val Ser Val Ser Asp Ala Pro Lys Ser Cys Val Thr Asp Cys Glu
            100                 105                 110

Glu Glu Ala Gly Thr Glu Ser Gln Gln Gly Thr Glu Ser Ser His Cys
        115                 120                 125

Lys Tyr Val Ala Glu Ser Val Met Ala Gln Ser Thr Gln Asn Val Asp
130                 135                 140

Tyr Ser Gln Leu Gln Glu Ile Ile Tyr Pro Glu Ser Ser Lys Leu Gly
145                 150                 155                 160

Glu Gly Gly Pro Glu Ser Leu Gly Pro Ser Glu Pro Lys Pro Arg Ser
                165                 170                 175

Pro Ser Thr Pro Pro Val Val Gln Met Pro Val Thr Leu Gln Pro
            180                 185                 190

Gln Thr Gln Val Arg Gln Ala Gln Thr Pro Arg Glu Asn Gln Val Glu
        195                 200                 205

Arg Asp Arg Val Ser Ile Pro Ala Met Pro Thr Gln Ile Gln Tyr Pro
210                 215                 220

Gln Tyr Gln Pro Val Glu Asn Lys Thr Gln Pro Leu Val Val Tyr Gln
225                 230                 235                 240

Tyr Arg Leu Pro Thr Glu Leu Gln Tyr Arg Pro Pro Ser Glu Val Gln
                245                 250                 255

Tyr Arg Pro Gln Ala Val Cys Pro Val Pro Asn Ser Thr Ala Pro Tyr
            260                 265                 270

Gln Gln Pro Thr Ala Met Ala Ser Asn Ser Pro Ala Thr Gln Asp Ala
        275                 280                 285

Ala Leu Tyr Pro Gln Pro Pro Thr Val Arg Leu Asn Pro Thr Ala Ser
290                 295                 300

Arg Ser Gly Gln Gly Gly Ala Leu His Ala Val Ile Asp Glu Ala Arg
305                 310                 315                 320

Lys Gln Gly Asp Leu Glu Ala Trp Arg Phe Leu Val Ile Leu Gln Leu
                325                 330                 335

Val Gln Ala Gly Glu Glu Thr Gln Val Gly Ala Pro Ala Arg Ala Glu
            340                 345                 350

Thr Arg Cys Glu Pro Phe Thr Met Lys Met Leu Lys Asp Ile Lys Glu
        355                 360                 365

Gly Val Lys Gln Tyr Gly Ser Asn Ser Pro Tyr Ile Arg Thr Leu Leu
370                 375                 380
```

```
Asp Ser Ile Ala His Gly Asn Arg Leu Thr Pro Tyr Asp Trp Glu Ile
385                 390                 395                 400

Leu Ala Lys Ser Ser Leu Ser Ser Gln Tyr Leu Gln Phe Lys Thr
            405                 410                 415

Trp Trp Ile Asp Gly Val Gln Glu Gln Val Arg Lys Asn Gln Ala Thr
            420                 425                 430

Lys Pro Thr Val Asn Ile Asp Ala Asp Gln Leu Leu Gly Thr Gly Pro
            435                 440                 445

Asn Trp Ser Thr Ile Asn Gln Gln Ser Val Met Gln Asn Glu Ala Ile
            450                 455                 460

Glu Gln Val Arg Ala Ile Cys Leu Arg Ala Trp Gly Lys Ile Gln Asp
465                 470                 475                 480

Pro Gly Thr Ala Phe Pro Ile Asn Ser Ile Arg Gln Gly Ser Lys Glu
            485                 490                 495

Pro Tyr Pro Asp Phe Val Ala Arg Leu Gln Asp Ala Ala Gln Lys Ser
            500                 505                 510

Ile Thr Asp Asp Asn Ala Arg Lys Val Ile Val Glu Leu Met Ala Tyr
            515                 520                 525

Glu Asn Ala Asn Pro Glu Cys Gln Ser Ala Ile Lys Pro Leu Lys Gly
            530                 535                 540

Lys Val Pro Ala Gly Val Asp Val Ile Thr Glu Tyr Val Lys Ala Cys
545                 550                 555                 560

Asp Gly Ile Gly Gly Ala Met His Lys Ala Met Leu Met Ala Gln Ala
            565                 570                 575

Met Arg Gly Leu Thr Leu Gly Gly Gln Val Arg Thr Phe Gly Lys Lys
            580                 585                 590

Cys Tyr Asn Cys Gly Gln Ile Gly His Leu Lys Arg Ser Cys Pro Val
            595                 600                 605

Leu Asn Lys Gln Asn Ile Ile Asn Gln Ala Ile Thr Ala Lys Asn Lys
            610                 615                 620

Lys Pro Ser Gly Leu Cys Pro Lys Cys Gly Lys Gly Lys His Trp Ala
625                 630                 635                 640

Asn Gln Cys His Ser Lys Phe Asp Lys Asp Gly Gln Pro Leu Ser Gly
            645                 650                 655

Asn Arg Lys Arg Gly Gln Pro Gln Ala Pro Gln Gln Thr Gly Ala Phe
            660                 665                 670

Pro Val Gln Leu Phe Val Pro Gln Gly Phe Gln Gly Gln Gln Pro Leu
            675                 680                 685

Gln Lys Ile Pro Pro Leu Gln Gly Val Ser Gln Leu Gln Gln Ser Asn
690                 695                 700

Ser Cys Pro Ala Pro Gln Gln Ala Ala Pro Gln
705                 710                 715

<210> SEQ ID NO 79
<211> LENGTH: 716
<212> TYPE: PRT
<213> ORGANISM: Artificial Sequence
<220> FEATURE:
<223> OTHER INFORMATION: Manipulated Gag

<400> SEQUENCE: 79

Met Gly Gln Thr Glu Ser Lys Tyr Ala Ser Tyr Leu Ser Phe Ile Lys
1               5                   10                  15

Ile Leu Leu Arg Arg Gly Gly Val Arg Ala Ser Thr Glu Asn Leu Ile
            20                  25                  30
```

-continued

```
Thr Leu Phe Gln Thr Ile Glu Gln Phe Cys Pro Trp Phe Pro Glu Gln
        35                  40                  45

Gly Thr Leu Asp Leu Lys Asp Trp Glu Lys Ile Gly Lys Glu Leu Lys
 50                  55                  60

Gln Ala Asn Arg Glu Gly Lys Ile Ile Pro Leu Thr Val Trp Asn Asp
 65                  70                  75                  80

Trp Ala Ile Ile Lys Ala Thr Leu Glu Pro Phe Gln Thr Gly Glu Asp
                 85                  90                  95

Ile Val Ser Val Ser Asp Ala Pro Lys Ser Cys Val Thr Asp Cys Glu
            100                 105                 110

Glu Glu Ala Gly Thr Glu Ser Gln Gln Gly Thr Glu Ser Ser His Cys
            115                 120                 125

Lys Tyr Val Ala Glu Ser Val Met Ala Gln Ser Thr Gln Asn Val Asp
        130                 135                 140

Tyr Ser Gln Leu Gln Glu Ile Ile Tyr Pro Glu Ser Ser Lys Leu Gly
145                 150                 155                 160

Glu Gly Gly Pro Glu Ser Leu Gly Pro Ser Glu Pro Lys Pro Arg Ser
                165                 170                 175

Pro Ser Thr Pro Pro Val Val Gln Met Pro Val Thr Leu Gln Pro
            180                 185                 190

Gln Thr Gln Val Arg Gln Ala Gln Thr Pro Arg Glu Asn Gln Val Glu
        195                 200                 205

Arg Asp Arg Val Ser Ile Pro Ala Met Pro Thr Gln Ile Gln Tyr Pro
210                 215                 220

Gln Tyr Gln Pro Val Glu Asn Lys Thr Gln Pro Leu Val Val Tyr Gln
225                 230                 235                 240

Tyr Arg Leu Pro Thr Glu Leu Gln Tyr Arg Pro Pro Ser Glu Val Gln
                245                 250                 255

Tyr Arg Pro Gln Ala Val Cys Pro Val Pro Asn Ser Thr Ala Pro Tyr
            260                 265                 270

Gln Gln Pro Thr Ala Met Ala Ser Asn Ser Pro Ala Thr Gln Asp Ala
        275                 280                 285

Ala Leu Tyr Pro Gln Pro Pro Thr Val Arg Leu Asn Pro Thr Ala Ser
        290                 295                 300

Arg Ser Gly Gln Gly Gly Ala Leu His Ala Val Ile Asp Glu Ala Arg
305                 310                 315                 320

Lys Gln Gly Asp Leu Glu Ala Trp Arg Phe Leu Val Ile Leu Gln Leu
                325                 330                 335

Val Gln Ala Gly Glu Glu Thr Gln Val Gly Ala Pro Ala Arg Ala Glu
            340                 345                 350

Thr Arg Cys Glu Pro Phe Thr Met Lys Met Leu Lys Asp Ile Lys Glu
        355                 360                 365

Gly Val Lys Gln Tyr Gly Ser Asn Ser Pro Tyr Ile Arg Thr Leu Leu
370                 375                 380

Asp Ser Ile Ala His Gly Asn Arg Leu Thr Pro Tyr Asp Trp Glu Ile
385                 390                 395                 400

Leu Ala Lys Ser Ser Leu Ser Ser Ser Gln Tyr Leu Gln Phe Lys Thr
                405                 410                 415

Trp Trp Ile Asp Gly Val Gln Glu Gln Val Arg Lys Asn Gln Ala Thr
            420                 425                 430

Lys Pro Thr Val Asn Ile Asp Ala Asp Gln Leu Leu Gly Thr Gly Pro
        435                 440                 445

Asn Trp Ser Thr Ile Asn Gln Gln Ser Val Met Gln Asn Glu Ala Ile
450                 455                 460
```

Glu Gln Val Arg Ala Ile Cys Leu Arg Ala Trp Gly Lys Ile Gln Asp
465                 470                 475                 480

Pro Gly Thr Ala Phe Pro Ile Asn Ser Ile Arg Gln Gly Ser Lys Glu
            485                 490                 495

Pro Tyr Pro Asp Phe Val Ala Arg Leu Gln Asp Ala Ala Gln Lys Ser
        500                 505                 510

Ile Thr Asp Asp Asn Ala Arg Lys Val Ile Val Glu Leu Met Ala Tyr
    515                 520                 525

Glu Asn Ala Asn Pro Glu Cys Gln Ser Ala Ile Lys Pro Leu Lys Gly
530                 535                 540

Lys Val Pro Ala Gly Val Asp Val Ile Thr Glu Tyr Val Lys Ala Cys
545                 550                 555                 560

Asp Gly Ile Gly Gly Ala Met His Lys Ala Met Leu Met Ala Gln Ala
                565                 570                 575

Met Arg Gly Leu Thr Leu Gly Gly Gln Val Arg Thr Phe Gly Lys Lys
            580                 585                 590

Cys Tyr Asn Cys Gly Gln Ile Gly His Leu Lys Arg Ser Cys Pro Val
        595                 600                 605

Leu Asn Lys Gln Asn Ile Ile Asn Gln Ala Ile Thr Ala Lys Asn Lys
    610                 615                 620

Lys Pro Ser Gly Leu Cys Pro Lys Cys Gly Lys Gly Lys His Trp Ala
625                 630                 635                 640

Asn Gln Cys His Ser Lys Phe Asp Lys Asp Gly Gln Pro Leu Ser Gly
                645                 650                 655

Asn Arg Lys Arg Gly Gln Pro Gln Ala Pro Gln Gln Thr Gly Ala Phe
            660                 665                 670

Pro Val Gln Leu Phe Val Pro Gly Phe Gly Gln Gln Pro Leu
        675                 680                 685

Gln Lys Ile Pro Pro Leu Gln Gly Val Ser Gln Leu Gln Ser Asn
    690                 695                 700

Ser Cys Pro Ala Pro Gln Gln Ala Ala Pro Gln Ala
705                 710                 715

<210> SEQ ID NO 80
<211> LENGTH: 6486
<212> TYPE: DNA
<213> ORGANISM: Artificial Sequence
<220> FEATURE:
<223> OTHER INFORMATION: pCMVKm2.gagopt PCAV vector

<400> SEQUENCE: 80
gccgcggaat tcgactcta ggccattgca tacgttgtat ctatatcata atatgtacat      60
ttatattggc tcatgtccaa tatgaccgcc atgttgacat tgattattga ctagttatta    120
atagtaatca attacggggt cattagttca tagcccatat atggagttcc gcgttacata    180
acttacggta aatggcccgc ctggctgacc gcccaacgac ccccgcccat tgacgtcaat    240
aatgacgtat gttcccatag taacgccaat agggactttc cattgacgtc aatgggtgga    300
gtatttacgg taaactgccc acttggcagt acatcaagtg tatcatatgc caagtccgcc    360
ccctattgac gtcaatgacg gtaaatggcc cgcctggcat tatgcccagt acatgacctt    420
acgggacttt cctacttggc agtacatcta cgtattagtc atcgctatta ccatggtgat    480
gcggttttgg cagtacacca atgggcgtgg atagcggttt gactcacggg gatttccaag    540
tctccacccc attgacgtca atgggagttt gttttggcac caaaatcaac gggactttcc    600
aaaatgtcgt aataaccccg ccccgttgac gcaaatgggc ggtaggcgtg tacggtggga    660

```
ggtctatata agcagagctc gtttagtgaa ccgtcagatc gcctggagac gccatccacg    720
ctgttttgac ctccatagaa gacaccggga ccgatccagc ctccgcggcc gggaacggtg    780
cattggaacg cggattcccc gtgccaagag tgacgtaagt accgcctata gactctatag    840
gcacacccct ttggctctta tgcatgctat actgtttttg gcttggggcc tatacacccc    900
cgcttcctta tgctataggt gatggtatag cttagcctat aggtgtgggt tattgaccat    960
tattgaccac tccccctattg gtgacgatac tttccattac taatccataa catggctctt   1020
tgccacaact atctctattg gctatatgcc aatactctgt ccttcagaga ctgacacgga   1080
ctctgtattt ttacaggatg gggtcccatt tattatttac aaattcacat atacaacaac   1140
gccgtccccc gtgcccgcag ttttttattaa acatagcgtg ggatctccac gcgaatctcg   1200
ggtacgtgtt ccggacatgg gctcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccgtcgt cgacgccacc atgggccaga ccgagagcaa   1680
gtacgccagc tacctgagct tcatcaagat cctgctgcgc gcggcggcg tgcgcgccag    1740 caccgagaac ctgatcaccc tgttccagac catcgagcag ttctgcccct ggttccccga   1800
gcagggcacc ctggacctga aggactggga gaagatcggc aaggagctga gcaggccaa    1860 ccgcgagggc aagatcatcc ccctgaccgt gtggaacgac tgggccatca tcaaggccac   1920
cctggagccc ttccagaccg gcgaggacat cgtgagcgtg agcgacgccc caagagctg    1980 cgtgaccgac tgcgaggagg aggccggcac cgagagccag cagggcaccg agagcagcca   2040
ctgcaagtac gtggccgaga gcgtgatggc ccagagcacc cagaacgtgg actcagcca    2100 gctgcaggag atcatctacc ccgagagcag caagctgggc gagggcggcc ccgagagcct   2160
gggccccagc gagcccaagc cccgcagccc cagcaccccc ccccccgtgg tgcagatgcc   2220
cgtgaccctg cagcccccaga cccaggtgcg ccaggcccag acccccgcg agaaccaggt   2280 ggagcgcgac cgcgtgagca tccccgccat gcccacccag atccagtacc ccagtacca    2340 gcccgtggag aacaagaccc agcccctggt ggtgtaccag taccgcctgc ccaccgagct   2400
gcagtaccgc ccccccagcg aggtgcagta ccgcccccag gccgtgtgcc ccgtgcccaa   2460
cagcaccgcc ccctaccagc agcccaccgc catggccagc aacagccccg ccacccagga   2520
cgccgccctg tacccccagc ccccccaccgt gcgcctgaac cccaccgcca gccgcagcgg   2580
ccagggcggc gccctgcacg ccgtgatcga cgaggcccgc aagcagggcg acctggaggc   2640
ctggcgcttc ctggtgatcc tgcagctggt gcaggccggc gaggagaccc aggtgggcgc   2700
ccccgcccgc gccgagaccc gctgcgagcc cttcaccatg aagatgctga aggacatcaa   2760
ggagggcgtg aagcagtacg gcagcaacag cccctacatc cgcaccctgc tggacagcat   2820
cgcccacggc aaccgcctga cccccctacga ctggagagatc ctggccaaga gcagcctgag   2880
cagcagccag tacctgcagt tcaagacctg gtggatcgac ggcgtgcagg agcaggtgcg   2940
caagaaccag gccaccaagc ccaccgtgaa catcgcgcc gaccagctgc tgggcaccgg   3000
ccccaactgg agcaccatca accagcagag cgtgatgcag aacgaggcca tcgagcaggt   3060
```

```
gcgcgccatc tgcctgcgcg cctggggcaa gatccaggac cccggcaccg ccttccccat   3120
caacagcatc cgccagggca gcaaggagcc ctaccccgac ttcgtggccc gcctgcagga   3180
cgccgcccag aagagcatca ccgacgacaa cgcccgcaag gtgatcgtgg agctgatggc   3240
ctacgagaac gccaaccccg agtgccagag cgccatcaag cccctgaagg gcaaggtgcc   3300
cgccggcgtg gacgtgatca ccgagtacgt gaaggcctgc gacggcatcg gcggcgccat   3360
gcacaaggcc atgctgatgg cccaggccat gcgcggcctg accctgggcg ccaggtgcg   3420 caccttcggc aagaagtgct acaactgcgc ccagatcggc cacctgaagc gcagctgccc   3480
cgtgctgaac aagcagaaca tcatcaacca ggccatcacc gccaagaaca gaagcccag   3540 cggcctgtgc cccaagtgcg gcaagggcaa gcactgggcc aaccagtgcc acagcaagtt   3600
cgacaaggac ggccagcccc tgagcggcaa ccgcaagcgc ggccagcccc aggcccccca   3660
gcagaccggc gccttccccg tgcagctgtt cgtgccccag ggcttccagg ccagcagcc   3720 cctgcagaag atcccccccc tgcagggcgt gagccagctg cagcagagca cagctgccc   3780 cgccccccag caggccgccc ccaggcctta agaattcaga ctcgagcaag tctagaaagc   3840
catggatatc ggatccacta cgcgttagag ctcgctgatc agcctcgact gtgccttcta   3900
gttgccagcc atctgttgtt tgcccctccc ccgtgccttc cttgaccctg gaaggtgcca   3960
ctcccactgt cctttcctaa taaaatgagg aaattgcatc gcattgtctg agtaggtgtc   4020
attctattct ggggggtggg gtggggcagg acagcaaggg ggaggattgg gaagacaata   4080
gcaggggggt gggcgaagaa ctccagcatg agatcccgc gctggaggat catccagccg   4140
gcgtcccgga aaacgattcc gaagcccaac cttttcataga aggcggcggt ggaatcgaaa   4200
tctcgtgatg gcaggttggg cgtcgcttgg tcggtcattt cgaaccccag agtcccgctc   4260
agaagaactc gtcaagaagg cgatagaagg cgatgcgctg cgaatcggga gcggcgatac   4320
cgtaaagcac gaggaagcgg tcagcccatt cgccgccaag ctcttcagca atatcacggg   4380
tagccaacgc tatgtcctga tagcggtccg ccacacccag ccggccacag tcgatgaatc   4440
cagaaaagcg gccatttttcc accatgatat tcggcaagca ggcatcgcca tgggtcacga   4500
cgagatcctc gccgtcgggc atgcgcgcct tgagcctggc gaacagttcg ctggcgcga   4560 gcccctgatg ctcttcgtcc agatcatcct gatcgacaag accggcttcc atccgagtac   4620
gtgctcgctc gatgcgatgt ttcgcttggt ggtcgaatgg gcaggtagcc ggatcaagcg   4680
tatgcagccg ccgcattgca tcagccatga tggatacttt ctcggcagga gcaaggtgag   4740
atgacaggag atcctgcccc ggcacttcgc ccaatagcag ccagtccctt cccgcttcag   4800
tgacaacgtc gagcacagct gcgcaaggaa cgcccgtcgt ggccagccac gatagccgcg   4860
ctgcctcgtc ctgcagttca ttcagggcac cggacaggtc ggtcttgaca aaaagaaccg   4920
ggcgcccctg cgctgacagc cggaacacgg cggcatcaga gcagccgatt gtctgttgtg   4980
cccagtcata gccgaatagc ctctccaccc aagcggccgg agaacctgcg tgcaatccat   5040
cttgttcaat catgcgaaac gatcctcatc ctgtctcttg atcagatctt gatccctgc   5100 gccatcagat ccttggcggc aagaaagcca tccagtttac tttgcagggc ttcccaacct   5160
taccagaggg cgccccagct ggcaattccg gttcgcttgc tgtccataaa accgcccagt   5220
ctagctatcg ccatgtaagc ccactgcaag ctacctgctt tctctttgcg cttgcgtttt   5280
cccttgtcca gatagcccag tagctgacat tcatccgggg tcagcaccgt ttctgcggac   5340
tggctttcta cgtgttccgc ttcctttagc agcccttgcg ccctgagtgc ttgcggcagc   5400
gtgaagctaa ttcatggtta aatttttgtt aaatcagctc attttttaac caataggccg   5460
```

-continued

```
aaatcggcaa aatcccttat aaatcaaaag aatagcccga gatagggttg agtgttgttc    5520
cagtttggaa caagagtcca ctattaaaga acgtggactc caacgtcaaa gggcgaaaaa    5580
ccgtctatca gggcgatggc cggatcagct tatgcggtgt gaaataccgc acagatgcgt    5640
aaggagaaaa taccgcatca ggcgctcttc cgcttcctcg ctcactgact cgctgcgctc    5700
ggtcgttcgg ctgcggcgag cggtatcagc tcactcaaag gcggtaatac ggttatccac    5760
agaatcaggg gataacgcag gaaagaacat gtgagcaaaa ggccagcaaa aggccaggaa    5820
ccgtaaaaag gccgcgttgc tggcgttttt ccataggctc cgcccccctg acgagcatca    5880
caaaaatcga cgctcaagtc agaggtggcg aaacccgaca ggactataaa gataccaggc    5940
gtttccccct ggaagctccc tcgtgcgctc tcctgttccg accctgccgc ttaccggata    6000
cctgtccgcc tttctccctt cgggaagcgt ggcgctttct catagctcac gctgtaggta    6060
tctcagttcg gtgtaggtcg ttcgctccaa gctgggctgt gtgcacgaac cccccgttca    6120
gcccgaccgc tgcgccttat ccggtaacta tcgtcttgag tccaacccgg taagacacga    6180
cttatcgcca ctggcagcag ccactggtaa caggattagc agagcgaggt atgtaggcgg    6240
tgctacagag ttcttgaagt ggtggcctaa ctacggctac actagaagga cagtatttgg    6300
tatctgcgct ctgctgaagc cagttacctt cggaaaaaga gttggtagct cttgatccgg    6360
caaacaaacc accgctggta gcggtggttt ttttgtttgc aagcagcaga ttacgcgcag    6420
aaaaaaagga tctcaagaag atcctttgat cttttctact gaacggtgat ccccaccgga    6480
attgcg                                                               6486
```

<210> SEQ ID NO 81
<211> LENGTH: 2103
<212> TYPE: DNA
<213> ORGANISM: Human endogenous retrovirus, K family (HERV-K)

<400> SEQUENCE: 81

```
atgaacccaa gcgagatgca agaaaagca cctccgcgga gacggagaca tcgcaatcga      60
gcaccgttga ctcacaagat gaacaaaatg gtgacgtcag aagaacagat gaagttgcca     120
tccaccaaga aggcagagcc gccaacttgg gcacaactaa agaagctgac gcagttagct     180
acaaaatatc tagagaacac aaaggtgaca caaaccccag agagtatgct gcttgcagcc     240
ttgatgattg tatcaatggt ggtaagtctc cctatgcctg caggagcagc tgcagctaac     300
tatacctact gggcctatgt gccttttccg cccttaattc gggcagtcac atggatggat     360
aatcctacag aagtatatgt taatgatagt gtatgggtac ctggccccat agatgatcgc     420
tgccctgcca aacctgagga gaagggatg atgataaata tttccattgg gtatcattat     480
cctcctattt gcctagggag agcaccagga tgtttaatgc ctgcagtcca aaattggttg     540
gtagaagtac ctactgtcag tcccatctgt agattcactt atcacatggt aagcgggatg     600
tcactcaggc cacgggtaaa ttatttacaa gacttttctt atcaaagatc attaaaattt     660
agacctaaag ggaaaccttg ccccaaggaa attcccaaag aatcaaaaaa tacagaagtt     720
ttagtttggg aagaatgtgt ggccaatagt gcggtgatat tacaaaacaa tgaattcgga     780
actattatag attgggcacc tcgaggtcaa ttctaccaca attgctcagg acaaactcag     840
tcgtgtccaa gtgcacaagt gagtccagct gttgatagcg acttaacaga agtttagac     900 aaacataagc ataaaaaatt gcagtctttc tacccttggg aatggggaga aaaggaatc     960 tctacccccaa gaccaaaaat agtaagtcct gtttctggtc ctgaacatcc agaattatgg    1020
aggcttactg tggcttcaca ccacattaga atttggtctg gaaatcaaac tttagaaaca    1080
```

```
agagatcgta agccatttta tactattgac ctgaattcca gtctaacagt tcctttacaa    1140
agttgcgtaa agccccctta tatgctagtt gtaggaaata tagttattaa accagactcc    1200
cagactataa cctgtgaaaa ttgtagattg cttacttgca ttgattcaac ttttaattgg    1260
caacaccgta ttctgctggt gagagcaaga gagggcgtgt ggatccctgt gtccatggac    1320
cgaccgtggg aggcctcgcc atccgtccat attttgactg aagtattaaa aggtgtttta    1380
aatagatcca aaagattcat ttttacttta attgcagtga ttatgggatt aattgcagtc    1440
acagctacgg ctgctgtagc aggagttgca ttgcactctt ctgttcagtc agtaaacttt    1500
gttaatgatt ggcaaaaaaa ttctacaaga ttgtggaatt cacaatctag tattgatcaa    1560
aaattggcaa atcaaattaa tgatcttaga caaactgtca tttggatggg agacagactc    1620
atgagcttag aacatcgttt ccagttacaa tgtgactgga atacgtcaga tttttgtatt    1680 acacccaaa tttataatga gtctgagcat cactgggaca tggttagacg ccatctacag    1740
ggaagagaag ataatctcac tttagacatt tccaaattaa agaacaaat tttcgaagca    1800 tcaaaagccc atttaaattt ggtgccagga actgaggcaa ttgcaggagt tgctgatggc    1860
ctcgcaaatc ttaaccctgt cacttgggtt aagaccattg aagtactac gattataaat    1920 ctcatattaa tccttgtgtg cctgttttgt ctgttgttag tctgcaggtg tacccaacag    1980
ctccgaagag acagcgacca tcgagaacgg gccatgatga cgatggcggt tttgtcgaaa    2040
agaaaagggg gaatgtggg gaaaagcaag agagatcaga ttgttactgt gtctgtggcc    2100
taa                                                                  2103
```

<210> SEQ ID NO 82
<211> LENGTH: 2103
<212> TYPE: DNA
<213> ORGANISM: Artificial Sequence
<220> FEATURE:
<223> OTHER INFORMATION: Modified env sequence

<400> SEQUENCE: 82

```
atgaaccca gcgagatgca gcgcaaggcc ccccccgcc gccgccgcca ccgcaaccgc     60 gccccctga cccacaagat gaacaagatg gtgaccagcg aggagcagat gaagctgccc    120
agcaccaaga aggccgagcc ccccacctgg gcccagctga agaagctgac ccagctggcc    180
accaagtacc tggagaacac caaggtgacc cagaccccg agagcatgct gctggccgcc    240
ctgatgatcg tgagcatggt ggtgagcctg cccatgcccg ccggcgccgc cgccgccaac    300
tacacctact gggcctacgt gcccttcccc cccctgatcc gcgccgtgac ctggatggac    360
aaccccaccg aggtgtacgt gaacgacagc gtgtgggtgc ccggccccat cgacgaccgc    420
tgccccgcca gcccgagga ggagggcatg atgatcaaca tcagcatcgg ctaccactac    480 cccccatct gcctgggccg cgccccggc tgcctgatgc ccgccgtgca gaactggctg    540
gtggaggtgc ccaccgtgag ccccatctgc cgcttcacct accacatggt gagcggcatg    600
agcctgcgcc ccgcgtgaa ctacctgcag gacttcagct accagcgcag cctgaagttc    660
cgccccaagg gcaagccctg ccccaaggag atccccaagg agagcaagaa caccgaggtg    720
ctggtgtggg aggagtgcgt ggccaacagc gccgtgatcc tgcagaacaa cgagttcggc    780
accatcatcg actgggcccc ccgcggccag ttctaccaca actgcagcgg ccagacccag    840
agctgcccca gcgccaggt gagccccgcc gtggacagcg acctgaccga gagcctggac    900
aagcacaagc acaagaagct gcagagcttc taccctgggg agtggggcga agggcatc     960 agcacccccc gccccaagat cgtgagcccc gtgagcggcc ccgagcaccc cgagctgtgg   1020
```

-continued

```
cgcctgaccg tggccagcca ccacatccgc atctggagcg gcaaccagac cctggagacc    1080
cgcgaccgca agcccttcta caccatcgac ctgaacagca gcctgaccgt gcccctgcag    1140
agctgcgtga agccccccta catgctggtg gtgggcaaca tcgtgatcaa gcccgacagc    1200
cagaccatca cctgcgagaa ctgccgcctg ctgacctgca tcgacagcac cttcaactgg    1260
cagcaccgca tcctgctggt gcgcgcccgc gagggcgtgt ggatccccgt gagcatggac    1320
cgcccctggg aggccagccc cagcgtgcac atcctgaccg aggtgctgaa gggcgtgctg    1380
aaccgcagca agcgcttcat cttcaccctg atcgccgtga tcatgggcct gatcgccgtg    1440
accgccaccg ccgccgtggc cggcgtggcc ctgcacagca gcgtgcagag cgtgaacttc    1500
gtgaacgact ggcagaagaa cagcacccgc ctgtggaaca gcagagcag catcgaccag    1560 aagctggcca accagatcaa cgacctgcgc cagaccgtga tctggatggg cgaccgcctg    1620
atgagcctgg agcaccgctt ccagctgcag tgcgactgga caccagcga cttctgcatc    1680 acccccaga tctacaacga gagcgagcac cactgggaca tggtgcgccg ccacctgcag    1740
ggccgcgagg acaacctgac cctggacatc agcaagctga aggagcagat cttcgaggcc    1800
agcaaggccc acctgaacct ggtgcccggc accgaggcca tcgccggcgt ggccgacggc    1860
ctggccaacc tgaaccccgt gacctgggtg aagaccatcg gcagcaccac catcatcaac    1920
ctgatcctga tcctggtgtg cctgttctgc ctgctgctgg tgtgccgctg cacccagcag    1980
ctgcgccgcg acagcgacca ccgcgagcgc gccatgatga ccatggccgt gctgagcaag    2040
cgcaagggcg gcaacgtggg caagagcaag cgcgaccaga tcgtgaccgt gagcgtggcc    2100
taa                                                                  2103
```

<210> SEQ ID NO 83
<211> LENGTH: 700
<212> TYPE: PRT
<213> ORGANISM: Human endogenous retrovirus, K family (HERV-K)

<400> SEQUENCE: 83

```
Met Asn Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
        50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
                100                 105                 110

Ile Arg Ala Val Thr Trp Met Asp Asn Pro Thr Glu Val Tyr Val Asn
            115                 120                 125

Asp Ser Val Trp Val Pro Gly Pro Ile Asp Asp Arg Cys Pro Ala Lys
        130                 135                 140

Pro Glu Glu Glu Gly Met Met Ile Asn Ile Ser Ile Gly Tyr His Tyr
145                 150                 155                 160

Pro Pro Ile Cys Leu Gly Arg Ala Pro Gly Cys Leu Met Pro Ala Val
                165                 170                 175
```

-continued

```
Gln Asn Trp Leu Val Glu Val Pro Thr Val Ser Pro Ile Cys Arg Phe
            180                 185                 190

Thr Tyr His Met Val Ser Gly Met Ser Leu Arg Pro Arg Val Asn Tyr
            195                 200                 205

Leu Gln Asp Phe Ser Tyr Gln Arg Ser Leu Lys Phe Arg Pro Lys Gly
            210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Ile Ile Asp Trp Ala Pro Arg Gly Gln Phe Tyr
            260                 265                 270

His Asn Cys Ser Gly Gln Thr Gln Ser Cys Pro Ser Ala Gln Val Ser
            275                 280                 285

Pro Ala Val Asp Ser Asp Leu Thr Glu Ser Leu Asp Lys His Lys His
            290                 295                 300

Lys Lys Leu Gln Ser Phe Tyr Pro Trp Glu Trp Gly Glu Lys Gly Ile
305                 310                 315                 320

Ser Thr Pro Arg Pro Lys Ile Val Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
            355                 360                 365

Ile Asp Leu Asn Ser Ser Leu Thr Val Pro Leu Gln Ser Cys Val Lys
            370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
            435                 440                 445

Val His Ile Leu Thr Glu Val Leu Lys Gly Val Leu Asn Arg Ser Lys
            450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
                485                 490                 495

Ser Val Asn Phe Val Asn Asp Trp Gln Lys Asn Ser Thr Arg Leu Trp
            500                 505                 510

Asn Ser Gln Ser Ser Ile Asp Gln Lys Leu Ala Asn Gln Ile Asn Asp
            515                 520                 525

Leu Arg Gln Thr Val Ile Trp Met Gly Asp Arg Leu Met Ser Leu Glu
            530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
                565                 570                 575

Arg His Leu Gln Gly Arg Glu Asp Asn Leu Thr Leu Asp Ile Ser Lys
            580                 585                 590

Leu Lys Glu Gln Ile Phe Glu Ala Ser Lys Ala His Leu Asn Leu Val
            595                 600                 605
```

```
Pro Gly Thr Glu Ala Ile Ala Gly Val Ala Asp Gly Leu Ala Asn Leu
    610             615             620

Asn Pro Val Thr Trp Val Lys Thr Ile Gly Ser Thr Thr Ile Ile Asn
625             630             635             640

Leu Ile Leu Ile Leu Val Cys Leu Phe Cys Leu Leu Leu Val Cys Arg
                645             650             655

Cys Thr Gln Gln Leu Arg Arg Asp Ser Asp His Arg Glu Arg Ala Met
            660             665             670

Met Thr Met Ala Val Leu Ser Lys Arg Lys Gly Gly Asn Val Gly Lys
        675             680             685

Ser Lys Arg Asp Gln Ile Val Thr Val Ser Val Ala
    690             695             700
```